United States Patent
Howard et al.

(10) Patent No.: US 9,821,074 B2
(45) Date of Patent: Nov. 21, 2017

(54) PYRROLOBENZODIAZEPINES AND CONJUGATES THEREOF

(71) Applicants: Spirogen Sàrl, St-Légier-Chiésaz (CH); Genentech, Inc., South San Francisco, CA (US)

(72) Inventors: Philip Wilson Howard, London (GB); John A. Flygare, South San Francisco, CA (US); Thomas Pillow, South San Francisco, CA (US); Binqing Wei, South San Francisco, CA (US)

(73) Assignees: Genentech, Inc., San Francisco, CA (US); MedImmue Limited (GB)

( * ) Notice: Subject to any disclaimer, the term of this patent is extended or adjusted under 35 U.S.C. 154(b) by 81 days.

(21) Appl. No.: 14/208,374

(22) Filed: Mar. 13, 2014

(65) Prior Publication Data

US 2014/0294868 A1    Oct. 2, 2014

Related U.S. Application Data

(60) Provisional application No. 61/778,771, filed on Mar. 13, 2013.

(51) Int. Cl.
*A61K 47/48* (2006.01)
*A61K 31/5517* (2006.01)
(Continued)

(52) U.S. Cl.
CPC .... *A61K 47/48638* (2013.01); *A61K 31/5517* (2013.01); *A61K 47/4863* (2013.01);
(Continued)

(58) Field of Classification Search
None
See application file for complete search history.

(56) References Cited

U.S. PATENT DOCUMENTS 6,562,806 B1   5/2003   Thurston et al.
6,608,192 B1   8/2003   Thurston et al.
(Continued)

FOREIGN PATENT DOCUMENTS

NL   WO 2011133039 A2 * 10/2011 ........... A61K 31/437
WO   WO 00/12506        3/2000
(Continued)

OTHER PUBLICATIONS

Jeffrey SC, et al., "A potent anti-CD70 antibody-drug conjugate combining a dimeric pyrrolobenzodiazepine drug with site-specific conjugation technology." Bioconjug Chem. Jul. 17, 2013;24(7): 1256-1263. Jun. 28, 2013.
(Continued)

*Primary Examiner* — Mark Halvorson
*Assistant Examiner* — Kauser Akhoon

(74) *Attorney, Agent, or Firm* — Michael Best & Friedrich, LLP; Lisa L. Mueller

(57) ABSTRACT

Conjugate compounds of formula (A):

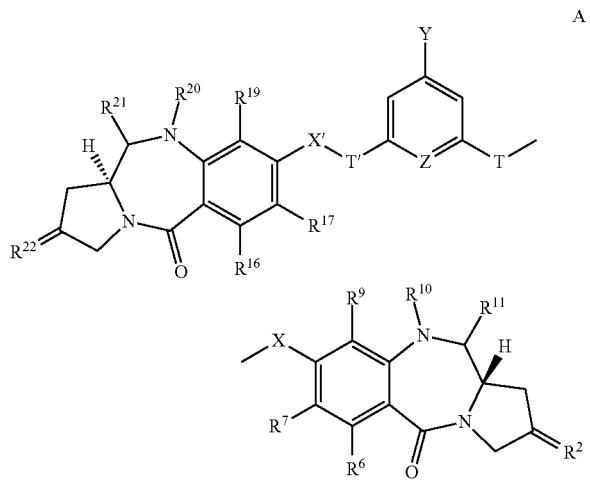

Figure 1:
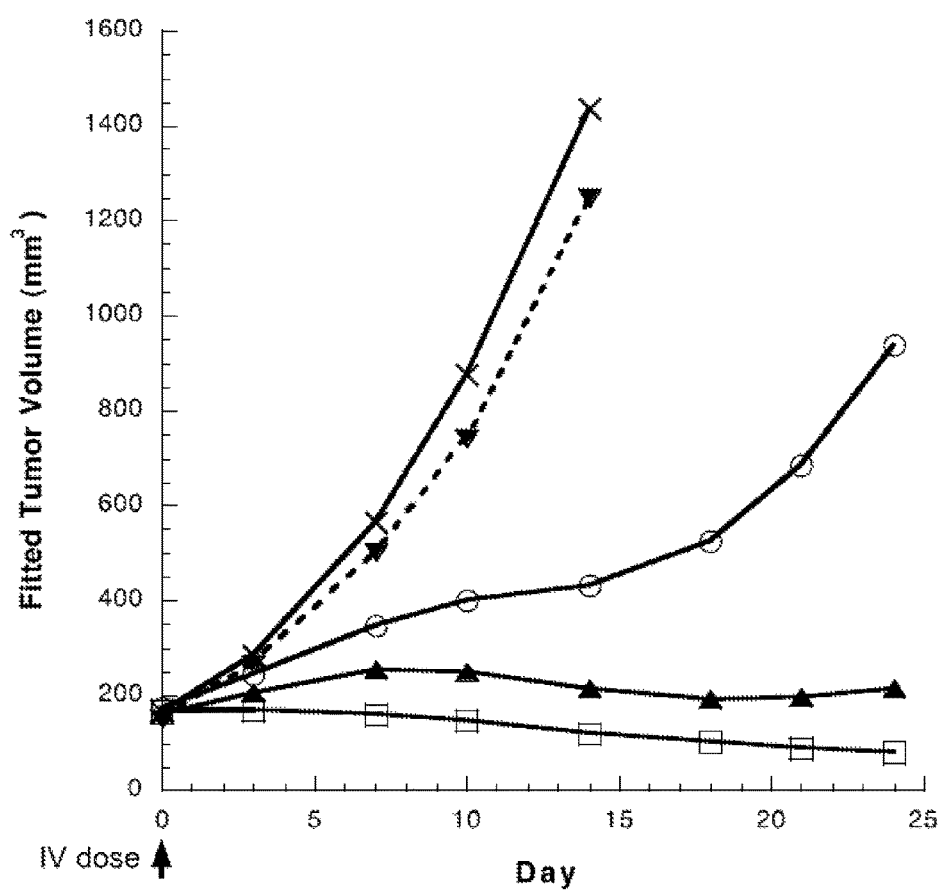

wherein:
$R^2$ is where $R^{36a}$ and $R^{36b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester or, when one of $R^{36a}$ and $R^{36b}$ is H, the other is selected from nitrile and a $C_{1-4}$ alkyl ester;
$R^6$ and $R^9$ are independently selected from H, R, OH, OR, SH, SR, $NH_2$, NHR, NRR', $NO_2$, $Me_3Sn$ and halo;
$R^7$ is independently selected from H, R, OH, OR, SH, SR, $NH_2$, NHR, NRR', $NO_2$, $Me_3Sn$ and halo;
Y is selected from formulae A1, A2, A3, A4, A5 and A6:

(Continued)

-continued

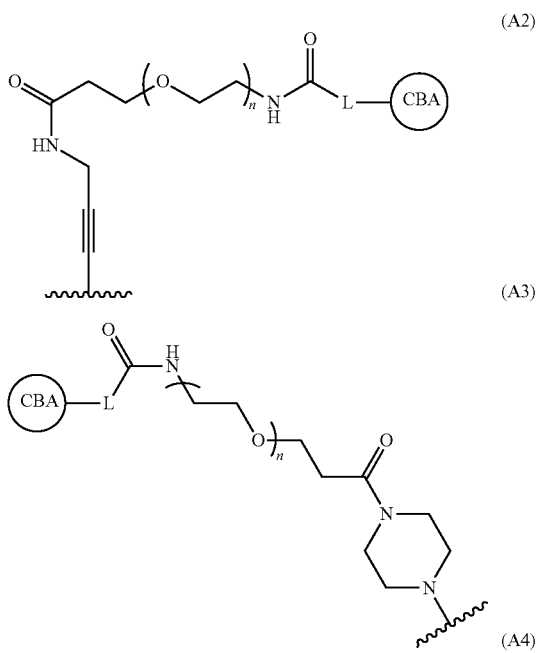

(A2)

(A3)

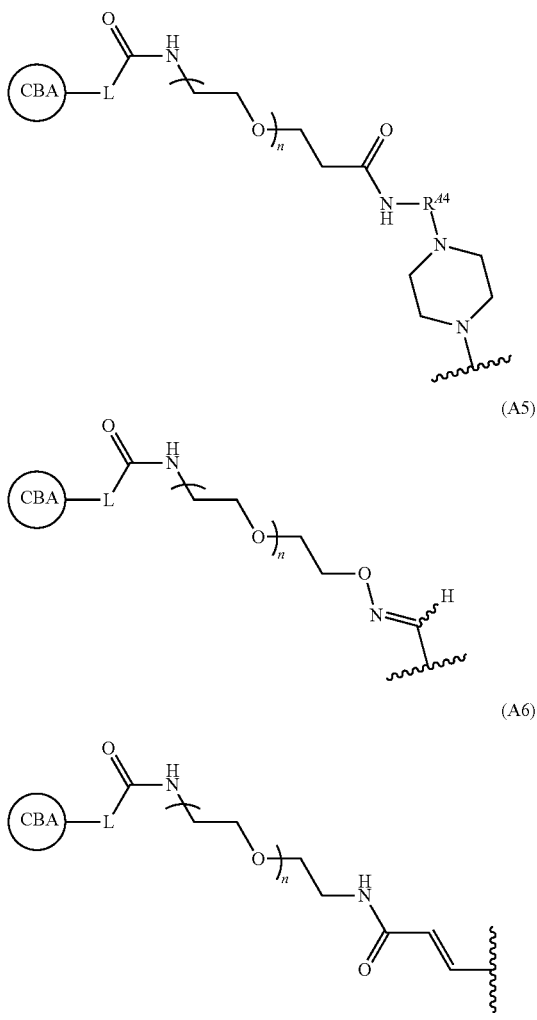

(A4)

(A5)

(A6)

L is a linker connected to a cell binding agent;
CBA is the cell binding agent;
n is an integer selected in the range of 0 to 48;
$R^{44}$ is a $C_{1-6}$ alkylene group; either
(a) $R^{10}$ is H, and $R^{11}$ is OH, $OR^A$, where $R^A$ is $C_{1-4}$ alkyl; or
(b) $R^{10}$ and $R^{11}$ form a nitrogen-carbon double bond between the nitrogen and carbon atoms to which they are bound; or
(c) $R^{10}$ is H and $R^{11}$ is $OSO_zM$, where z is 2 or 3 and M is a monovalent pharmaceutically acceptable cation;
R and R' are each independently selected from optionally substituted $C_{1-12}$ alkyl, $C_{3-20}$ heterocyclyl and $C_{5-20}$ aryl groups, and optionally in relation to the group NRR', R and R' together with the nitrogen atom to which they are attached form an optionally substituted 4-, 5-, 6- or 7-membered heterocyclic ring;
wherein $R^{16}$, $R^{17}$, $R^{19}$, $R^{20}$, $R^{21}$ and $R^{22}$ are as defined for $R^6$, $R^7$, $R^9$, $R^{10}$, $R^{11}$ and $R^2$ respectively;
wherein Z is CH or N;
wherein T and T' are independently selected from a single bond or a $C_{1-9}$ alkylene, which chain may be interrupted by one or more heteroatoms e.g. O, S, N(H), NMe, provided that the number of atoms in the shortest chain of atoms between X and X' is 3 to 12 atoms; and
X and X' are independently selected from O, S and N(H).

8 Claims, 3 Drawing Sheets

(51) Int. Cl.
*C07D 519/00* (2006.01)
*C07D 487/04* (2006.01)

(52) U.S. Cl.
CPC .. *A61K 47/48384* (2013.01); *A61K 47/48546* (2013.01); *A61K 47/48561* (2013.01); *A61K 47/48569* (2013.01); *A61K 47/48584* (2013.01); *A61K 47/48715* (2013.01); *C07D 487/04* (2013.01); *C07D 519/00* (2013.01)

(56) References Cited

U.S. PATENT DOCUMENTS

| | | |
|---|---|---|
| 6,660,742 B2 | 12/2003 | Lee et al. |
| 6,747,144 B1 | 6/2004 | Thurston et al. |
| 6,909,006 B1 | 6/2005 | Thurston et al. |
| 7,049,311 B1 | 5/2006 | Thurston et al. |
| 7,067,511 B2 | 6/2006 | Thurston et al. |
| 7,265,105 B2 | 9/2007 | Thurston et al. |
| 7,407,951 B2 | 8/2008 | Thurston et al. |
| 7,429,658 B2 | 9/2008 | Howard et al. |
| 7,528,126 B2 | 5/2009 | Howard et al. |
| 7,557,099 B2 | 7/2009 | Howard et al. |
| 7,612,062 B2 | 11/2009 | Gregson et al. |
| 7,704,924 B2 | 4/2010 | Thurston et al. |
| 7,741,319 B2 | 6/2010 | Howard et al. |
| 8,034,808 B2 | 10/2011 | Delavault et al. |
| 8,487,092 B2 | 7/2013 | Howard et al. |
| 8,501,934 B2 | 8/2013 | Howard et al. |
| 8,592,576 B2 | 11/2013 | Howard et al. |
| 8,633,185 B2 | 1/2014 | Howard et al. |
| 8,637,664 B2 | 1/2014 | Howard et al. |
| 8,697,688 B2 | 4/2014 | Howard et al. |
| 8,829,184 B2 | 9/2014 | Howard et al. |
| 8,940,733 B2 | 1/2015 | Howard et al. |
| 9,102,704 B2 | 8/2015 | Howard |
| 2003/0195196 A1 | 10/2003 | Thurston et al. |
| 2004/0198722 A1 | 10/2004 | Thurston et al. |
| 2007/0154906 A1 | 7/2007 | Martin et al. |
| 2007/0191349 A1 | 8/2007 | Howard et al. |
| 2007/0249591 A1 | 10/2007 | Howard et al. |
| 2008/0090812 A1 | 4/2008 | Pepper et al. |

(56) References Cited

U.S. PATENT DOCUMENTS

| | | |
|---|---|---|
| 2009/0036431 A1 | 2/2009 | Gauzy et al. |
| 2009/0274713 A1 | 11/2009 | Chari et al. |
| 2009/0304710 A1 | 12/2009 | Park et al. |
| 2010/0028346 A1 | 2/2010 | Lutz et al. |
| 2010/0047257 A1 | 2/2010 | Blanc et al. |
| 2010/0203007 A1 | 8/2010 | Li et al. |
| 2010/0316656 A1 | 12/2010 | Bouchard et al. |
| 2011/0039969 A1 | 2/2011 | Muratoglu et al. |
| 2011/0160192 A1 | 6/2011 | Howard et al. |
| 2011/0195021 A1 | 8/2011 | Deckert et al. |
| 2011/0195022 A1 | 8/2011 | Deckert et al. |
| 2011/0256157 A1 | 10/2011 | Howard et al. |
| 2012/0233172 A1 | 9/2012 | Skillcorn et al. |
| 2012/0238731 A1 | 9/2012 | Fishkin et al. |
| 2013/0028917 A1 | 1/2013 | Howard et al. |
| 2013/0028919 A1 | 1/2013 | Howard et al. |
| 2013/0137659 A1 | 5/2013 | Commercon et al. |
| 2013/0244171 A1 | 9/2013 | Yamasaki et al. |
| 2013/0266595 A1 | 10/2013 | Flygare et al. |
| 2013/0266596 A1 | 10/2013 | Li et al. |
| 2013/0302359 A1 | 11/2013 | Li et al. |
| 2013/0304357 A1 | 11/2013 | Koci et al. |
| 2014/0030279 A1 | 1/2014 | Polakis et al. |
| 2014/0030280 A1 | 1/2014 | Polakis et al. |
| 2014/0066435 A1 | 3/2014 | Howard et al. |
| 2014/0088089 A1 | 3/2014 | Chari |
| 2014/0120118 A1 | 5/2014 | Howard |
| 2014/0127239 A1 | 5/2014 | Howard |
| 2014/0155590 A1 | 6/2014 | Commercon et al. |
| 2014/0234346 A1 | 8/2014 | Howard |
| 2014/0274907 A1 | 9/2014 | Howard et al. |
| 2014/0286970 A1 | 9/2014 | Jeffrey et al. |
| 2014/0302066 A1 | 10/2014 | Jeffrey et al. |
| 2015/0111880 A1 | 4/2015 | Howard et al. |
| 2015/0126495 A1 | 5/2015 | Howard et al. |
| 2015/0133435 A1 | 5/2015 | Howard et al. |
| 2015/0158869 A1 | 6/2015 | Howard |
| 2015/0183883 A1 | 7/2015 | Asundi |
| 2015/0265722 A1 | 9/2015 | Van Berkel |
| 2015/0273077 A1 | 10/2015 | Van Berkel |
| 2015/0273078 A1 | 10/2015 | Van Berkel |
| 2015/0274737 A1 | 10/2015 | Howard et al. |
| 2015/0283258 A1 | 10/2015 | Van Berkel |
| 2015/0283262 A1 | 10/2015 | Van Berkel |
| 2015/0283263 A1 | 10/2015 | Van Berkel |
| 2015/0297746 A1 | 10/2015 | Van Berkel |
| 2015/0315196 A1 | 11/2015 | Howard et al. |
| 2015/0344482 A1 | 12/2015 | Howard et al. |
| 2016/0015828 A1 | 1/2016 | Torgor |
| 2016/0031887 A1 | 2/2016 | Howard et al. |

FOREIGN PATENT DOCUMENTS

| | | |
|---|---|---|
| WO | WO 00/12507 | 3/2000 |
| WO | WO 00/12508 | 3/2000 |
| WO | WO 00/12509 | 3/2000 |
| WO | WO 01/16104 | 3/2001 |
| WO | WO 2004/043963 | 5/2004 |
| WO | WO 2005/023814 | 3/2005 |
| WO | WO 2005/042535 | 5/2005 |
| WO | WO 2005/085177 | 9/2005 |
| WO | WO 2005/085250 | 9/2005 |
| WO | WO 2005/085251 | 9/2005 |
| WO | WO 2005/085259 | 9/2005 |
| WO | WO 2005/085260 | 9/2005 |
| WO | WO 2005/105113 | 11/2005 |
| WO | WO 2005/110423 | 11/2005 |
| WO | WO 2006/111759 | 10/2006 |
| WO | WO 2007/039752 | 4/2007 |
| WO | WO 2007/085930 | 8/2007 |
| WO | WO 2008/050140 | 5/2008 |
| WO | WO 2009/016516 | 2/2009 |
| WO | WO 2009/060208 | 5/2009 |
| WO | WO 2009/060215 | 5/2009 |
| WO | WO 2010/010347 | 1/2010 |
| WO | WO 2010/043877 | 4/2010 |
| WO | WO 2010/043880 | 4/2010 |
| WO | WO 2010/091150 | 8/2010 |
| WO | WO 2011/023883 | 3/2011 |
| WO | WO 2011/128650 | 10/2011 |
| WO | WO 2011/130598 | 10/2011 |
| WO | WO 2011/130613 | 10/2011 |
| WO | WO 2011/130616 | 10/2011 |
| WO | WO 2012/014147 | 2/2012 |
| WO | WO 2012/112687 | 8/2012 |
| WO | WO 2012/112708 | 8/2012 |
| WO | WO 2012/128868 | 9/2012 |
| WO | WO 2013/041606 | 3/2013 |
| WO | WO 2013/053871 | 4/2013 |
| WO | WO 2013/053872 | 4/2013 |
| WO | WO 2013/053873 | 4/2013 |
| WO | WO 2013/055987 | 4/2013 |
| WO | WO 2013/055990 | 4/2013 |
| WO | WO 2013/055993 | 4/2013 |
| WO | WO 2013/164592 | 11/2013 |
| WO | WO 2013/164593 | 11/2013 |
| WO | WO 2014/011518 | 1/2014 |
| WO | WO 2014/011519 | 1/2014 |
| WO | WO 2014/022679 | 2/2014 |
| WO | WO 2014/057072 | 4/2014 |
| WO | WO 2014/057073 | 4/2014 |
| WO | WO 2014/057074 | 4/2014 |
| WO | WO 2014/057113 | 4/2014 |
| WO | WO 2014/057114 | 4/2014 |
| WO | WO 2014/057115 | 4/2014 |
| WO | WO 2014/057117 | 4/2014 |
| WO | WO 2014/057118 | 4/2014 |
| WO | WO 2014/057119 | 4/2014 |
| WO | WO 2014/057120 | 4/2014 |
| WO | WO 2014/057122 | 4/2014 |
| WO | WO 2014/096365 | 6/2014 |
| WO | WO 2014/096368 | 6/2014 |
| WO | WO 2014/130879 | 8/2014 |
| WO | WO 2014/140174 | 9/2014 |
| WO | WO 2014/140862 | 9/2014 |
| WO | WO 2014/159981 | 10/2014 |
| WO | WO 2014/174111 | 10/2014 |
| WO | WO 2015/052321 | 4/2015 |
| WO | WO 2015/052322 | 4/2015 |
| WO | WO 2015/052532 | 4/2015 |
| WO | WO 2015/052533 | 4/2015 |
| WO | WO 2015/052534 | 4/2015 |
| WO | WO 2015/052535 | 4/2015 |
| WO | WO 2015/095124 | 6/2015 |
| WO | WO 2015/159076 | 10/2015 |

OTHER PUBLICATIONS

International Search Report and Written Opinion for Application No. PCT/2014/025564 dated Jan. 27, 2015 (9 pages).
U.S. Appl. No. 14/995,944, filed Jan. 14, 2016, Howard et al.
International Search Report and Written Opinion for Application No. PCT/US2014/025564 dated Jan. 27, 2015.

* cited by examiner

SEQUENCE LISTING

```
<160> NUMBER OF SEQ ID NOS: 55

<210> SEQ ID NO 1
<211> LENGTH: 16
<212> TYPE: PRT
<213> ORGANISM: Artificial sequence
<220> FEATURE:
<223> OTHER INFORMATION: Synthetic sequence: Antibody drug conjugate CDR
      L1

<400> SEQUENCE: 1

Arg Ser Ser Glu Thr Leu Val His Ser Ser Gly Asn Thr Tyr Leu Glu
1               5                   10                  15

<210> SEQ ID NO 2
<211> LENGTH: 7
<212> TYPE: PRT
<213> ORGANISM: Artificial sequence
<220> FEATURE:
<223> OTHER INFORMATION: Synthetic sequence: Antibody drug conjugate CDR
      L2

<400> SEQUENCE: 2

Arg Val Ser Asn Arg Phe Ser
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic sequence: Antibody drug conjugate CDR
      L3

<400> SEQUENCE: 3

Phe Gln Gly Ser Phe Asn Pro Leu Thr
1               5

<210> SEQ ID NO 4
<211> LENGTH: 10
<212> TYPE: PRT
<213> ORGANISM: Artificial sequence
<220> FEATURE:
<223> OTHER INFORMATION: Synthetic sequence: Antibody drug conjugate CDR
      H1

<400> SEQUENCE: 4

Gly Phe Ser Phe Ser Asp Phe Ala Met Ser
1               5                   10

<210> SEQ ID NO 5
<211> LENGTH: 18
<212> TYPE: PRT
<213> ORGANISM: Artificial sequence
<220> FEATURE:
<223> OTHER INFORMATION: Synthetic sequence: Antibody drug conjugate CDR
      H2

<400> SEQUENCE: 5

Ala Thr Ile Gly Arg Val Ala Phe His Thr Tyr Tyr Pro Asp Ser Met
```

```
                1               5                  10                  15

Lys Gly

<210> SEQ ID NO 6
<211> LENGTH: 13
<212> TYPE: PRT
<213> ORGANISM: Artificial sequence
<220> FEATURE:
<223> OTHER INFORMATION: Synthetic sequence: Antibody drug conjugate CDR
      H3

<400> SEQUENCE: 6

Ala Arg His Arg Gly Phe Asp Val Gly His Phe Asp Phe
1               5                  10

<210> SEQ ID NO 7
<211> LENGTH: 113
<212> TYPE: PRT
<213> ORGANISM: Artificial sequence
<220> FEATURE:
<223> OTHER INFORMATION: Synthetic sequence: Antibody drug conjugate VL

<400> SEQUENCE: 7

Asp Ile Gln Met Thr Gln Ser Pro Ser Ser Leu Ser Ala Ser Val Gly
1               5                  10                  15

Asp Arg Val Thr Ile Thr Cys Arg Ser Ser Glu Thr Leu Val His Ser
                20                  25                  30

Ser Gly Asn Thr Tyr Leu Glu Trp Tyr Gln Gln Lys Pro Gly Lys Ala
            35                  40                  45

Pro Lys Leu Leu Ile Tyr Arg Val Ser Asn Arg Phe Ser Gly Val Pro
        50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Phe Asn Pro Leu Thr Phe Gly Gln Gly Thr Lys Val Glu Ile Lys
                100                 105                 110

Arg

<210> SEQ ID NO 8
<211> LENGTH: 120
<212> TYPE: PRT
<213> ORGANISM: Artificial sequence
<220> FEATURE:
<223> OTHER INFORMATION: Synthetic sequence: Antibody drug conjugate VH

<400> SEQUENCE: 8

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Ser Phe Ser Asp Phe
                20                  25                  30

Ala Met Ser Trp Val Arg Gln Ala Pro Gly Lys Gly Leu Glu Trp Val
            35                  40                  45

Ala Thr Ile Gly Arg Val Ala Phe His Thr Tyr Tyr Pro Asp Ser Met
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg His Arg Gly Phe Asp Val Gly His Phe Asp Phe Trp Gly Gln
                100                 105                 110

Gly Thr Leu Val Thr Val Ser Ser
        115                 120

<210> SEQ ID NO 9
<211> LENGTH: 219
<212> TYPE: PRT
<213> ORGANISM: Artificial sequence
<220> FEATURE:
<223> OTHER INFORMATION: Synthetic sequence: Antibody drug conjugate
      light chain

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Thr Leu Val His Ser
                20                  25                  30

Ser Gly Asn Thr Tyr Leu Glu Trp Tyr Gln Gln Lys Pro Gly Lys Ala
            35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Phe Asn Pro Leu Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
    210                 215

<210> SEQ ID NO 10
<211> LENGTH: 450
<212> TYPE: PRT
<213> ORGANISM: Artificial sequence
<220> FEATURE:
<223> OTHER INFORMATION: Synthetic sequence: Antibody drug conjugate
      heavy chain

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
                20                  25                  30

Ala Met Ser Trp Val Arg Gln Ala Pro Gly Lys Gly Leu Glu Trp Val
            35                  40                  45

```
Ala Thr Ile Gly Arg Val Ala Phe His Thr Tyr Tyr Pro Asp Ser Met
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg His Arg Gly Phe Asp Val Gly His Phe Asp Phe Trp Gly Gln
             100                 105                 110
Gly Thr Leu Val Thr Val Ser Ser Cys Ser Thr Lys Gly Pro Ser Val
             115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Lys
450
```

```
<210> SEQ ID NO 11
<211> LENGTH: 16
<212> TYPE: PRT
<213> ORGANISM: Artificial sequence
<220> FEATURE:
<223> OTHER INFORMATION: Synthetic sequence: Antibody drug conjugate
      light chain hypervariable region HVR-L1

<400> SEQUENCE: 11

Arg Ser Ser Gln Ser Ile Val His Ser Val Gly Asn Thr Phe Leu Glu
1               5                   10                  15

<210> SEQ ID NO 12
<211> LENGTH: 7
<212> TYPE: PRT
<213> ORGANISM: Artificial sequence
<220> FEATURE:
<223> OTHER INFORMATION: Synthetic sequence: Antibody drug conjugate
      light chain hypervariable region HVR-L2

<400> SEQUENCE: 12

Lys Val Ser Asn Arg Phe Ser
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic sequence: Antibody drug conjugate
      light chain hypervariable region HVR-L3

<400> SEQUENCE: 13

Phe Gln Gly Ser Gln Phe Pro Tyr Thr
1               5

<210> SEQ ID NO 14
<211> LENGTH: 10
<212> TYPE: PRT
<213> ORGANISM: Artificial sequence
<220> FEATURE:
<223> OTHER INFORMATION: Synthetic sequence: Antibody drug conjugate
      heavy chain hypervariable region HVR-H1

<400> SEQUENCE: 14

Gly Tyr Glu Phe Ser Arg Ser Trp Met Asn
1               5                   10

<210> SEQ ID NO 15
<211> LENGTH: 18
<212> TYPE: PRT
<213> ORGANISM: Artificial sequence
<220> FEATURE:
<223> OTHER INFORMATION: Synthetic sequence: Antibody drug conjugate
      heavy chain hypervariable region HVR-H2

<400> SEQUENCE: 15

Gly Arg Ile Tyr Pro Gly Asp Gly Asp Thr Asn Tyr Ser Gly Lys Phe
1               5                   10                  15

Lys Gly

<210> SEQ ID NO 16
<211> LENGTH: 11
<212> TYPE: PRT
<213> ORGANISM: Artificial sequence
<220> FEATURE:
<223> OTHER INFORMATION: Synthetic sequence: Antibody drug conjugate
      heavy chain hypervariable region HVR-H3
```

```
<400> SEQUENCE: 16

Asp Gly Ser Ser Trp Asp Trp Tyr Phe Asp Val
1               5                   10

<210> SEQ ID NO 17
<211> LENGTH: 16
<212> TYPE: PRT
<213> ORGANISM: Artificial sequence
<220> FEATURE:
<223> OTHER INFORMATION: Synthetic sequence: Anti-CD33 antibody HVR-L1

<400> SEQUENCE: 17

Arg Ser Ser Gln Ser Leu Leu His Ser Asn Gly Tyr Asn Tyr Leu Asp
1               5                   10                  15

<210> SEQ ID NO 18
<211> LENGTH: 7
<212> TYPE: PRT
<213> ORGANISM: Artificial sequence
<220> FEATURE:
<223> OTHER INFORMATION: Synthetic sequence: Anti-CD33 antibody HVR-L2

<400> SEQUENCE: 18

Leu Gly Val Asn Ser Val Ser
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic sequence: Anti-CD33 antibody HVR-L3

<400> SEQUENCE: 19

Met Gln Ala Leu Gln Thr Pro Trp Thr
1               5

<210> SEQ ID NO 20
<211> LENGTH: 5
<212> TYPE: PRT
<213> ORGANISM: Artificial sequence
<220> FEATURE:
<223> OTHER INFORMATION: Synthetic sequence: Anti-CD33 antibody HVR-H1

<400> SEQUENCE: 20

Asn His Ala Ile Ser
1               5

<210> SEQ ID NO 21
<211> LENGTH: 17
<212> TYPE: PRT
<213> ORGANISM: Artificial sequence
<220> FEATURE:
<223> OTHER INFORMATION: Synthetic sequence: Anti-CD33 antibody HVR-H2

<400> SEQUENCE: 21

Gly Ile Ile Pro Ile Phe Gly Thr Ala Asn Tyr Ala Gln Lys Phe Gln
1               5                   10                  15

Gly

<210> SEQ ID NO 22
<211> LENGTH: 7
<212> TYPE: PRT
<213> ORGANISM: Artificial sequence
<220> FEATURE:
```

<223> OTHER INFORMATION: Synthetic sequence: Anti-CD33 antibody HVR-H3

<400> SEQUENCE: 22

Glu Trp Ala Asp Val Phe Asp
1               5

<210> SEQ ID NO 23
<211> LENGTH: 112
<212> TYPE: PRT
<213> ORGANISM: Artificial sequence
<220> FEATURE:
<223> OTHER INFORMATION: Synthetic sequence: Anti-CD33 antibody VL

<400> SEQUENCE: 23

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Val Asn Ser Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 24
<211> LENGTH: 117
<212> TYPE: PRT
<213> ORGANISM: Artificial sequence
<220> FEATURE:
<223> OTHER INFORMATION: Synthetic sequence: Anti-CD33 antibody VH

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Asn His
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Phe
65                  70                  75                  80

Met Glu Leu Ser Ser Leu Arg Ser Glu Asp Thr Ala Val Tyr Tyr Cys
                85                  90                  95

Ala Arg Glu Trp Ala Asp Val Phe Asp Ile Trp Gly Gln Gly Thr Met
            100                 105                 110

Val Thr Val Ser Ser
        115

<210> SEQ ID NO 25
<211> LENGTH: 11
<212> TYPE: PRT
<213> ORGANISM: Artificial sequence
<220> FEATURE:
<223> OTHER INFORMATION: Synthetic sequence: Anti-CD33 antibody HVR-L1

```
<400> SEQUENCE: 25

Arg Ala Ser Gln Gly Ile Arg Asn Asp Leu Gly
1               5                   10

<210> SEQ ID NO 26
<211> LENGTH: 7
<212> TYPE: PRT
<213> ORGANISM: Artificial sequence
<220> FEATURE:
<223> OTHER INFORMATION: Synthetic sequence: Anti-CD33 antibody HVR-L2

<400> SEQUENCE: 26

Ala Ala Ser Ser Leu Gln Ser
1               5

<210> SEQ ID NO 27
<211> LENGTH: 9
<212> TYPE: PRT
<213> ORGANISM: Artificial sequence
<220> FEATURE:
<223> OTHER INFORMATION: Synthetic sequence: Anti-CD33 antibody HVR-L3

<400> SEQUENCE: 27

Leu Gln His Asn Ser Tyr Pro Trp Thr
1               5

<210> SEQ ID NO 28
<211> LENGTH: 5
<212> TYPE: PRT
<213> ORGANISM: Artificial sequence
<220> FEATURE:
<223> OTHER INFORMATION: Synthetic sequence: Anti-CD33 antibody HVR-H1

<400> SEQUENCE: 28

Gly Asn Tyr Met Ser
1               5

<210> SEQ ID NO 29
<211> LENGTH: 16
<212> TYPE: PRT
<213> ORGANISM: Artificial sequence
<220> FEATURE:
<223> OTHER INFORMATION: Synthetic sequence: Anti-CD33 antibody HVR-H2

<400> SEQUENCE: 29

Leu Ile Tyr Ser Gly Asp Ser Thr Tyr Tyr Ala Asp Ser Val Lys Gly
1               5                   10                  15

<210> SEQ ID NO 30
<211> LENGTH: 10
<212> TYPE: PRT
<213> ORGANISM: Artificial sequence
<220> FEATURE:
<223> OTHER INFORMATION: Synthetic sequence: Anti-CD33 antibody HVR-H3

<400> SEQUENCE: 30

Asp Gly Tyr Tyr Val Ser Asp Met Val Val
1               5                   10

<210> SEQ ID NO 31
<211> LENGTH: 107
<212> TYPE: PRT
<213> ORGANISM: Artificial sequence
<220> FEATURE:
<223> OTHER INFORMATION: Synthetic sequence: Anti-CD33 antibody VL
```

```
<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 32
<211> LENGTH: 118
<212> TYPE: PRT
<213> ORGANISM: Artificial sequence
<220> FEATURE:
<223> OTHER INFORMATION: Synthetic sequence: Anti-CD33 antibody VH

<400> SEQUENCE: 32

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
50                  55                  60

Gly Arg Phe Asn Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115

<210> SEQ ID NO 33
<211> LENGTH: 107
<212> TYPE: PRT
<213> ORGANISM: Artificial sequence
<220> FEATURE:
<223> OTHER INFORMATION: Synthetic sequence: Anti-CD33 antibody VL

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60
```

```
Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Leu Glu Ile Lys
            100                 105
```

<210> SEQ ID NO 34
<211> LENGTH: 118
<212> TYPE: PRT
<213> ORGANISM: Artificial sequence
<220> FEATURE:
<223> OTHER INFORMATION: Synthetic sequence: Anti-CD33 antibody VH

<400> SEQUENCE: 34

```
Glu Val Gln Leu Val Glu Ser Gly Gly Ala Leu Ile Gln Pro Gly Gly
 1               5                  10                  15

Ser Leu Arg Leu Ser Cys Val Ala Ser Gly Phe Thr Ile Ser Gly Asn
                 20                  25                  30

Tyr Met Ser Trp Val Arg Gln Ala Pro Gly Lys Gly Leu Glu Trp Val
             35                  40                  45

Ser Leu Ile Tyr Ser Gly Asp Ser Thr Tyr Tyr Ala Asp Ser Val Lys
 50                  55                  60

Gly Arg Phe Thr Ile Ser Arg Asp Ile Ser Lys Asn Thr Val Tyr Leu
 65                  70                  75                  80

Gln Met Asn Ser Leu Arg Val Glu Asp Thr Ala Val Tyr Tyr Cys Val
                 85                  90                  95

Arg Asp Gly Tyr Tyr Val Ser Asp Met Val Val Trp Gly Lys Gly Thr
            100                 105                 110

Thr Val Thr Val Ser Ser
        115
```

<210> SEQ ID NO 35
<211> LENGTH: 107
<212> TYPE: PRT
<213> ORGANISM: Artificial sequence
<220> FEATURE:
<223> OTHER INFORMATION: Synthetic sequence: Anti-CD33 antibody VL

<400> SEQUENCE: 35

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Leu Glu Ile Lys
            100                 105
```

<210> SEQ ID NO 36
<211> LENGTH: 118
<212> TYPE: PRT
<213> ORGANISM: Artificial sequence

```
<220> FEATURE:
<223> OTHER INFORMATION: Synthetic sequence: Anti-CD33 antibody VH

<400> SEQUENCE: 36

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Ser Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115

<210> SEQ ID NO 37
<211> LENGTH: 107
<212> TYPE: PRT
<213> ORGANISM: Artificial sequence
<220> FEATURE:
<223> OTHER INFORMATION: Synthetic sequence: Anti-CD33 antibody VL

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 38
<211> LENGTH: 118
<212> TYPE: PRT
<213> ORGANISM: Artificial sequence
<220> FEATURE:
<223> OTHER INFORMATION: Synthetic sequence: Anti-CD33 antibody VH

<400> SEQUENCE: 38

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45
```

Ser Leu Ile Tyr Ser Gly Asp Ser Thr Tyr Tyr Ala Asp Ser Val Lys
            50                  55                  60

Gly Arg Phe Ala Ile Ser Arg Asp Ile Ser Lys Asn Thr Val Tyr Leu
 65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
                100                 105                 110

Thr Val Thr Val Ser Ser
        115

<210> SEQ ID NO 39
<211> LENGTH: 112
<212> TYPE: PRT
<213> ORGANISM: Artificial sequence
<220> FEATURE:
<223> OTHER INFORMATION: Synthetic sequence: Anti-LGR5 antibody VL

<400> SEQUENCE: 39

Asp Ile Val Met Thr Gln Ser Pro Asp Ser Leu Ala Val Ser Leu Gly
 1                   5                  10                  15

Glu Arg Ala Thr Ile Asn Cys Arg Ala Ser Glu Ser Val Asp Asn Tyr
                20                  25                  30

Gly Asn Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Tyr
                85                  90                  95

Glu Asp Pro Phe Thr Phe Gly Gln Gly Thr Lys Val Glu Ile Lys Arg
                100                 105                 110

<210> SEQ ID NO 40
<211> LENGTH: 118
<212> TYPE: PRT
<213> ORGANISM: Artificial sequence
<220> FEATURE:
<223> OTHER INFORMATION: Synthetic sequence: Anti-LGR5 antibody VH

<400> SEQUENCE: 40

Glu Val Gln Leu Val Gln Ser Gly Ala Glu Val Lys Lys Pro Gly Ala
 1                   5                  10                  15

Ser Val Lys Val Ser Cys Lys Ala Ser Gly Tyr Thr Phe Ser Ala Tyr
                20                  25                  30

Trp Ile Glu Trp Val Arg Gln Ala Pro Gly Gln Gly Leu Glu Trp Ile
            35                  40                  45

Gly Glu Ile Leu Pro Gly Ser Asp Ser Thr Asp Tyr Asn Glu Lys Phe
 50                  55                  60

Lys Val Arg Ala Thr Phe Thr Ser Asp Thr Ser Thr Ser Thr Val Tyr
 65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
                100                 105                 110

Leu Val Thr Val Ser Ser
        115

```
<210> SEQ ID NO 41
<211> LENGTH: 108
<212> TYPE: PRT
<213> ORGANISM: Artificial sequence
<220> FEATURE:
<223> OTHER INFORMATION: Synthetic sequence: Anti-LGR5 antibody VL

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Pro Pro
                85                  90                  95

Thr Phe Gly Gln Gly Thr Lys Val Glu Ile Lys Arg
            100                 105

<210> SEQ ID NO 42
<211> LENGTH: 116
<212> TYPE: PRT
<213> ORGANISM: Artificial sequence
<220> FEATURE:
<223> OTHER INFORMATION: Synthetic sequence: Anti-LGR5 antibody VH

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ser Ile Ser Trp Val Arg Gln Ala Pro Gly Lys Gly Leu Glu Trp Val
        35                  40                  45

Ala Glu Ile Tyr Pro Pro Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Lys Ala Arg Leu Phe Phe Asp Tyr Trp Gly Gln Gly Thr Leu Val
            100                 105                 110

Thr Val Ser Ser
        115

<210> SEQ ID NO 43
<211> LENGTH: 15
<212> TYPE: PRT
<213> ORGANISM: Artificial sequence
<220> FEATURE:
<223> OTHER INFORMATION: Synthetic sequence: Anti-LGR5 antibody HVR-L1

<400> SEQUENCE: 43

Arg Ala Ser Glu Ser Val Asp Asn Tyr Gly Asn Ser Phe Met His
1               5                   10                  15
```

```
<210> SEQ ID NO 44
<211> LENGTH: 7
<212> TYPE: PRT
<213> ORGANISM: Artificial sequence
<220> FEATURE:
<223> OTHER INFORMATION: Synthetic sequence: Anti-LGR5 antibody HVR-L2

<400> SEQUENCE: 44

Leu Ala Ser Asn Leu Glu Ser
1               5

<210> SEQ ID NO 45
<211> LENGTH: 9
<212> TYPE: PRT
<213> ORGANISM: Artificial sequence
<220> FEATURE:
<223> OTHER INFORMATION: Synthetic sequence: Anti-LGR5 antibody HVR-L3

<400> SEQUENCE: 45

Gln Gln Asn Tyr Glu Asp Pro Phe Thr
1               5

<210> SEQ ID NO 46
<211> LENGTH: 10
<212> TYPE: PRT
<213> ORGANISM: Artificial sequence
<220> FEATURE:
<223> OTHER INFORMATION: Synthetic sequence: Anti-LGR5 antibody HVR-H1

<400> SEQUENCE: 46

Gly Tyr Thr Phe Ser Ala Tyr Trp Ile Glu
1               5                   10

<210> SEQ ID NO 47
<211> LENGTH: 17
<212> TYPE: PRT
<213> ORGANISM: Artificial sequence
<220> FEATURE:
<223> OTHER INFORMATION: Synthetic sequence: Anti-LGR5 antibody HVR-H2

<400> SEQUENCE: 47

Glu Ile Leu Pro Gly Ser Asp Ser Thr Asp Tyr Asn Glu Lys Phe Lys
1               5                   10                  15

Val

<210> SEQ ID NO 48
<211> LENGTH: 9
<212> TYPE: PRT
<213> ORGANISM: Artificial sequence
<220> FEATURE:
<223> OTHER INFORMATION: Synthetic sequence: Anti-LGR5 antibody HVR-H3

<400> SEQUENCE: 48

Gly Gly His Tyr Gly Ser Leu Asp Tyr
1               5

<210> SEQ ID NO 49
<211> LENGTH: 11
<212> TYPE: PRT
<213> ORGANISM: Artificial sequence
<220> FEATURE:
<223> OTHER INFORMATION: Synthetic sequence: Anti-LGR5 antibody HVR-L1

<400> SEQUENCE: 49

Arg Ala Ser Gln Asp Val Ser Thr Ala Val Ala
1               5                   10
```

<210> SEQ ID NO 50
<211> LENGTH: 7
<212> TYPE: PRT
<213> ORGANISM: Artificial sequence
<220> FEATURE:
<223> OTHER INFORMATION: Synthetic sequence: Anti-LGR5 antibody HVR-L2

<400> SEQUENCE: 50

Ser Ala Ser Phe Leu Tyr Ser
1               5

<210> SEQ ID NO 51
<211> LENGTH: 9
<212> TYPE: PRT
<213> ORGANISM: Artificial sequence
<220> FEATURE:
<223> OTHER INFORMATION: Synthetic sequence: Anti-LGR5 antibody HVR-L3

<400> SEQUENCE: 51

Gln Gln Ser Tyr Thr Thr Pro Pro Thr
1               5

<210> SEQ ID NO 52
<211> LENGTH: 10
<212> TYPE: PRT
<213> ORGANISM: Artificial sequence
<220> FEATURE:
<223> OTHER INFORMATION: Synthetic sequence: Anti-LGR5 antibody HVR-H1

<400> SEQUENCE: 52

Gly Phe Thr Phe Thr Ser Tyr Ser Ile Ser
1               5                   10

<210> SEQ ID NO 53
<211> LENGTH: 17
<212> TYPE: PRT
<213> ORGANISM: Artificial sequence
<220> FEATURE:
<223> OTHER INFORMATION: Synthetic sequence: Anti-LGR5 antibody HVR-H2

<400> SEQUENCE: 53

Glu Ile Tyr Pro Pro Gly Gly Tyr Thr Asp Tyr Ala Asp Ser Val Lys
1               5                   10                  15

Gly

<210> SEQ ID NO 54
<211> LENGTH: 7
<212> TYPE: PRT
<213> ORGANISM: Artificial sequence
<220> FEATURE:
<223> OTHER INFORMATION: Synthetic sequence: Anti-LGR5 antibody HVR-H3

<400> SEQUENCE: 54

Ala Arg Leu Phe Phe Asp Tyr
1               5

<210> SEQ ID NO 55
<211> LENGTH: 21
<212> TYPE: PRT
<213> ORGANISM: Artificial Sequence
<220> FEATURE:
<223> OTHER INFORMATION: Synthetic sequence: A20FMDV-Cys

<400> SEQUENCE: 55

Asn Ala Val Pro Asn Leu Arg Gly Asp Leu Gln Val Leu Ala Gln Lys

| 1 | | | 5 | | 10 | | 15 |
|---|---|---|---|---|---|---|---|
Val Ala Arg Thr Cys
20

PYRROLOBENZODIAZEPINES AND CONJUGATES THEREOF

The present invention relates to pyrrolobenzodiazepines (PBDs), in particular pyrrolobenzodiazepines having a linker group connected to a cell binding agent.

BACKGROUND TO THE INVENTION

Pyrrolobenzodiazepines

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994); Antonow, D. and Thurston, D. E., *Chem. Rev.* 2011 111 (4), 2815-2864). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102) (Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

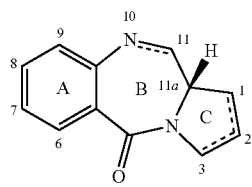

They differ in the number, type and position of substituents, in both their aromatic A rings and pyrrolo C rings, and in the degree of saturation of the C ring. In the B-ring there is either an imine (N═C), a carbinolamine(NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

A particularly advantageous pyrrolobenzodiazepine compound is described by Gregson et al. (*Chem. Commun.* 1999, 797-798) as compound 1, and by Gregson et al. (*J. Med. Chem.* 2001, 44, 1161-1174) as compound 4a. This compound, also known as SJG-136, is shown below:

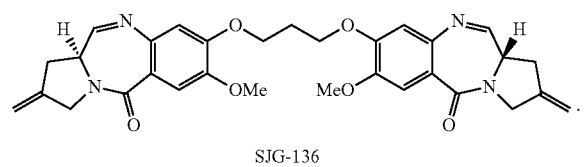

SJG-136

Other dimeric PBD compounds, such as those bearing C2 aryl substituents in WO 2005/085251, have been disclosed, an example being:

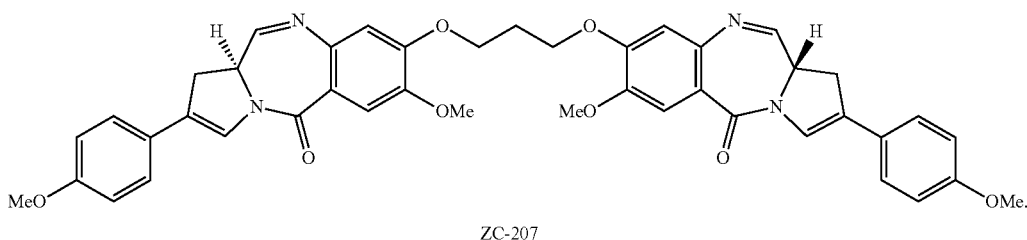 [SMILES: COc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

ZC-207

These compounds have been shown to be highly useful cytotoxic agents.

Antibody-Drug Conjugates

Antibody therapy has been established for the targeted treatment of patients with cancer, immunological and angiogenic disorders (Carter, P. (2006) Nature Reviews Immunology 6:343-357). The use of antibody-drug conjugates (ADC), i.e. immunoconjugates, for the local delivery of cytotoxic or cytostatic agents, i.e. drugs to kill or inhibit tumor cells in the treatment of cancer, targets delivery of the drug moiety to tumors, and intracellular accumulation therein, whereas systemic administration of these unconjugated drug agents may result in unacceptable levels of toxicity to normal cells as well as the tumor cells sought to be eliminated (Xie et al (2006) Expert. Opin. Biol. Ther. 6(3):281-291; Kovtun et al (2006) Cancer Res. 66(6):3214-3121; Law et al (2006) Cancer Res. 66(4):2328-2337; Wu et al (2005) Nature Biotech. 23(9):1137-1145; Lambert J. (2005) Current Opin. in Pharmacol. 5:543-549; Hamann P. (2005) Expert Opin. Ther. Patents 15(9):1087-1103; Payne, G. (2003) Cancer Cell 3:207-212; Trail et al (2003) Cancer Immunol. Immunother. 52:328-337; Syrigos and Epenetos (1999) Anticancer Research 19:605-614).

Maximal efficacy with minimal toxicity is sought thereby. Efforts to design and refine ADC have focused on the selectivity of monoclonal antibodies (mAbs) as well as drug mechanism of action, drug-linking, drug/antibody ratio (loading), and drug-releasing properties (Junutula, et al., 2008b Nature Biotech., 26(8):925-932; Dornan et al (2009) Blood 114(13):2721-2729; U.S. Pat. No. 7,521,541; U.S. Pat. No. 7,723,485; WO2009/052249; McDonagh (2006) Protein Eng. Design & Sel. 19(7): 299-307; Doronina et al (2006) Bioconj. Chem. 17:114-124; Erickson et al (2006) Cancer Res. 66(8):1-8; Sanderson et al (2005) Clin. Cancer Res. 11:843-852; Jeffrey et al (2005) J. Med. Chem. 48:1344-1358; Hamblett et al (2004) Clin. Cancer Res. 10:7063-7070). Drug moieties may impart their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

PBDs in ADCs

Dimeric PBDs have been disclosed as the drugs in drug conjugates. For example, in WO 2011/130598, dimer PBD compounds having linker groups for connection to a cell binding agent, such as an antibody, are disclosed where the linker group is attached to one of the available N10 positions, and are generally cleaved by action of an enzyme on the linker group.

By contrast, in WO 2011/130613 and WO 2011/130616, dimer PBD compounds having linker groups for connection to a cell binding agent, such as an antibody, are disclosed where the linker group is attached via an aromatic group at one of the C2 positions, and are generally cleaved by action of an enzyme on the linker group. Such antibody drug conjugates are also described in Flygare, J., et al, Chem. Biol. Drug Des. 81: 113-121 (2013), which also describes other types of antibody drug conjugates.

A further approach is described in WO 2007/085930, wherein tomaymycin-like dimers have a linker group for connection to a cell binding agent, such as an antibody, where the linker group is attached to the tether between the tomaymycin units, and are generally cleaved by action of an enzyme on the linker group.

The present inventors have developed a novel approach to forming PBD conjugates with cell binding agents, and in particular PBD antibody conjugates.

SUMMARY OF THE INVENTION

In a general aspect the present invention provides a conjugate comprising a PBD dimer compound with a linker for connecting to a cell binding agent, wherein the linker has a triazole, piperazine, propargylene or oxime group attached to a phenylene or pyridylene in the bridge linking the two PBD monomers. The cell binding agent is preferably an antibody.

In a first aspect, the present invention provides novel conjugate compounds of formula (A):

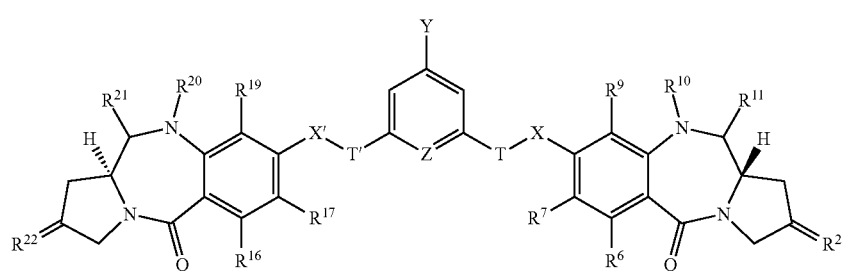

wherein:
$R^2$ is

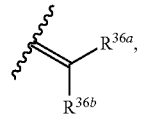

where $R^{36a}$ and $R^{36b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester or, when one of $R^{36a}$ and $R^{36b}$ is H, the other is selected from nitrile and a $C_{1-4}$ alkyl ester;

$R^6$ and $R^9$ are independently selected from H, R, OH, OR, SH, SR, $NH_2$, NHR, NRR', $NO_2$, $Me_3Sn$ and halo;

$R^7$ is independently selected from H, R, OH, OR, SH, SR, $NH_2$, NHR, NRR', $NO_2$, $Me_3Sn$ and halo;

Y is selected from formulae A1, A2, A3, A4, A5 and A6:

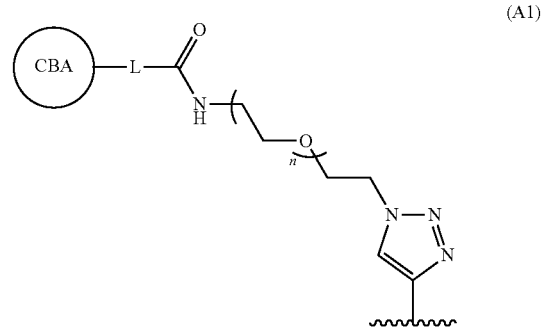

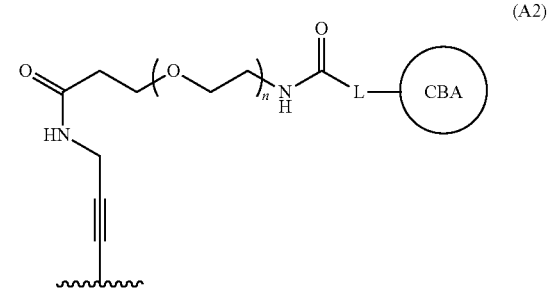

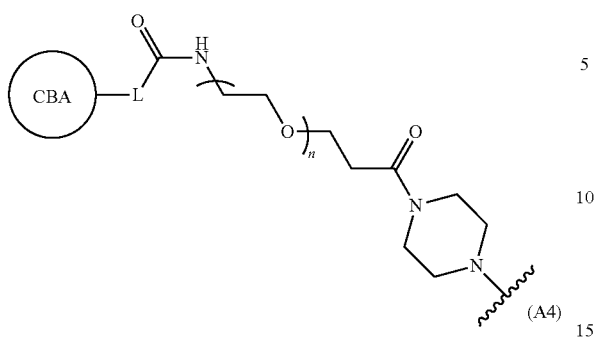

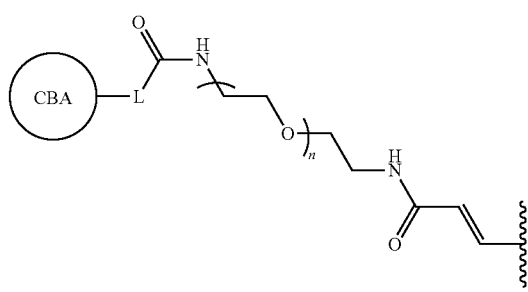

L is a linker connected to a cell binding agent;
CBA is the cell binding agent;
n is an integer selected in the range of 0 to 48;
$R^{A4}$ is a $C_{1-6}$ alkylene group; either
(a) $R^{10}$ is H, and $R^{11}$ is OH, $OR^A$, where $R^A$ is $C_{1-4}$ alkyl; or
(b) $R^{10}$ and $R^{11}$ form a nitrogen-carbon double bond between the nitrogen and carbon atoms to which they are bound; or
(c) $R^{10}$ is H and $R^{11}$ is $OSO_zM$, where z is 2 or 3 and M is a monovalent pharmaceutically acceptable cation;

R and R' are each independently selected from optionally substituted $C_{1-12}$ alkyl, $C_{3-20}$ heterocyclyl and $C_{5-20}$ aryl groups, and optionally in relation to the group NRR', R and R' together with the nitrogen atom to which they are attached form an optionally substituted 4-, 5-, 6- or 7-membered heterocyclic ring;
wherein $R^{16}$, $R^{17}$, $R^{19}$, $R^{20}$, $R^{21}$ and $R^{22}$ are as defined for $R^6$, $R^7$, $R^9$, $R^{10}$, $R^{11}$ and $R^{12}$ respectively;
wherein Z is CH or N;
wherein T and T' are independently selected from a single bond or a $C_{1-9}$ alkylene, which chain may be interrupted by one or more heteroatoms e.g. O, S, N(H), NMe, provided that the number of atoms in the shortest chain of atoms between X and X' is 3 to 12 atoms; and
X and X' are independently selected from O, S and N(H).
Thus formula A is selected from the following formulae A-I, A-II, A-III, A-IV, A-V and A-VI depending on Y:

| Y | A |
|---|---|
| A1 | 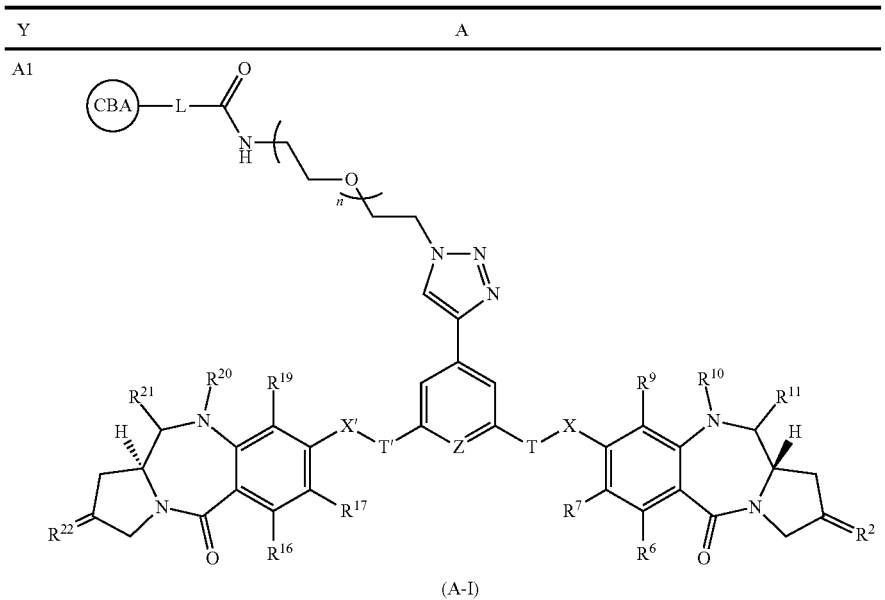 (A-I) |

-continued
| Y | A |
|---|---|
| A2 | 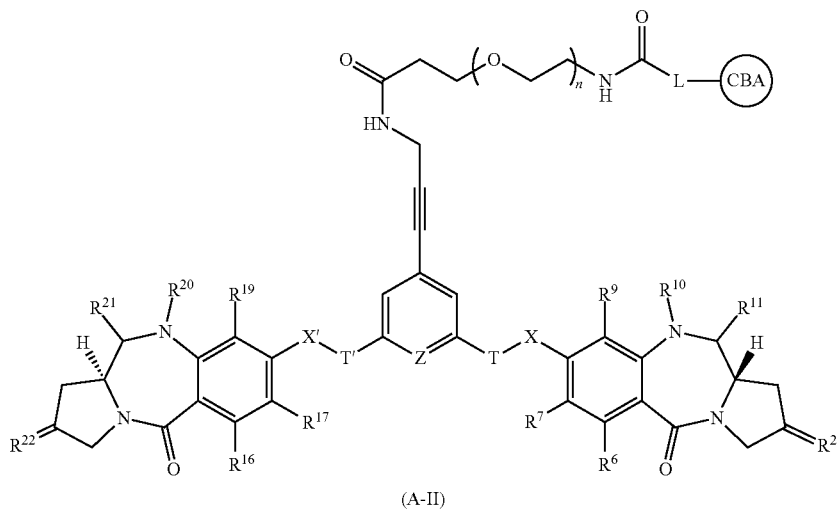<br>(A-II) |
| A3 | 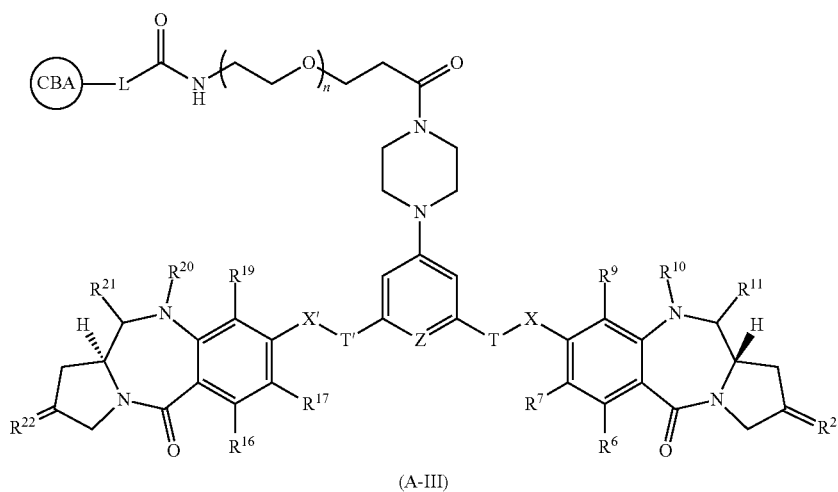<br>(A-III) |
| A4 | 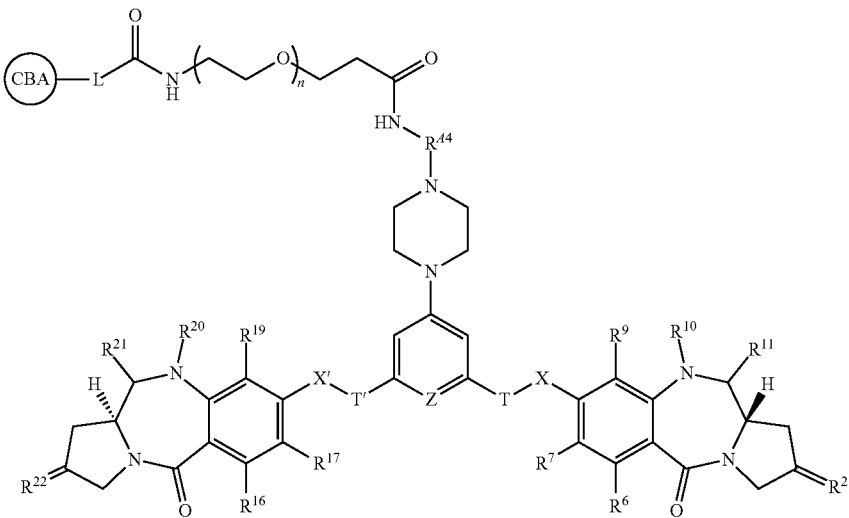<br>(A-IV) |

| Y | A |
|---|---|
| A5 | 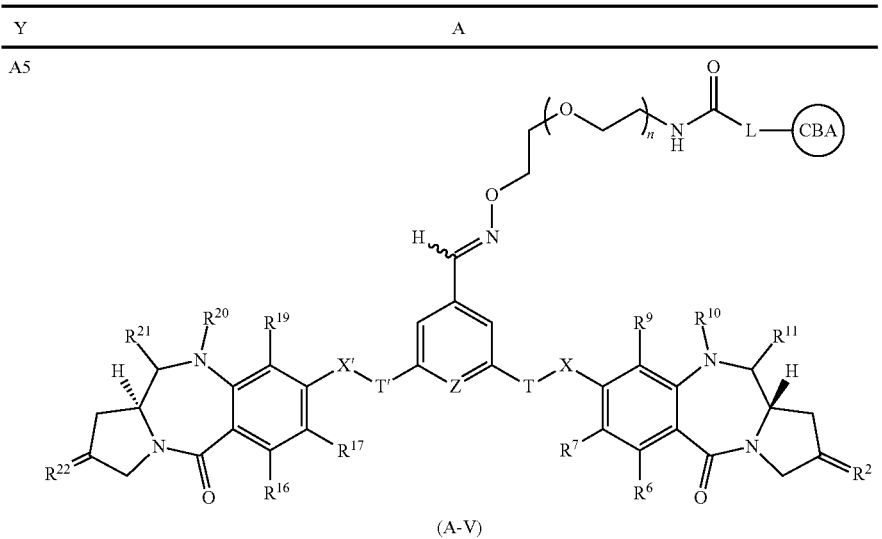 |
| | (A-V) |
| A6 | 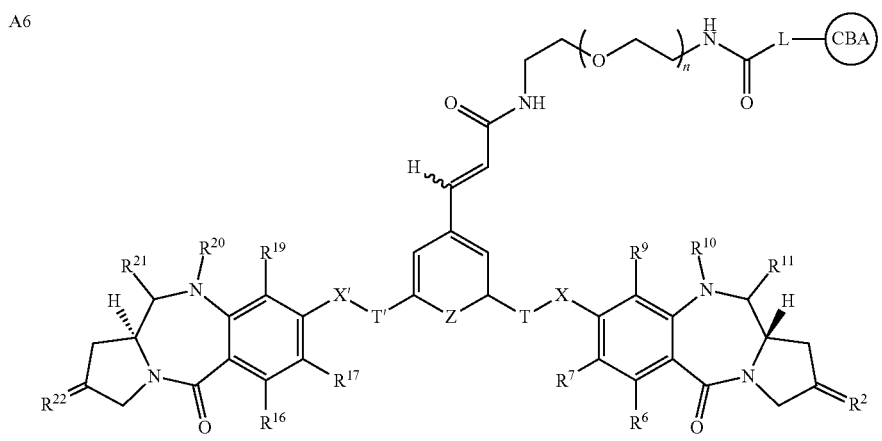 |
A second aspect of the present invention provides novel drug-linker compounds of formula (B):
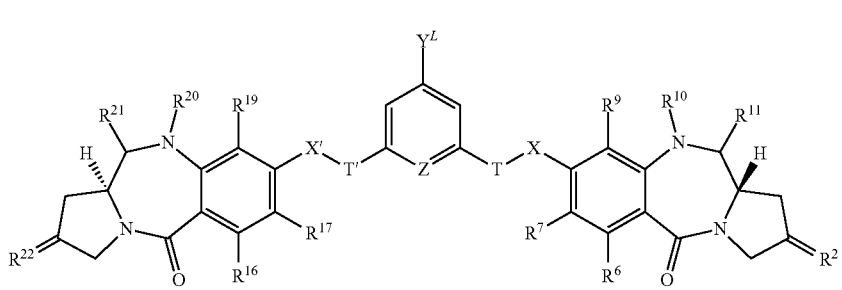
Where all the groups are as defined in the first aspect of the invention; and
$Y^L$ is selected from a group of formulae B1, B2, B3, B4, B5 and B6:

(B1)
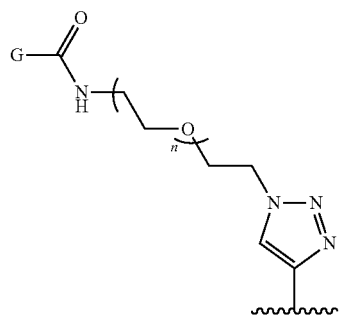
(B2)
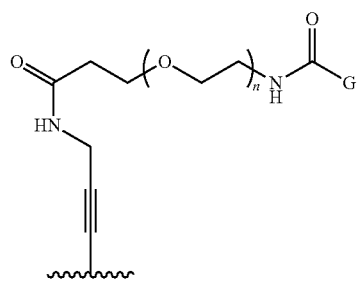
(B3)
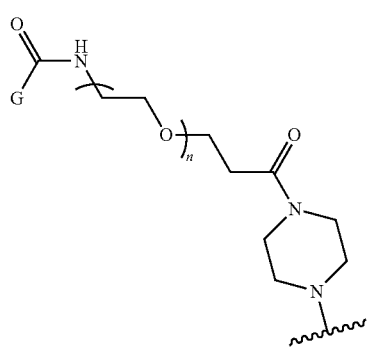
(B4)
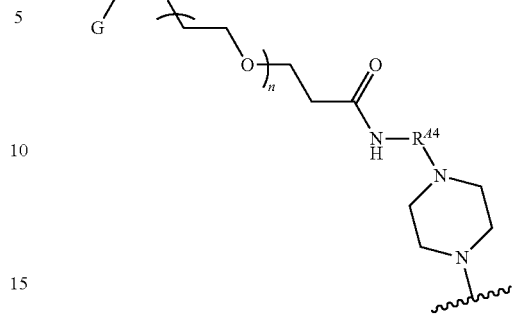
(B5)
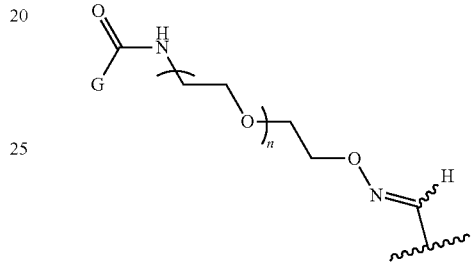
(B6)
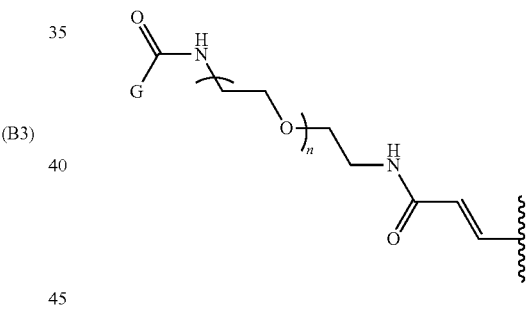
where G is a reactive group for connecting to a cell binding agent.
A third aspect of the present invention provides compounds of formula (C) which may be used in the preparation of the compounds and conjugate compounds of the invention:
C
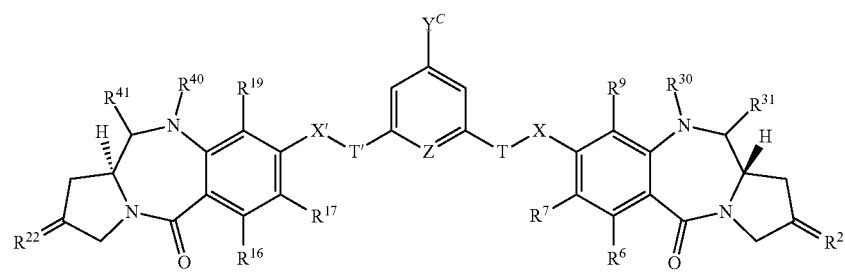

where $Y^C$ is selected from a group of formulae C1, C2, C3, C4 and C5:

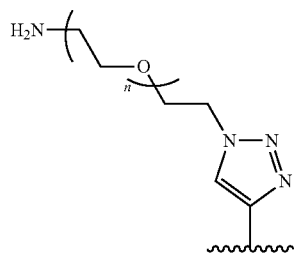
(C1)

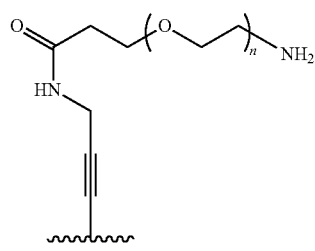
(C2)

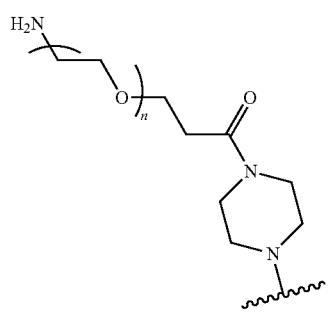
(C3)

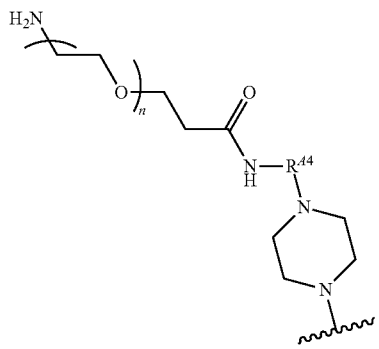
(C4)

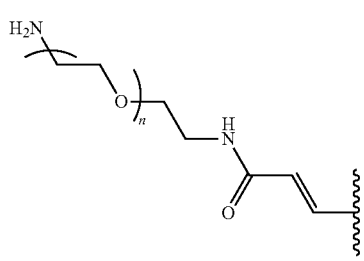
(C5)

(C6)
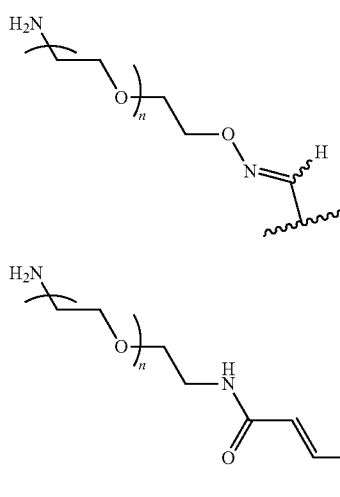

either
- (a) $R^{30}$ is H, and $R^{31}$ is OH, $OR^A$, where $R^A$ is $C_{1-4}$ alkyl; or
- (b) $R^{30}$ and $R^{31}$ form a nitrogen-carbon double bond between the nitrogen and carbon atoms to which they are bound; or
- (c) $R^{30}$ is H and $R^{31}$ is $OSO_zM$, where z is 2 or 3 and M is a monovalent pharmaceutically acceptable cation; or
- (d) $R^{30}$ is a nitrogen protecting group and $R^{31}$ is $OProt^O$, where $Prot^O$ is a hydroxy protecting group; and $R^{40}$ and $R^{41}$ are as defined for $R^{30}$ and $R^{31}$ respectively; and all the remaining groups are as defined in the first aspect of the invention.

A fourth aspect of the present invention provides compounds of formula (D) which may be used in the preparation of the compounds of the second and third aspects of the invention:

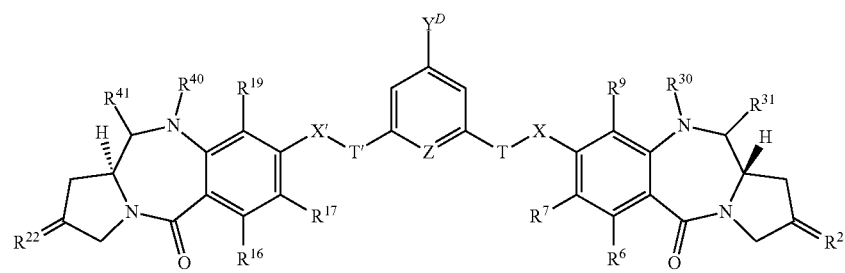

D $Y^D$ is selected from a group of formulae D2, D3, D4 and D6:

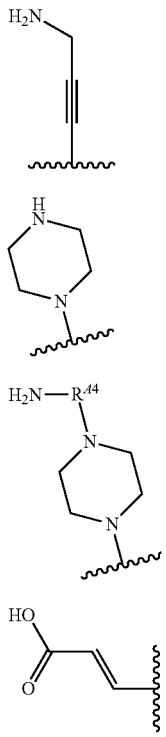

(D2)

(D3)

(D4)

(D6)

and all the remaining groups are as defined in the third aspect of the invention.

A fifth aspect of the present invention provides compounds of formula (E) which may be used in the preparation of the compounds of the second, third and fourth aspects of the invention:

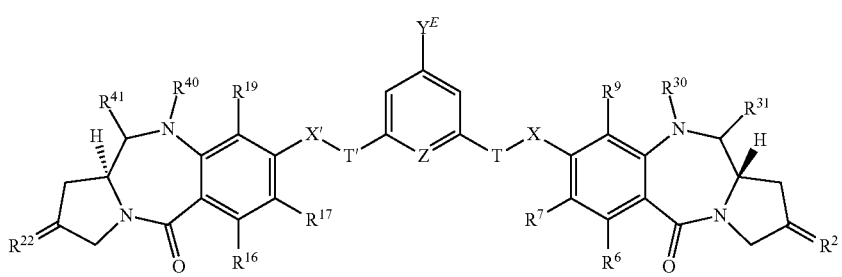

E $Y^E$ is selected from a group of formulae E1, E2 and E5:

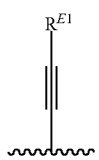

(E1)

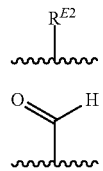

(E2)

(E5)

where $R^{E1}$ is selected from H and TMS;

$R^{E2}$ is selected from Br, Cl and I; and all the remaining groups are as defined in the third aspect of the invention.

A sixth aspect of the present invention provides the use of a compound of the first aspect of the invention in a method of medical treatment. The fourth aspect also provides a pharmaceutical composition comprising a compound of the first aspect, and a pharmaceutically acceptable excipient.

A seventh aspect of the present invention provides a compound of the first aspect of the invention or a pharmaceutical composition of the fourth aspect of the invention for use in a method of treatment of a proliferative disease. The fifth aspect also provides the use of a compound of the first aspect in a method of manufacture of a medicament for the treatment of a proliferative disease, and a method of treating a mammal having a proliferative disease, comprising administering an effective amount of a compound of the first aspect or a pharmaceutical composition of the fourth aspect.

An eight aspect of the present invention provides a method of synthesis of a compound of the first aspect of the present invention, comprising the step of conjugating a drug-linker of the second aspect with a cell-binding agent.

The present invention also provides the synthesis of compounds of the second aspect of the invention from compounds of the third, fourth or fifth aspect of the invention by reacting them with suitable reagents.

DETAILED DESCRIPTION OF THE INVENTION

The present invention provides a conjugate comprising a PBD dimer connected through the dimer bridging portion via a specified linker to a cell binding agent.

The present invention is suitable for use in providing a PBD conjugate to a preferred site in a subject.

Nitrogen Protecting Groups

Nitrogen protecting groups are well known in the art. Preferred nitrogen protecting groups for use in the present invention are carbamate protecting groups that have the general formula:

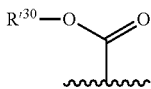

wherein R'³⁰ is an optionally substituted alkyl (e.g. $C_{1-20}$ alkyl), aryl (e.g. $C_{5-20}$ aryl) or heteroaryl (e.g. $C_{3-20}$ heterocyclyl) group.

A large number of possible carbamate nitrogen protecting groups are listed on pages 706 to 772 of Greene's Protective Groups in Organic Synthesis, 4th Edition, John Wiley & Sons, Inc., 2007 (ISBN 978-0-471-69754-1), which is incorporated herein by reference.

Particularly preferred protecting groups include Alloc, Troc, Teoc, BOC, TcBOC, Fmoc, 1-Adoc and 2-Adoc.

Hydroxyl Protecting Groups

Hydroxyl protecting groups are well known in the art. A large number of suitable groups are described on pages 24 to 298 of Greene's Protective Groups in Organic Synthesis, 4th Edition, John Wiley & Sons, Inc., 2007 (ISBN 978-0-471-69754-1), which is incorporated herein by reference.

Classes of particular interest include silyl ethers, methyl ethers, alkyl ethers, benzyl ethers, esters, benzoates, carbonates, and sulfonates. Particularly preferred hydroxyl protecting groups include THP.

Preferences

The following preferences may apply to all aspects of the invention as described above, or may relate to a single aspect. The preferences may be combined together in any combination.

$R^2$

In some embodiments, $R^{36a}$ and $R^{36b}$ are both H.

In other embodiments, $R^{36a}$ and $R^{36b}$ are both methyl.

In further embodiments, one of $R^{36a}$ and $R^{36b}$ is H, and the other is selected from $C_{1-4}$ saturated alkyl, $C_{2-3}$ alkenyl, which alkyl and alkenyl groups are optionally substituted. In some of these further embodiments, the group which is not H may be selected from methyl and ethyl.

$R^{22}$

The above preferences for $R^2$ apply equally to $R^{22}$.

$R^6$

In one embodiment, $R^6$ is independently selected from H, R, OH, OR, SH, SR. $NH_2$, NHR, NRR', $NO_2$, $Me_3Sn$— and Halo.

In one embodiment, $R^6$ is independently selected from H, OH, OR, SH, $NH_2$, $NO_2$ and Halo.

In one embodiment, $R^6$ is independently selected from H and Halo.

In one embodiment, $R^6$ is independently H.

In one embodiment, $R^6$ and $R^7$ together form a group —O—$(CH_2)_p$—O—, where p is 1 or 2.

These embodiments also apply to $R^{16}$.

$R^7$ $R^7$ is independently selected from H, R, OH, OR, SH, SR, $NH_2$, NHR, NRR', $NO_2$, $Me_3Sn$ and halo.

In one embodiment, $R^7$ is independently OR.

In one embodiment, $R^7$ is independently $OR^{7A}$, where $R^{7A}$ is independently optionally substituted $C_{1-6}$ alkyl.

In one embodiment, $R^{7A}$ is independently optionally substituted saturated $C_{1-6}$ alkyl.

In one embodiment, $R^{7A}$ is independently optionally substituted $C_{2-4}$ alkenyl.

In one embodiment, $R^{7A}$ is independently Me.

In one embodiment, $R^{7A}$ is independently $CH_2Ph$.

In one embodiment, $R^{7A}$ is independently allyl.

These embodiments also apply to $R^{17}$.

$R^9$

In one embodiment, $R^9$ is independently selected from H, R, OH, OR, SH, SR. $NH_2$, NHR, NRR', $NO_2$, $Me_3Sn$— and Halo.

In one embodiment, $R^9$ is independently H.

In one embodiment, $R^9$ is independently R or.

These embodiments also apply to $R^{19}$.

N10-C11

In some embodiments, $R^{10}$ is H, and $R^{11}$ is OH, $OR^A$, where $R^A$ is $C_{1-4}$ alkyl. In some of these embodiments, $R^{11}$ is OH. In others of these embodiments, $R^{11}$ is $OR^A$, where $R^A$ is $C_{1-4}$ alkyl. In some of these embodiments, $R^A$ is methyl.

In some embodiments, $R^{10}$ and $R^{11}$ form a nitrogen-carbon double bond between the nitrogen and carbon atoms to which they are bound.

In some embodiments, $R^{10}$ is H and $R^{11}$ is $OSO_zM$, where z is 2 or 3 and M is a monovalent pharmaceutically acceptable cation. In some of these embodiments. M is a monovalent pharmaceutically acceptable cation, and may be $Na^+$. Furthermore, in some embodiments z is 3.

The above preferences apply equally to $R^{20}$ and $R^{21}$.

In some embodiments, $R^{30}$ is H, and $R^{31}$ is OH, $OR^A$, where $R^A$ is $C_{1-4}$ alkyl. In some of these embodiments, $R^{31}$ is OH. In others of these embodiments, $R^{31}$ is $OR^A$, where $R^A$ is $C_{1-4}$ alkyl. In some of these embodiments, $R^A$ is methyl.

In some embodiments, $R^{30}$ and $R^{31}$ form a nitrogen-carbon double bond between the nitrogen and carbon atoms to which they are bound.

In some embodiments, $R^{30}$ is H and $R^{31}$ is $OSO_zM$, where z is 2 or 3 and M is a monovalent pharmaceutically acceptable cation. In some of these embodiments, M is a monovalent pharmaceutically acceptable cation, and may be $Na^+$. Furthermore, in some embodiments z is 3.

In some embodiments, $R^{30}$ is a nitrogen protecting group and $R^{31}$ is $OProt^O$, where $Prot^O$ is a hydroxy protecting group.

In some of these embodiments, the nitrogen protecting group may be selected from Alloc, Troc, Teoc, BOC, TcBOC, Fmoc, 1-Adoc and 2-Adoc, and more preferably be Boc.

In some of these embodiments, the nitrogen protecting group may be THP.

For compounds of formula D, it may be preferred that $R^{30}$ and $R^{31}$ form a nitrogen-carbon double bond between the nitrogen and carbon atoms to which they are bound.

For compounds of formula E, it may be preferred that $R^{30}$ is a nitrogen protecting group and $R^{31}$ is OProt$^O$, where Prot$^O$ is a hydroxy protecting group.

For compounds of formula C, where $Y^C$ is of formula C2, C3 or C4, it may be preferred that $R^{30}$ and $R^{31}$ form a nitrogen-carbon double bond between the nitrogen and carbon atoms to which they are bound.

For compounds of formula C, where $Y^C$ is of formula C1 or C5, it may be preferred that $R^{30}$ is a nitrogen protecting group and $R^{31}$ is OProt$^O$, where Prot$^O$ is a hydroxy protecting group.

The above preferences apply equally to $R^{40}$ and $R^{41}$.

T and T'

Each of T and T' is independently selected from a single bond or a $C_{1-9}$ alkylene group, which chain may be interrupted by one or more heteroatoms, e.g. O, S, N(H) and/or NMe, provided that the number of atoms in the shortest chain of atoms between X and X' is 3 to 12 atoms.

In one embodiment, each alkylene group of T and T' is optionally interrupted by one or more heteroatoms selected from O, S, and NMe.

In one embodiment, each of T and T'' is independently selected from a single bond and a $C_{1-9}$ alkylene group.

In one embodiment, T is selected from a single bond, $C_1$, $C_2$, $C_3$ and a $C_4$ alkylene group and T' is selected from a single bond, $C_1$, $C_2$, $C_3$ and a $C_4$ alkylene group.

In one embodiment, T is selected from a single bond, $C_1$, and a $C_2$ alkylene group and T' is selected from a single bond, $C_1$, and a $C_2$ alkylene group.

In one embodiment, T is selected from a single bond and a $C_1$ alkylene group and T' is selected from a single bond and a $C_1$ alkylene group.

In one embodiment, T is a single bond and T' is a single bond.

In one embodiment, T is a $C_1$ alkylene group and T' is a $C_1$ alkylene group.

In some embodiments, T and T' are the same.

The alkylene groups listed above may be optionally interrupted by one or more heteroatoms.

The alkylene groups listed above may be unsubstituted linear aliphatic alkylene groups.

X

In one embodiment, X is selected from O, S, or N(H).

Preferably, X is O.

Dimers

In some embodiments, the groups $R^{22}$, $R^{16}$, $R^{17}$, $R^{19}$, $R^{20}$ and $R^{21}$ are the same as the groups $R^2$, $R^6$, $R^9$, $R^7$, $R^{10}$ and $R^{11}$ respectively. In these embodiments, the PBD monomer units have the same substituents.

Particularly preferred compounds of the first aspect of the present invention may be of formula Ia:

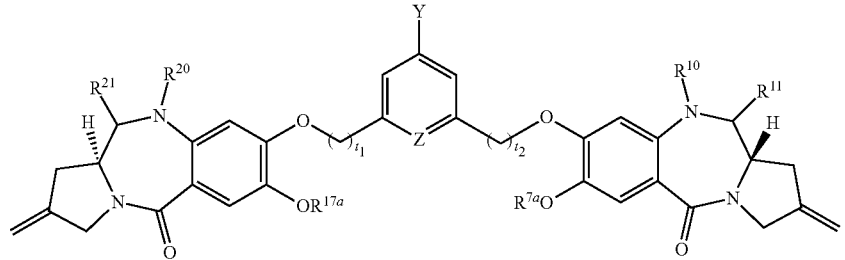

Ia where
$R^{10}$, $R^{11}$, $R^{20}$, $R^{21}$ and Y are as defined above;
$t_1$ and $t_2$ are an independently selected from 0, 1 and 2
$R^{7a}$ and $R^{17a}$ are independently selected from methyl and phenyl.

Particularly preferred compounds of the second aspect of the present invention may be of formula IIa:

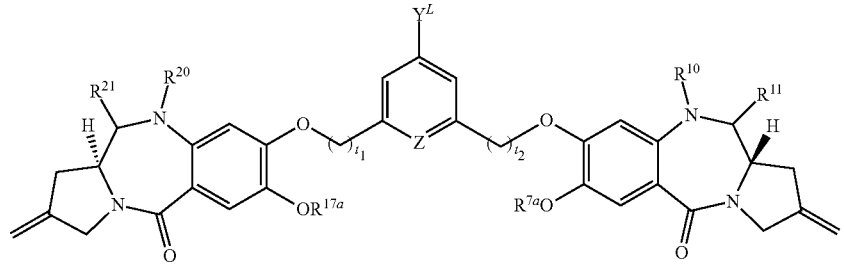

IIa where
$R^{10}$, $R^{11}$, $R^{20}$, $R^{21}$ and $Y^L$ are as defined above;
$t_1$ and $t_2$ are an independently selected from 0, 1 and 2
$R^{7a}$ and $R^{17a}$ are independently selected from methyl and phenyl.

Particularly preferred compounds of the third aspect of the present invention may be of formula IIIa:

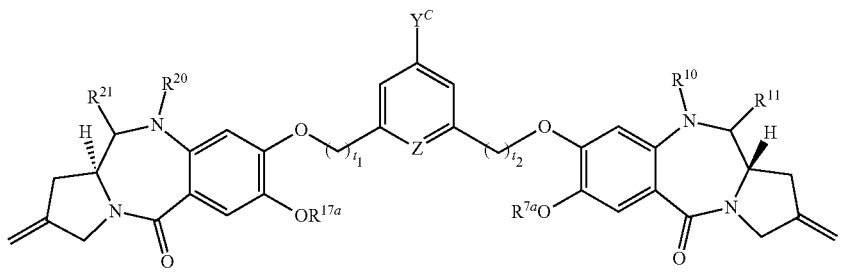

IIIa where
$R^{10}$, $R^{11}$, $R^{20}$, $R^{21}$ and $Y^C$ are as defined above;
$t_1$ and $t_2$ are an independently selected from 0, 1 and 2
$R^{7a}$ and $R^{17a}$ are independently selected from methyl and phenyl.

n (Y, $Y^L$)

In some embodiments, n (in Y or $Y^L$) is an integer between 0 and 24.

In some embodiments, n (in Y or $Y^L$) is an integer between 0 and 12.

In some embodiments, n (in Y or $Y^L$) is an integer between 0 and 8.

In some embodiments, n (in Y or $Y^L$) is an integer between 0 and 6.

In some embodiments, n (in Y or $Y^L$) is 0.
In some embodiments, n (in Y or $Y^L$) is 1.
In some embodiments, n (in Y or $Y^L$) is 2.
In some embodiments, n (in Y or $Y^L$) is 3.
In some embodiments, n (in Y or $Y^L$) is 4.
In some embodiments, n (in Y or $Y^L$) is 5.
In some embodiments, n (in Y or $Y^L$) is 6.
In some embodiments, n (in Y or $Y^L$) is 7.
In some embodiments, n (in Y or $Y^L$) is 8.
In some embodiments, n (in Y or $Y^L$) is 9.
In some embodiments, n (in Y or $Y^L$) is 10.
In some embodiments, n (in Y or $Y^L$) is 11.
In some embodiments, n (in Y or $Y^L$) is 12.
In some embodiments, n (in Y or $Y^L$) is 13.
In some embodiments, n (in Y or $Y^L$) is 14.
In some embodiments, n (in Y or $Y^L$) is 15.

In some embodiments when Y is A1, or $Y^L$ is B1, n may be selected from 3 and 6.

In some embodiments when Y is A2, or $Y^L$ is B2, n may be selected from 4 and 6.

In some embodiments when Y is A3, or $Y^L$ is B3, n may be 4.

In some embodiments when Y is A4, or $Y^L$ is B4, n may be 4.

In some embodiments when Y is A5, or $Y^L$ is B5, n may be 11.

In some embodiments when Y is A6, or $Y^L$ is B6, n may be 2.

L and G

L is a linker connected to the cell binding agent in the conjugate compound. G is a reactive group for connecting the PBD dimer to the cell binding agent to form the conjugate compound.

Preferably, the linker/reactive group contains an electrophilic functional group for reaction with a nucleophilic functional group on the cell binding agent. Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) maleimide groups (ii) activated disulfides, (iii) active esters such as NHS (N-hydroxysuccinimide) esters, HOBt (N-hydroxybenzotriazole) esters, haloformates, and acid halides; (iv) alkyl and benzyl halides such as haloacetamides; and (v) aldehydes, ketones, carboxyl, and, some of which are exemplified as follows:

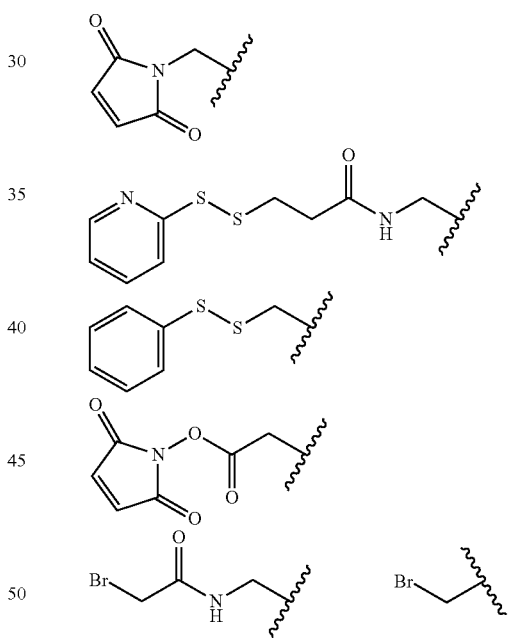

Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids. In some embodiments, a Linker has a reactive nucleophilic group which is reactive with an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydroxyl, hydrazine, thiosemicarbazone, hydrazine carboxylate, and arylhydrazide. The electrophilic group on an antibody provides a convenient site for attachment to a Linker.

In one embodiment, the group L is:

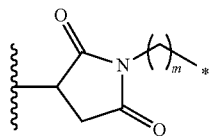

where the asterisk indicates the point of attachment to the rest of group Y, the wavy line indicates the point of attachment to the cell binding agent, and m is an integer selected from the range 0 to 6. In one embodiment, m is selected from 2, 3, 4 and 5.

In one embodiment, the connection between the cell binding agent and L is through a thiol residue of the cell binding agent and a maleimide group of L.

In one embodiment, the connection between the cell binding agent and L is:

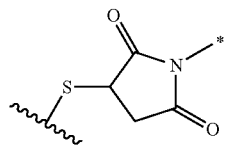 [SMILES: *SC1CC(=O)N(C)C1=O]

where the asterisk indicates the point of attachment to the remaining portion of the L group or the remaining portion of the Y group and the wavy line indicates the point of attachment to the remaining portion of the cell binding agent. In this embodiment, the S atom is typically derived from the cell binding agent.

In each of the embodiments above, an alternative functionality may be used in place of the maleimide-derived group shown below:

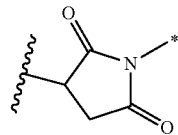 [SMILES: *C1CC(=O)N(C)C1=O]

where the wavy line indicates the point of attachment to the cell binding agent as before, and the asterisk indicates the bond to the remaining portion of the L group or the remaining portion of the Y group.

In one embodiment, the maleimide-derived group is replaced with the group:

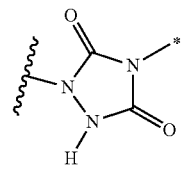 [SMILES: *n1[nH]c(=O)n(C)c1=O]

where the wavy line indicates point of attachment to the cell binding agent, and the asterisk indicates the bond to the remaining portion of the L group or the remaining portion of the Y group.

In one embodiment, the maleimide-derived group is replaced with a group, which optionally together with the cell binding agent, is selected from:

—C(=O)NH—,
—C(=O)O—,
—NHC(=O)—,
—OC(=O)—,
—OC(=O)O—,
—NHC(=O)O—,
—OC(=O)NH—,
—NHC(=O)NH—,
—NHC(=O)NH,
—C(=O)NHC(=O)—,
—S—,
—S—,
—CH$_2$C(=O)—
—C(=O)CH$_2$—,
=N—NH—, and
—NH—N=.

In one embodiment, the maleimide-derived group is replaced with a group, which optionally together with the cell binding agent, is selected from:

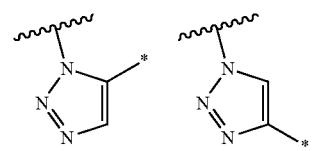 [SMILES: *c1cnnn1* ; *c1cn(*)nn1]

where the wavy line indicates either the point of attachment to the cell binding agent or the bond to the remaining portion of the L group or the remaining portion of the Y group, and the asterisk indicates the other of the point of attachment to the cell binding agent or the bond to the remaining portion of the L group or the remaining portion of the Y group.

Other groups that can be used as L for connecting the remaining portion of the Y group to the cell binding agent are described in WO 2005/082023.

Thus, in embodiments of the present invention, L is of formula:

-L$^A$-(CH$_2$)$_m$—         (L1)

Where m is from 0 to 6; and
L$^A$ is selected from:

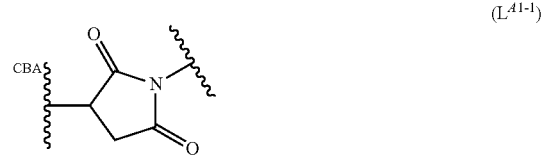

(L$^{A1-1}$)

-continued

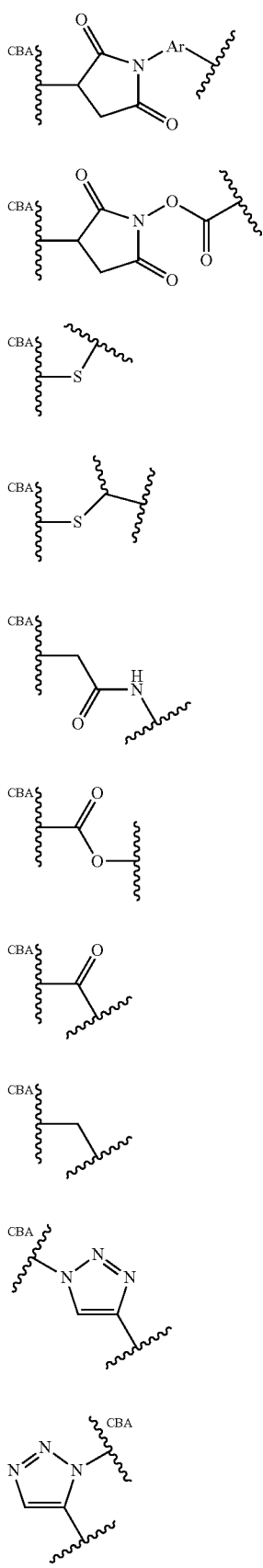

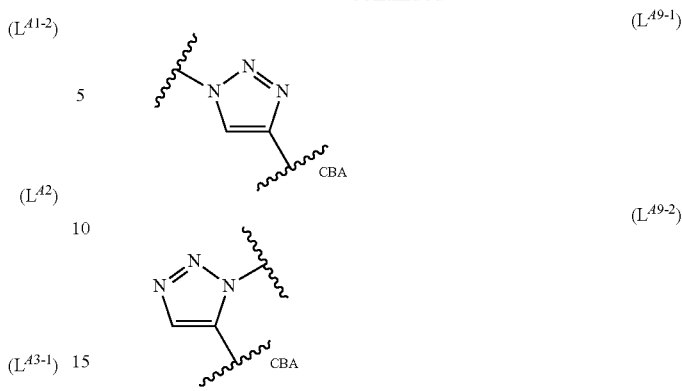

where Ar is $C_{5-6}$ arylene group, e.g. phenylene.

In some embodiments where L is L1, m may be 2, 3 or 5.
In some embodiments where L is L1, $L^A$ may be $L^{A1-1}$.
In embodiments of the present invention, L is of formula:

$$-L^A-(CH_2)_m-O- \qquad (L2)$$

Where m is from 0 to 6; and
$L^A$ is selected from the groups above.

Without wishing to be bound by theory, such a group may be cleaved from the antibody such that the carbamate group yields a terminal amine.

In some embodiments where L is L2, $L^A$ may be $L^{A3-2}$.
In some embodiments where L is L2, m may be 1.
In embodiments of the present invention, L is of formula:

$$-L^A-(CH_2)_q-O-C(=O)-NH-(CH_2)_p- \qquad (L3)$$

Where q is from 1 to 3, and p is from 1 to 3; and
$L^A$ is selected from the groups above.

Without wishing to be bound by theory, such a group may be cleaved from the antibody such that the carbamate group yields the group: $H_2N-(CH_2)_p-$ (L3').

In some embodiments where L is L3, q may be 1, and p may be 2.

In some embodiments where L is L3, $L^A$ may be selected from $L^{A7}$, $L^{AB-1}$ and $L^{A8-2}$.

In embodiments of the present invention, L is of formula:

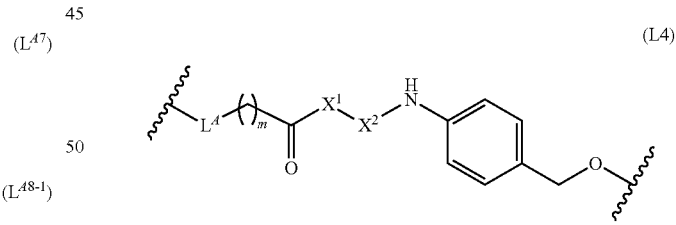

Where m is from 0 to 6;
$X^1$ and $X^2$ are amino acid groups, selected from natural amino acids, which may be modified;
$L^A$ is selected from the groups above.

The natural amino acids may be selected such that the dipeptide group is cathpesin labile.

In one embodiment, the group $-X_1-X_2-$ is selected from:
-Phe-Lys-,
-Val-Ala-,
-Val-Lys-,
-Ala-Lys-,
-Val-Cit-, -Phe-Cit-,
-Leu-Cit-,
-Ile-Cit-,
-Phe-Arg-,
-Trp-Cit-
where Cit is citrulline.

Preferably, the group —$X_1$-$X_2$— is selected from:
-Phe-Lys-,
-Val-Ala-,
-Val-Lys-,
-Ala-Lys-,
-Val-Cit-.

Most preferably, the group —$X_1$-$X_2$— is -Phe-Lys- or -Val-Ala-.

In some embodiments where L is L4, m may be 1.

Other dipeptide combinations may be used, including those described by Dubowchik et al., *Bioconjugate Chemistry*, 2002, 13, 855-869, which is incorporated herein by reference.

In one embodiment, the amino acid side chain is derivatised, where appropriate. For example, an amino group or carboxy group of an amino acid side chain may be derivatised.

In one embodiment, an amino group $NH_2$ of a side chain amino acid, such as lysine, is a derivatised form selected from the group consisting of NHR and NRR'.

In one embodiment, a carboxy group COOH of a side chain amino acid, such as aspartic acid, is a derivatised form selected from the group consisting of COOR, $CONH_2$, CONHR and CONRR'.

In one embodiment, the amino acid side chain is chemically protected, where appropriate.

The side chain protecting group may be a group as discussed below in relation to the group $R^L$. The present inventors have established that protected amino acid sequences are cleavable by enzymes. For example, it has been established that a dipeptide sequence comprising a Boc side chain-protected Lys residue is cleavable by cathepsin.

Protecting groups for the side chains of amino acids are well known in the art and are described in the Novabiochem Catalog. Additional protecting group strategies are set out in Protective Groups in Organic Synthesis, Greene and Wuts.

Possible side chain protecting groups are shown below for those amino acids having reactive side chain functionality:

Arg: Z, Mtr, Tos;
Asn: Trt, Xan;
Asp: Bzl, t-Bu;
Cys: Acm, Bzl, Bzl-OMe, Bzl-Me, Trt;
Glu: Bzl, t-Bu;
Gln: Trt, Xan;
His: Boc, Dnp, Tos, Trt;
Lys: Boc, Z—Cl, Fmoc, Z, Alloc;
Ser: Bzl, TBDMS, TBDPS;
Thr: Bz;
Trp: Boc;
Tyr: Bzl, Z, Z—Br.

Thus, in embodiments of the present invention, G is of formula:

$$G^A\text{-}(CH_2)_m— \quad (G1)$$

Where m is from 0 to 6; and
$G^A$ is selected from:

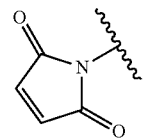

(G$^{A1\text{-}1}$)

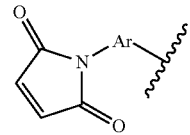

(G$^{A1\text{-}2}$)

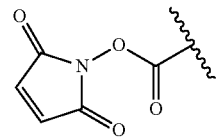

(G$^{A2}$)

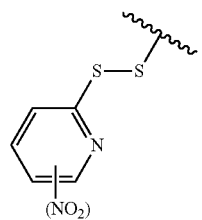

(G$^{A3\text{-}1}$)

where the $NO_2$ group is optional

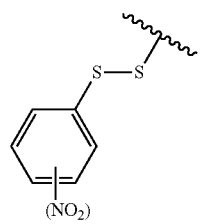

(G$^{A3\text{-}2}$)

where the $NO_2$ group is optional

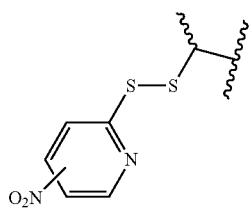

(G$^{A3\text{-}3}$)

where the $NO_2$ group is optional

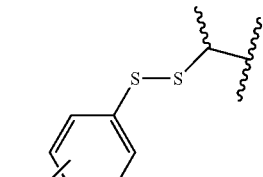

(G$^{A3\text{-}4}$)

where the $NO_2$ group is optional

-continued

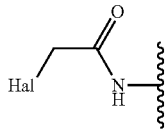 (G44)

Where Hal = I, Br, Cl

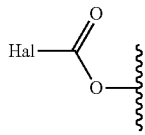 (G45)

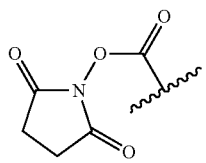 (G46)

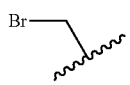 (G47)

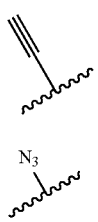 (G48)

(G49)

where Ar represents a $C_{5-6}$ arylene group, e.g. phenylene.

In some embodiments where G is G1, m may be 2, 3 or 5.

In some embodiments where G is G1, $G^4$ may be $G^{41-1}$.

In embodiments of the present invention, G is of formula:

$$G^4\text{-}(CH_2)_m\text{---}O\text{---} \quad (G2)$$

Where m is from 0 to 6; and
$G^4$ is selected from the groups above.
In some embodiments where G is G2, $G^4$ may be $G^{3-2}$.
In some embodiments where G is G2, m may be 1.
In embodiments of the present invention, G is of formula:

$$G^4\text{-}(CH_2)_q\text{---}O\text{---}C(=\!O)\text{---}NH\text{---}(CH_2)_p\text{---} \quad (G3)$$

Where q is from 1 to 3, and p is from 1 to 3; and
$G^4$ is selected from the groups above.
In some embodiments where G is G3, q may be 1, and p may be 2.
In some embodiments where G is G3, $G^4$ may be selected from $G^{47}$ and $G^{48}$.
In embodiments of the present invention, G is of formula:

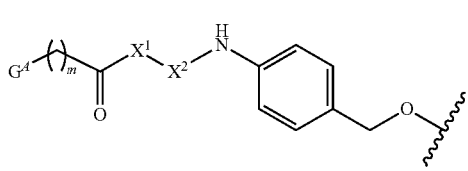 (G4)

Where m is from 0 to 6;
$X^1$ and $X^2$ are as defined above for L4;
$G^4$ is selected from the groups above.
R and R'
In one embodiment, R is independently selected from optionally substituted $C_{1-12}$ alkyl, $C_{3-2}$ heterocyclyl and $C_{5-20}$ aryl groups. These groups are each defined in the substituents section below.

In one embodiment, R is independently optionally substituted $C_{1-12}$ alkyl.
In one embodiment, R is independently optionally substituted $C_{3-20}$ heterocyclyl.
In one embodiment, R is independently optionally substituted $C_{5-20}$ aryl.
In one embodiment, R is independently optionally substituted $C_{1-12}$ alkyl.
The preferences for R apply also to R'.
In some embodiments of the invention there is provided a compound having a substituent group —NRR'. In one embodiment, R and R' together with the nitrogen atom to which they are attached form an optionally substituted 4-, 5-, 6- or 7-membered heterocyclic ring. The ring may contain a further heteroatom, for example N, O or S.

In one embodiment, the heterocyclic ring is itself substituted with a group R. Where a further N heteroatom is present, the substituent may be on the N heteroatom.
$R^{44}$
In one embodiment, $R^{44}$ is a $C_{2-4}$ alkylene group.
In one embodiment, $R^{44}$ is a $C_2$ alkylene group.
In one embodiment, $R^{44}$ is a $C_3$ alkylene group.
In one embodiment, $R^{44}$ is an unsubstituted $C_{1-6}$ alkylene group.
In one embodiment, $R^{44}$ is a linear $C_{1-6}$ alkylene group.
In one embodiment, $R^{44}$ is selected from the group consisting of —$CH_2CH_2$—, —$CH_2CH_2CH_2$— and —$CH_2CH_2CH_2CH_2$—

Cell Binding Agent

A cell binding agent may be of any kind, and include peptides and non-peptides. These can include antibodies or a fragment of an antibody that contains at least one binding site, lymphokines, hormones, growth factors, nutrient-transport molecules, or any other cell binding molecule or substance.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) *Jour. of Immunology* 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology,* 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2. IgG3, IgG4, IgA1 and IgA2) or subclass of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) *Nature* 256:495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) *Proc. Natl. Acad. Sci. USA,* 81:6851-6855). Chimeric antibodies include "primatized" antibodies comprising variable domain antigen-binding sequences derived from a non-human primate (e.g. Old World Monkey or Ape) and human constant region sequences.

An "intact antibody" herein is one comprising a VL and VH domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

Examples of cell binding agents include those agents described for use in WO 2007/085930, which is incorporated herein.

The cell binding agent may be, or comprise, a polypeptide. The polypeptide may be a cyclic polypeptide. The cell binding agent may be antibody. Thus, in one embodiment, the present invention provides an antibody-drug conjugate (ADC).

Drug Loading

The drug loading is the average number of PBD drugs per antibody. Drug loading may range from 1 to 8 drugs (D) per antibody (Ab), i.e. where 1, 2, 3, 4, 5, 6, 7, and 8 drug moieties are covalently attached to the antibody. Compositions of ADC include collections of antibodies conjugated with a range of drugs, from 1 to 8. The average number of drugs per antibody in preparations of ADC from conjugation reactions may be characterized by conventional means such as mass spectroscopy, ELISA assay, electrophoresis, and HPLC. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g. p>5, may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with the drug-linker intermediate (D-L) or linker reagent. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio) of an ADC may be controlled in several different manners, including: (i) limiting the molar excess of drug-linker intermediate (D-L) or linker reagent relative to antibody, (ii) limiting the conjugation reaction time or temperature, and (iii) partial or limiting reductive conditions for cysteine thiol modification.

Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114 (13):2721-2729; U.S. Pat. No. 7,521,541; U.S. Pat. No. 7,723,485; WO2009/052249, Shen et al (2012) Nature Biotech., 30(2):184-191; Junutula et al (2008) Jour of Immun. Methods 332:41-52). The engineered cysteine thiols may react with linker reagents or the drug-linker reagents of the present invention which have thiol-reactive, electrophilic groups such as maleimide or alpha-halo amides to form ADC with cysteine engineered antibodies (ThioMabs) and the PBD drug moieties. The location of the drug moiety can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. A drug loading near 2 can be achieved and near homogeneity of the conjugation product ADC.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

Thus the antibody-drug conjugate compositions of the invention include mixtures of antibody-drug conjugate compounds where the antibody has one or more PBD drug moieties and where the drug moieties may be attached to the antibody at various amino acid residues.

In one embodiment, the average number of dimer pyrrolobenzodiazepine groups per cell binding agent is in the range 1 to 20. In some embodiments the range is selected from 1 to 8, 2 to 8, 2 to 6, 2 to 4, and 4 to 8.

In some embodiments, there is one dimer pyrrolobenzodiazepine groups per cell binding agent.

Peptides

In one embodiment, the cell binding agent is a linear or cyclic peptide comprising 4-20, preferably 6-20, contiguous amino acid residues. In this embodiment, it is preferred that one cell binding agent is linked to one monomer or dimer pyrrolobenzodiazepine compound.

In one embodiment the cell binding agent comprises a peptide that binds integrin $\alpha_v\beta_6$. The peptide may be selective for $\alpha_v\beta_6$ over XYS.

In one embodiment the cell binding agent comprises the A20FMDV-Cys polypeptide. The A20FMDV-Cys has the sequence: NAVPNLRGDLQVLAQKVARTC (SEQ ID NO:55). Alternatively, a variant of the A20FMDV-Cys sequence may be used wherein one, two, three, four, five, six, seven, eight, nine or ten amino acid residues is substituted with another amino acid residue.

In one embodiment the antibody is a monoclonal antibody; chimeric antibody; humanized antibody; fully human antibody; or a single chain antibody. One embodiment the antibody is a fragment of one of these antibodies having biological activity. Examples of such fragments include Fab, Fab', F(ab')₂ and Fv fragments.

In these embodiments, each antibody may be linked to one or several dimer pyrrolobenzodiazepine groups. The preferred ratios of pyrrolobenzodiazepine to cell binding agent are given above.

The antibody may be a domain antibody (DAB).

In one embodiment, the antibody is a monoclonal antibody.

Antibodies for use in the present invention include those antibodies described in WO 2005/082023 which is incorporated herein. Particularly preferred are those antibodies for tumour-associated antigens. Examples of those antigens known in the art include, but are not limited to, those tumour-associated antigens set out in WO 2005/082023. See, for instance, pages 41-55.

The conjugates of the invention are designed to target tumour cells via their cell surface antigens. The antigens are usually normal cell surface antigens which are either over-expressed or expressed at abnormal times. Ideally the target antigen is expressed only on proliferative cells (preferably tumour cells), however this is rarely observed in practice. As a result, target antigens are usually selected on the basis of differential expression between proliferative and healthy tissue.

Tumor-associated antigens (TAA) are known in the art, and can prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of TAA include, but are not limited to, TAA (1)-(36) listed below. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI). Nucleic acid and protein sequences corresponding to TAA (1)-(36) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Tumor-Associated Antigens (1)-(36):

(1) BMPR1B (bone morphogenetic protein receptor-type IB, Genbank accession no. NM_001203) ten Dijke, P., et al Science 264 (5155):101-104 (1994), Oncogene 14 (11): 1377-1382 (1997)); WO2004/063362 (Claim 2); WO2003/042661 (Claim 12); US2003/134790-A1 (Page 38-39); WO2002/102235 (Claim 13; Page 296); WO2003/055443 (Page 91-92); WO2002/99122 (Example 2; Page 528-530); WO2003/029421 (Claim 6); WO2003/024392 (Claim 2; FIG. 112); WO2002/98358 (Claim 1; Page 183); WO2002/54940 (Page 100-101); WO2002/59377(Page 349-350); WO2002/30268 (Claim 27; Page 376); WO2001/48204 (Example; FIG. 4); NP_001194 bone morphogenetic protein receptor, type IB/pid=NP_001194.1. Cross-references: MIM:603248; NP_001194.1; AY065994

Figure 3:
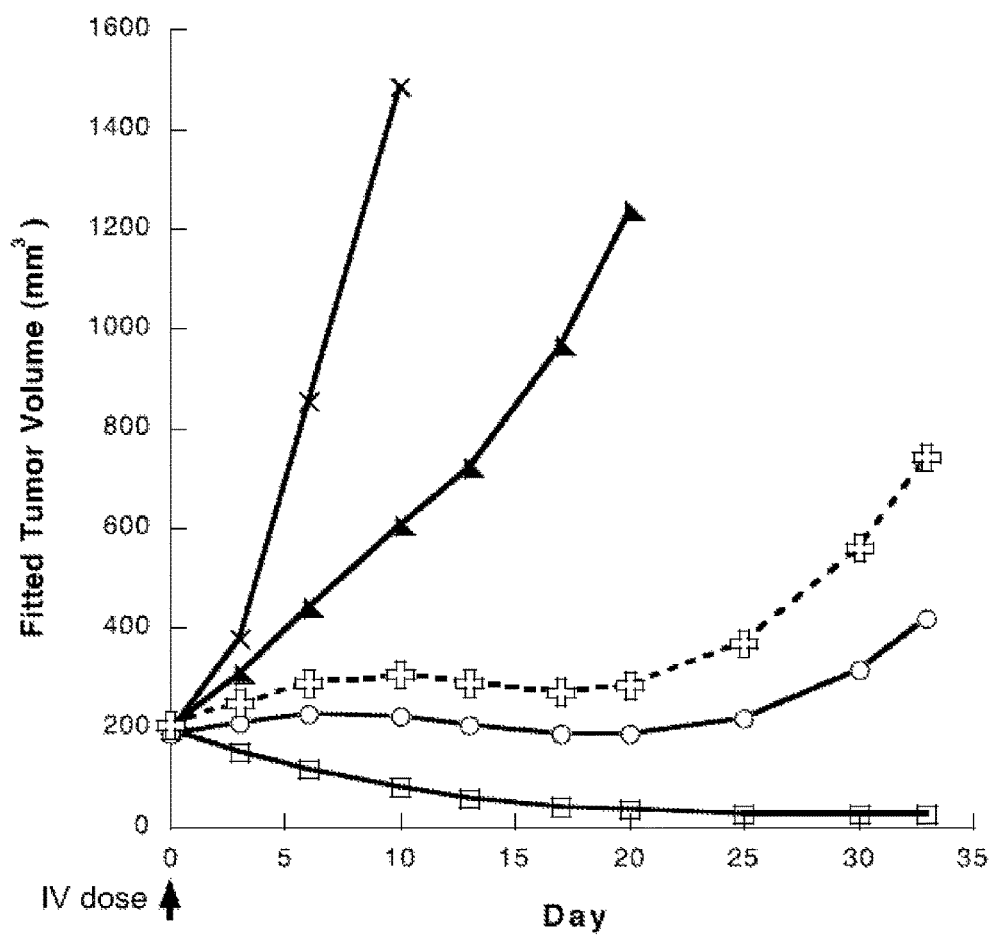

(2) E16 (LAT1, SLC7A5, Genbank accession no. NM_003486) Biochem. Biophys. Res. Commun. 255 (2), 283-288 (1999), Nature 395 (6699):288-291 (1998), Gaugitsch, H. W., et al (1992) J. Biol. Chem. 267 (16):11267-11273); WO2004/048938 (Example 2); WO2004/032842 (Example IV); WO2003/042661 (Claim 12); WO2003/016475 (Claim 1); WO2002/78524 (Example 2); WO2002/99074 (Claim 19; Page 127-129); WO2002/86443 (Claim 27; Pages 222, 393); WO2003/003906 (Claim 10; Page 293); WO2002/64798 (Claim 33; Page 93-95); WO2000/14228 (Claim 5; Page 133-136); US2003/224454 (FIG. 3); WO2003/025138 (Claim 12; Page 150); NP_003477 solute carrier family 7 (cationic amino acid transporter, y+system), member 5/pid=NP_003477.3—Homo sapiens; Cross-references: MIM:600182; NP_003477.3; NM_015923; NM_003486_1

Figure 2:
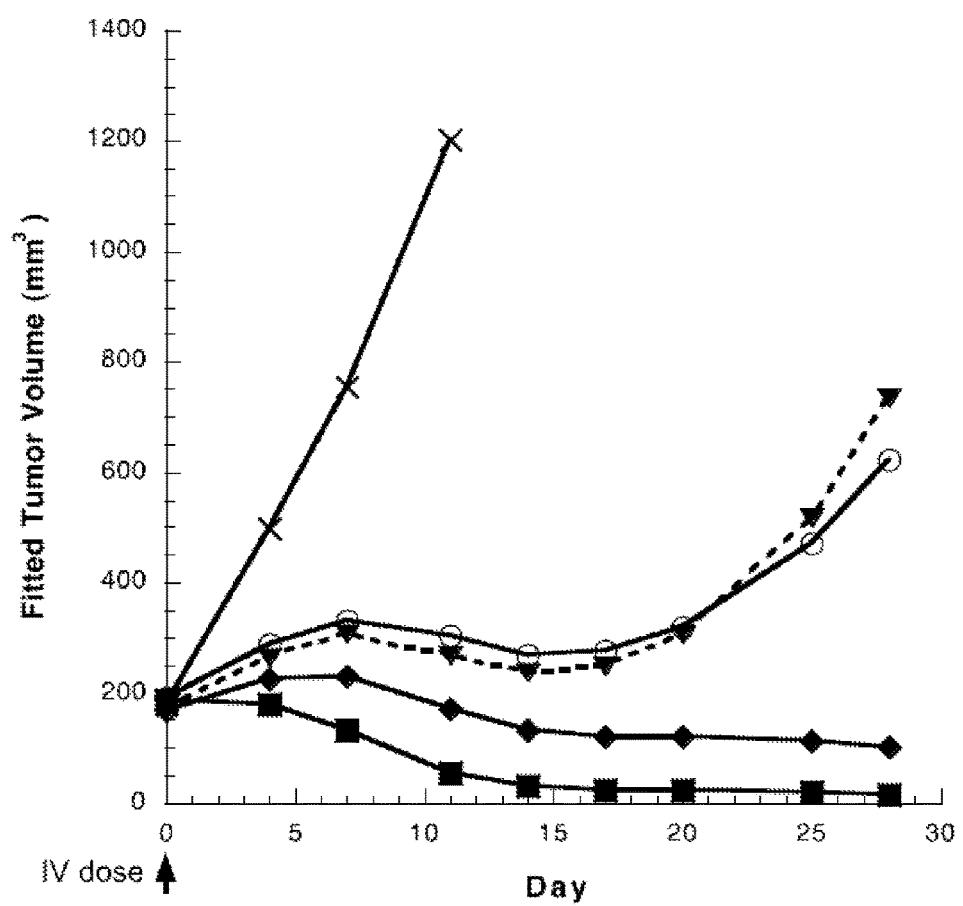

(3) STEAP1 (six transmembrane epithelial antigen of prostate, Genbank accession no. NM_012449); Cancer Res. 61 (15), 5857-5860 (2001), Hubert, R. S., et al (1999) Proc. Natl. Acad. Sci. U.S.A. 96 (25):14523-14528); WO2004/065577 (Claim 6): WO2004/027049 (FIG. 1L); EP1394274 (Example 11); WO2004/016225 (Claim 2); WO2003/042661 (Claim 12); US2003/157089 (Example 5); US2003/185830 (Example 5); US2003/064397 (FIG. 2); WO2002/89747 (Example 5; Page 618-619); WO2003/022995 (Example 9; FIG. 13A, Example 53; Page 173, Example 2; FIG. 2A); NP_036581 six transmembrane epithelial antigen of the prostate; Cross-references: MIM:604415; NP_036581.1; NM_012449_1

(4) 0772P(CA125, MUC16, Genbank accession no. AF361486); J. Biol. Chem. 276 (29):27371-27375 (2001)); WO2004/045553 (Claim 14); WO2002/92836 (Claim 6: FIG. 12); WO2002/83866 (Claim 15; Page 116-121); US2003/124140 (Example 16); Cross-references: GI:34501467; AAK74120.3; AF361486_1

(5) MPF (MPF, MSLN, SMR, megakaryocyte potentiating factor, mesothelin, Genbank accession no. NM_005823) Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003/101283 (Claim 14); (WO2002/102235 (Claim 13; Page 287-288); WO2002/101075 (Claim 4; Page 308-309); WO2002/71928 (Page 320-321): WO94/10312 (Page 52-57); Cross-references: MIM:601051; NP_005814.2; NM_005823_1

(6) Napi3b (NAPI-3B, NaPi2B, NPTIIb, SLC34A2, solute carrier family 34 (sodium phosphate), member 2, type II sodium-dependent phosphate transporter 3b, Genbank accession no. NM_006424) J. Biol. Chem. 277 (22):19665-19672 (2002), Genomics 62 (2):281-284 (1999), Feild, J. A., et al (1999) Biochem. Biophys. Res. Commun. 258 (3):578-582); WO2004/022778 (Claim 2); EP1394274 (Example 11); WO2002/102235 (Claim 13; Page 326); EP0875569 (Claim 1; Page 17-19): WO2001/57188 (Claim 20; Page 329): WO2004/032842 (Example IV); WO2001/75177 (Claim 24; Page 139-140); Cross-references: MIM:604217; NP_006415.1; NM_006424_1. In certain embodiments, conjugate compounds of the invention comprise anti-NaPi2B antibodies. In one embodiment of the invention, an anti-NaPi2B antibody of an ADC of the invention comprise (a) CDR L1 of SEQ ID NO:1; (b) CDR L2 of SEQ ID NO:2; (c) CDR L3 of SEQ ID NO:3; (d) CDR H1 of SEQ ID NO:4; (e) CDR H2 of SEQ ID NO:5; (f) CDR H3 of SEQ ID NO:6. In one embodiment, the antibody comprises the VH and VL sequences in SEQ ID NO:8 and SEQ ID NO:7, respectively, including post-translational modifications of those sequences. In one embodiment, the antibody comprises the heavy chain and light chain sequences in SEQ ID NO:10 and SEQ ID NO:9, respectively, including post-translational modifications of those sequences.

SEQ ID NO: 1    RSSETLVHSSGNTYLE

SEQ ID NO: 2    RVSNRFS

SEQ ID NO: 3    FQGSFNPLT

SEQ ID NO: 4    GFSFSDFAMS

SEQ ID NO: 5    ATIGRVAFHTYYPDSMKG

SEQ ID NO: 6    ARHRGFDVGHFDF

SEQ ID NO: 7    DIQMTQSPSSLSASVGDRVTITCRSSETLVHSSGNT
                YLEWYQQKPGKAPKLLIYRVSNRFSGVPSRFSGSGS
                GTDFTLTISSLQPEDFATYYCFQGSFNPLTFGQGTK
                VEIKR

SEQ ID NO: 8    EVQLVESGGGLVQPGGSLRLSCAASGFSFSDFAMSW
                VRQAPGKGLEWVATIGRVAFHTYYPDSMKGRFTISR
                DNSKNTLYLQMNSLRAEDTAVYYCARHRGFDVGHFD
                FWGQGTLVTVSS

SEQ ID NO: 9    DIQMTQSPSSLSASVGDRVTITCRSSETLVHSSGNT
                YLEWYQQKPGKAPKLLIYRVSNRFSGVPSRFSGSGS
                GTDFTLTISSLQPEDFATYYCFQGSFNPLTFGQGTK
                VEIKRTVAAPSVFIFPPSDEQLKSGTASVVCLLNNF
                YPREAKVQWKVDNALQSGNSQESVTEQDSKDSTYSL
                SSTLTLSKADYEKHKVYACEVTHQGLSSPVTKSFNR
                GEC

SEQ ID NO: 10   EVQLVESGGGLVQPGGSLRLSCAASGFSFSDFAMSW
                VRQAPGKGLEWVATIGRVAFHTYYPDSMKGRFTISR
                DNSKNTLYLQMNSLRAEDTAVYYCARHRGFDVGHFD
                FWGQGTLVTVSSCSTKGPSVFPLAPSSKSTSGGTAA
                LGCLVKDYFPEPVTVSWNSGALTSGVHTFPAVLQSS
                GLYSLSSVVTVPSSSLGTQTYICNVNHKPSNTKVDK
                KVEPKSCDKTHTCPPCPAPELLGGPSVFLFPPKPKD
                TLMISRTPEVTCVVVDVSHEDPEVKFNWYVDGVEVH
                NAKTKPREEQYNSTYRVVSVLTVLHQDWLNGKEYKC
                KVSNKALPAPIEKTISKAKGQPREPQVYTLPPSREE
                MTKNQVSLTCLVKGFYPSDIAVEWESNGQPENNYKT
                TPPVLDSDGSFFLYSKLTVDKSRWQQGNVFSCSVMH
                EALHNHYTQKSLSLSPGK (7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878); Nagase T., et al (2000) DNA Res. 7 (2):143-150); WO2004/000997 (Claim 1); WO2003/003923 (Claim 1); WO2002/06339 (Claim 1; Page 50); WO2001/88133 (Claim 1; Page 41-43, 48-58); WO2003/054152 (Claim 20);

WO2003/101400 (Claim 11); Accession: Q9P283; EMBL; AB040878; BAA95969.1. Genew; HGNC:10737

(8) PSCA hlg (2700050C12Rik, C530008O16Rik, RIKEN cDNA 2700050C12, RIKEN cDNA 2700050C12 gene, Genbank accession no. AY358628); Ross et al (2002) *Cancer Res.* 62:2546-2553; US2003/129192 (Claim 2); US2004/044180 (Claim 12); US2004/044179 (Claim 11); US2003/096961 (Claim 11); US2003/232056 (Example 5); WO2003/105758 (Claim 12); US2003/206918 (Example 5); EP1347046 (Claim 1); WO2003/025148 (Claim 20); Cross-references: GI:37182378; AAQ88991.1; AY358628_1

(9) ETBR (Endothelin type B receptor, Genbank accession no. AY275463); Nakamuta M., et al *Biochem. Biophys. Res. Commun.* 177, 34-39, 1991; Ogawa Y., et al *Biochem. Biophys. Res. Commun.* 178, 248-255, 1991; Arai H., et al *Jpn. Circ. J.* 56, 1303-1307, 1992; Arai H., et al *J. Biol. Chem.* 268, 3463-3470, 1993; Sakamoto A., Yanagisawa M., et al *Biochem. Biophys. Res. Commun.* 178, 656-663, 1991; Elshourbagy N. A., et al *J. Biol. Chem.* 268, 3873-3879, 1993; Haendler B., et al *J. Cardiovasc. Pharmacol.* 20, s1-S4, 1992: Tsutsumi M., et al *Gene* 228, 43-49, 1999; Strausberg R. L., et al *Proc. Natl. Acad. Sci. U.S.A.* 99, 16899-16903, 2002; Bourgeois C., et al *J. Clin. Endocrinol. Metab.* 82, 3116-3123, 1997; Okamoto Y., et al *Biol. Chem.* 272, 21589-21596, 1997; Verheij J. B., et al *Am. J. Med. Genet.* 108, 223-225, 2002; Hofstra R. M. W., et al *Eur. J. Hum. Genet.* 5, 180-185, 1997; Puffenberger E. G., et al *Cell* 79, 1257-1266, 1994; Attie T., et al, *Hum. Mol. Genet.* 4, 2407-2409, 1995; Auricchio A., et al *Hum. Mol. Genet.* 5:351-354, 1996; Amiel J., et al *Hum. Mol. Genet.* 5, 355-357, 1996; Hofstra R. M. W., et al *Nat. Genet.* 12, 445-447, 1996; Svensson P. J., et al *Hum. Genet.* 103, 145-148, 1998: Fuchs S., et al *Mol. Med.* 7, 115-124, 2001; Pingault V., et al (2002) *Hum. Genet.* 111, 198-206; WO2004/045516 (Claim 1); WO2004/048938 (Example 2); WO2004/040000 (Claim 151); WO2003/087768 (Claim 1); WO2003/016475 (Claim 1); WO2003/016475 (Claim 1); WO2002/61087 (FIG. 1); WO2003/016494 (FIG. 6); WO2003/025138 (Claim 12; Page 144): WO2001/98351 (Claim 1; Page 124-125); EP0522868 (Claim 8; FIG. 2); WO2001/77172 (Claim 1; Page 297-299); US2003/109676; U.S. Pat. No. 6,518,404 (FIG. 3); U.S. Pat. No. 5,773,223 (Claim 1a; Col 31-34); WO2004/001004

(10) MSG783 (RNF124, hypothetical protein FLJ20315, Genbank accession no. NM_017763); WO2003/104275 (Claim 1); WO2004/046342 (Example 2); WO2003/042661 (Claim 12); WO2003/083074 (Claim 14; Page 61); WO2003/018621 (Claim 1); WO2003/024392 (Claim 2: FIG. 93): WO2001/66689 (Example 6); Cross-references: LocusID:54894; NP_060233.2; NM_017763_1

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138); Lab. Invest. 82 (11):1573-1582 (2002)); WO2003/087306; US2003/064397 (Claim 1; FIG. 1); WO2002/72596 (Claim 13; Page 54-55); WO2001/72962 (Claim 1; FIG. 4B); WO2003/104270 (Claim 11); WO2003/104270 (Claim 16); US2004/005598 (Claim 22); WO2003/042661 (Claim 12); US2003/060612 (Claim 12; FIG. 10); WO2002/26822 (Claim 23; FIG. 2); WO2002/16429 (Claim 12; FIG. 10); Cross-references: GI:22655488; AAN04080.1; AF455138_1

(12) TrpM4 (BR22450. FLJ20041, TRPM4, TRPM4B, transient receptor potential cation channel, subfamily M, member 4, Genbank accession no. NM_017636); Xu, X. Z., et al *Proc. Natl. Acad. Sci. U.S.A.* 98 (19):10692-10697 (2001), *Cell* 109 (3):397-407 (2002), *J. Biol. Chem.* 278 (33):30813-30820 (2003)); US2003/143557 (Claim 4); WO2000/40614 (Claim 14; Page 100-103); WO2002/10382 (Claim 1; FIG. 9A); WO2003/042661 (Claim 12); WO2002/30268 (Claim 27; Page 391); US2003/219806 (Claim 4); WO2001/62794 (Claim 14; FIG. 1A-D); Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212); Ciccodicola, A., et al *EMBO J.* 8 (7):1987-1991 (1989), *Am. J. Hum. Genet.* 49 (3):555-565 (1991)); US2003/224411 (Claim 1); WO2003/083041 (Example 1); WO2003/034984 (Claim 12); WO2002/88170 (Claim 2; Page 52-53); WO2003/024392 (Claim 2; FIG. 58); WO2002/16413 (Claim 1; Page 94-95, 105); WO2002/22808 (Claim 2; FIG. 1); U.S. Pat. No. 5,854,399 (Example 2; Col 17-18); U.S. Pat. No. 5,792,616 (FIG. 2); Cross-references: MIM:187395; NP_003203.1; NM_003212_1

(14) CD21 (CR2 (Complement receptor 2) or C3DR (C3d/Epstein Barr virus receptor) or Hs.73792 Genbank accession no. M26004); Fujisaku et al (1989) *J. Biol. Chem.* 264 (4):2118-2125); Weis J. J., et al *J. Exp. Med.* 167, 1047-1066, 1988; Moore M., et al *Proc. Natl. Acad. Sci. U.S.A.* 84, 9194-9198, 1987; Barel M., et al *Mol. Immunol.* 35, 1025-1031, 1998; Weis J. J., et al *Proc. Natl. Acad. Sci. U.S.A.* 83, 5639-5643, 1986; Sinha S. K., et al (1993) *J. Immunol.* 150, 5311-5320; WO2004/045520 (Example 4); US2004/005538 (Example 1); WO2003/062401 (Claim 9); WO2004/045520 (Example 4); WO91/02536 (FIG. 9.1-9.9); WO2004/020595 (Claim 1); Accession: P20023: Q13866; Q14212; EMBL; M26004; AAA35786.1.

(15) CD79b (CD79B, CD79β, IGb (immunoglobulin-associated beta), B29, Genbank accession no. NM_000626 or 11038674); *Proc. Natl. Acad. Sci. U.S.A.* (2003) 100 (7):4126-4131, *Blood* (2002) 100 (9):3068-3076, Muller et al (1992) *Eur. J. Immunol.* 22 (6):1621-1625); WO2004/016225 (claim 2, FIG. 140); WO2003/087768, US2004/101874 (claim 1, page 102); WO2003/062401 (claim 9); WO2002/78524 (Example 2); US2002/150573 (claim 5, page 15); U.S. Pat. No. 5,644,033; WO2003/048202 (claim 1, pages 306 and 309); WO 99/58658, U.S. Pat. No. 6,534,482 (claim 13, FIG. 17A/B); WO2000/55351 (claim 11, pages 1145-1146); Cross-references: MIM:147245; NP_000617.1; NM_000626_1

(16) FcRH2 (IFGP4, IRTA4, SPAP1A (SH2 domain containing phosphatase anchor protein Ia), SPAP1B, SPAP1C, Genbank accession no. NM_030764, AY358130); *Genome Res.* 13 (10):2265-2270 (2003), *Immunogenetics* 54 (2):87-95 (2002), *Blood* 99 (8):2662-2669 (2002), *Proc. Natl. Acad. Sci. U.S.A.* 98 (17):9772-9777 (2001), Xu, M. J., et al (2001) *Biochem. Biophys. Res. Commun.* 280 (3):768-775; WO2004/016225 (Claim 2); WO2003/077836; WO2001/38490 (Claim 5; FIG. 18D-1-18D-2); WO2003/097803 (Claim 12); WO2003/089624 (Claim 25); Cross-references: MIM:606509; NP_110391.2; NM_030764_1

(17) HER2 (ErbB2, Genbank accession no. M11730); Coussens L., et al *Science* (1985) 230(4730):1132-1139); Yamamoto T., et al *Nature* 319, 230-234, 1986; Semba K., et al *Proc. Natl. Acad. Sci. U.S.A.* 82, 6497-6501, 1985; Swierz J. M., et al *J. Cell Biol.* 165, 869-880, 2004; Kuhns J. J., et al *J. Biol. Chem.* 274, 36422-36427, 1999; Cho H.-S., et al *Nature* 421, 756-760, 2003; Ehsani A., et al (1993) *Genomics* 15, 426-429; WO2004/048938 (Example 2); WO2004/027049 (FIG. 11); WO2004/009622; WO2003/081210; WO2003/089904 (Claim 9); WO2003/016475 (Claim 1); US2003/118592; WO2003/008537 (Claim 1);

WO2003/055439 (Claim 29; FIG. 1A-B); WO2003/025228 (Claim 37; FIG. 5C); WO2002/22636 (Example 13; Page 95-107); WO2002/12341 (Claim 68; FIG. 7); WO2002/13847 (Page 71-74); WO2002/14503 (Page 114-117); WO2001/53463 (Claim 2; Page 41-46); WO2001/41787 (Page 15); WO2000/44899 (Claim 52; FIG. 7); WO2000/20579 (Claim 3; FIG. 2); U.S. Pat. No. 5,869,445 (Claim 3; Col 31-38); WO9630514 (Claim 2; Page 56-61); EP1439393 (Claim 7); WO2004/043361 (Claim 7); WO2004/022709; WO2001/00244 (Example 3; FIG. 4); Accession: P04626; EMBL; M11767; AAA35808.1. EMBL; M11761; AAA35808.1. In certain embodiments, conjugate compounds of the invention comprise anti-HER2 antibodies. In one embodiment of the invention, an anti-HER2 antibody of an ADC of the invention comprises a humanized anti-HER2 antibody, e.g., huMAb4D5-1, huMAb4D5-2, huMAb4D5-3, huMAb4D5-4, huMAb4D5-5, huMAb4D5-6, huMAb4D5-7 and huMAb4D5-8, as described in Table 3 of U.S. Pat. No. 5,821,337. Those antibodies contain human framework regions with the complementarity-determining regions of a murine antibody (4D5) that binds to HER2. The humanized antibody huMAb4D5-8 is also referred to as trastuzumab, commercially available under the tradename HERCEPTIN. In another embodiment of the invention, an anti-HER2 antibody of an ADC of the invention comprises a humanized anti-HER2 antibody, e.g., humanized 2C4, as described in U.S. Pat. No. 7,862,817. An exemplary humanized 2C4 antibody is pertuzumab, commercially available under the tradename PERJETA.

(18) NCA (CEACAM6, Genbank accession no. M18728); Barnett T., et al *Genomics* 3, 59-66, 1988; Tawaragi Y., et al *Biochem. Biophys. Res. Commun.* 150, 89-96, 1988; Strausberg R. L., et al *Proc. Natl. Acad. Sci. U.S.A.* 99:16899-16903, 2002; WO2004/063709; EP1439393 (Claim 7); WO2004/044178 (Example 4): WO2004/031238; WO2003/042661 (Claim 12); WO2002/78524 (Example 2); WO2002/86443 (Claim 27; Page 427); WO2002/60317 (Claim 2); Accession: P40199; Q14920; EMBL; M29541; AAA59915.1. EMBL; M18728

(19) MDP (DPEP1, Genbank accession no. BC017023); Proc. Natl. Acad. Sci. U.S.A. 99 (26):16899-16903 (2002)); WO2003/016475 (Claim 1); WO2002/64798 (Claim 33; Page 85-87); JP05003790 (FIG. 6-8); WO99/46284 (FIG. 9); Cross-references: MIM:179780; AAH17023.1; BC017023_1

(20) IL20Rα (IL20Ra, ZCYTOR7, Genbank accession no. AF184971); Clark H. F., et al *Genome Res.* 13, 2265-2270, 2003; Mungall A. J., et al *Nature* 425, 805-811, 2003; Blumberg H., et al *Cell* 104, 9-19, 2001; Dumoutier L., et al *J. Immunol.* 167, 3545-3549, 2001; Parrish-Novak J., et al *J. Biol. Chem.* 277, 47517-47523, 2002; Pletnev S., et al (2003) *Biochemistry* 42:12617-12624; Sheikh F., et al (2004) *J. Immunol.* 172, 2006-2010; EP1394274 (Example 11); US2004/005320 (Example 5); WO2003/029262 (Page 74-75); WO2003/002717 (Claim 2; Page 63); WO2002/22153 (Page 45-47); US2002/042366 (Page 20-21); WO2001/46261 (Page 57-59); WO2001/46232 (Page 63-65): WO98/37193 (Claim 1; Page 55-59); Accession: ☐9UHF4; Q6UWA9; Q96SH8; EMBL; AF184971; AAF01320.1.

(21) Brevican (BCAN, BEHAB, Genbank accession no. AF229053); Gary S. C., et al *Gene* 256, 139-147, 2000; Clark H. F., et al *Genome Res.* 13, 2265-2270, 2003; Strausberg R. L., et al *Proc. Natl. Acad. Sci. U.S.A.* 99, 16899-16903, 2002; US2003/186372 (Claim 11); US2003/186373 (Claim 11); US2003/119131 (Claim 1; FIG. 52); US2003/119122 (Claim 1; FIG. 52); US2003/119126 (Claim 1); US2003/119121 (Claim 1; FIG. 52); US2003/119129 (Claim 1); US2003/119130 (Claim 1); US2003/119128 (Claim 1; FIG. 52); US2003/119125 (Claim 1); WO2003/016475 (Claim 1); WO2002/02634 (Claim 1)

(22) EphB2R (DRT, ERK, Hek5, EPHT3, Tyro5, Genbank accession no. NM_004442); Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42); Cross-references: MIM:600997; NP_004433.2; NM_004442_1

(23) ASLG659 (B7h, Genbank accession no. AX092328); US2004/0101899 (Claim 2); WO2003104399 (Claim 11): WO2004000221 (FIG. 3): US2003/165504 (Claim 1); US2003/124140 (Example 2); US2003/065143 (FIG. 60); WO2002/102235 (Claim 13; Page 299); US2003/091580 (Example 2); WO2002/10187 (Claim 6; FIG. 10); WO2001/94641 (Claim 12; FIG. 7b); WO2002/02624 (Claim 13; FIG. 1A-1B); US2002/034749 (Claim 54; Page 45-46); WO2002/06317 (Example 2; Page 320-321, Claim 34; Page 321-322); WO2002/71928 (Page 468-469); WO2002/02587 (Example 1; FIG. 1); WO2001/40269 (Example 3; Pages 190-192); WO2000/36107 (Example 2; Page 205-207); WO2004/053079 (Claim 12); WO2003/004989 (Claim 1); WO2002/71928 (Page 233-234, 452-453); WO 01/16318

(24) PSCA (Prostate stem cell antigen precursor, Genbank accession no. AJ297436); Reiter R. E., et al *Proc. Natl. Acad. Sci. U.S.A.* 95, 1735-1740, 1998; Gu Z., et al *Oncogene* 19, 1288-1296, 2000; *Biochem. Biophys. Res. Commun.* (2000) 275(3):783-788; WO2004/022709; EP1394274 (Example 11); US2004/018553 (Claim 17); WO2003/008537 (Claim 1); WO2002/81646 (Claim 1; Page 164); WO2003/003906 (Claim 10; Page 288); WO2001/40309 (Example 1; FIG. 17); US2001/055751 (Example 1; FIG. 1b); WO2000/32752 (Claim 18; FIG. 1); WO98/51805 (Claim 17; Page 97); WO98/51824 (Claim 10; Page 94); WO98/40403 (Claim 2; FIG. 1B); Accession: 043653; EMBL; AF043498; AAC39607.1

(25) GEDA (Genbank accession No. AY260763); AAP14954 lipoma HMGIC fusion-partner-like protein/pid=AAP14954.1—*Homo sapiens* (human); WO2003/054152 (Claim 20); WO2003/000842 (Claim 1); WO2003/023013 (Example 3, Claim 20); US2003/194704 (Claim 45); Cross-references: GI:30102449; AAP14954.1: AY260763_1 (26) BAFF-R (B cell-activating factor receptor, BLyS receptor 3, BR3, Genbank accession No. AF116456); BAFF receptor/pid=NP_443177.1—*Homo sapiens*: Thompson, J. S., et al *Science* 293 (5537), 2108-2111 (2001); WO2004/058309; WO2004/011611; WO2003/045422 (Example; Page 32-33); WO2003/014294 (Claim 35; FIG. 6B); WO2003/035846 (Claim 70; Page 615-616); WO2002/94852 (Col 136-137); WO2002/38766 (Claim 3; Page 133); WO2002/24909 (Example 3; FIG. 3); Cross-references: MIM:606269; NP_443177.1; NM_052945_1; AF132600

(27) CD22 (B-cell receptor CD22-B isoform, BL-CAM, Lyb-8, Lyb8, SIGLEC-2, FLJ22814, Genbank accession No. AK026467); Wilson et al (1991) *J. Exp. Med.* 173:137-146; WO2003/072036 (Claim 1; FIG. 1); Cross-references: MIM:107266; NP_001762.1; NM_001771_1. In certain embodiments, conjugate compounds of the invention comprise anti-CD22 antibodies. In one embodiment of the invention, an anti-CD22 antibody of an ADC of the invention comprise three light chain hypervariable regions (HVR- L1, HVR-L2 and HVR-L3) and three heavy chain hypervariable regions (HVR-H1, HVR-H2 and HVR-H3), according to U.S. Pat. No. 8,226,945:

```
HVR-L1
                                    (SEQ ID NO: 11)
RSSQSIVHSVGNTFLE

HVR-L2
                                    (SEQ ID NO: 12)
KVSNRFS

HVR-L3
                                    (SEQ ID NO: 13)
FQGSQFPYT

HVR-H1
                                    (SEQ ID NO: 14)
GYEFSRSWMN

HVR-H2
                                    (SEQ ID NO: 15)
GRIYPGDGDTNYSGKFKG

HVR-H3
                                    (SEQ ID NO: 16)
DGSSWDWYFDV
```

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10); WO2003/088808, US2003/0228319; WO2003/062401 (claim 9); US2002/150573 (claim 4, pages 13-14); WO99/58658 (claim 13, FIG. 16); WO92/07574 (FIG. 1); U.S. Pat. No. 5,644,033; Ha et al (1992) *J. Immunol.* 148(5):1526-1531; Müller et al (1992) *Eur. J. Immunol.* 22:1621-1625; Hashimoto et al (1994) *Immunogenetics* 40(4):287-295; Preud'homme et al (1992) *Clin. Exp. Immunol.* 90(1):141-146; Yu et al (1992) *J. Immunol.* 148(2) 633-637; Sakaguchi et al (1988) *EMBO J.* 7(11): 3457-3464

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1); WO2004/040000; WO2004/015426; US2003/105292 (Example 2); U.S. Pat. No. 6,555,339 (Example 2); WO2002/61087 (FIG. 1); WO2001/57188 (Claim 20, page 269); WO2001/72830 (pages 12-13); WO2000/22129 (Example 1, pages 152-153, Example 2, pages 254-256); WO99/28468 (claim 1, page 38); U.S. Pat. No. 5,440,021 (Example 2, col 49-52); WO94/28931 (pages 56-58); WO92/17497 (claim 7, FIG. 5); Dobner et al (1992) *Eur. J. Immunol.* 22:2795-2799; Barella et al (1995) *Biochem. J.* 309:773-779

(30) HLA-DOB (Beta subunit of MHC class II molecule (Ia antigen) that binds peptides and presents them to CD4+ T lymphocytes); 273 aa, pI: 6.56, MW: 30820.TM: 1 [P] Gene Chromosome: 6p21.3, Genbank accession No. NP_002111.1); Tonnelle et al (1985) *EMBO J.* 4(11):2839-2847; Jonsson et al (1989) *Immunogenetics* 29(6):411-413; Beck et al (1992) *J. Mol. Biol.* 228:433-441; Strausberg et al (2002) *Proc. Natl. Acad. Sci. USA* 99:16899-16903; Servenius et al (1987) *J. Biol. Chem.* 262:8759-8766; Beck et al (1996) *J. Mol. Biol.* 255:1-13; Naruse et al (2002) *Tissue Antigens* 59:512-519; WO99/58658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) *Immunogenetics* 30(1):66-68; Larhammar et al (1985) *J. Biol. Chem.* 260(26):14111-14119

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3. Genbank accession No. NP_002552.2); Le et al (1997) *FEBS Lett.* 418(1-2):195-199; WO2004/047749; WO2003/072035 (claim 10); Touchman et al (2000) *Genome Res.* 10:165-173; WO2002/22660 (claim 20); WO2003/093444 (claim 1); WO2003/087768 (claim 1); WO2003/029277 (page 82)

(32) CD72 (B-cell differentiation antigen CD72, Lyb-2); 359 aa, pI: 8.66, MW: 40225, TM: 1 [P] Gene Chromosome: 9p13.3, Genbank accession No. NP_001773.1); WO2004042346 (claim 65); WO2003/026493 (pages 51-52, 57-58); WO2000/75655 (pages 105-106); Von Hoegen et al (1990) *J. Immunol.* 144(12):4870-4877; Strausberg et al (2002) *Proc. Natl. Acad. Sci. USA* 99:16899-16903.

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1); US2002/193567; WO97/07198 (claim 11, pages 39-42); Miura et al (1996) *Genomics* 38(3):299-304; Miura et al (1998) *Blood* 92:2815-2822; WO2003/083047; WO97/44452 (claim 8, pages 57-61); WO2000/12130 (pages 24-26)

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1); WO2003/077836; WO2001/38490 (claim 6, FIG. 18E-1-18-E-2); Davis et al (2001) *Proc. Natl. Acad. Sci. USA* 98(17):9772-9777; WO2003/089624 (claim 8); EP1347046 (claim 1); WO2003/089624 (claim 7)

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88, MW: 106468, TM: 1 [P] Gene Chromosome: 1q21, Genbank accession No. Human: AF343662, AF343663, AF343664, AF343665, AF369794, AF397453, AK090423, AK090475, AL834187, AY358085; Mouse: AK089756. AY158090, AY506558; NP_112571.1; WO2003/024392 (claim 2, FIG. 97); Nakayama et al (2000) *Biochem. Biophys. Res. Commun.* 277(1):124-127; WO2003/077836; WO2001/38490 (claim 3, FIG. 18B-1-18B-2)

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436; WO2004/074320; JP2004113151; WO2003/042661; WO2003/009814; EP1295944 (pages 69-70); WO2002/30268 (page 329); WO2001/90304; US2004/249130; US2004/022727; WO2004/063355; US2004/197325; US2003/232350; US2004/005563; US2003/124579; Horie et al (2000)

*Genomics* 67:146-152; Uchida et al (1999) *Biochem. Biophys. Res. Commun.* 266:593-602; Liang et al (2000) *Cancer Res.* 60:4907-12; Glynne-Jones et al (2001) *Int J Cancer.* October 15; 94(2):178-84.

(37) CD33 (CD33 molecule, SIGLEC-3, SIGLEC3, p67; CD33 antigen (gp67); gp67; myeloid cell surface antigen CD33; sialic acid binding Ig-like lectin 3; sialic acid-binding Ig-like lectin); Nucleotide: Genbank accession no. M_23197; Genbank version no. NM_23197.1 GI:180097; Genbank record update date: Jun. 23, 2010 08:47 AM; Polypeptide: Genbank accession no. AAA51948; Genbank version no. AAA51948.1 GI:188098: Genbank record update date: Jun. 23, 2010 08:47 AM; Simmons D., et al *J. Immunol.* 141 (8), 2797-2800 (1988); *Antibodies: H195* (Lintuzumab)—Raza A., et al *Leuk Lymphoma.* 2009 August; 50(8):1336-44; U.S. Pat. No. 6,759,045 (Seattle Genetics/Immunomedics); mAb OKT9: Sutherland, D. R. et al. *Proc Natl Acad Sci USA* 78(7): 4515-4519 1981, Schneider, C., et al *J Biol Chem* 257, 8516-8522 (1982); mAb E6: Hoogenboom, H. R., et al *J Immunol* 144, 3211-3217 (1990); U.S. Pat. No. 6,590,088 (Human Genome Sciences)—for example, SEQ ID NOs: 1 and 2 and ATCC accession no. 97521; U.S. Pat. No. 7,557,189 (Immunogen)—For example, an antibody or fragment thereof comprising a heavy chain variable region which comprises three CDRs having the amino acid sequences of SEQ ID NOs:1-3 and a light chain variable region comprising three CDRs having the amino acid sequences of SEQ ID NOs:4-6.

In some embodiments, the anti-CD33 antibody comprises (a) HVR-H1 comprising the amino acid sequence of SEQ ID NO:20; (b) HVR-H2 comprising the amino acid sequence of SEQ ID NO:21; (c) HVR-H3 comprising the amino acid sequence of SEQ ID NO:22; (d) HVR-L1 comprising the amino acid sequence of SEQ ID NO:17; (e) HVR-L2 comprising the amino acid sequence of SEQ ID NO:18; and (f) HVR-L3 comprising the amino acid sequence of SEQ ID NO:19.

In some embodiments, the anti-CD33 antibody comprises the VH and VL sequences in SEQ ID NO:24 and SEQ ID NO:23, respectively, including post-translational modifications of those sequences.

In some embodiments, the anti-CD33 antibody comprises (a) HVR-H1 comprising the amino acid sequence of SEQ ID NO:28; (b) HVR-H2 comprising the amino acid sequence of SEQ ID NO:29; (c) HVR-H3 comprising the amino acid sequence of SEQ ID NO:30; (d) HVR-L1 comprising the amino acid sequence of SEQ ID NO:25; (e) HVR-L2 comprising the amino acid sequence of SEQ ID NO:26; and (f) HVR-L3 comprising the amino acid sequence of SEQ ID NO:27.

In some embodiments, the anti-CD33 antibody comprises the VH and VL sequences in SEQ ID NO:32 and SEQ ID NO:31, respectively, including post-translational modifications of those sequences. In some embodiments, the anti-CD33 antibody comprises the VH and VL sequences in SEQ ID NO:34 and SEQ ID NO:33, respectively, including post-translational modifications of those sequences. In some embodiments, the anti-CD33 antibody comprises the VH and VL sequences in SEQ ID NO:36 and SEQ ID NO:35, respectively, including post-translational modifications of those sequences. In one embodiment, In some embodiments, the anti-CD33 antibody comprises the VH and VL sequences in SEQ ID NO:38 and SEQ ID NO:37, respectively, including post-translational modifications of those sequences.

| | | |
|---|---|---|
| 15G15.33 HVR-L1 | RSSQSLLHSNGYNYLD | SEQ ID NO: 17 |
| 15G15.33 HVR-L2 | LGVNSVS | SEQ ID NO: 18 |
| 15G15.33 HVR-L3 | MQALQTPWT | SEQ ID NO: 19 |
| 15G15.33 HVR-H1 | NHAIS | SEQ ID NO: 20 |
| 15G15.33 HVR-H2 | GIIPIFGTANYAQKFQG | SEQ ID NO: 21 |
| 15G15.33 HVR-H3 | EWADVFD | SEQ ID NO: 22 |
| 15G15.33 VL | EIVLTQSPLSLPVTPGEPASISCRSSQSLLHSN GYNYLDWYLQKPGQSPQLLIYLGVNSVSGVPDR FSGSGSGTDFTLKISRVEAEDVGVYYCMQALQT PWTFGQGTKVEIK | SEQ ID NO: 23 |
| 15G15.33 VH | QVQLVQSGAEVKKPGSSVKVSCKASGGIFSNHA ISWVRQAPGQGLEWMGGIIPIFGTANYAQKFQG RVTITADESTSTAFMELSSLRSEDTAVYYCARE WADVFDIWGQGTMVTVSS | SEQ ID NO: 24 |
| 9C3-HVR L1 | RASQGIRNDLG | SEQ ID NO: 25 |
| 9C3-HVR L2 | AASSLQS | SEQ ID NO: 26 |
| 9C3-HVR L3 | LQHNSYPWT | SEQ ID NO: 27 |
| 9C3-HVR H1 | GNYMS | SEQ ID NO: 28 |
| 9C3-HVR H2 | LIYSGDSTYYADSVKG | SEQ ID NO: 29 |
| 9C3-HVR H3 | DGYYVSDMVV | SEQ ID NO: 30 |
| 9C3 VL | DIQMTQSPSSLSASVGDRVTITCRASQGIRNDL GWYQQKPGKAPKRLIYAASSLQSGVPSRFSGSG SGTEFTLTISSLQPEDFATYYCLQHNSYPWTFG QGTKLEIK | SEQ ID NO: 31 |
| 9C3 VH | EVQLVESGGALIQPGGSLRLSCVASGFTISGNY MSWVRQAPGKGLEWVSLIYSGDSTYYADSVKGR FNISRDISKNTVYLQMNSLRVEDTAVYYCVRDG YYVSDMVVWGKGTTVTVSS | SEQ ID NO: 32 |
| 9C3.2 VL | DIQMTQSPSSLSASVGDRVTITCRASQGIRNDL GWYQQKPGKAPKRLIYAASSLQSGVPSRFSGSG SGTEFTLTISSLQPEDFATYYCLQHNSYPWTFG QGTKLEIK | SEQ ID NO: 33 |
| 9C3.2 VH | EVQLVESGGALIQPGGSLRLSCVASGFTISGNY MSWVRQAPGKGLEWVSLIYSGDSTYYADSVKGR FTISRDISKNTVYLQMNSLRVEDTAVYYCVRDG YYVSDMVVWGKGTTVTVSS | SEQ ID NO: 34 |
| 9C3.3 VL | DIQMTQSPSSLSASVGDRVTITCRASQGIRNDL GWYQQKPGKAPKRLIYAASSLQSGVPSRFSGSG SGTEFTLTISSLQPEDFATYYCLQHNSYPWTFG QGTKLEIK | SEQ ID NO: 35 |
| 9C3.3 VH | EVQLVESGGALIQPGGSLRLSCVASGFTISGNY MSWVRQAPGKGLEWVSLIYSGDSTYYADSVKGR FSISRDISKNTVYLQMNSLRVEDTAVYYCVRDG YYVSDMVVWGKGTTVTVSS | SEQ ID NO: 36 |
| 9C3.4 VL | DIQMTQSPSSLSASVGDRVTITCRASQGIRNDL GWYQQKPGKAPKRLIYAASSLQSGVPSRFSGSG SGTEFTLTISSLQPEDFATYYCLQHNSYPWTFG QGTKLEIK | SEQ ID NO: 37 |

| | | |
|---|---|---|
| 9C3.4 VH | EVQLVESGGALIQPGGSLRLSCVASGFTISGNY MSWVRQAPGKGLEWVSLIYSGDSTYYADSVKGR FAISRDISKNTVYLQMNSLRVEDTAVYYCVRDG YYVSDMVVWGKGTTVTVSS | SEQ ID NO: 38 |

(38) LGR5/GPR49; Nucleotide: Genbank accession no. NM_003667; Genbank version no. NM_003667.2 GI:24475886; Genbank record update date: Jul. 22, 2012 03:38 PM; Polypeptide: Genbank accession no. NP_003658; Genbank version no. NP_003658.1 GI:4504379; Genbank record update date: Jul. 22, 2012 03:38 PM.

In some embodiments, the anti-LGR5 antibody comprises (a) HVR-H1 comprising the amino acid sequence of SEQ ID NO: 46; (b) HVR-H2 comprising the amino acid sequence of SEQ ID NO: 47; (c) HVR-H3 comprising the amino acid sequence of SEQ ID NO: 48; (d) HVR-L1 comprising the amino acid sequence of SEQ ID NO: 43; (e) HVR-L2 comprising the amino acid sequence of SEQ ID NO: 44; and (f) HVR-L3 comprising the amino acid sequence of SEQ ID NO: 45.

In one embodiment, the antibody comprises the VH and VL sequences in SEQ ID NO: 40 and SEQ ID NO: 39, respectively, including post-translational modifications of those sequences.

In some embodiments, the anti-LGR5 comprises (a) HVR-H1 comprising the amino acid sequence of SEQ ID NO: 52; (b) HVR-H2 comprising the amino acid sequence of SEQ ID NO: 53; (c) HVR-H3 comprising the amino acid sequence of SEQ ID NO: 54; (d) HVR-L1 comprising the amino acid sequence of SEQ ID NO: 49; (e) HVR-L2 comprising the amino acid sequence of SEQ ID NO: 50; and (f) HVR-L3 comprising an amino acid sequence selected from SEQ ID NO: 51.

In some embodiments, the anti-LgR5 antibody comprises a VH as in any of the embodiments provided above, and a VL as in any of the embodiments provided above. In one embodiment, the antibody comprises the VH and VL sequences in SEQ ID NO:42 and SEQ ID NO:41, respectively, including post-translational modifications of those sequences.

| | | |
|---|---|---|
| 8E11 VL | DIVMTQSPDS LAVSLGERAT INCRASESVD NYGNSFMHWY QQKPGQPPKL LIYLASNLES GVPDRFSGSG SGTDFTLTIS SLQAEDVAVY YCQQNYEDPF TFGQGTKVEI KR | SEQ ID NO: 39 |
| 8E11 VH | EVQLVQSGAE VKKPGASVKV SCKASGYTFS AYWIEWVRQA PGQGLEWIGE ILPGSDSTDY NEKFKVRATF TSDTSTSTVY LELSSLRSED TAVYYCARGG HYGSLDYWGQ GTLVTVSS | SEQ ID NO: 40 |
| YW353 VL | DIQMTQSPSS LSASVGDRVT ITCRASQDVS TAVAWYQQKP GKAPKLLIYS ASFLYSGVPS RFSGSGSGTD FTLTISSLQP EDFATYYCQQ SYTTPPTFGQ GTKVEIKR | SEQ ID NO: 41 |
| YW353 VH | EVQLVESGGG LVQPGGSLRL SCAASGFTFT SYSISWVRQA PGKGLEWVAE IYPPGGYTDY ADSVKGRFTI SADTSKNTAY LQMNSLRAED TAVYYCAKAR LFFDYWGQGT LVTVSS | SEQ ID NO: 42 |
| 8E11-HVR L1 | RASESVDNYG NSFMH | SEQ ID NO: 43 |
| 8E11-HVR L2 | LASNLES | SEQ ID NO: 44 |
| 8E11-HVR L3 | QQNYEDPFT | SEQ ID NO: 45 |
| 8E11-HVR H1 | GYTFSAYWIE | SEQ ID NO: 46 |
| 8E11-HVR H2 | EILPGSDSTD YNEKFKV | SEQ ID NO: 47 |
| 8E11-HVR H3 | GGHYGSLDY | SEQ ID NO: 48 |
| YW353 HVR L1 | RASQDVSTAV A | SEQ ID NO: 49 |
| YW353 HVR L2 | SASFLYS | SEQ ID NO: 50 |
| YW353 HVR L3 | QQSYTTPPT | SEQ ID NO: 51 |
| YW353 HVR H1 | GFTFTSYSIS | SEQ ID NO: 52 |
| YW353 HVR H2 | EIYPPGGYTD YADSVKG | SEQ ID NO: 53 |
| YW353 HVR H3 | ARLFFDY | SEQ ID NO: 54 |

The parent antibody may also be a fusion protein comprising an albumin-binding peptide (ABP) sequence (Dennis et al. (2002) "Albumin Binding As A General Strategy For Improving The Pharmacokinetics Of Proteins" *J Biol. Chem.* 277:35035-35043; WO 01/45746). Antibodies of the invention include fusion proteins with ABP sequences taught by: (i) Dennis et al (2002) *J Biol. Chem.* 277:35035-35043 at Tables III and IV, page 35038; (ii) US 2004/0001827 at [0076]; and (iii) WO 01/45746 at pages 12-13, and all of which are incorporated herein by reference.

In one embodiment, the antibody has been raised to target specific the tumour related antigen $\alpha_v\beta_6$.

The cell binding agent may be labelled, for example to aid detection or purification of the agent either prior to incorporation as a conjugate, or as part of the conjugate. The label may be a biotin label. In another embodiment, the cell binding agent may be labelled with a radioisotope.

Substituents

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

In a preferred embodiment, the substituents described herein (which include optional substituents) are limited to those groups that are not reactive to a cell binding agent. The link to the cell binding agent in the present case is formed from the bridge between the two PBD moieties through a linker group to the cell binding agent. Reactive functional groups located at other parts of the PBD structure may be capable of forming additional bonds to the cell binding agent (this may be referred to as crosslinking). These additional bonds may alter transport and biological activity of the conjugate. Therefore, in some embodiment, the additional substituents are limited to those lacking reactive functionality.

In one embodiment, the substituents are selected from the group consisting of R, OR, SR, NRR', NO$_2$, halo, CO$_2$R, COR, CONH$_2$, CONHR, and CONRR'.

In one embodiment, the substituents are selected from the group consisting of R, OR, SR, NRR', NO$_2$, CO$_2$R, COR, CONH$_2$, CONHR, and CONRR'.

In one embodiment, the substituents are selected from the group consisting of R, OR, SR, NRR', NO$_2$, and halo.

In one embodiment, the substituents are selected from the group consisting of R, OR, SR, NRR', and NO$_2$.

Any one of the embodiment mentioned above may be applied to any one of the substituents described herein. Alternatively, the substituents may be selected from one or more of the groups listed below.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

An alkyl group may optionally be interrupted by one or more heteroatoms selected from O, N(H) and S. Such groups may be referred to as "heteroalkyl".

$C_{2-12}$ Heteroalkyl: The term "$C_{2-12}$ heteroalkyl" as used herein, pertains to a monovalent moiety obtained by removing a hydrogen atom from a carbon atom of a hydrocarbon compound having from 2 to 12 carbon atoms, and one or more heteroatoms selected from O, N(H) and S, preferably O and S.

Examples of heteroalkyl groups include, but are not limited to those comprising one or more ethylene glycol units of the type —(OCH$_2$CH$_2$)—. The terminal of a heteroalkyl group may be the primary form of a heteroatom, e.g. —OH, —SH or —NH$_2$. In a preferred embodiment, the terminal is —CH$_3$.

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —CH$_2$—C≡CH).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds:
norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_3S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_5$); and,
$N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocycyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R$^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

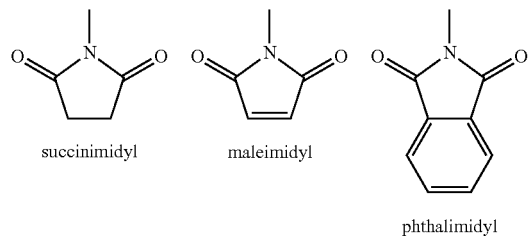

succinimidyl    maleimidyl    phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

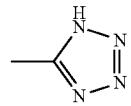

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$alkyl group. Examples of imino groups include, but are not limited to, =NH, =NMe, and =NEt.

Amidine (amidino): —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.
Thioether (sulfide): —SR, wherein R is a thioether substituent, for example, a $C_{1-7}$ alkyl group (also referred to as a $C_{1-7}$alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a $C_{1-7}$ alkyl group, a $C_{3-2}$ heterocyclyl group, or a $C_{5-20}$ aryl group, preferably a $C_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a $C_{1-7}$ alkyl group, a $C_{3-20}$ heterocyclyl group, or a $C_{5-20}$ aryl group, preferably a $C_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocycyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a $C_{1-7}$ alkyl group, a $C_{3-20}$ heterocyclyl group, or a $C_{5-20}$ aryl group, preferably a $C_{1-7}$ alkyl group or a $C_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphate groups include, but are not limited to, —OP(=O)(OCH$_3$)$_2$, —OP(=O)(OCH$_2$CH$_3$)$_2$, —OP(=OXO-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^{22}$, where R$^1$ and R$^2$ are phosphoramidite substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^{22}$, where R$^1$ and R$^2$ are phosphoramidate substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Alkylene $C_{3-12}$ alkylene: The term "$C_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the subclasses alkenylene, alkynylene, cycloalkylene, etc., discussed below.

Examples of linear saturated $C_{3-12}$ alkylene groups include, but are not limited to, —(CH$_2$)$_n$— where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH$_2$CH$_2$CH$_2$CH$_2$— (heptylene).

Examples of branched saturated $C_{3-12}$ alkylene groups include, but are not limited to, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated $C_{3-12}$ alkylene groups ($C_{3-12}$ alkenylene, and alkynylene groups) include, but are not limited to, —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH$_2$—CH=CH—, —CH=CH—CH$_2$—CH$_2$—CH=CH—, and —CH$_2$—C≡C—CH$_2$—.

Examples of branched partially unsaturated $C_{3-12}$ alkylene groups ($C_{3-12}$ alkenylene and alkynylene groups) include, but are not limited to, —C(CH$_3$)=CH—, —C(CH$_3$)=CH—CH$_2$—, —CH=CH—CH(CH$_3$)— and —C≡C—CH(CH$_3$)—.

Examples of alicyclic saturated $C_{3-12}$ alkylene groups ($C_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated $C_{3-12}$ alkylene groups ($C_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

The invention includes compounds where a solvent adds across the imine bond of the PBD moiety, which is illustrated below where the solvent is water or an alcohol (R$^A$OH, where R$^A$ is $C_{1-4}$ alkyl):

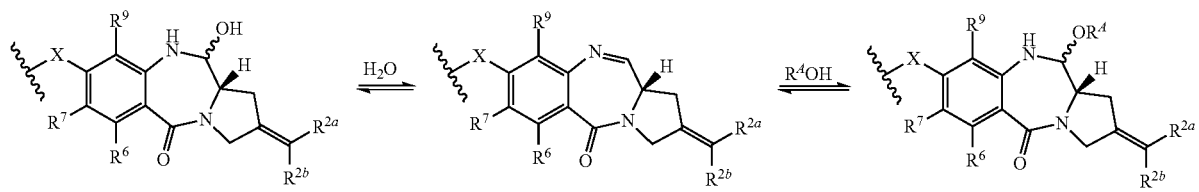

These forms can be called the carbinolamine and carbinolamine ether forms of the PBD (as described in the section relating to $R^{10}$ above). The balance of these equilibria depend on the conditions in which the compounds are found, as well as the nature of the moiety itself.

These particular compounds may be isolated in solid form, for example, by lyophilisation.

Isomers

Certain compounds of the invention may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

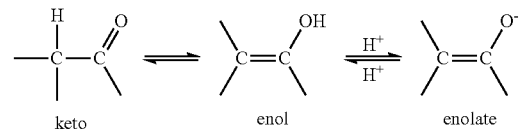

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Examples of isotopes that can be incorporated into compounds of the invention include isotopes of hydrogen, carbon, nitrogen, oxygen, phosphorous, fluorine, and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Biological Activity
In Vitro Cell Proliferation Assays

Generally, the cytotoxic or cytostatic activity of an antibody-drug conjugate (ADC) is measured by: exposing mammalian cells having receptor proteins, e.g. HER2, to the antibody of the ADC in a cell culture medium; culturing the cells for a period from about 6 hours to about 5 days; and measuring cell viability. Cell-based in vitro assays are used to measure viability (proliferation), cytotoxicity, and induction of apoptosis (caspase activation) of an ADC of the invention.

The in vitro potency of antibody-drug conjugates can be measured by a cell proliferation assay. The CellTiter-Glo® Luminescent Cell Viability Assay is a commercially available (Promega Corp., Madison, Wis.), homogeneous assay method based on the recombinant expression of *Coleoptera luciferase* (U.S. Pat. Nos. 5,583,024; 5,674,713 and 5700670). This cell proliferation assay determines the number of viable cells in culture based on quantitation of the ATP present, an indicator of metabolically active cells (Crouch et al (1993) *J. Immunol. Meth.* 160:81-88: U.S. Pat. No. 6,602,677). The CellTiter-Glo® Assay is conducted in 96 well format, making it amenable to automated high-throughput screening (HTS) (Cree et al (1995) *AntiCancer Drugs* 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons.

In Vivo Efficacy

The in vivo efficacy of antibody-drug conjugates (ADC) of the invention can be measured by tumor xenograft studies in mice. For example, the in vivo efficacy of an anti-HER2 ADC of the invention can be measured by a high expressing HER2 transgenic explant mouse model. An allograft is propagated from the Fo5 mmtv transgenic mouse which does not respond to, or responds poorly to, HERCEPTIN® therapy. Subjects were treated once with ADC at certain dose levels (mg/kg) and PBD drug exposure ($\mu g/m^2$); and placebo buffer control (Vehicle) and monitored over two weeks or more to measure the time to tumor doubling, log cell kill, and tumor shrinkage.

Use

The conjugates of the invention may be used to provide a PBD conjugate at a target location.

The target location is preferably a proliferative cell population. The antibody is an antibody for an antigen present in a proliferative cell population.

In one embodiment the antigen is absent or present at a reduced level in a non-proliferative cell population compared to the amount of antigen present in the proliferative cell population, for example a tumour cell population.

The target location may be in vitro, in vivo or ex vivo.

The antibody-drug conjugate (ADC) compounds of the invention include those with utility for anticancer activity. In particular, the compounds include an antibody conjugated, i.e. covalently attached by a linker, to a PBD moiety.

At the target location the linker may not be cleaved. The antibody-drug conjugate (ADC compounds of the invention may have a cytotoxic effect without the cleavage of the linker to release a PBD drug moiety. The antibody-drug conjugates (ADC) of the invention selectively deliver cytotoxic agent to tumor tissue whereby greater selectivity, i.e. a lower efficacious dose, may be achieved.

Thus, in one aspect, the present invention provides a conjugate compound as described herein for use in therapy.

In a further aspect there is also provides a conjugate compound as described herein for use in the treatment of a proliferative disease. A second aspect of the present invention provides the use of a conjugate compound in the manufacture of a medicament for treating a proliferative disease.

One of ordinary skill in the art is readily able to determine whether or not a candidate conjugate treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Cancers of particular interest include, but are not limited to, leukemias and ovarian cancers.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

In one embodiment, the treatment is of a pancreatic cancer.

In one embodiment, the treatment is of a tumour having $\alpha_v\beta_6$ integrin on the surface of the cell.

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant tumors; leukemia, haematological, and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the ADC compounds may be used in treatment include rheumatologic disorders (such as, for example, rheumatoid arthritis. Sjögren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g. Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Methods of Treatment

The conjugates of the present invention may be used in a method of therapy. Also provided is a method of treatment, comprising administering to a subject in need of treatment a therapeutically-effective amount of a conjugate compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound of the invention may be administered alone or in combination with other treatments, either simultaneously or sequentially dependent upon the condition to be treated. Examples of treatments and therapies include, but are not limited to, chemotherapy (the administration of active agents, including, e.g. drugs, such as chemotherapeutics); surgery; and radiation therapy.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARA-SAR™, SCH 66336, Schering Plough), sorafenib (NEXA-VAR®, BAY43-9006, Bayer Labs), gefitinib (IRESSA®, AstraZeneca), irinotecan (CAMPTOSAR®, CPT-11, Pfizer), tipifamib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gamma1I, calicheamicin omega1l (*Angew Chem. Intl. Ed. Engl.* (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the conjugates of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Pharmaceutical compositions according to the present invention, and for use in accordance with the present invention, may comprise, in addition to the active ingredient, i.e. a conjugate compound, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringers Injection, Lactated Ringer's Injection. Preservatives, stabilisers, buffers, antioxidants and/or other additives may be included, as required.

Formulations

While it is possible for the conjugate compound to be used (e.g., administered) alone, it is often preferable to present it as a composition or formulation.

In one embodiment, the composition is a pharmaceutical composition (e.g., formulation, preparation, medicament) comprising a conjugate compound, as described herein, and a pharmaceutically acceptable carrier, diluent, or excipient.

In one embodiment, the composition is a pharmaceutical composition comprising at least one conjugate compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives*, 2nd Edition (eds. M. Ash and I. Ash), 2001 (Synapse Information Resources, Inc., Endicott, N.Y., USA), *Remington's Pharmaceutical Sciences*, 20th edition, pub. Lippincott, Williams & Wilkins, 2000; and *Handbook of Pharmaceutical Excipients*, 2nd edition, 1994.

Another aspect of the present invention pertains to methods of making a pharmaceutical composition comprising admixing at least one [$^{11}$C]-radiolabelled conjugate or conjugate-like compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable." as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the conjugate compound, and compositions comprising the conjugate compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the conjugate compound is administered to a human patient according to the following dosage regime: about 50 or about 75 mg, 3 or 4 times daily.

In one embodiment, the conjugate compound is administered to a human patient according to the following dosage regime: about 100 or about 125 mg, 2 times daily.

The dosage amounts described above may apply to the conjugate (including the PBD moiety and the linker to the antibody) or to the effective amount of PBD compound provided, for example the amount of compound that is releasable after cleavage of the linker.

For the prevention or treatment of disease, the appropriate dosage of an ADC of the invention will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises a course of administering an initial loading dose of about 4 mg/kg, followed by additional doses every week, two weeks, or three weeks of an ADC. Other dosage regimens may be useful. The progress of this therapy is easily monitored by conventional techniques and assays.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

Preparation of Antibody Drug Conjugates

Antibody drug conjugates may be prepared by several routes, employing organic chemistry reactions, conditions, and reagents known to those skilled in the art, including: (1) reaction of a nucleophilic group of an antibody with a bivalent linker reagent to form antibody-linker intermediate Ab-L, via a covalent bond, followed by reaction with an activated drug moiety reagent; and (2) reaction of a drug moiety reagent with a linker reagent, to form drug-linker reagent D-L, via a covalent bond, followed by reaction with the nucleophilic of an antibody. Conjugation methods (1) and (2) may be employed with a variety of antibodies, and linkers to prepare the antibody-drug conjugates of the invention.

Nucleophilic groups on antibodies include, but are not limited to side chain thiol groups, e.g. cysteine. Thiol groups are nucleophilic and capable of reacting to form covalent bonds with electrophilic groups on linker moieties such as those of the present invention. Certain antibodies have reducible interchain disulfides, i.e. cysteine bridges. Antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Each cysteine disulfide bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

In one embodiment, the patient is a population where each patient has a tumour having $\alpha_v\beta_6$ integrin on the surface of the cell.

Synthesis

One possible synthesis route to a dimer intermediate of formula IV is shown below:

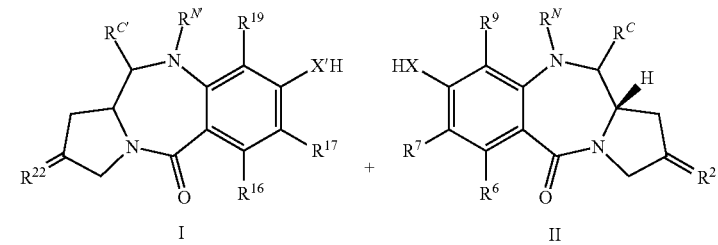

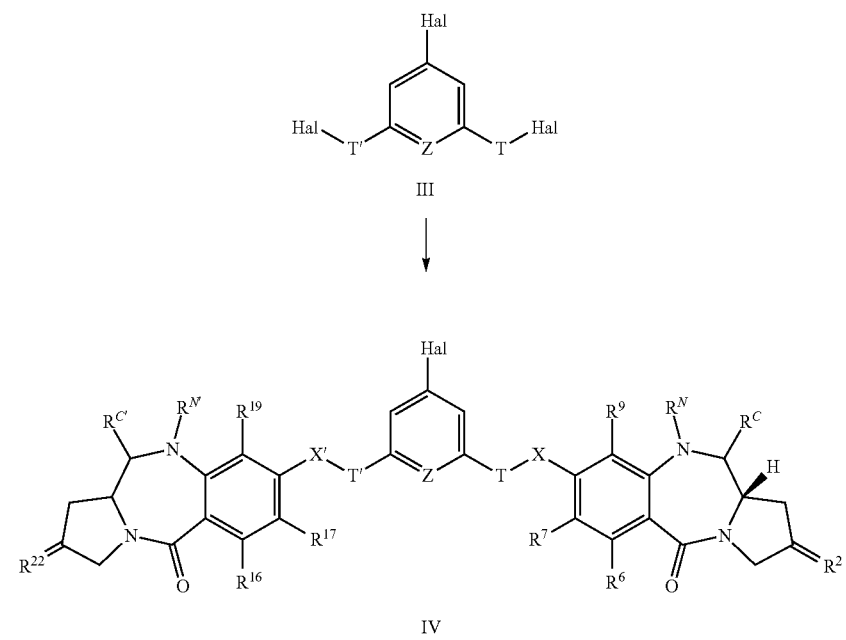

Intermediate IV can be used to make intermediate VII

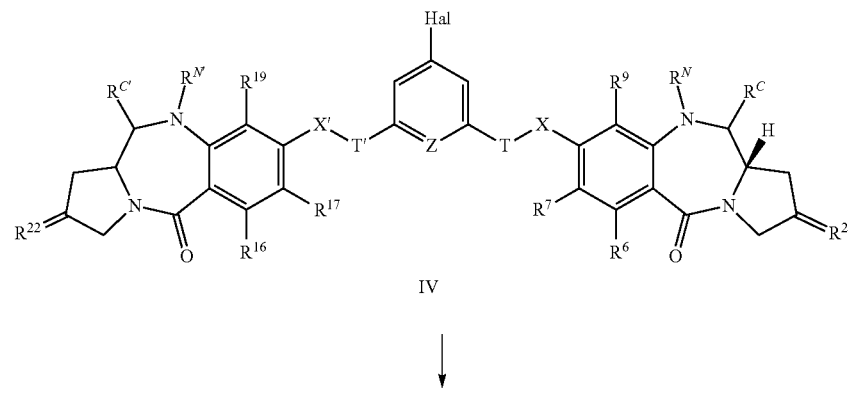

-continued
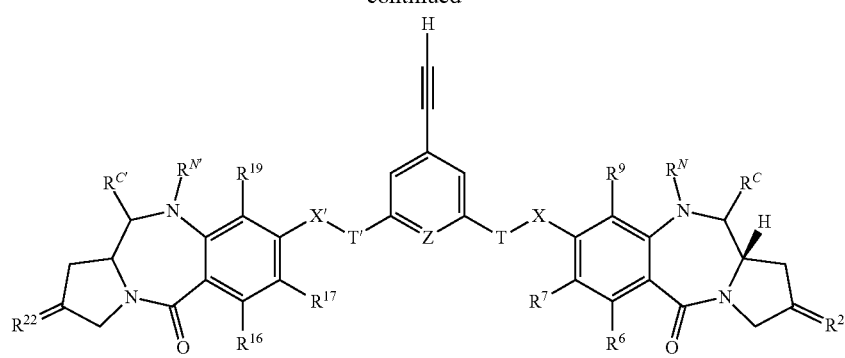
V
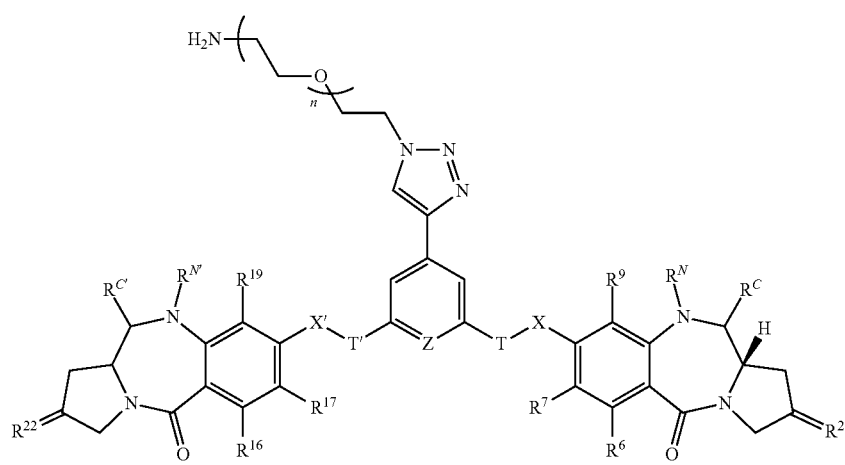
VI
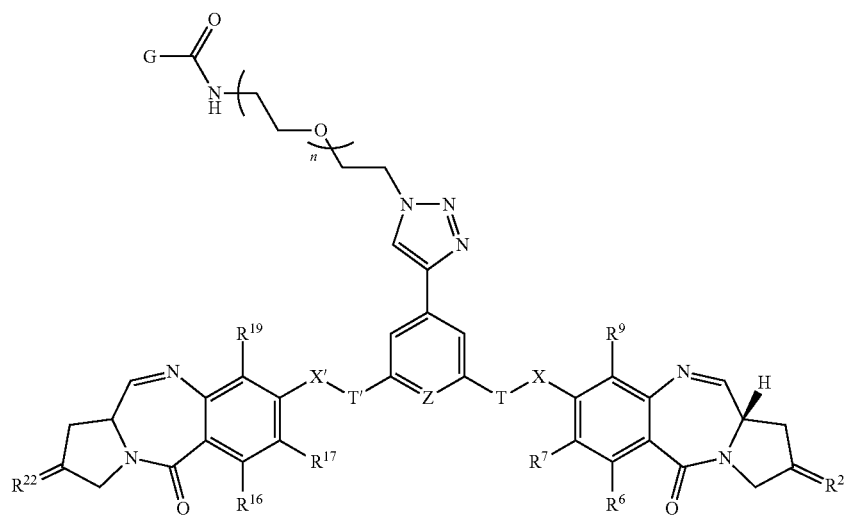
VII

Intermediate IV can be used to make intermediate IX:
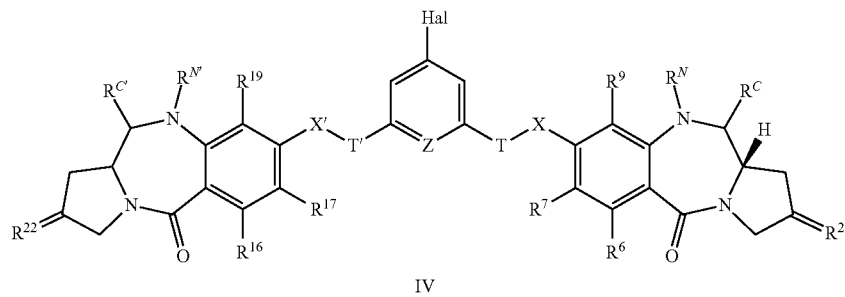
IV
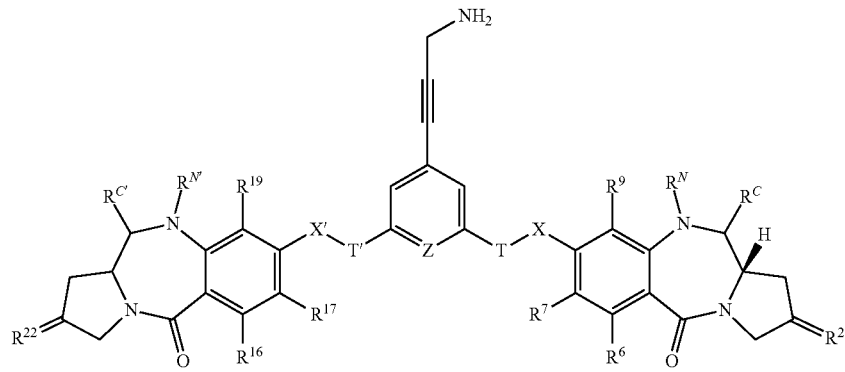
VIII
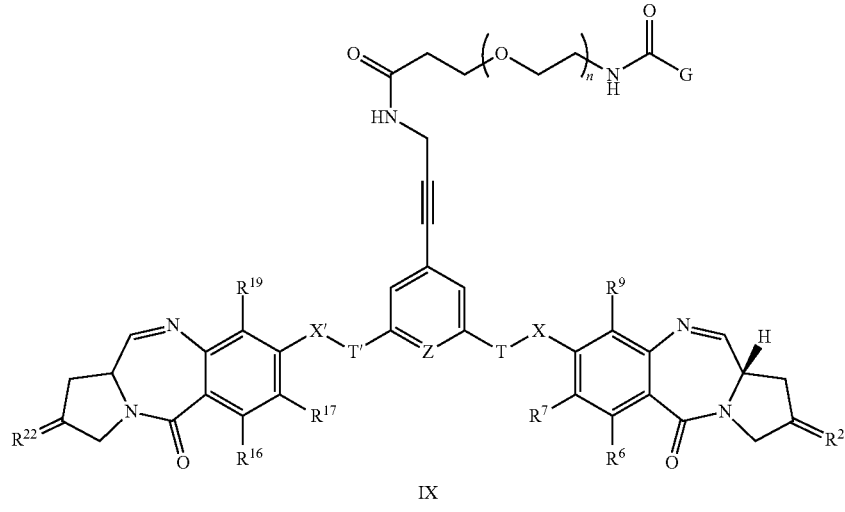
IX Alternatively, intermediate IV can be coupled with intermediate X to make intermediate IX:
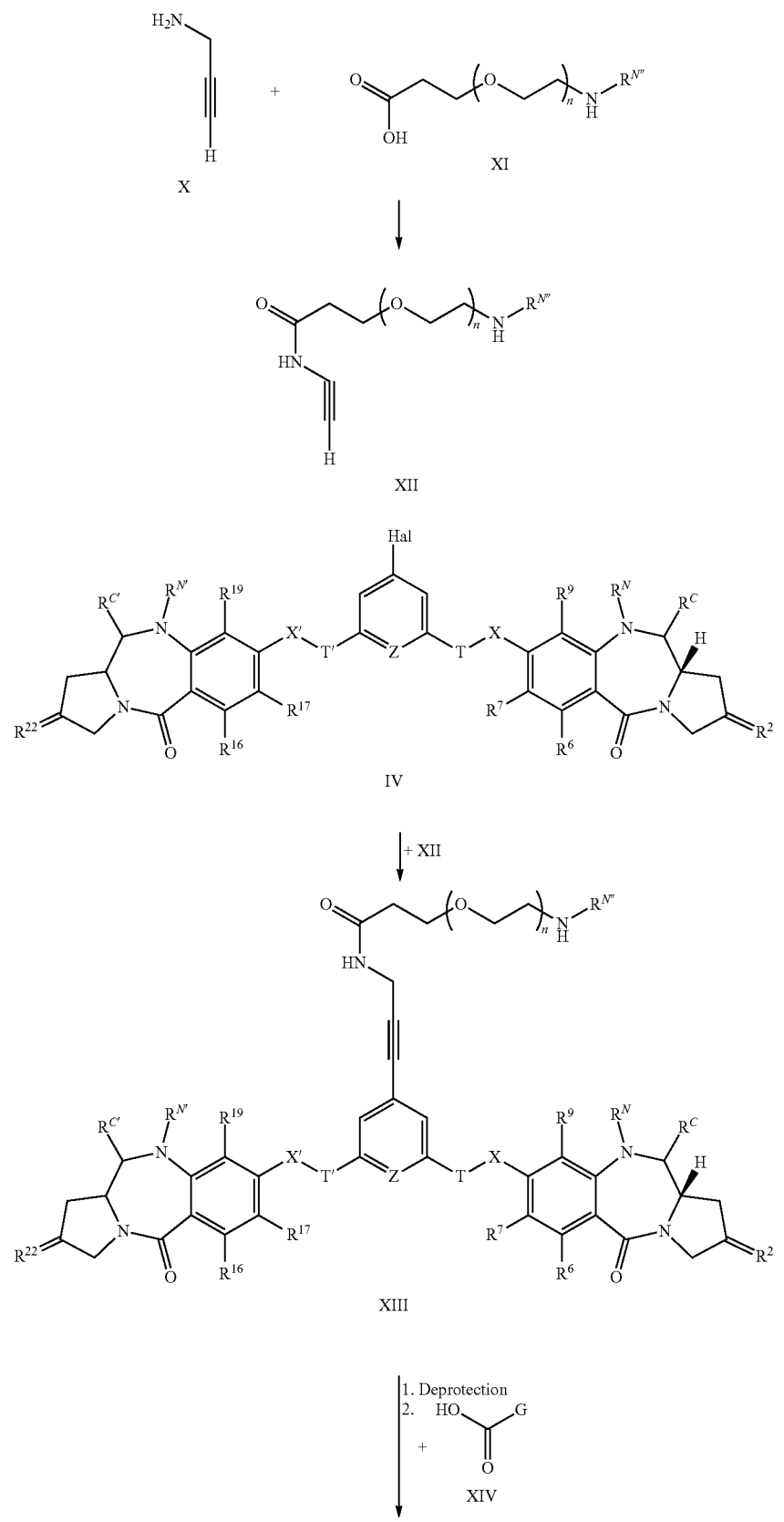

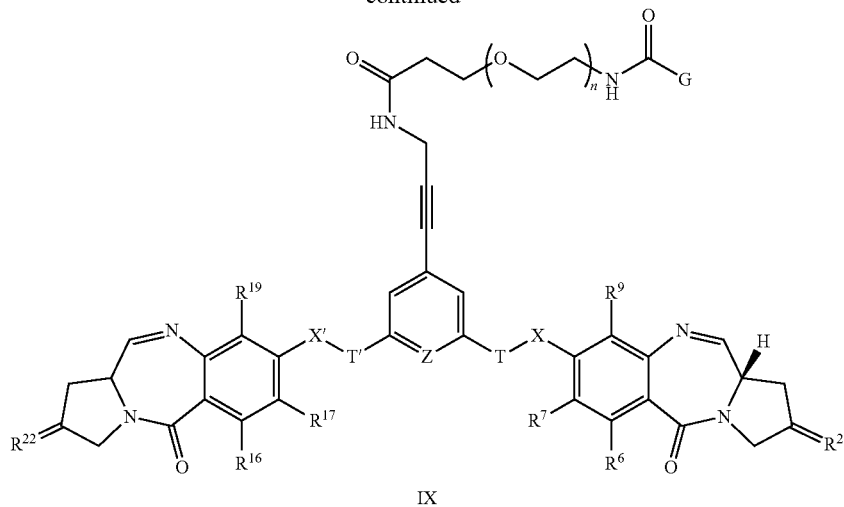
IX
Intermediate IV can be used to make intermediate XVI
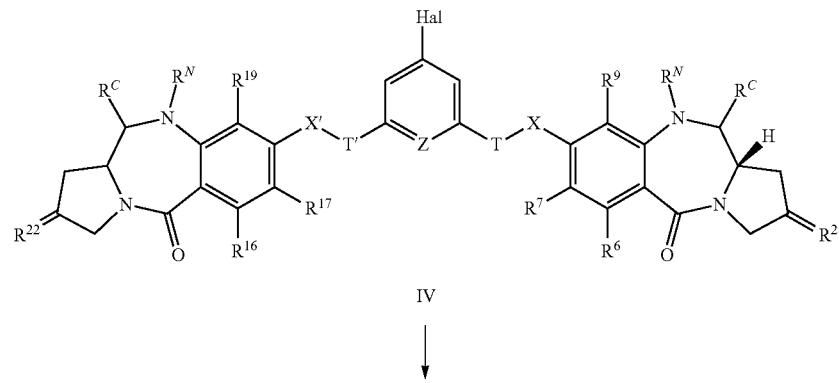
IV
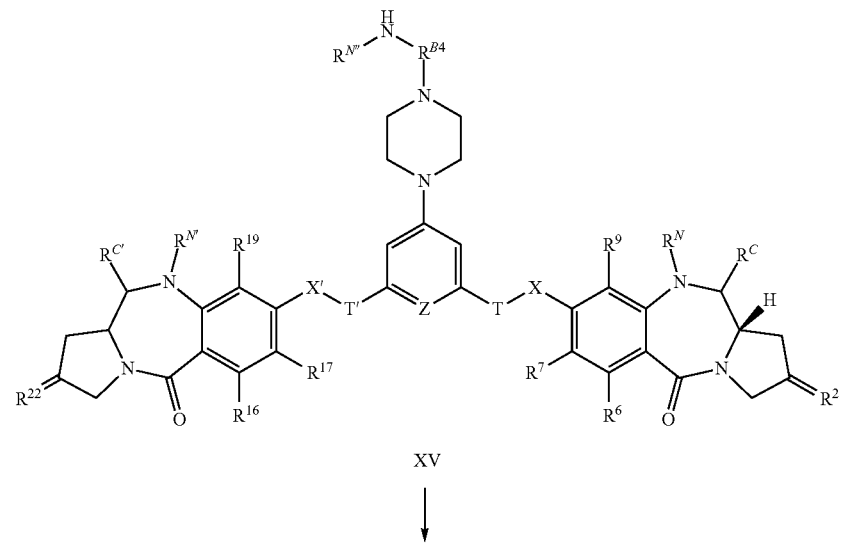
XV

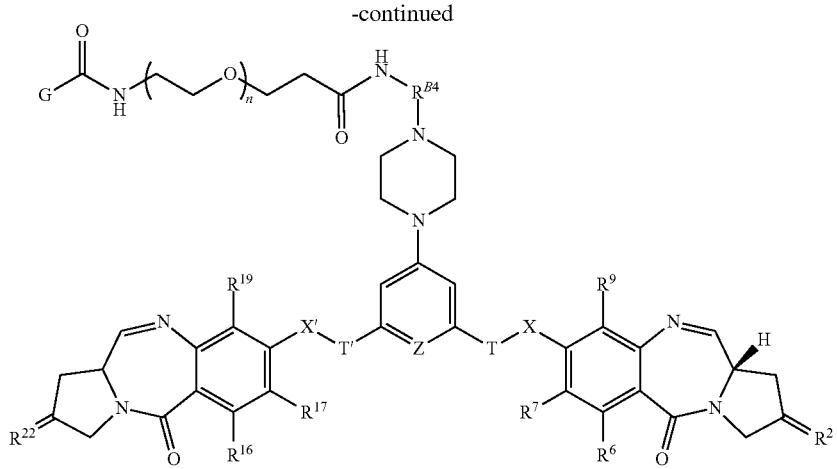
XVI
Intermediate IV can be used to make intermediate XIX
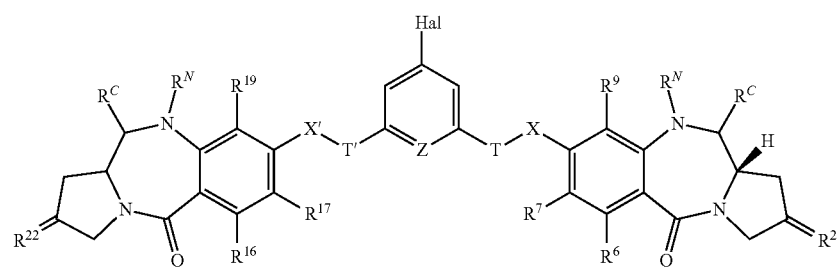
IV
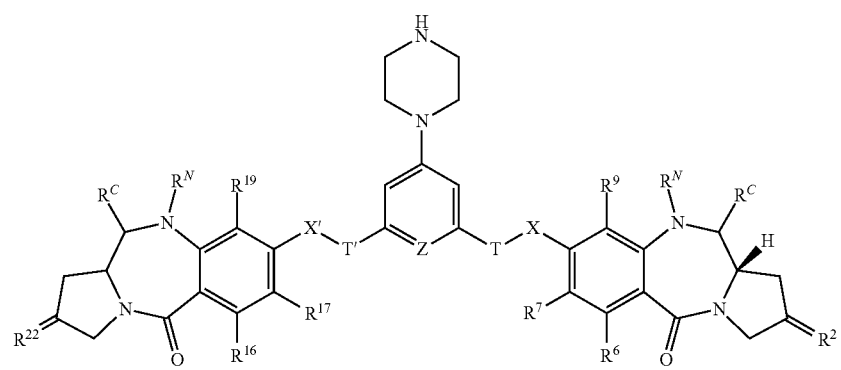
XVII
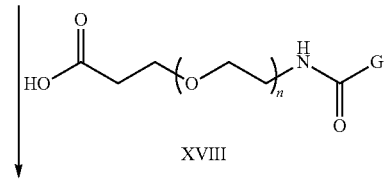
XVIII

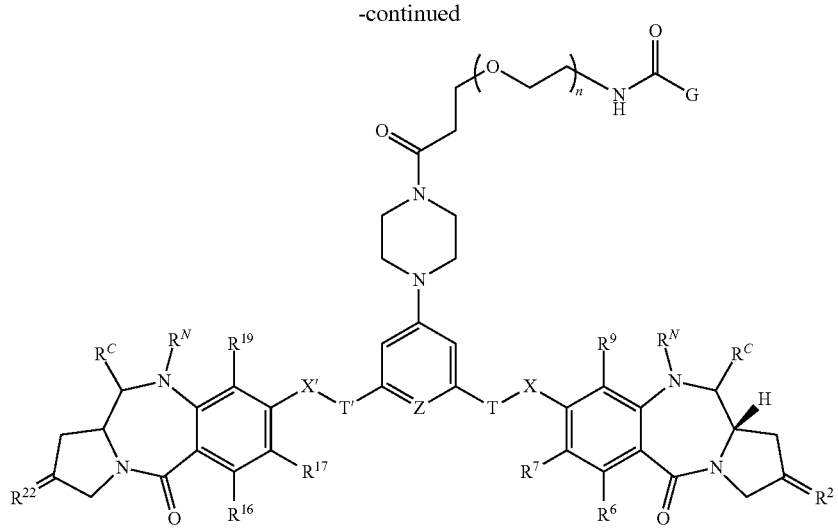
XIX
One possible synthesis route to a dimer intermediate of formula XIV is shown below:
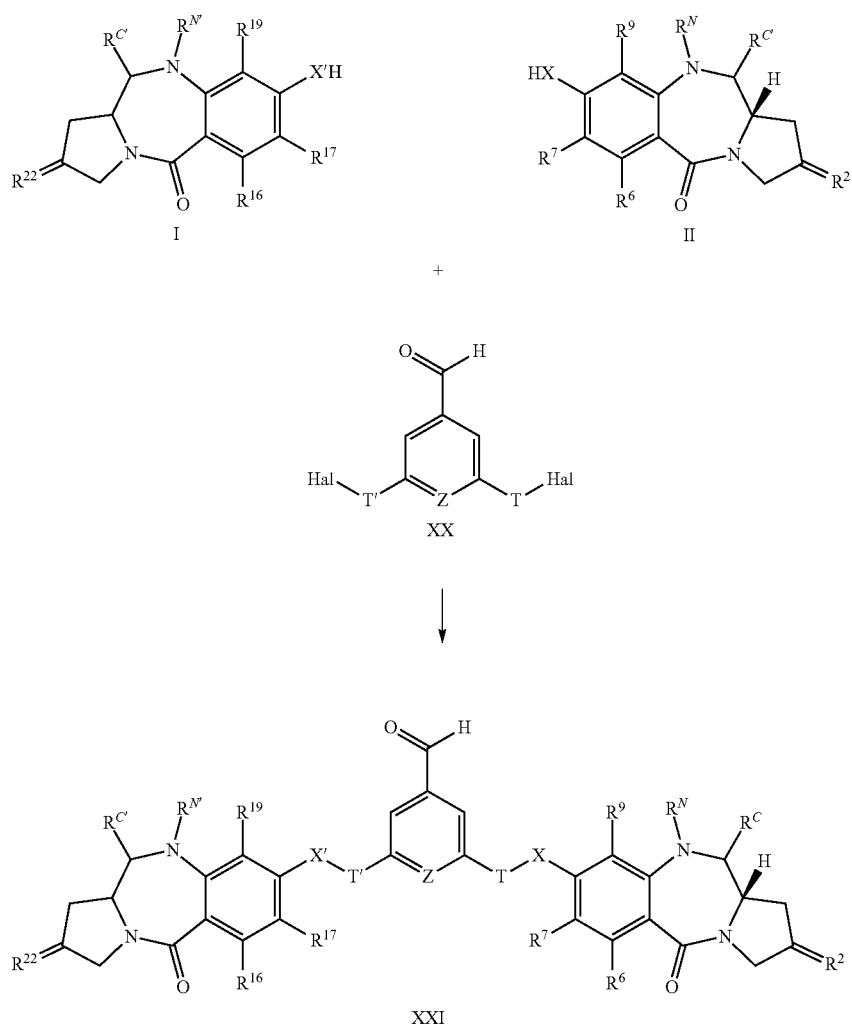

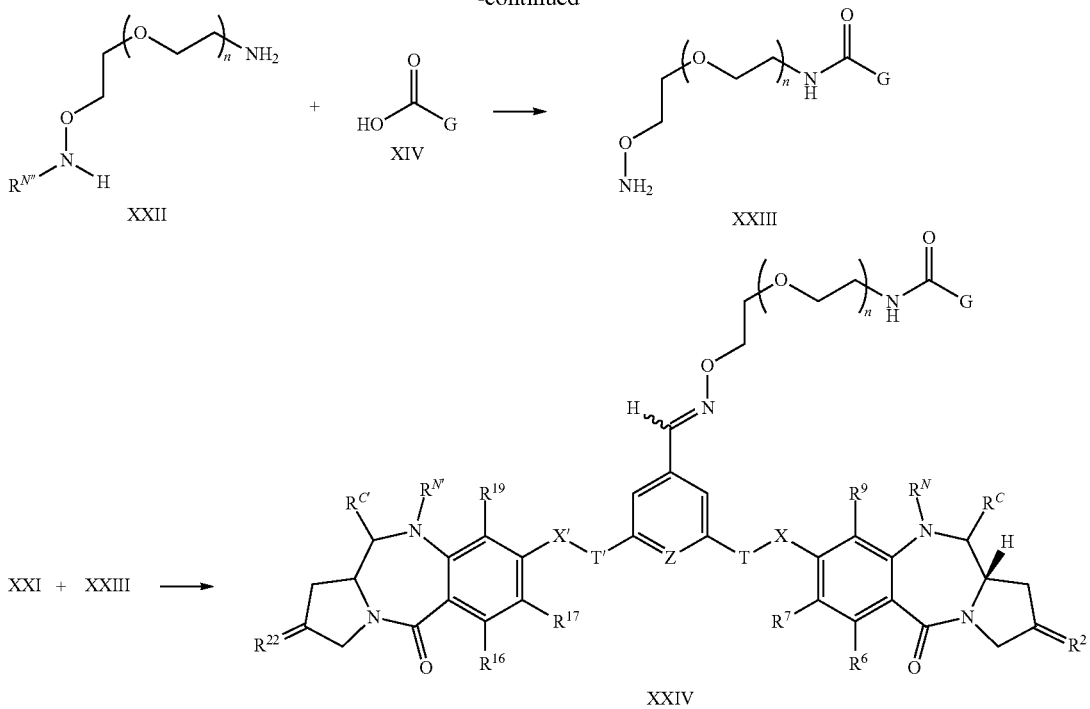
Intermediate XXI can be used to make intermediate XXVII:
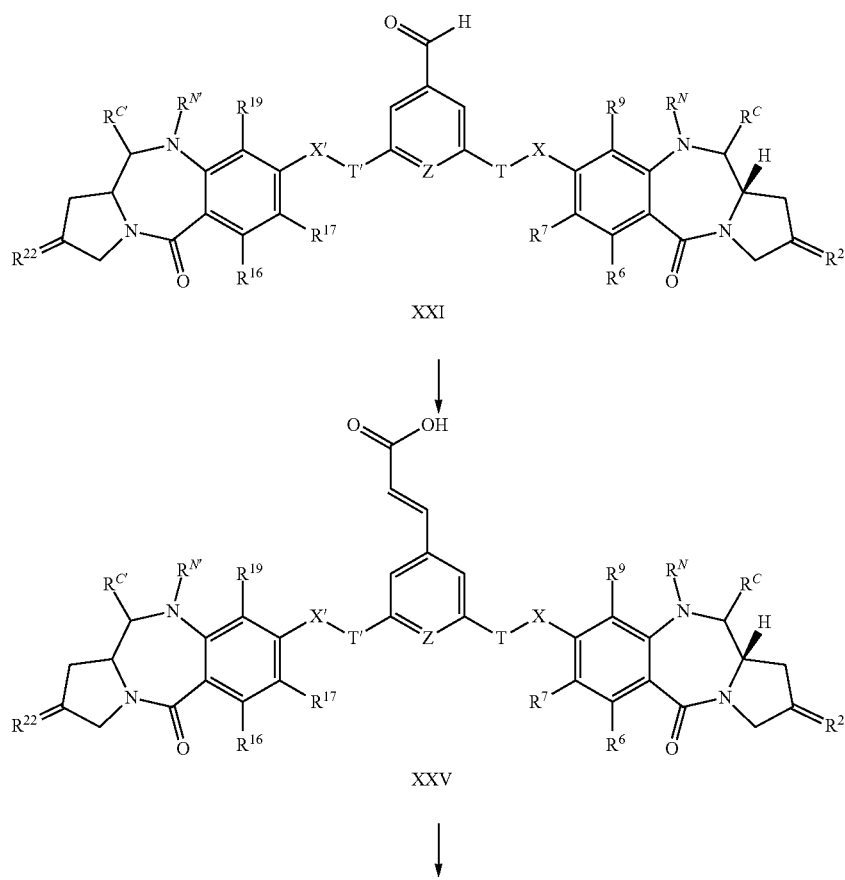

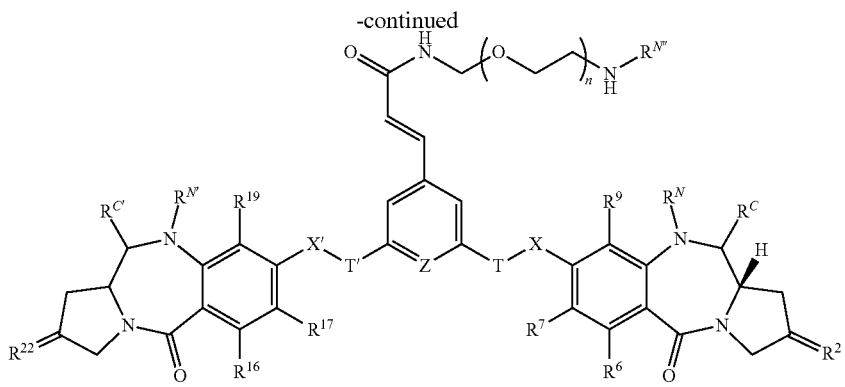

XXVI

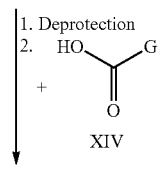

1. Deprotection
2.

XIV

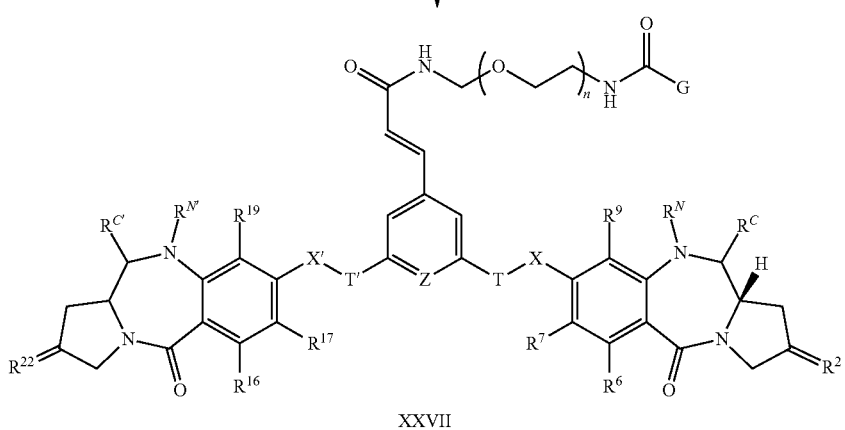

XXVII

In the above schemes, $R^N$, $R^{N'}$ and $R^{N''}$ each independently represent a nitrogen protecting group. $R^C$ and $R^{C'}$ each independently represent OH or $OProt^O$, where $Prot^O$ is a hydroxy protecting group. Protecting groups are well known in the art. $R^N$, $R^{N'}$ and $R^{N''}$ may be, for example. BOC. $Prot^O$ may be THP. It may be the protection of the N10-C11 imine bonds is removed at a different stage in the synthesis methods to that shown above, dependent on the chemistries employed.

In general, the compounds and conjugates can be prepared by first linking two PBD monomers with a phenylene or pyridylene dimer bridge to produce intermediate IV or XXI. The halogen group on the aryl ring in the dimer bridge of intermediate IV may then be used to form the tether (including linker group G or L) to connect the PBD dimer to the cell binding agent.

In more detail, two PBD monomers with —XH and —X'H groups at the C8 position of each PBD monomer (intermediates I and II, respectively) may be reacted with -T-Hal and -T'-Hal groups on intermediate III or intermediate XX. Such a method of synthesis allows for the PBD monomers to be different and so the resulting PBD dimer is asymmetrical. Equally, the PBD monomers may be the same.

PBD dimer intermediate IV may be used to provide the compounds and conjugates of the present invention by reacting the aryl halogen group in the bridge in a number of ways.

First, intermediate IV can be used in a Sonogishira cross-coupling reaction to provide an acetylene group on the aryl group of the dimer bridge. Sonogishira cross-coupling reactions are well known in the art for coupling a terminal alkyne with an aryl halide in the presence of a palladium catalyst, such as $Pd(Ph_3)_4$, a copper catalyst, such as CuI, and a base, such as diethylamine.

When acetylene is to be used as the terminal acetylene, one side of the acetylene molecule is typically protected with, for example, TMS in order to prevent cross-linking of the PBD dimers. Once the Sonogishira reaction is complete, the TMS group can be cleaved to provide alkyne intermediate V.

Intermediate V can be reacted with an azido compound to form a triazole derivative in an azide-alkyne Huisgen cycloaddition. Such a reaction may be catalysed by a copper catalyst. To form the compounds and conjugates of the present invention, the azide is bonded to an ethylene group and a variable number of PEG groups. The azide may be terminated with an amine group to react further. Reaction of intermediate V with an amino-azide compound will provide intermediate VI.

The free amine group of intermediate VI can then be reacted with a carboxylic acid group of a linker group for connecting to a cell binding unit to form the amido group linking the PBD dimer to the linker group G or L to provide compound VII.

The linker/reactive group, G, of intermediate VII can be conjugated to a cell binding agent to provide conjugates of the present invention.

As an alternative Sonogishira reaction, intermediate IV can be coupled to an acetylamine, such as propargylamine in the presence of palladium and copper catalysts and base. Such a reaction provides part of a tether attached to the PBD dimer bridge where the aclyne group is preserved and a free terminal amine is available for further reaction. For example, the reaction of intermediate IV with propargylamine provides intermediate VIII.

The terminal amine of intermediate VIII can be reacted with, for example, a carboxylic acid group attached to a linker/reactive group G (for connecting to a cell binding agent) to provide intermediate IX.

As an alternative synthesis of intermediate IX, the carboxylic acid group of intermediate XI can be reacted with propargylamine to form intermediate XII. Reaction of intermediate IV with intermediate XII in a Sonogoshira reaction yields intermediate XIII.

The protected amine group terminated the variable PEG chain can be deprotected and reacted with the carboxylic acid group of intermediate XIV in order to couple the linker/reactive group G onto the PBD dimer and produce intermediate XIV.

Intermediate IV may also used in a cross-coupling amination reaction, such as a Buchwald-Hartwig amination. A carbon-nitrogen bond is formed via a palladium-catalysed cross-coupling of an amine with an aryl halide. A number of palladium catalysts for use in such cross-coupling reactions are known, such as Pd(Ph$_3$)$_4$ or RuPhos/RuPhosPd.

Reaction of intermediate IV with a piperizine functionlised with a protected propan-1-amine provides intermediate XV. The protected amine of intermediate XV can be further reacted with, for example, a carboxylic acid group attached to a linker/reactive group, G, for connecting to a cell binding agent to provide intermediate XVI.

Cross-coupling amination reaction, such as a Buchwald-Hartwig amination, of intermediate IV with a partially protected piperazine followed by deprotection (for example with trifluoroacetic acid) provides intermediate XVII.

The deprotected piperazine amine group of intermediate XVII can be reacted with a carboxylic acid group in intermediate XVIII to provide intermediate XIX.

Intermediate XXI can be used to form the oxime intermediate XXIV. For example, a partially protected PEG-diamine, intermediate XXII, may be reacted with the carboxylic acid group of intermediate XIV. Deprotection yields intermediate XIII.

Reaction of intermediates XXI and XXIII yields oxime intermediate XXIV. The syn and anti oximes can be resolved using preparative HPLC.

Intermediate XXI can also be used to form the acrylamide intermediate XXVII. For example, the aldehyde intermediate XXI can be reacted with malonic acid in a Knoevenagel condensation to yield the acrylic acid intermediate XXV. This can be reacted with a partially protected PEG-diamine to yield intermediate XXVI. Deprotectopm and coupling with intermediate XIV yield the acrylamide intermediate XXVII.

The synthesis of PBD compounds containing two imine moieties is extensively discussed in the following references, which discussions are incorporated herein by reference:
a) WO 00/12508 (pages 14 to 30);
b) WO 2005/023814 (pages 3 to 10); and
c) WO 2005/085259 (pages 31 to 39).

EXAMPLES

General Experimental Methods

Optical rotations were measured on an ADP 220 polarimeter (Bellingham Stanley Ltd.) and concentrations (c) are given in g/100 mL. Melting points were measured using a digital melting point apparatus (Electrothermal). IR spectra were recorded on a Perkin-Elmer Spectrum 1000 FT IR Spectrometer. $^1$H and $^{13}$C NMR spectra were acquired at 300 K using a Bruker Avance NMR spectrometer at 400 and 100 MHz, respectively. Chemical shifts are reported relative to TMS (δ=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). Mass spectroscopy (MS) data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0: Source temperature (° C.), 100; Desolvation Temperature (° C.), 200; Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument. Thin Layer Chromatography (TLC) was performed on silica gel aluminium plates (Merck 60, F$_{254}$), and flash chromatography utilised silica gel (Merck 60, 230-400 mesh ASTM). All chemicals and solvents were purchased from Sigma-Aldrich and were used as supplied without further purification.

General LC/MS conditions: The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B within 3 min. The composition was held for 0.5 min at 95% B, and then returned to 5% B in 0.3 minutes. Total gradient run time equals 5 min. Flow rate 3.0 mL/min, 400 µL was split via a zero dead volume tee piece which passes into the mass spectrometer. Wavelength detection range: 220 to 400 nm. Function type: diode array (535 scans). Column: Phenomenex® Onyx Monolithic C18 50×4.60 mm.

The analytical LC/MS conditions for Example 5 to 11 were as follows: Positive mode electrospray mass spectrometry was performed using a Shimadzu Nexera®/Prominence® LCMS-2020. Mobile phases used were solvent A (H$_2$O with 0.1% formic acid) and solvent B (CH$_3$CN with 0.1% formic acid). Gradient: Initial composition 5% B held over 0.25 min, then increased from 5% B to 100% B over a 2 min period. The composition was held for 0.50 min at 100% B, then returned to 5% B in 0.05 min and held there for 0.05 min. The total duration of the gradient run was 3.0 min. Flow rate was 0.8 mL/min. Detection was at 214 and 254 nm. Column: Waters Acquity UPLC® BEH Shield RP18 1.7 µm 2.1×50 mm at 50° C.

The preparative HPLC conditions for Example 5 to 11 were as follows: Reverse-phase ultra-fast high-performance liquid chromatography (UFLC) was carried out on a Shimadzu Prominence® machine using Phenomenex® Gemini NX 5μ C18 columns (at 50° C.) of the following dimensions: 150×4.6 mm for analysis, and 150×21.2 mm for preparative work. Eluents used were solvent A (H₂O with 0.1% formic acid) and solvent B (CH₃CN with 0.1% formic acid). All UFLC experiments were performed with gradient conditions: From 0 to 30 min the composition of B was increased from 0 to 100% and held at 100% B for a further 2 min. The composition of B was decreased from 100% to 0% from 32.0 min to 32.1 min and held at 0% B until 35.0 min. The total duration of the gradient run was 35.0 min. Flow rates used were 1.0 mL/min for analytical, and 20.0 mL/min for preparative HPLC. Detection was at 254 and 280 nm.

Example 1

(a) (11S,11aS,11'S, 11a'S)-di-tert-butyl 8,8'-(((5-halo-1,3-phenylene)bis(methylene))bis(oxy))bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (2a, 2b, 2c)

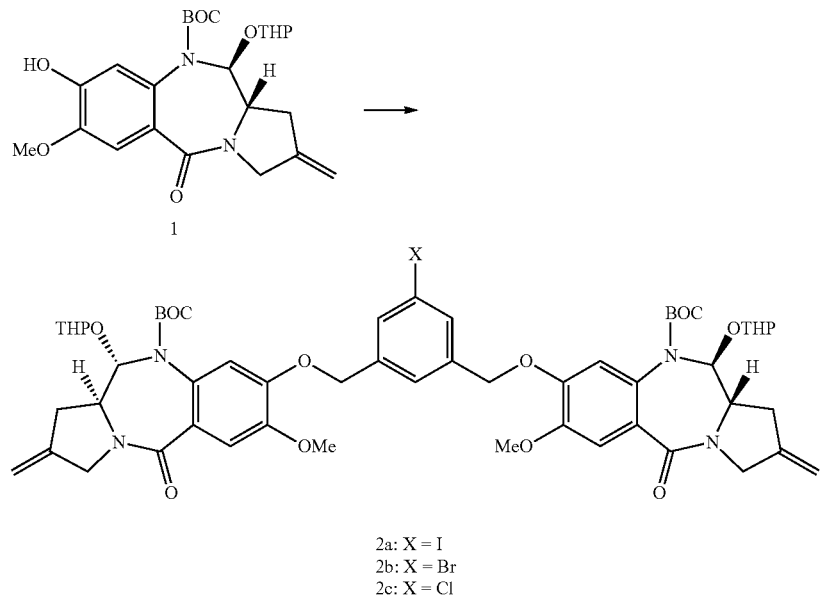

2a: X = I
2b: X = Br
2c: X = Cl (i) (11S,11aS,11'S,11a'S)-di-tert-butyl 8,8'-(((5-iodo-1,3-phenylene)bis(methylene))bis(oxy))bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (2a)

1,3-bis(bromomethyl)-5-iodobenzene (2.00 g, 5.20 mmol) was added to a stirred solution of Boc/THP-protected PBD capping unit 1 (4.75 g, 10.3 mmol), TBAI (190 mg, 0.52 mmol) and K₂CO₃ (1.42 g, 10.3 mmol) in dry DMF (60 mL). The reaction mixture was heated to 60° C. and stirred under an argon atmosphere for 3 hours at which point analysis by LC/MS revealed substantial product formation at retention time 4.15 min (ES+) m/z 1171 ([M+Na]⁺, ~10% relative intensity). The reaction mixture was allowed to cool to room temperature and the DMF was removed by evaporation in vacuo. The resulting residue was partitioned between water (50 mL) and EtOAc (50 mL) and the aqueous phase was extracted with EtOAc (3×20 mL). The combined organic layers were washed with water (2×20 mL), brine (50 mL), dried (MgSO₄), filtered and evaporated in vacuo to provide the crude product. Purification by flash chromatography (gradient elution: 50:50 v/v EtOAc/hexane to 80:20 v/v EtOAc/hexane) gave the bis-ether 2a as a white foam (5.42 g, 91% yield).

(ii) (11S,11aS,11'S,11a'S)-di-tert-butyl 8,8'-(((5-bromo-1,3-phenylene)bis(methylene))bis(oxy))bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (2b)

1-bromo-3,5-bis(bromomethyl)benzene (1.54 g, 4.53 mmol) was added to a stirred solution of Boc/THP-protected PBD capping unit 1 (4.20 g, 9.06 mmol), TBAI (167 mg, 0.45 mmol) and K₂CO₃ (1.25 g, 9.06 mmol) in dry DMF (52 mL). The reaction mixture was heated to 60° C. and stirred under an argon atmosphere for 5 hours at which point analysis by LC/MS revealed substantial product formation at retention time 4.10 min (ES+) m/z 1101 ([M+H]⁺, ~70% relative intensity). The reaction mixture was allowed to cool to room temperature and the DMF was removed by evaporation in vacuo. The resulting residue was partitioned between water (60 mL) and EtOAc (60 mL) and the aqueous phase was extracted with EtOAc (3×25 mL). The combined organic layers were washed with water (30 mL), brine (50 mL), dried (MgSO₄), filtered and evaporated in vacuo to provide the crude product. Purification by flash chromatography (gradient elution: 50:50 v/v EtOAc/hexane to 100% EtOAc) gave the bis-ether 2b as a white foam (3.37 g, 68% yield).

(iii) (11S,11aS,11'S, 11a'S)-di-tert-butyl 8,8'-(((5-chloro-1,3-phenylene)bis(methylene))bis(oxy))bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (2c)

1,3-bis(bromomethyl)-5-chlorobenzene (1.42 g, 4.80 mmol) was added to a stirred solution of Boc/THP-protected PBD capping unit 1 (4.42 g, 9.60 mmol), TBAI (177 mg, 0.48 mmol) and K₂CO₃ (1.33 g, 9.60 mmol) in dry DMF (55 mL). The reaction mixture was heated to 60° C. and stirred under an argon atmosphere for 1.5 hours at which point analysis by LC/MS revealed substantial product formation at retention time 4.08 min (ES+) m/z 1057 ([M+H]⁺, ~30% relative intensity). The reaction mixture was allowed to cool to room temperature and the DMF was removed by evaporation in vacuo. The resulting residue was partitioned between water (60 mL) and EtOAc (60 mL) and the aqueous phase was extracted with EtOAc (3×20 mL). The combined organic layers were washed with water (20 mL), brine (40 mL), dried (MgSO₄), filtered and evaporated in vacuo to provide the crude product. Purification by flash chromatography (gradient elution: 50:50 v/v EtOAc/hexane to 80:20 v/v EtOAc/hexane) gave the bis-ether 2c as a white foam (5.10 g, 99% yield).

(b) (11S,11aS,11'S,11a'S)-di-tert-butyl 8,8'-(((5-ethynyl-1,3-phenylene)bis(methylene))bis(oxy))bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (4)

mmol), TMS-acetylene (278 μL, 191 mg, 1.96 mmol), CuI (5.0 mg, 26.1 μmol), diethylamine (1.35 mL, 956 mg, 13.1 mmol) and oven-dried 4 Å molecular sieve pellets in dry DMF (5.6 mL) in an oven-dried sealable vessel. The mixture was degassed and flushed with argon 3 times then heated in a microwave at 100° C. for 30 minutes at which point analysis by LC/MS revealed complete consumption of starting material and substantial product formation at retention time 4.37 min (ES+) m/z 1142 ([M+Na]⁺, ~40% relative intensity). Peak at retention time 3.97 min (ES+) m/z 1069 ([M+Na]⁺, ~60% relative intensity) observed which corresponds to TMS-cleavage under LC/MS conditions. The reaction mixture was allowed to cool to room temperature and was then filtered through a sinter to remove the sieves (washed with DMF). The filtrate was evaporated in vacuo and the resulting residue subjected to flash chromatography (gradient elution: 50:50 v/v EtOAc/hexane to 80:20 v/v EtOAc/hexane) to provide the TMS-acetylene 3 as a yellow foam (691 mg, 95% yield).

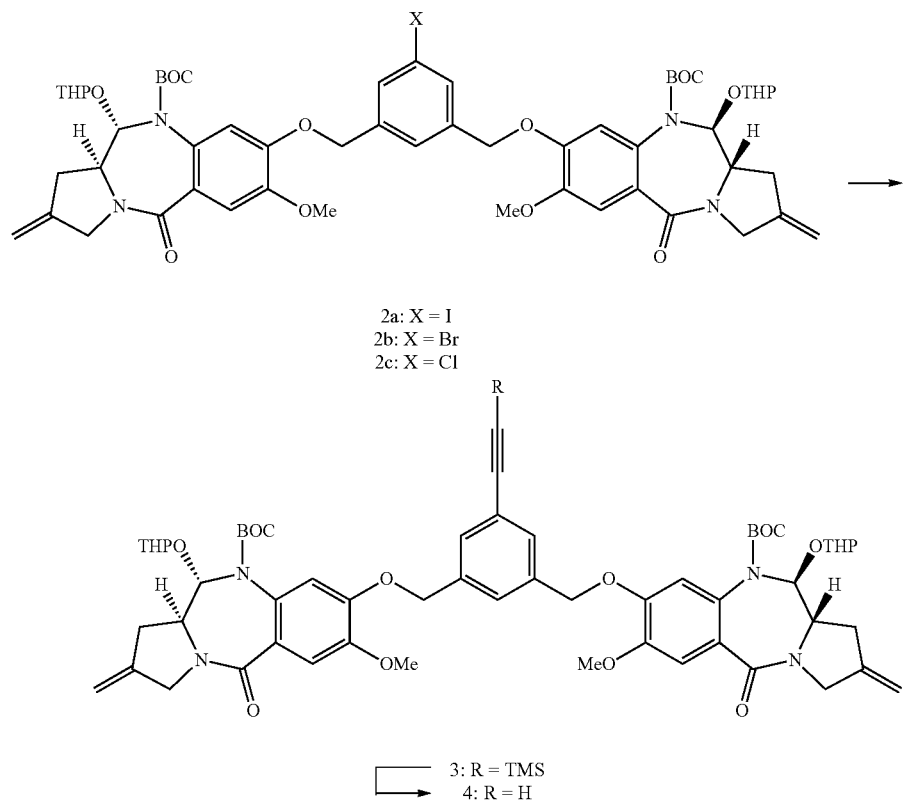

2a: X = I
2b: X = Br
2c: X = Cl

3: R = TMS
4: R = H (i) (11S,11aS,11'S,11a'S)-di-tert-butyl 8,8'-(((5-((trimethylsilyl)ethynyl)-1,3-phenylene)bis(methylene))bis(oxy))bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (3)

A catalytic amount of Pd(PPh₃)₄ (15.0 mg, 13.1 μmol) was added to a mixture of the bis-ether 2a (750 mg, 0.65

(ii) (11S,11aS,11'S,11a'S)-di-tert-butyl 8,8'-(((5-ethynyl-1,3-phenylene)bis(methylene))bis(oxy))bis(7-methoxy-2-methylene-5-oxo-11-((tetrahydro-2H-pyran-2-yl)oxy)-2,3,11,11a-tetrahydro-11H-pyrrolo[2,1-c][1,4]benzodiazepine-10(5H)-carboxylate) (4)

Solid K₂CO₃ (383 mg, 2.77 mmol) was added to a stirred solution of the TMS-protected compound 3 (1.55 g, 1.39 mmol) in MeOH (20 mL). After 3 hours stirring at room temperature the reaction was deemed to be complete as judged by LC/MS [desired product peak at retention time 4.00 min (ES+) m/z 1047 ([M+H]+, ~30% relative intensity)]. The MeOH was removed by evaporation in vacuo and the resulting residue was partitioned between water (60 mL) and EtOAc (60 mL). The layers were separated and the aqueous phase was extracted with EtOAc (3×20 mL). The combined organic layers were washed with water (30 mL), brine (30 mL), dried (MgSO4), filtered and evaporated in vacuo to provide the crude product. Purification by flash chromatography (gradient elution: 50:50 v/v EtOAc/hexane to 80:20 v/v EtOAc/hexane) gave the acetylene 4 as an orange foam (1.13 g, 78% yield).

(c) (11S,11aS,11'S, 11a'S)-di-tert-butyl 8,8'-(((5-(1-(2-(2-(2-(2-aminoethoxy)ethoxy)ethoxy)ethyl)-1H-1,2,3-triazol-4-yl)-1,3-phenylene)bis(methylene))bis(oxy))bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (5)

Solid CuSO4.5H2O (13.0 mg, 52.0 μmol) and (+)-sodium L-ascorbate (41.0 mg, 0.21 mmol) were added to a stirred solution of 11-Azido-3,6,9-trioxaundecan-1-amine (227 mg, 207 μL, 1.04 mmol) and the alkyne 4 (1.09 g, 1.04 mmol) in tert-BuOH (6 mL) and H2O (6 mL) at room temperature. A colour change from yellow to green was observed as the reaction progressed. After stirring for 16 hours analysis by LC/MS revealed a substantial of amount of desired product formed corresponding to peak at retention time 3.12 min (ES+) m/z 1265 ([M+H]+, ~100% relative intensity). [NOTE: On some occasions reaction progress stalled, however, the reaction was driven to completion upon addition of further CuSO4.5H2O (0.05 equivalents) and (+)-sodium L-ascorbate (0.2 equivalents)]. The reaction mixture was partitioned (without shaking of the separating funnel) between water (50 mL) and EtOAc (50 mL). The aqueous phase was extracted with EtOAc (3×15 mL) and the combined organic layers were washed with water (30 mL), brine (50 mL), dried (MgSO4), filtered and evaporated in vacuo to provide the crude product 5 as a green foam (1.32 g, 100% crude yield). The crude product was carried through to next step without further purification.

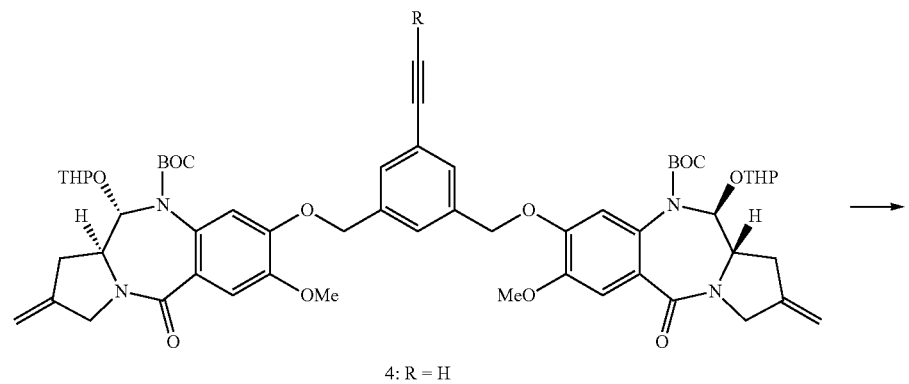

4: R = H

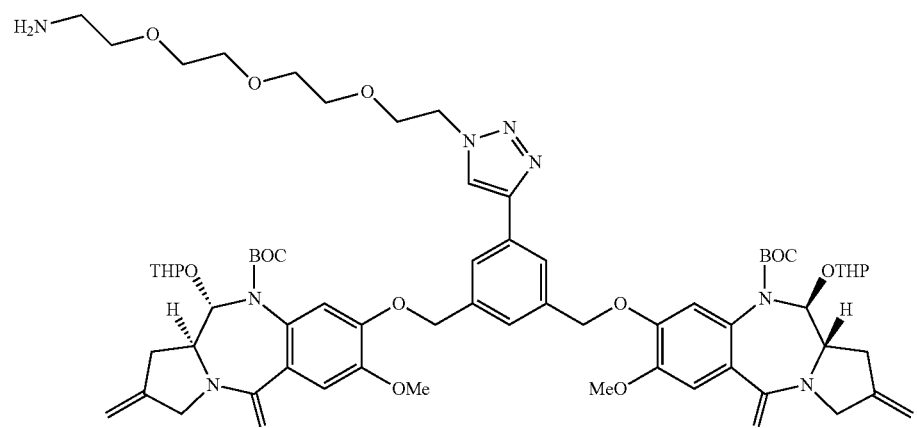

5

(d) (11S,11aS,11'S, 11a'S)-di-tert-butyl 8,8'-(((5-(1-(18-(2,5-dioxo-2,5-dihydro-1H-pyrrol-1-yl)-13-oxo-3,6,9-trioxa-12-azaoctadecyl)-1H-1,2,3-triazol-4-yl)-1,3-phenylene)bis(methylene))bis(oxy))bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (6)

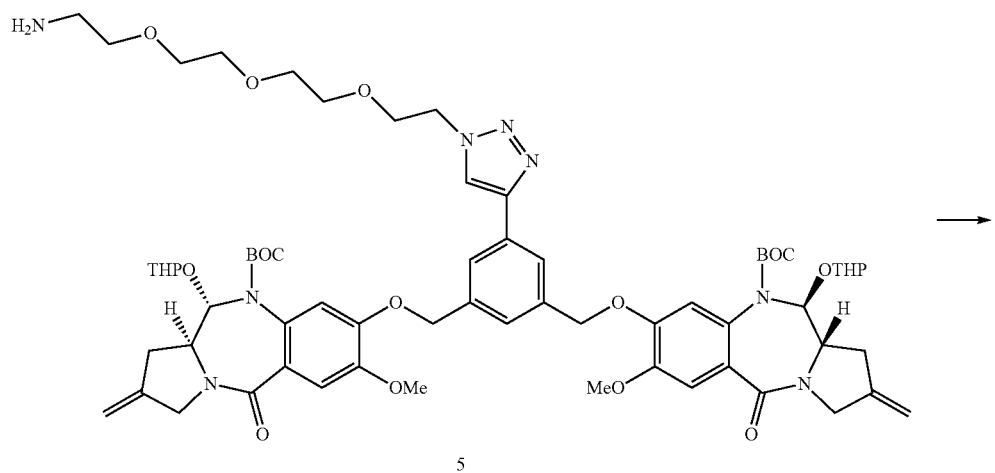

5

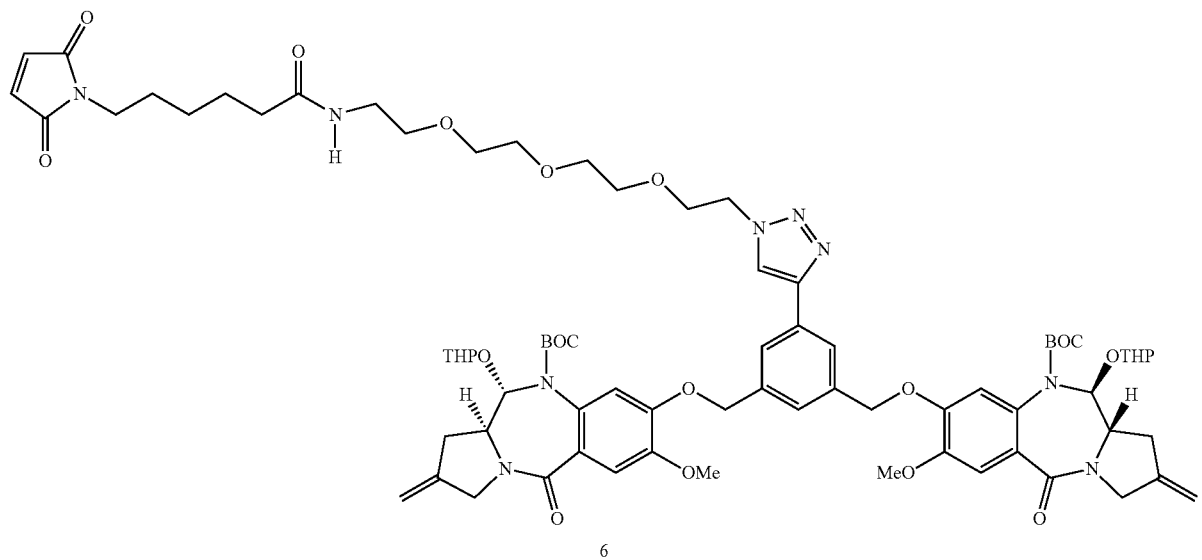

6

Solid 6-maleimidohexanoic acid N-hydroxysuccinimide ester (327 mg, 1.06 mmol) was added to a stirred solution of the primary amine 5 (1.28 g, 1.01 mmol) in dry DCM (30 mL) at room temperature. Progress was monitored by LC/MS and after 3 days stirring the reaction proceeded no further, a substantial amount of desired product was observed at retention time 3.65 min (ES+) m/z 1458 ([M+H]$^+$, ~100% relative intensity) accompanied by unreacted starting material at retention time 3.15 min. The reaction mixture was treated with silica gel and the solvent removed by evaporation in vacuo. The resulting residue was subjected to flash chromatography (gradient elution: 100% DCM to 97:3 v/v DCM/MeOH) to give the maleimide 6 as a foam (658 mg, 45% yield).

(e) N-(2-(2-(2-(2-(4-(3,5-bis((((S)-7-methoxy-2-methylene-5-oxo-2,3,5,11a-tetrahydro-1H-pyrrolo[2,1-c][1,4]benzodiazepin-8-yl)oxy)methyl)phenyl)-1H-1,2,3-triazol-1-yl)ethoxy)ethoxy)ethoxy)ethyl)-6-(2,5-dioxo-2,5-dihydro-1H-pyrrol-1-yl)hexanamide (7)

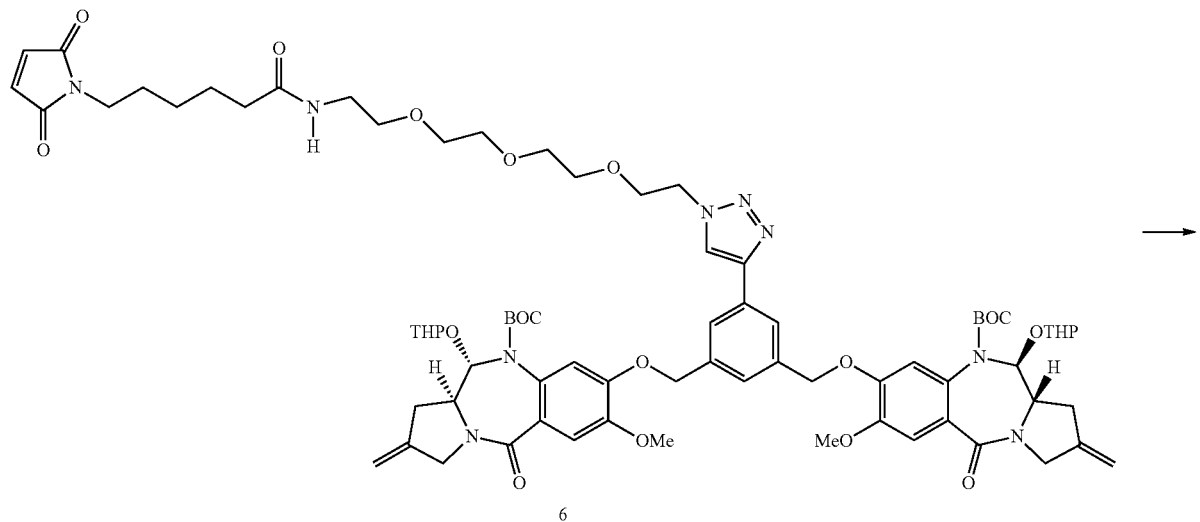

6

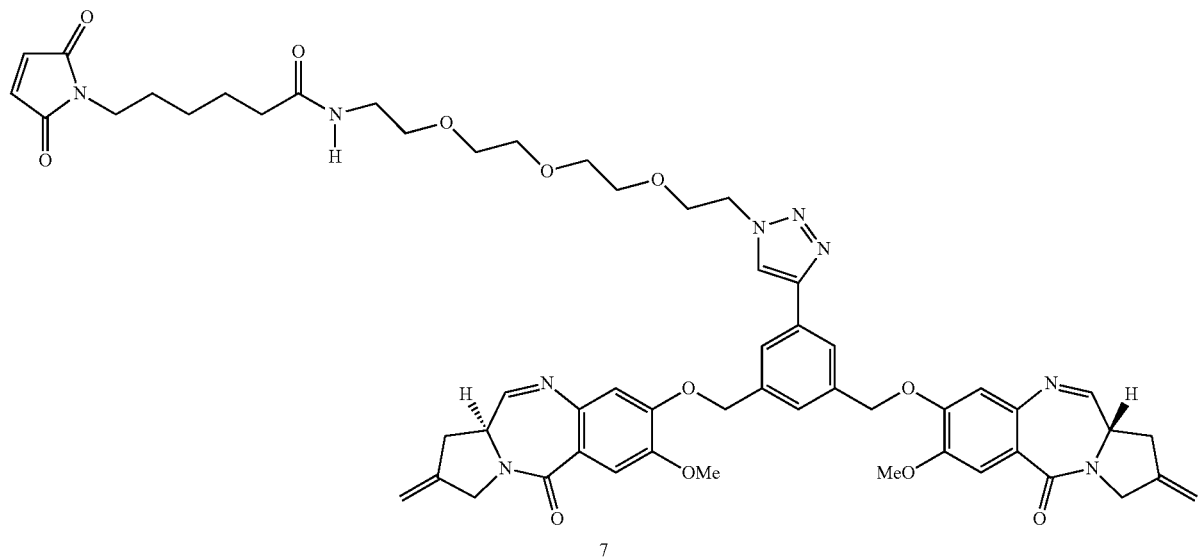

7

A solution of 95:5 v/v TFA/H$_2$O (5 mL) was added to a sample of the Boc/THP-protected compound 6 (428 mg, 0.29 mmol) at 0° C. (ice/acetone). After stirring at 0° C. for 1 hour the reaction was deemed complete as judged by LC/MS, desired product peak at retention time 2.72 min (ES+) m/z 1054 ([M+H]$^+$, ~70% relative intensity). The reaction mixture was kept cold and added drop wise to a chilled saturated aqueous solution of NaHCO$_3$ (100 mL). The mixture was extracted with DCM (3×30 mL) and the combined organic layers washed with H$_2$O (20 mL), brine (40 mL), dried (MgSO$_4$), filtered and evaporated in vacuo to provide the crude product. Purification by flash chromatography (gradient elution: 100% CHCl$_3$ to 96:4 v/v CHCl$_3$/MeOH) gave 7 as an orange foam (163 mg, 53% yield).

Example 2

(a) (11S,11aS,11'S, 11a'S)-di-tert-butyl 8,8'-(((5-(3-aminoprop-1-yn-1-yl)-1,3-phenylene)bis(methylene))bis(oxy))bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (8)

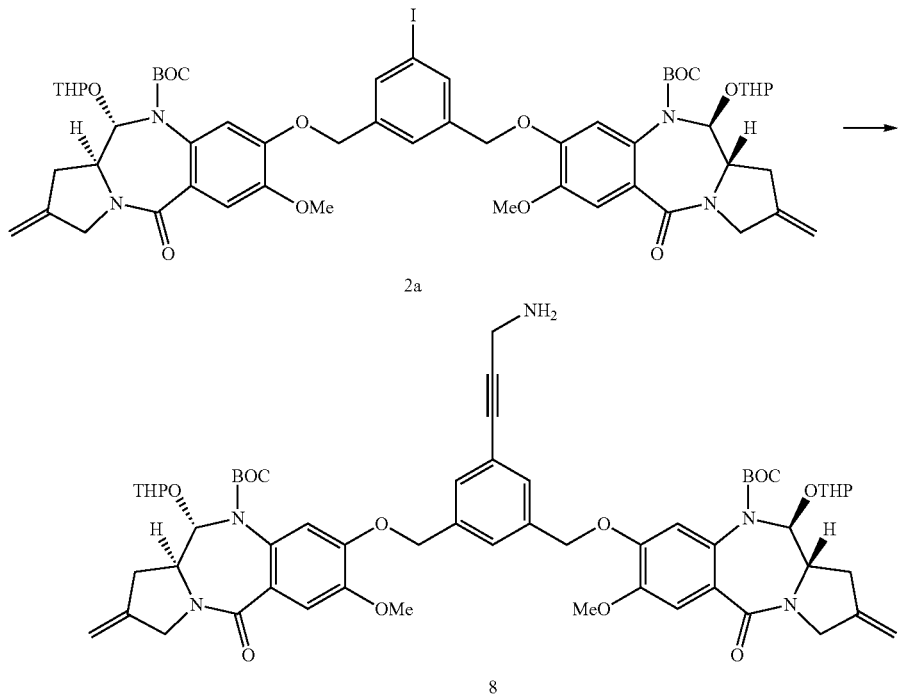

A catalytic amount of Pd(PPh$_3$)$_4$ (5.0 mg, 4.2 µmol) was added to a mixture of the bis-ether 2a (242 mg, 0.21 mmol), propargylamine (41 µL, 35 mg, 0.63 mmol), CuI (1.6 mg, 8.4 µmol), diethylamine (0.42 mL, 309 mg, 4.22 mmol) and oven-dried 4 Å molecular sieve pellets in dry DMF (1.8 mL) in an oven-dried sealable vessel. The mixture was degased and flushed with argon 3 times then heated in a microwave at 100° C. for 3 minutes at which point analysis by LC/MS revealed complete consumption of starting material and substantial product formation at retention time 3.18 min (ES+) m/z 1076 ([M+H]$^+$, ~60% relative intensity). The reaction mixture was allowed to cool to room temperature and was then filtered through a sinter to remove the sieves (washed with DMF). The filtrate was evaporated in vacuo to provide the unstable crude product 8 which was used immediately in the next step without purification or analysis.

(b) (11S,11aS,11'S,11a'S)-di-tert-butyl 8,8'-(((5-(1-(2,5-dioxo-2,5-dihydro-1H-pyrrol-1-yl)-3,19-dioxo-7,10,13,16-tetraoxa-4,20-diazatricos-22-yn-23-yl)-1,3-phenylene)bis(methylene))bis(oxy))bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (9)

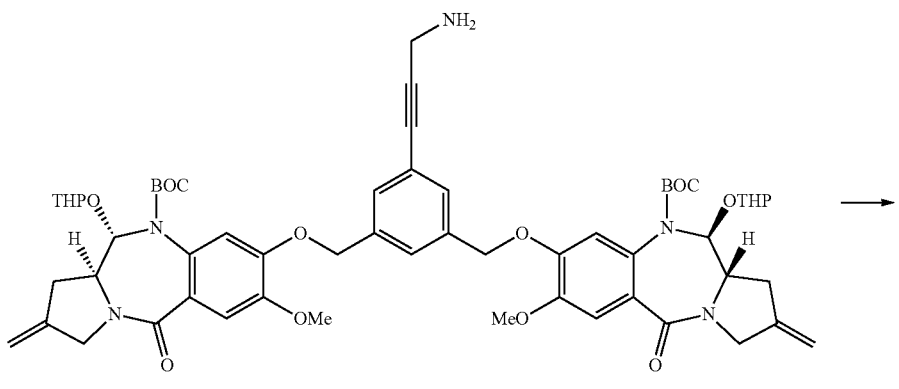

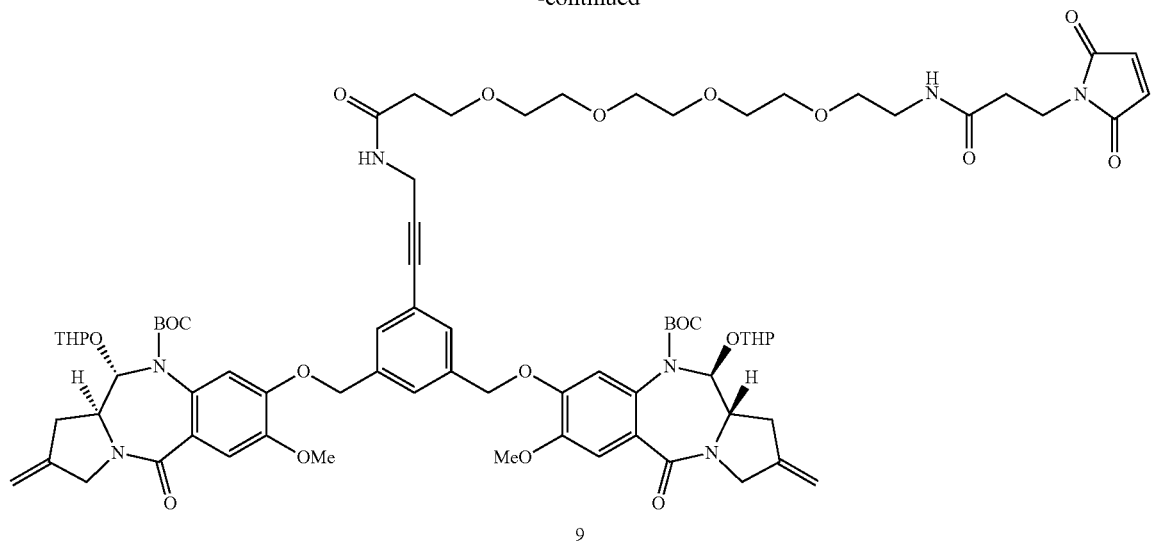

9

MAL-dPEG®4-acid (88 mg, 0.21 mmol) was added to a stirred solution of EDCI (41 mg, 0.21 mmol) and the crude primary amine 8 in dry DCM (4 mL) at room temperature. The reaction mixture was stirred under an argon atmosphere for 3 hours at which point analysis by LC/MS showed a substantial amount of desired product at retention time 3.58 min (ES+) m/z 1475 ([M+H]$^+$, ~10% relative intensity), 1498 ([M+Na]$^+$, ~5% relative intensity) accompanied by a side product at retention time 3.85 min. The reaction mixture was diluted with DCM (30 mL) and washed with H$_2$O (3×10 mL), brine (20 mL), dried (MgSO$_4$), filtered and evaporated in vacuo to provide the crude product. Purification by flash chromatography (gradient elution: 100% DCM to 96:4 v/v DCM/MeOH) gave the maleimide 9 as a foam (67 mg, 22% yield over 2 steps).

(c) N-(3-(3,5-bis((((S)-7-methoxy-2-methylene-5-oxo-2,3,5,1a-tetrahydro-1H-pyrrolo[2,1-c][1,4]benzodiazepin-8-yl)oxy)methyl)phenyl)prop-2-yn-1-yl)-1-(3-(2,5-dioxo-2,5-dihydro-1H-pyrrol-1-yl)propanamido)-3,6,9,12-tetraoxapentadecan-15-amide (10)

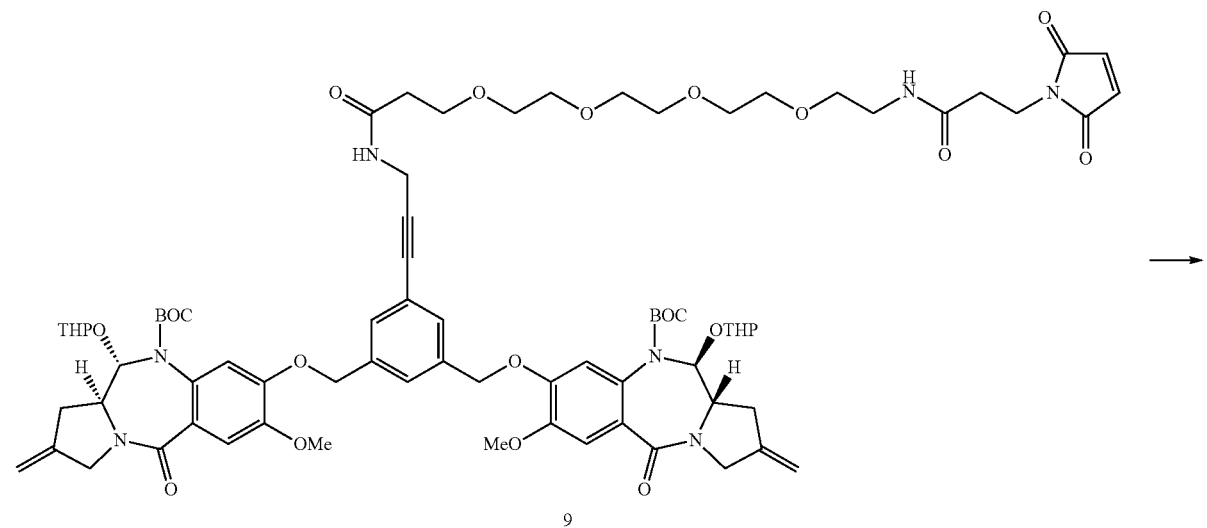

9

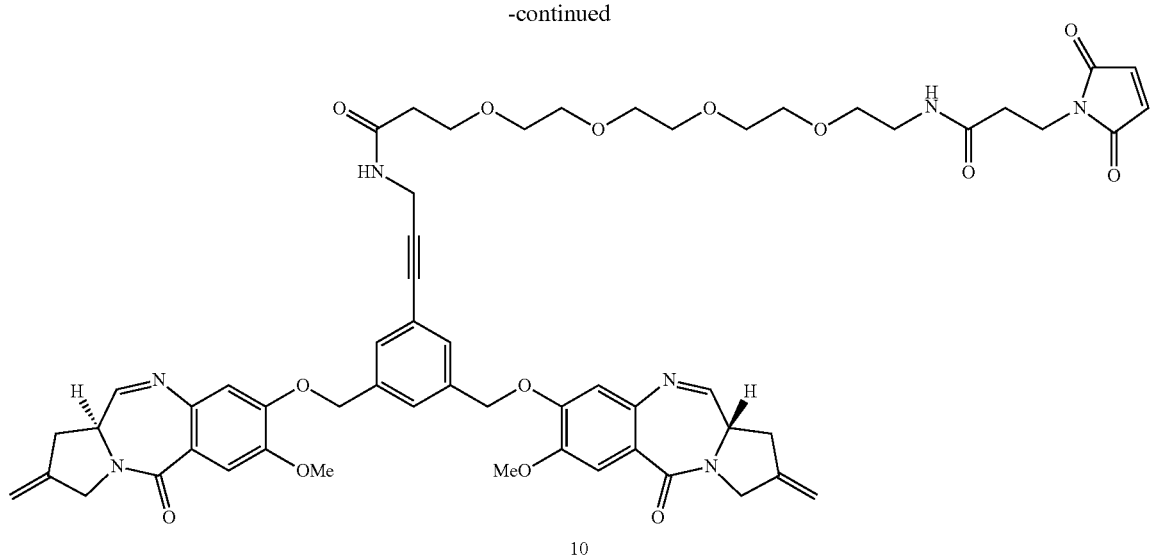

10

A solution of 95:5 v/v TFA/H$_2$O (1 mL) was added to a sample of the Boc/THP-protected compound 9 (67 mg, 45.5 μmol) at 0° C. (ice/acetone). After stirring at 0° C. for 1.5 hours, the reaction was deemed complete as judged by LC/MS, desired product peak at retention time 2.67 min (ES+) m/z 1070 ([M+H]$^+$, ~5% relative intensity). The reaction mixture was kept cold and added drop wise to a chilled saturated aqueous solution of NaHCO$_3$ (50 mL). The mixture was extracted with DCM (3×15 mL) and the combined organic layers washed with brine (40 mL), dried (MgSO$_4$), filtered and evaporated in vacuo to provide the crude product. Purification by flash chromatography (gradient elution: 100% CHCl$_3$ to 96:4 v/v CHCl$_3$/MeOH) gave 10 as an orange foam (12 mg, 24% yield).

Example 3

(a) (11S,11aS,11'S, 11a'S)-di-tert-butyl 8,8'-(((5-(4-(3-((tert-butoxycarbonyl)amino)propyl)piperazin-1-yl)-1,3-phenylene)bis(methylene))bis(oxy))bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (11)

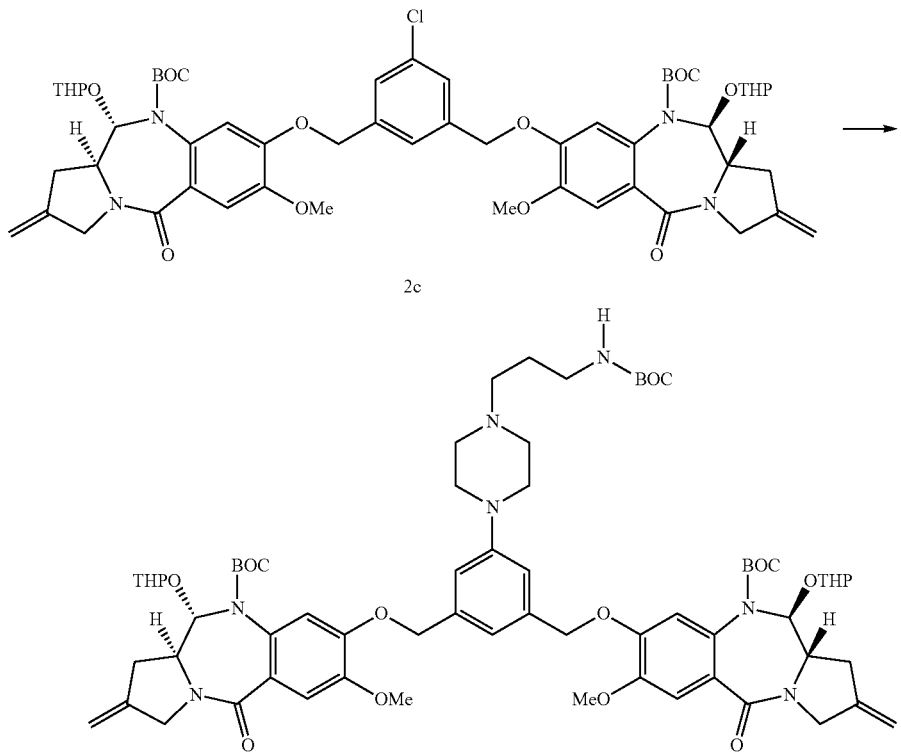

11

A sample of the bis-ether 2c (250 mg, 0.24 mmol), NaO'Bu (57 mg, 0.59 mmol), RuPhos (11 mg, 23.7 μmol) and RuPhosPd (19 mg, 23.7 μmol) were added to an oven-dried sealable tube (which was allowed to cool in a desicator). The mixture was degased and flushed with argon 3 times before the addition of dry THF (5 mL) and then allowed to stir under an inert atmosphere for ~10 minutes until the red colour had discharged. A solution of 3-(piperazin-1-yl)propan-1-amine (58 mg, 0.26 mmol) in dry THF (1 mL) was added and the mixture again degased and flushed with argon 3 times. The reaction mixture was heated at 80° C. in a pre-heated oil bath for 2.5 hours at which point analysis by LC/MS revealed a 3-component mixture: desired product at retention time 3.35 min (ES+) m/z 1264 ([M+H]+, ~60% relative intensity), major side product at retention time 3.95 min (de-chlorinated analogue of 2c) and shoulder 4.13 min (trace starting material). After being allowed to cool to room temperature the reaction mixture was partitioned between water (20 mL) and EtOAc (20 mL). The aqueous phase was extracted with EtOAc (3×15 mL) and the combined organic layers were washed with water (30 mL), brine (50 mL), dried (MgSO$_4$), filtered and evaporated in vacuo to provide the crude product. Purification by flash chromatography (gradient elution: 100% DCM to 95:5 v/v DCM/MeOH) gave the piperazine 11 as a foam (152 mg, 25% yield).

(b) (11aS,11a'S)-8,8'-(((5-(4-(3-aminopropyl)piperazin-1-yl)-1,3-phenylene)bis(methylene))bis(oxy))bis(7-methoxy-2-methylene-2,3-dihydro-1H-pyrrolo[2,1-c][1,4]benzodiazepin-5(11aH)-one) (12)

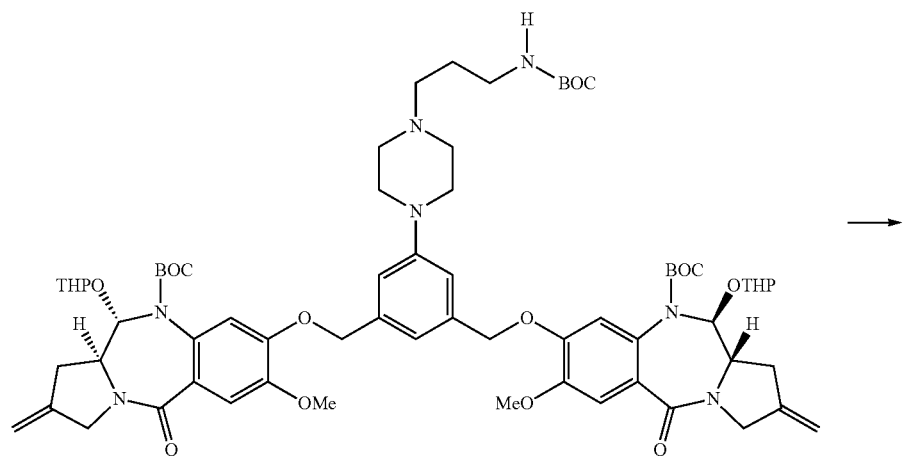

11

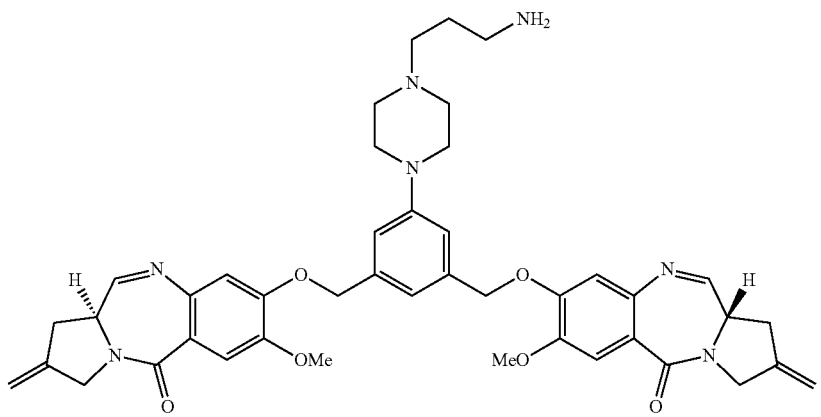

12

A solution of 95:5 v/v TFA/H$_2$O (2 mL) was added to a sample of the Boc/THP-protected compound 11 (142 mg, 0.11 mmol) at 0° C. (ice/acetone). After stirring at 0° C. for 1 hour, reaction was deemed complete as judged by LC/MS, desired product peak at retention time 2.23 min (ES+) m/z 778 ([M+H$_2$O]$^+$, ~5% relative intensity). The reaction mixture was kept cold and added drop-wise to a chilled saturated aqueous solution of NaHCO$_3$ (50 mL). The mixture was extracted with DCM (3×20 mL) and the combined organic layers washed with brine (15 mL), dried (MgSO$_4$), filtered and evaporated in vacuo to provide the crude product 12 as a waxy solid (22.6 mg). Note that during the NaHCO$_3$ neutralisation step the desired product precipitated out of solution as a waxy solid which was only partially soluble in DCM. Additional product was obtained by dissolving DCM-insoluble solids in DMF followed by evaporation in vacuo. The resulting oily residue was triturated with diethylether to provide a solid which was dried in vacuo to provide additional crude 12 (54.4 mg, total amount=77 mg, 85% yield) which was carried through to the next step without further purification or analysis.

(c) N-(3-(4-(3,5-bis((((S)-7-methoxy-2-methylene-5-oxo-2,3,5,11a-tetrahydro-1H-pyrrolo[2,1-c][1,4]benzodiazepin-8-yl)oxy)methyl)phenyl)piperazin-1-yl)propyl)-1-(3-(2,5-dioxo-2,5-dihydro-1H-pyrrol-1-yl)propanamido)-3,6,9,12-tetraoxapentadecan-15-amide (13)

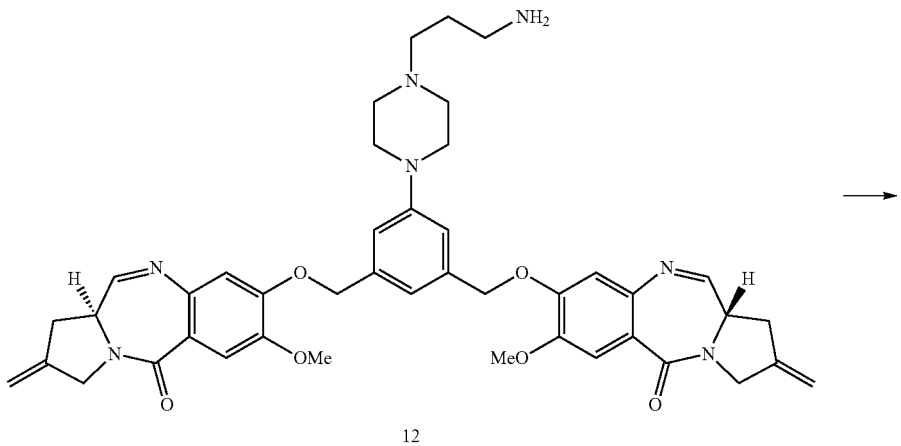

12

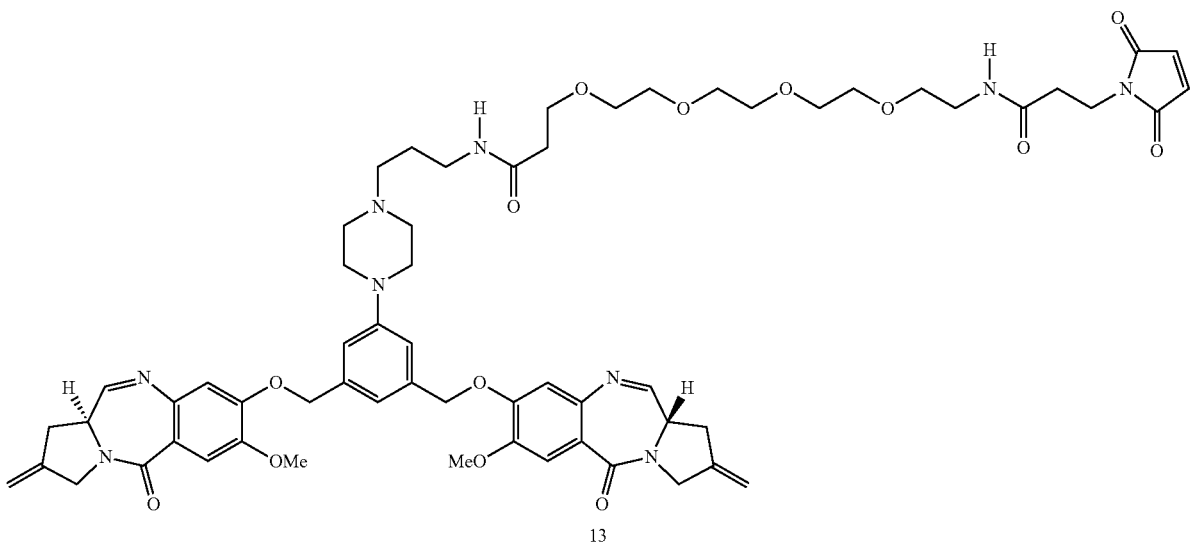

13

MAL-dPEG®4-acid (42 mg, 0.10 mmol) was added to a stirred solution of EDCI (20 mg, 0.10 mmol) and the crude primary amine 12 (77 mg, 0.10 mmol) in dry DCM (4 mL) at room temperature. The reaction mixture was stirred under an argon atmosphere for 3 hours at which point analysis by LC/MS showed complete consumption of starting material, a substantial amount of desired product at retention time 2.42 min (ES+) m/z 1176 ([M+H$_2$O]$^+$, ~5% relative intensity) and excess MAL-dPEG®4-acid at retention time 2.05 min (weak signal on diode array but detectable on ES+/ES−). The reaction mixture was diluted with DCM (30 mL) and washed with H$_2$O (15 mL), brine (20 mL), dried (MgSO$_4$), filtered and evaporated in vacuo to provide the crude product. Purification by flash chromatography (gradient elution: 100% CHCl$_3$ to 93:7 v/v CHCl$_3$/MeOH) gave the maleimide 13 as a foam (46 mg, 55%). Note that trace amounts of excess MAL-dPEG®4-acid could not be removed using flash chromatography.

Example 4

(a) (11S,11aS,11'S, 11a'S)-di-tert-butyl 8,8'-(((5-(4-(tert-butoxycarbonyl)piperazin-1-yl)-1,3-phenylene)bis(methylene))bis(oxy))bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (14)

2-Dicyclohexylphosphino-2',6'-diisopropoxybiphenyl (18 mg, 38 µmol, 0.2 eq), chloro(2-dicyclohexylphosphino-2',6'-diisopropoxy-1,1'-biphenyl)[2-(2'-amino-1,1'-biphenyl)]palladium(II) (18 mg, 22 µmol, 0.12 eq), caesium carbonate (0.36 g, 1.1 mmol, 5.0 eq) and iodo derivative (2a) (0.307 g, 0.27 mmol, 1.0 eq) were placed in a microwave vial which was evacuated and flushed with Argon (×3). Anhydrous THF (5 mL) was added followed by tert-butyl piperazine-1-carboxylate (70 mg, 0.37 mmol, 1.1 eq) and the resultant mixture was heated at 85° C. for 4 h then overnight at room temperature. The reaction mixture was diluted with saturated sodium hydrogen carbonate and extracted with ethylacetate (3×100 mL). The combined ethylacetate extracts were washed with brine (100 mL), dried (MgSO$_4$) and evaporated under reduced pressure. The product 14 was purified by flash column chromatography [CHCl$_3$/MeOH 0% to 1.5% in 0.5% increments](0.111 g, 51%) Analytical Data: RT 4.12 min; MS (ES$^+$) m/z (relative intensity) 1207 ([M+1]$^+$, 30).

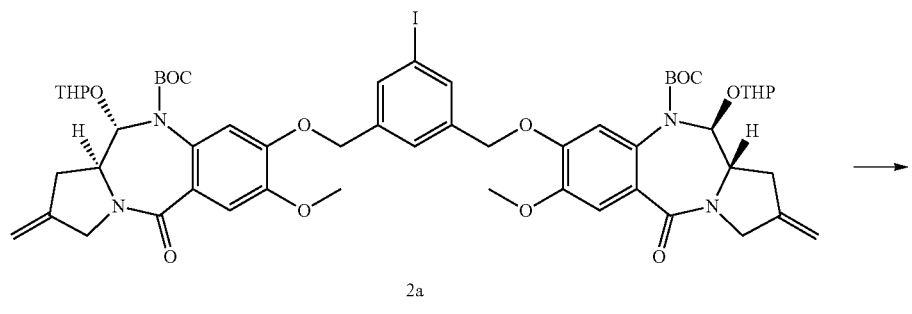

2a

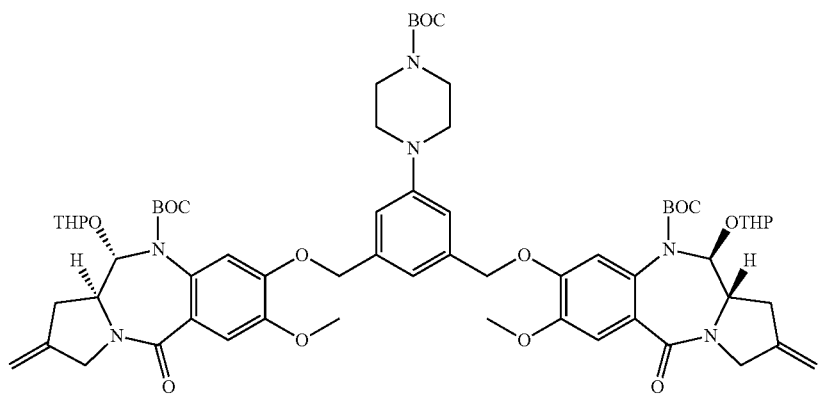

14

(b) (11aS,11a'S)-8,8'-(((5-(piperazin-1-yl)-1,3-phenylene)bis(methylene))bis(oxy))bis(7-methoxy-2-methylene-2,3-dihydro-1H-pyrrolo[2,1-c][1,4]-benzodiazepin-5(11aH)-one) (15)

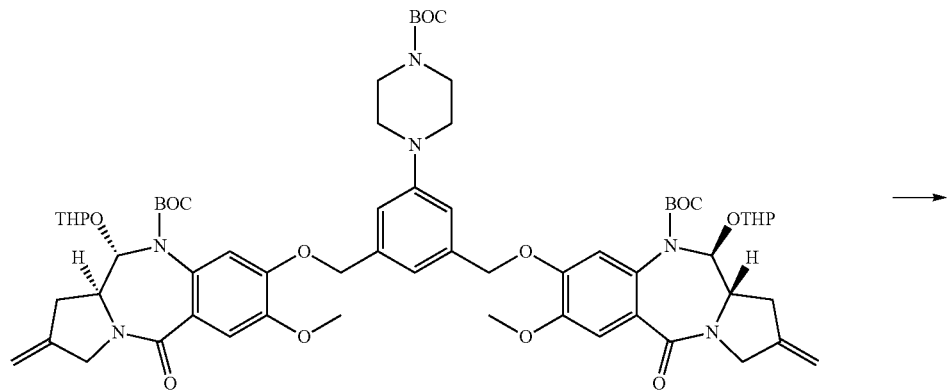

14

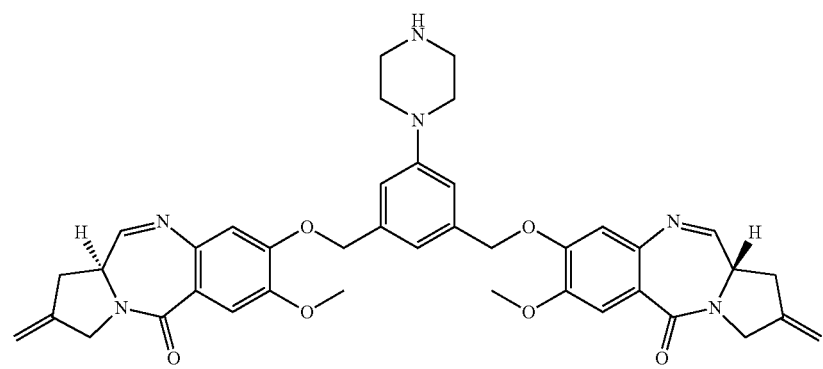

15

A cold (ice bath) solution of 95% trifluoroacetic acid (4 mL) was added to compound (14) (0.2 g, 0.165 mmol, 1 eq.) which had been cooled in an ice bath. The solution was stirred at 0° C. for 30 min when reaction was shown to be complete by LCMS. The reaction mixture was added dropwise to a mixture of ice and saturated sodium bicarbonate solution to neutralise the trifluoroacetic acid. The mixture was extracted with DCM (4×75 mL) and the combined extracts were washed with water (100 mL) saturated brine (100 mL), dried (MgSO$_4$) and evaporated under reduced pressure to give the product 15 as a yellow solid which was used without further purification (0.116 g, 100%)

Analytical Data: RT 2.33 min; MS (ES$^+$) m/z (relative intensity) 703 ([M+1]$^+$, 100).

(c) N-(15-(4-(3,5-bis((((S)-7-methoxy-2-methylene-5-oxo-2,3,5,11a-tetrahydro-1H-pyrrolo[2,1-c][1,4]benzodiazepin-8-yl)oxy)methyl)phenyl)piperazin-1-yl)-15-oxo-3,6,9,12-tetraoxapentadecyl)-3-(2,5-dioxo-2,5-dihydro-1H-pyrrol-1-yl)propanamide (17)

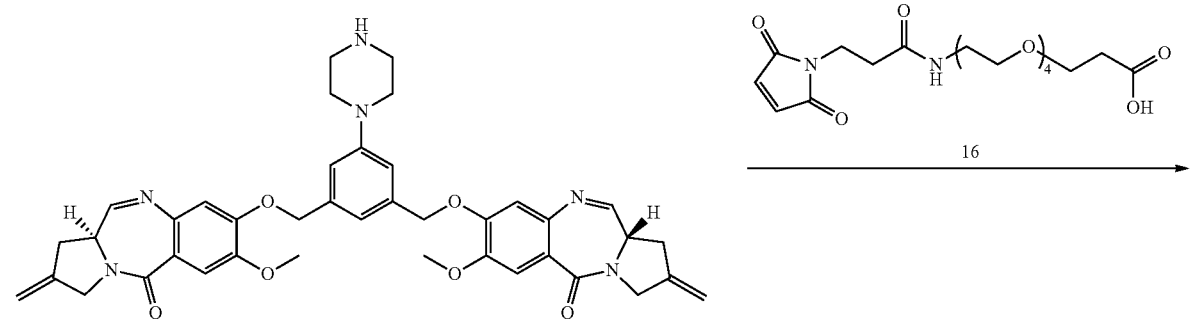

15

-continued

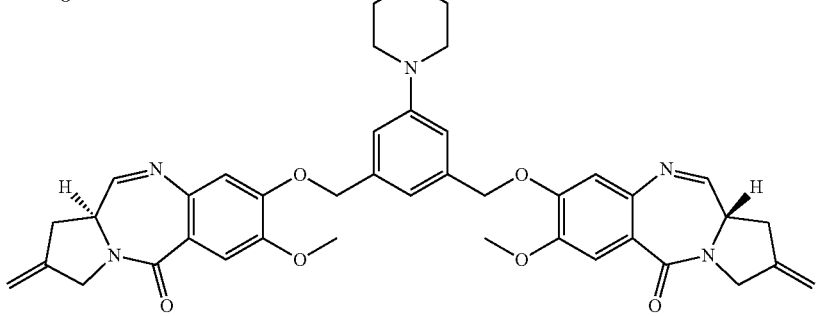

17

N-(3-Dimethylaminopropyl)-N'-ethylcarbodiimide hydrochloride (35 mg, 0.18 mmol, 1.1 eq) was added to a solution of compound (15) (116 mg, 0.165 mmol, 1.0 eq) and 1-(2,5-dioxo-2,5-dihydro-1H-pyrrol-1-yl)-3-oxo-7,10,13,16-tetraoxa-4-azanonadecan-19-oic acid (16) (69 mg, 0.165 mmol, 1.0 eq) in anhydrous DCM (5 mL) under Argon. The resultant solution was stirred at room temperature for 2 h. The reaction mixture was diluted with DCM (50 mL), washed with water (100 mL), saturated sodium hydrogen carbonate solution (100 mL), water (100 mL), brine (100 mL), dried (MgSO$_4$) and evaporated under reduced pressure.

Purification by flash column chromatography [CHCl$_3$/MeOH 0% to 5% in 1% increments] gave the product 17 as a yellow glass (0.058 g, 32%)

Analytical Data: $[\alpha]^{18}_D = [+628°]$ (c=0.25, CHCl$_3$); RT 2.65 min; MS (ES$^+$) m/z (relative intensity) 1101 ([M+1]$^+$, 40)

Example 5

(a) tert-butyl (42-(2,5-dioxo-2,5-dihydro-1H-pyrrol-1-yl)-37-oxo-3,6,9,12,15,18,21,24,27,30,33-undecaoxa-36-azadotetracontyl)oxycarbamate (19)

6-Maleimidohexanoic acid (64 mg, 0.30 mmol) was added to a stirred solution of EDCI (64 mg, 0.33 mmol) and the primary amine 18 (200 mg, 0.30 mmol) in dry DCM (6 mL) at room temperature. The reaction mixture was stirred under an argon atmosphere for 16 hours at which point analysis by LC/MS showed a substantial amount of desired product at retention time 1.38 min {(ES$^+$) m/z 854 ([M+H]$^+$, ~30% relative intensity), 877 ([M+Na]$^+$, ~100% relative intensity)} accompanied by unreacted 18 at retention time 1.07 min, note that both starting material and product had weak UV absorption (214 and 254 nm) and were best detected on ES$^+$ TIC. Additional 6-maleimidohexanoic acid (32 mg, 0.15 mmol) and EDCI (32 mg, 0.17 mmol) were added to the stirred mixture until starting material was completely consumed (as judged by LC/MS). The reaction mixture was diluted with DCM (100 mL) and washed with H$_2$O (3×30 mL), brine (40 mL), dried (MgSO$_4$), filtered and evaporated in vacuo to provide the crude product. Purification by flash chromatography (gradient elution in 1% increments: 100% DCM to 96:4 v/v DCM/MeOH) gave the amide 19 as an oil (214 mg, 83% yield).

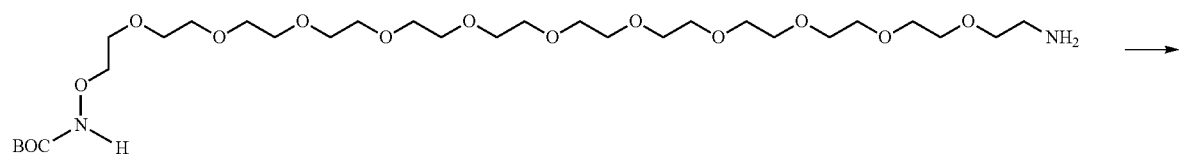

18

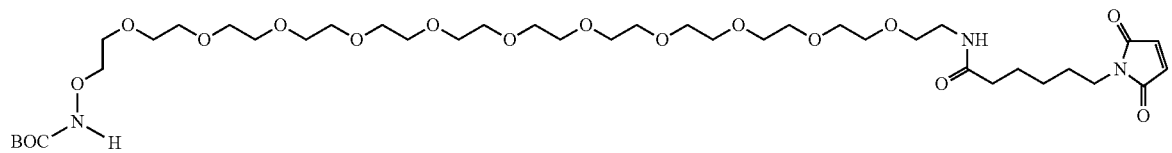

19

(b) N-(35-(aminooxy)-3,6,9,12,15,18,21,24,27,30,
33-undecaoxapentatriacontyl)-6-(2,5-dioxo-2,5-di-
hydro-1H-pyrrol-1-yl)hexanamide (20)

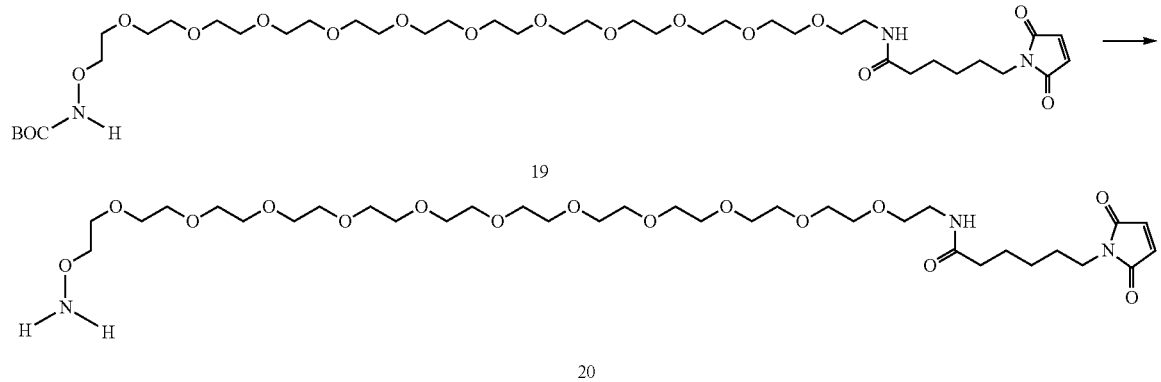

A solution of 95:5 v/v TFA/H$_2$O (2 mL) was added to a sample of the Boc/THP-protected compound 19 (214 mg, 0.25 mmol) at 0° C. (ice/acetone). After stirring at 0° C. for 1 hour the reaction was deemed complete as judged by LC/MS, desired product peak at retention time 1.06 min {(ES$^+$) m/z 754 ([M+H]$^+$, ~100% relative intensity)}, note that both starting material and product had weak UV absorption (214 and 254 nm) and were best detected on ES$^+$ TIC. The reaction mixture was kept cold and added drop wise to a chilled saturated aqueous solution of NaHCO$_3$ (100 mL). The mixture was extracted with DCM (3×30 mL) and the combined organic layers washed with brine (50 mL), dried (MgSO$_4$), filtered and evaporated in vacuo to provide the oxyamine 20 as an oil (161 mg, 85% yield) which was carried through to the next step without further purification.

(c) (11S,11aS,11'S,11a'S)-di-tert-butyl 8,8'-(((5-
formyl-1,3-phenylene)bis(methylene))bis(oxy))bis
(7-methoxy-2-methylene-5-oxo-11-((tetrahydro-2H-
pyran-2-yl)oxy)-2,3,11,11a-tetrahydro-1H-pyrrolo[2,
1-c][1,4]benzodiazepine-10(5H)-carboxylate) (21)

3,5-bis(bromomethyl)benzaldehyde (260 mg, 0.90 mmol) [Enrique Di'ez-Barra et al J. Org. Chem. 2001, 66, 5664-5670] was added to a stirred solution of Boc/THP-protected PBD capping unit 7 (826 mg, 1.79 mmol), TBAI (33 mg, 89.7 µmol) and K$_2$CO$_3$ (247 mg, 1.79 mmol) in dry DMF (12 mL). The reaction mixture was heated to 60° C. and stirred under an argon atmosphere for 2.5 hours at which point analysis by LC/MS revealed substantial product formation at retention time 1.92 min {(ES$^+$) m/z 1051 ([M+H]$^+$, ~65% relative intensity) 1073 ([M+Na]$^+$, ~25% relative intensity)}. The reaction mixture was allowed to cool to room temperature and the DMF was removed by evaporation in vacuo. The resulting residue was partitioned between water (50 mL) and EtOAc (50 mL) and the aqueous phase was extracted with EtOAc (3×15 mL). The combined organic layers were washed with water (2×20 mL), brine (30 mL), dried (MgSO$_4$), filtered and evaporated in vacuo to provide the crude product. Purification by flash chromatography (gradient elution in 10% increments: 50:50 v/v EtOAc/hexane to 80:20 v/v EtOAc/hexane) gave the bis-ether 21 as a white foam (717 mg, 76% yield). Note that 21 was isolated as a mixture of diasteroisomers arising from THP protecting group.

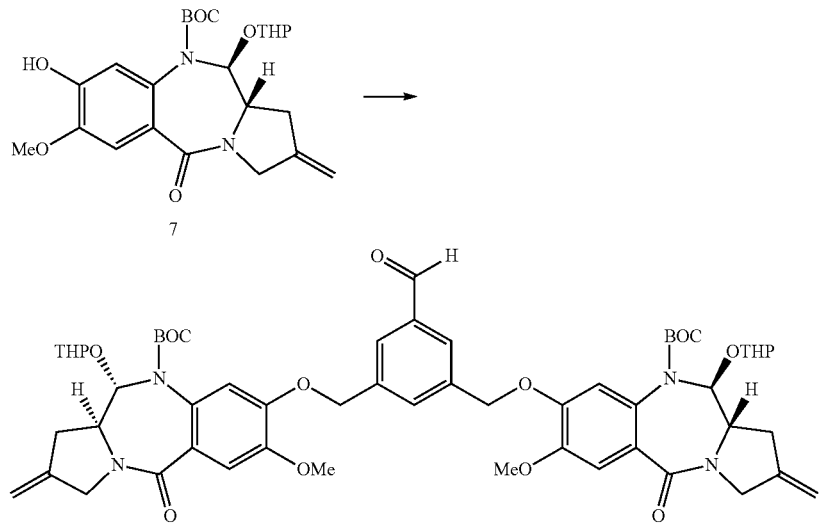

(d) (11S,11aS,11'S, 11a'S)-di-tert-butyl 8,8'-(((5-((syn/anti)-45-(2,5-dioxo-2,5-dihydro-1H-pyrrol-1-yl)-40-oxo-3,6,9,12,15,18,21,24,27,30,33,36-dodecaoxa-2,39-diazapentatetracont-1-en-1-yl)-1,3-phenylene)bis(methylene))bis(oxy))bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (22)

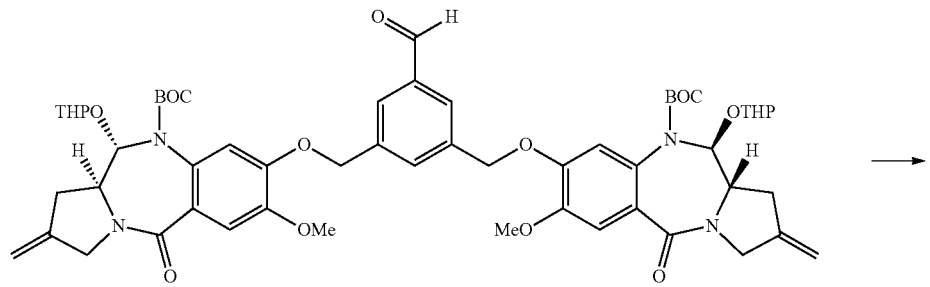

21

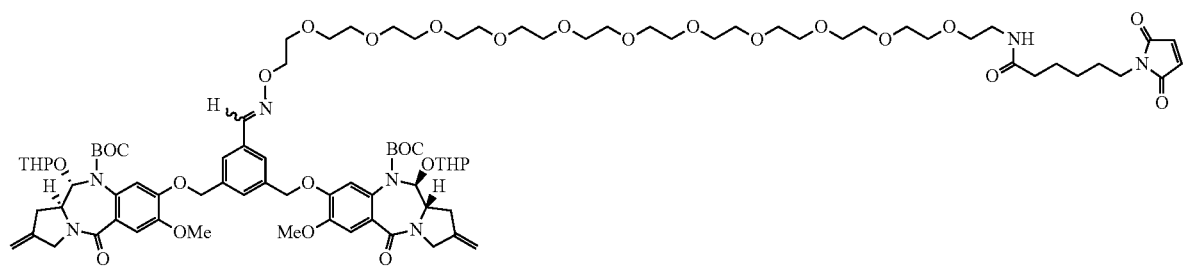

22

PTSA (4.1 mg, 21.4 μmol) was added to a stirred solution of the aldehyde 21 (224 mg, 0.21 mmol) and the oxy-amine 20 (161 mg, 0.21 mmol) in dry DCM (3 mL) at 0° C. (ice/acetone). The reaction mixture was allowed to stir at 0° C. under an argon atmosphere and stirring for 3 hours analysis by LC/MS revealed complete consumption of oxyamine 20 (retention time 1.06 min), presence of desired product {retention time 1.85 min (ES$^+$) m/z 1787 ([M+H]$^+$, ~25% relative intensity) 1810 ([M+Na]$^+$, ~90% relative intensity)} and unreacted aldehyde 21 (retention time 1.91 min). In order to avoid unwanted THP cleavage (observed in earlier test reactions), the reaction was quenched at this point although aldehyde had not been completely consumed: The mixture was diluted with DCM (50 mL) and washed with NaHCO$_3$ (3×15 mL), brine (30 mL), dried (MgSO$_4$), filtered and evaporated in vacuo to provide the crude product. Purification by flash chromatography (gradient elution in 1% increments: 100% DCM to 96:4 v/v DCM/MeOH) gave the syn/anti oximes 22 as a white foam (215 mg, 56% yield). Unreacted aldehyde 21 (83 mg) was recovered during flash chromatography. Note that 22 was isolated as a mixture of diastereoisomers arising from THP protecting group.

(e) N-((syn/anti)-1-(3,5-bis((((S)-7-methoxy-2-methylene-5-oxo-2,3,5,11a-tetrahydro-1H-pyrrolo[2,1-c][1,4]benzodiazepin-8-yl)oxy)methyl)phenyl)-3,6,9,12,15,18,21,24,27,30,33,36-dodecaoxa-2-azaoctatriacont-1-en-38-yl)-6-(2,5-dioxo-2,5-dihydro-1H-pyrrol-1-yl)hexanamide (23)

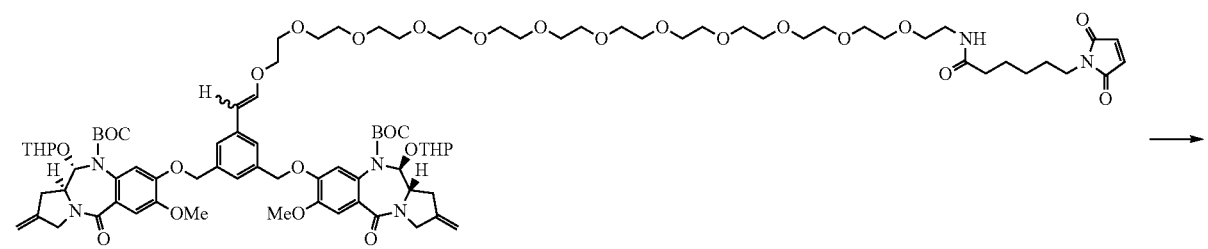

22

-continued

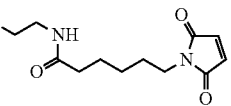
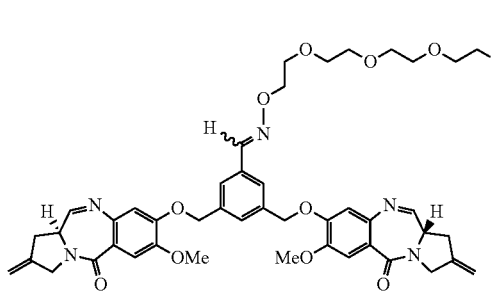

23

A solution of 95:5 v/v TFA/H₂O (1 mL) was added to a sample of the Boc/THP-protected compound 22 (204 mg, 0.11 mmol) at 0° C. (ice/acetone). After stirring at 0° C. for 30 minutes, the reaction was deemed complete as judged by LC/MS, desired product peak at retention time 1.42 min {(ES⁺) m/z 1383 ([M+H]⁺, <5% relative intensity)}. The reaction mixture was kept cold and added drop wise to a chilled saturated aqueous solution of NaHCO₃ (50 mL). The mixture was extracted with DCM (3×15 mL) and the combined organic layers washed with brine (30 mL), dried (MgSO₄), filtered and evaporated in vacuo to provide the crude product. Purification by flash chromatography (gradient elution in 1% increments: 100% CHCl₃ to 96:4 v/v CHCl₃/MeOH) gave the deprotected syn/anti oximes 23 as a yellow thin film (85 mg, 54% yield). Analysis by reverse-phase ultra-high-performance liquid chromatography (see General Information section for conditions) revealed predominantly two peaks at 16.15 min (syn isomer, minor component) and 16.42 min (anti isomer, major component).

(f) N-((anti)-1-(3,5-bis((((S)-7-methoxy-2-methyl-ene-5-oxo-2,3,5,11a-tetrahydro-1H-pyrrolo[2,1-c][1,4]benzodiazepin-8-yl)oxy)methyl)phenyl)-3,6,9,12,15,18,21,24,27,30,33,36-dodecaoxa-2-azaoctatriacont-1-en-38-yl)-6-(2,5-dioxo-2,5-dihydro-1H-pyrrol-1-yl)hexanamide (24)

24

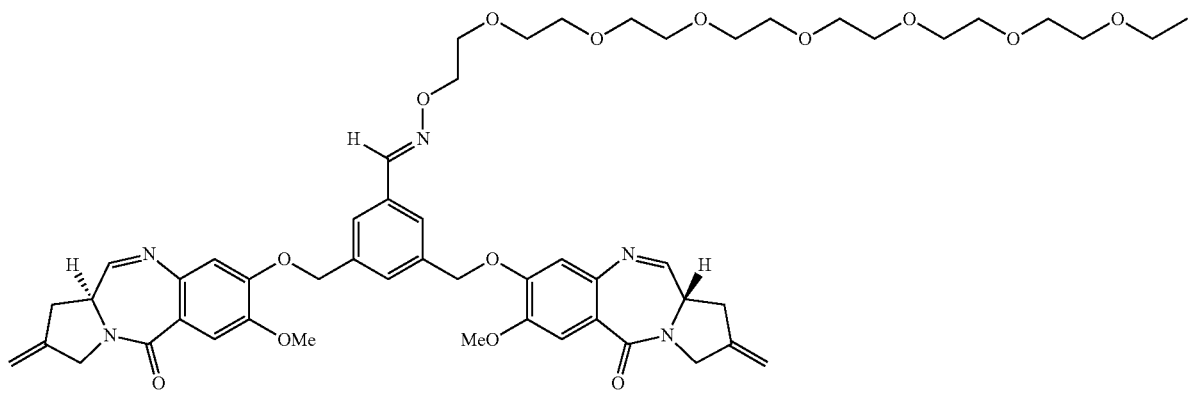
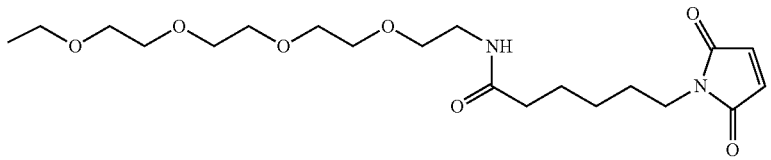

Compound 23 was subjected to purification by preparative HPLC (see general information section for conditions). The peak eluting at a retention time of 16.42 min was isolated and lyophilised to provide the anti-oxime 24 (9.9 mg): ¹H NMR (400 MHz, CDCl₃) δ 8.12 (s, 1H), 7.66 (d, 2H, J=4.4 Hz), 7.62-7.59 (m, 2H), 7.53-7.51 (m, 3H), 6.82 (s, 2H), 6.68 (s, 2H), 6.16 (br s, 2H), 5.25-5.14 (m, 8H), 4.33 (t, 2H, J=4.8 Hz), 4.28 (br s, 4H), 3.96 (s, 6H), 3.90-3.84 (m, 2H), 3.82-3.78 (m, 2H), 3.67-3.49 (m, 43H), 3.46-3.42 (m, 2H), 3.15-3.08 (m, 2H), 2.98-2.90 (m, 2H), 2.16 (t, 2H, J=7.6 Hz), 1.70-1.54 (m, 4H), 1.36-1.24 (m, 2H).

(g) N-((syn)-1-(3,5-bis((((S)-7-methoxy-2-methyl-ene-5-oxo-2,3,5,11a-tetrahydro-1H-pyrrolo[2,1-c][1,4]benzodiazepin-8-yl)oxy)methyl)phenyl)-3,6,9,12,15,18,21,24,27,30,33,36-dodecaoxa-2-azaoctatriacont-1-en-38-yl)-6-(2,5-dioxo-2,5-dihydro-1H-pyrrol-1-yl)hexanamide (25)

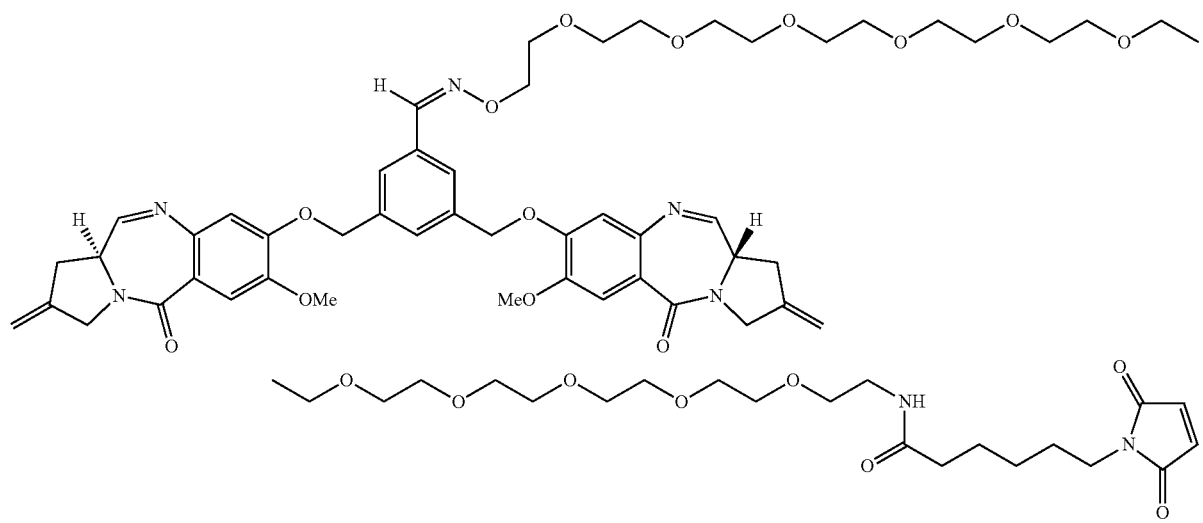

25

Compound 23 was subjected to purification by preparative HPLC (see general information section for conditions). The peak eluting at a retention time of 16.15 min was isolated and lyophilised to provide the syn-oxime 25 (5.2 mg): ¹H NMR (400 MHz, CDCl₃) δ 7.93-7.91 (m, 2H), 7.66 (d, 2H, J=4.4 Hz), 7.57-7.55 (m, 1H), 7.52 (s, 2H), 7.32 (s, 1H), 6.82 (s, 2H), 6.68 (s, 2H), 6.18 (br s, 2H), 5.26-5.14 (m, 8H), 4.35 (t, 2H, J=5.1 Hz), 4.28 (br s, 4H), 3.96 (s, 6H), 3.90-3.84 (m, 2H), 3.81 (t, 2H, J=5.1 Hz), 3.68-3.48 (m, 43H), 3.46-3.42 (m, 2H), 3.15-3.07 (m, 2H), 2.97-2.90 (m, 2H), 2.16 (t, 2H, J=7.6 Hz), 1.70-1.54 (m, 4H), 1.36-1.24 (m, 2H).

Example 6

(a) Di-tert-butyl 8,8'-(((5-(1-amino-15-oxo-3,6,9,12-tetraoxa-16-azanonadec-18-yn-19-yl)-1,3-phenylene)bis(methylene))bis(oxy))(11S,11aS,11'S,11a'S)-bis(7-methoxy-2-methylene-5-oxo-11-((tetrahydro-2H-pyran-2-yl)oxy)-2,3,11,11a-tetrahydro-1H-pyrrolo[2,1-c][1,4]benzo diazepine-10(5H)-carboxylate) (29)

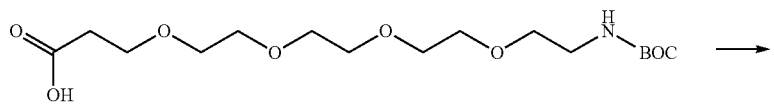

26

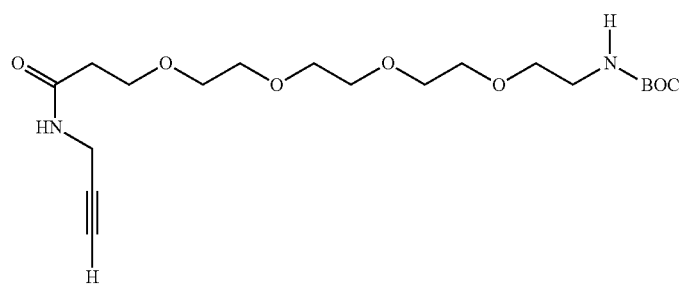

27

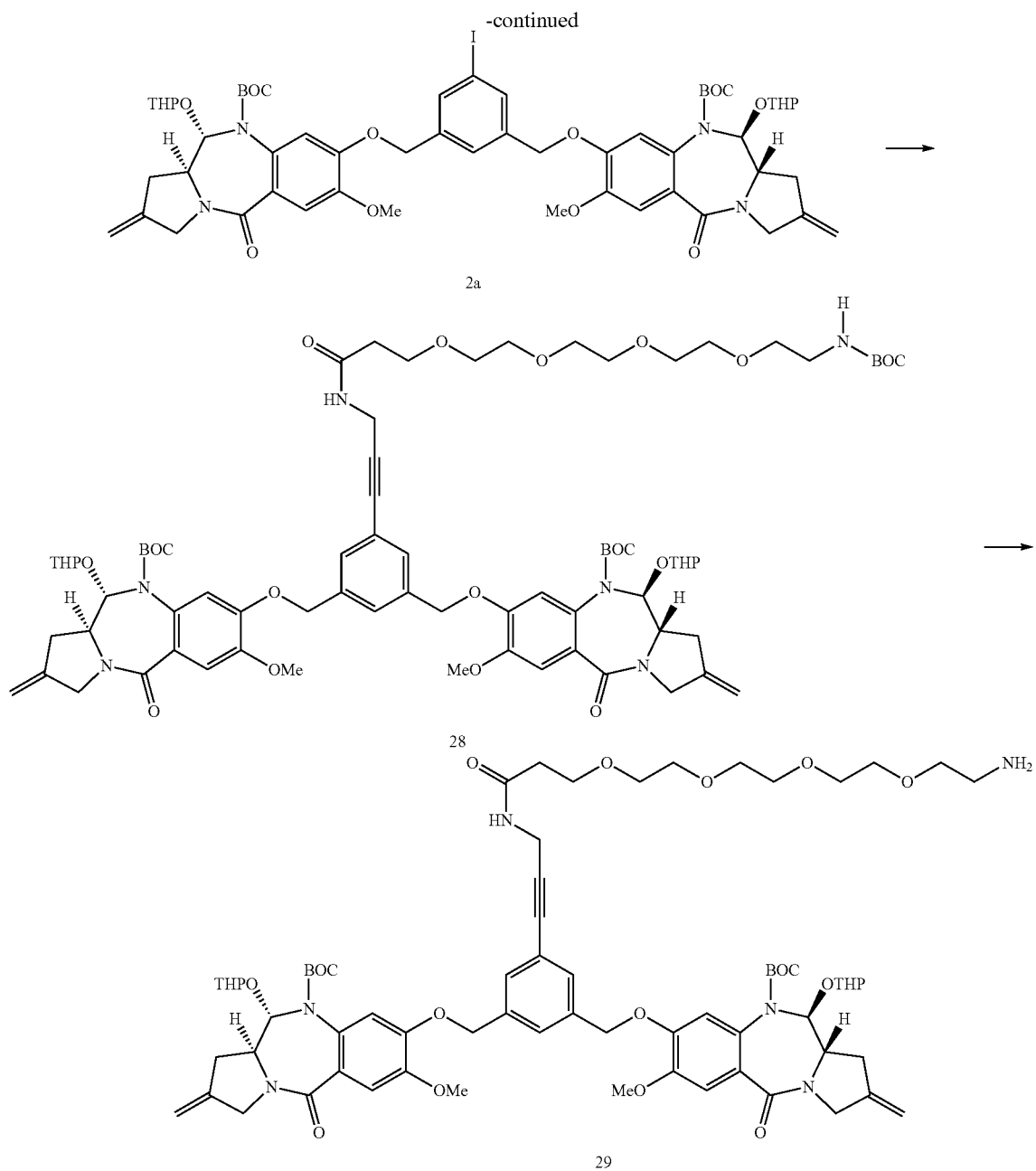

(i) tert-Butyl (15-oxo-3,6,9,12-tetraoxa-16-azanon-adec-18-yn-1-yl)carbamate (27)

EDCI (263 mg, 1.37 mmol) was added to a stirred solution of t-boc-N-amido-dPEG®₄-acid (26) (500 mg, 1.37 mmol, Stratech Scientific Limited) and propargylamine (88 μL, 76 mg, 1.37 mmol) in dry DCM (10 mL) at room temperature. The reaction mixture was stirred under an argon atmosphere for 16 hours at which point analysis by LC/MS showed a substantial amount of desired product at retention time 1.26 minutes (ES+) m/z 403 ([M+H]⁺, ~50% relative intensity), 425 ([M+Na]⁺, ~100% relative intensity), note that both starting material and product had weak UV absorption (214 and 254 nm) and were best detected on ES+TIC. The reaction mixture was diluted with DCM (100 mL) and washed with H₂O (30 mL), brine (40 mL), dried (MgSO₄), filtered and evaporated in vacuo to provide the crude product. Purification by flash chromatography (gradient elution in 1% increments: 100% DCM to 98:2 v/v DCM/MeOH) gave the amide 27 as an oil (392 mg, 71% yield).

(ii) Di-tert-butyl 8,8'-(((5-(2,2-dimethyl-4,20-dioxo-3,8,11,14,17-pentaoxa-5,21-diazatetracos-23-yn-24-yl)-1,3-phenylene)bis(methylene))bis(oxy))(11S, 11aS,11'S, 11a'S)-bis(7-methoxy-2-methylene-5-oxo-11-((tetrahydro-2H-pyran-2-yl)oxy)-2,3,11,11a-tetrahydro-H-pyrrolo[2,1-c][1,4]benzodiazepine-10 (5H)-carboxylate) (28)

A catalytic amount of Pd(PPh₃)₄ (23.0 mg, 19.5 μmol) was added to a mixture of the iodoaryl compound 2a (1.02 g, 0.89 mmol), Boc-acetylene 27 (393 mg, 0.98 mmol), CuI (7.4 mg, 39.1 μmol), diethylamine (2.02 mL, 1.43 g, 19.5 mmol) and oven-dried 4 Å molecular sieve pellets in dry DMF (9 mL) in an oven-dried sealable vessel. The mixture was degased and flushed with argon 3 times then heated in a microwave at 100° C. for 26 minutes at which point analysis by LC/MS revealed substantial product formation at retention time 1.89 minutes (ES+) m/z 1446 ([M+Na]+, ~100% relative intensity, 1424 ([M+H]+, ~15% relative intensity). The reaction mixture was allowed to cool to room temperature and was then filtered through a sinter to remove the sieves (washed with DMF). The filtrate was evaporated in vacuo and the resulting residue dissolved in DCM (100 mL) and washed with $H_2O$ (20 mL), brine (30 mL), dried ($MgSO_4$), filtered and evaporated in vacuo to give the crude product. Purification by flash chromatography (gradient elution in 1% increments: 100% DCM to 97:3 v/v DCM/MeOH) provided the alkyne 28 as a yellow foam (882 mg, 70% yield).

(iii) Di-tert-butyl 8,8'-(((5-(1-amino-15-oxo-3,6,9,12-tetraoxa-16-azanonadec-18-yn-19-yl)-1,3-phenylene)bis(methylene))bis(oxy))(11S,11aS,11'S,11a'S)-bis(7-methoxy-2-methylene-5-oxo-11-((tetrahydro-2H-pyran-2-yl)oxy)-2,3,11,11a-tetrahydro-1H-pyrrolo[2,1-c][1,4]benzo diazepine-10(5H)-carboxylate) (29)

TBDMSOTf (1.42 mL, 1.64 g, 6.2 mmol) was added to a stirred solution of the tri-Boc protected compound 28 (882 mg, 0.62 mmol) and 2,6-lutidine (0.96 mL, 883 mg, 8.25 mmol) in dry DCM (15 mL) at room temperature. The reaction mixture was allowed to stir under an argon atmosphere for 16 hours during which time analysis by LC/MS revealed formation of the TBS carbamate at retention time 2.09 minutes (ES+) m/z 1504 ([M+Na]+, ~100% relative intensity). The reaction mixture was diluted with DCM (60 mL) and washed with saturated $NH_4Cl$ (2×20 mL), $H_2O$ (20 mL), brine (30 mL), dried ($MgSO_4$), filtered and evaporated in vacuo to give the crude TBS carbamate. The product was re-dissolved in THF (15 mL) and treated with a solution of TBAF (744 μL of a 1.0M solution in THF, 0.744 mmol) at room temperature. The reaction mixture was allowed to stir for 1 hour at room temperature at which point analysis by LC/MS revealed substantial product formation at retention time 1.45 minutes (ES+) m/z 1324 ([M+H]+, ~60% relative intensity) along with product corresponding to 1 N10Boc/1 THP cleaved at retention time 1.29 minutes (ES+) m/z 1121 ([M+H]+, ~10% relative intensity), 1138 ([M++$H_2O$]+, ~20% relative intensity) and product corresponding to 2 N10 Boc/2 THP cleaved at retention time 1.12 minutes (ES+) m/z 919 ([M+H]+, ~2.5% relative intensity), 937 ([M+$H_2O$]+, ~3% relative intensity), 955 ([M+$2H_2O$]+, ~5% relative intensity). The THF was removed by evaporation in vacuo and the resulting residue re-dissolved in DCM (60 mL) and washed with saturated $NH_4Cl$ (2×20 mL), $H_2O$ (20 mL), brine (30 mL), dried ($MgSO_4$), filtered and evaporated in vacuo to give the key amine 29 as a pinkish foam.

(b) (R)-2-(pyridin-2-yldisulfanyl)propyl (19-(3,5-bis((((S)-7-methoxy-2-methylene-5-oxo-2,3,5,11a-tetrahydro-1H-pyrrolo[2,1-c][1,4]benzodiazepin-8-yl)oxy)methyl)phenyl)-15-oxo-3,6,9,12-tetraoxa-16-azanonadec-18-yn-1-yl)carbamate (33)

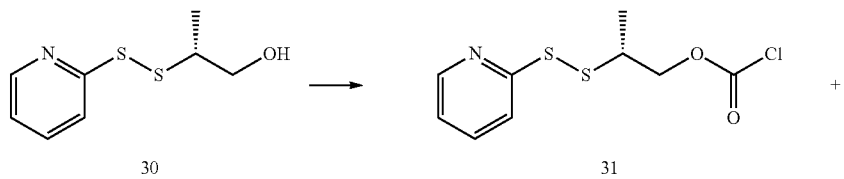

30

31

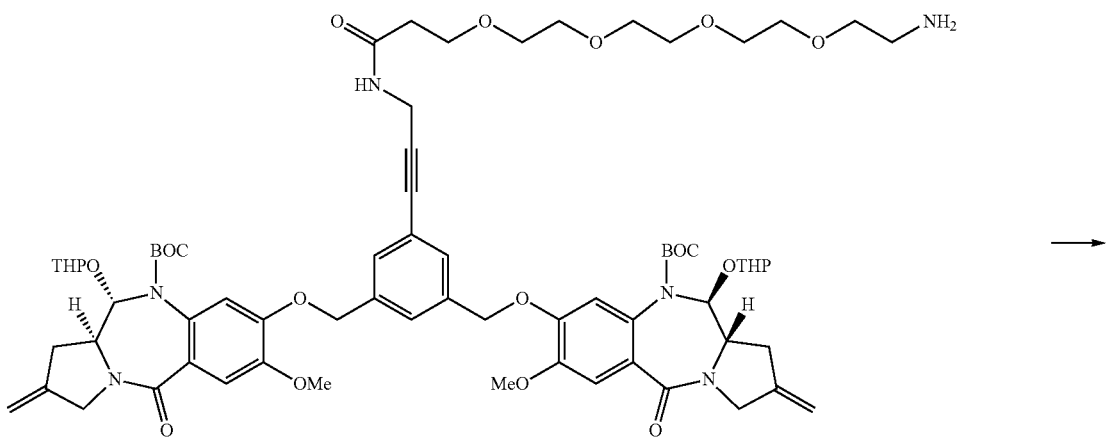

29

-continued

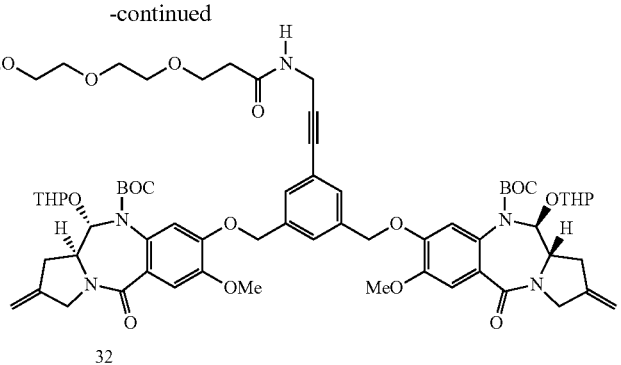

32

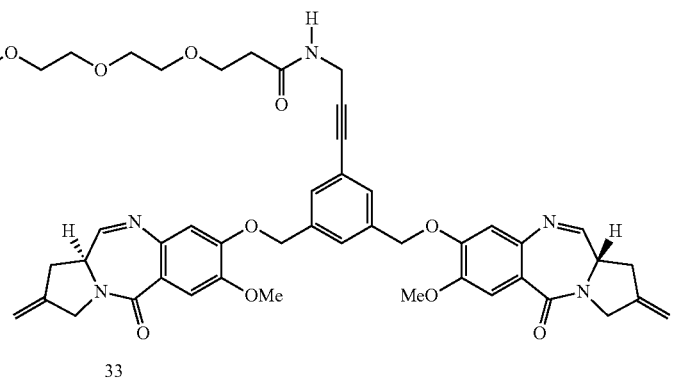

33

(i) (R)-2-(pyridin-2-yldisulfanyl)propyl carbonochloridate (31)

Triphosgene (9.36 mg, 31.5 µmol) was added to a stirred solution of (R)-2-(pyridin-2-yldisulfanyl)propan-1-ol (30) (18 mg, 0.09 mmol) and pyridine (6.7 µL, 6.6 mg, 0.08 mmol) in dry DCM (1 mL). The reaction mixture was allowed to stir under an argon atmosphere for 30 minutes after which time the solvent was removed by evaporation in vacuo to provide the crude chloroformate 31 as a white foam. Note: The product was carried through to the next step without purification or analysis.

(ii) Di-tert-butyl 8,8'-(((5-((R)-5,21-dioxo-2-(pyridin-2-yldisulfanyl)-4,9,12,15,18-pentaoxa-6,22-diazapentacos-24-yn-25-yl)-1,3-phenylene)bis(methylene))bis(oxy))(11S,11aS,11'S, 11a'S)-bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (32)

A solution of 31 (~23 mg, ~0.09 mmol) in dry DCM (1 mL) was added drop-wise to a stirred solution of amine 29 (~116 mg, ~0.09 mmol) and pyridine (7.8 µL, 7.7 mg, 0.1 mmol) in dry DCM (1 mL) at room temperature. The reaction mixture was allowed to stir under an argon atmosphere for 3 hours at which point analysis by LC/MS (Kinetex® column) revealed substantial product formation at retention time 2.02 minutes (ES+) m/z 1550 ([M+H]+, ~20% relative intensity) along with persistence of unreacted starting material 29 at retention time 1.51 minutes. The solvent was removed by evaporation in vacuo to provide the crude carbamate 32 which was carried through to the next step without further purification or analysis.

(iii) (R)-2-(pyridin-2-yldisulfanyl)propyl (19-(3,5-bis((((S)-7-methoxy-2-methylene-5-oxo-2,3,5,11a-tetrahydro-1H-pyrrolo[2,1-c][1,4]benzodiazepin-8-yl)oxy)methyl)phenyl)-15-oxo-3,6,9,12-tetraoxa-16-azanonadec-18-yn-1-yl)carbamate (33)

A solution of 95:5 v/v TFA/H$_2$O (1 mL) was added to a crude sample of the Boc/THP-protected compound 32 (~136 mg, 88 µmol) at 0° C. (ice/acetone). After stirring at 0° C. for 1 hour the reaction was deemed complete as judged by LC/MS (Kinetex® column), desired product peak at retention time 1.42 minutes (ES+) m/z 1146 ([M+H]+, ~90% relative intensity). The reaction mixture was kept cold and added drop-wise to a chilled saturated aqueous solution of NaHCO$_3$ (50 mL). The mixture was extracted with DCM (3×15 mL) and the combined organic layers washed with brine (20 mL), dried (MgSO$_4$), filtered and evaporated in vacuo to provide the crude product. Purification by flash chromatography (gradient elution: 100% CHCl$_3$ to 95:5 v/v CHCl$_3$/MeOH) gave 33 as a film (10 mg, 7% yield): LC/MS (15-minute run), retention time 5.79 minutes (ES+) m/z 1146 ([M+H]+, ~8% relative intensity); $^1$H NMR (400 MHz, CDCl$_3$) δ 8.44 (d, 1H, J=4.8 Hz), 7.75-7.58 (m, 2H), 7.66 (d, 2H, J=4.4 Hz), 7.52 (s, 2H), 7.45-7.40 (m, 3H), 7.08-7.05 (m, 1H), 6.95-6.85 (m, 1H), 6.79 (s, 2H), 5.43-5.41 (m, 1H), 5.23-5.09 (m, 8H), 4.30-4.23 (m, 6H), 4.19-4.10 (m, 4H), 3.97-3.94 (m, 2H), 3.96 (s, 6H), 3.91-3.85 (m, 2H), 3.75 (t, 2H, J=5.8 Hz), 3.66-3.58 (m, 8H), 3.52 (t, 2H, J=5.1 Hz), 3.34-3.30 (m, 2H), 3.23-3.08 (m, 3H), 2.96-2.90 (m, 2H), 2.52 (t, 2H, J=5.7 Hz), 1.31 (d, 3H, J=7.0 Hz).

Example 7

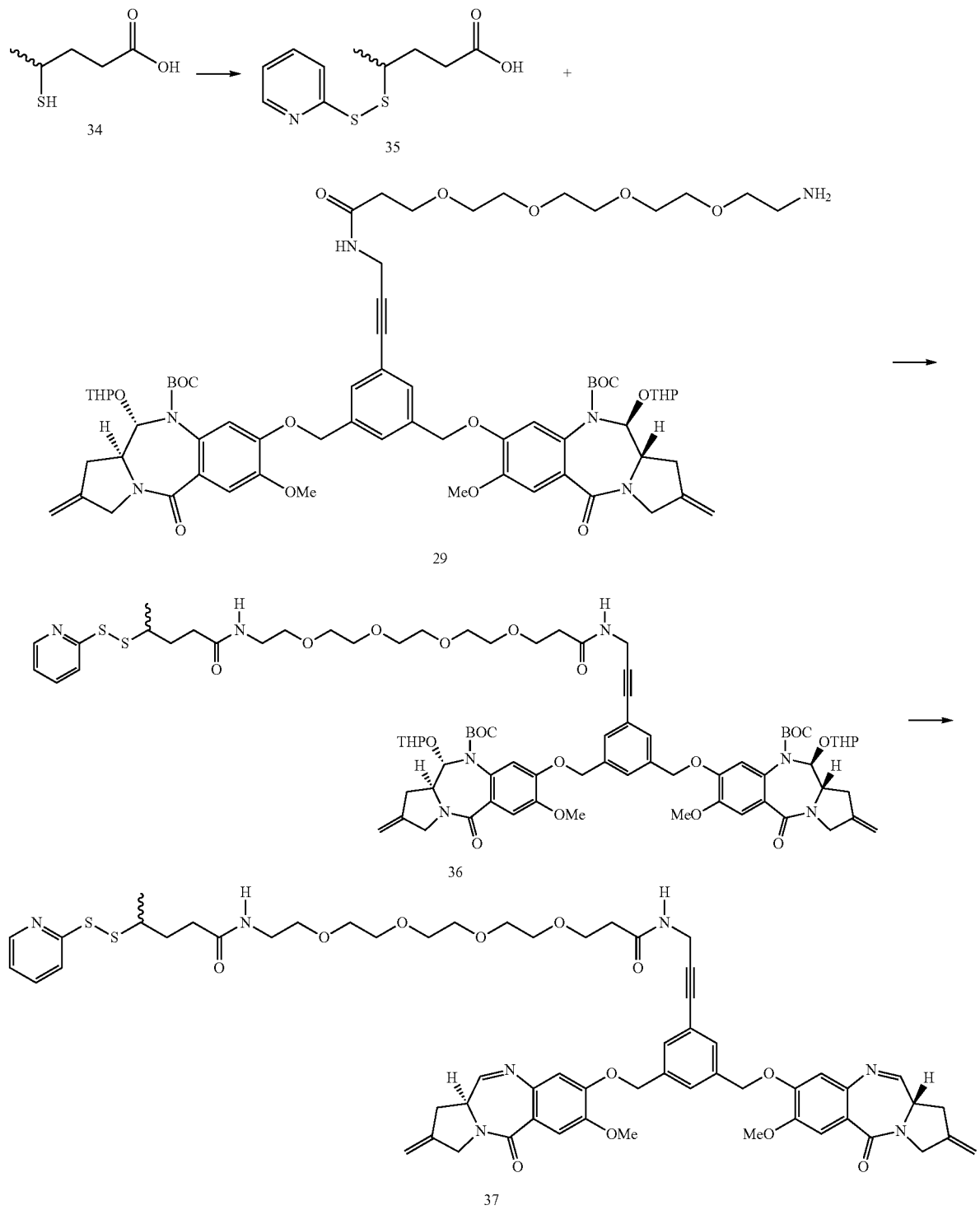

(a) (±)-4-(pyridin-2-yldisulfanyl)pentanoic acid (35)

Adrithiol™-2 (176 m, 0.86 mmol) was added to a stirred solution of (±)-4-mercaptopentanoic acid 34 (107 mg, 0.80 mmol, Aurora Fine Chemicals LLC) in EtOH (2 mL) at room temperature. The reaction mixture was allowed to stir for 16 hours under an argon atmosphere at which point analysis by LC/MS revealed substantial product formation at retention time 1.32 minutes (ES+) m/z 244 ([M+H]+, ~95% relative intensity). The solvent was removed by evaporation in vacuo and the resulting residue purified by flash chromatography (gradient elution: 90:10 v/v hexane/EtOAc to 80:20 v/v hexane/EtOAc) to give 35 as a white solid (92 mg, 47% yield).

(b) (±)-Di-tert-butyl 8,8'-(((5-(5,21-dioxo-24-(pyridin-2-yldisulfanyl)-8,11,14,17-tetraoxa-4,20-diazapentacos-1-yn-1-yl)-1,3-phenylene)bis(methylene))bis(oxy)) (11S,11aS,11'S, 11a'S)-bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (36)

EDCI (22 mg, 0.12 mmol) was added to a stirred solution of (±)-4-(pyridin-2-yldisulfanyl)pentanoic acid (35) (26 mg, 0.10 mmol) and amine 29 (~139 mg, 0.1 mmol) in dry DCM (2 mL) at room temperature. The reaction mixture was stirred under an argon atmosphere for 20 hours at which point analysis by LC/MS showed a substantial amount of desired product (split peak) at retention time 1.88 minutes (ES+) m/z 1548 ([M+H]$^+$, ~40% relative intensity) along with product corresponding to 1 N10Boc/1 THP cleaved at retention time 1.67 minutes (ES+) m/z 1346 ([M+H]$^+$, ~20% relative intensity), 1138 ([M+H$_2$O]$^+$, ~20% relative intensity) and product corresponding to 2 N10 Boc/2 THP cleaved at retention time 1.43 minutes (ES+ M+ not observed). The reaction mixture was diluted with DCM (30 mL) and washed with H$_2$O (15 mL), brine (20 mL), dried (MgSO$_4$), filtered and evaporated in vacuo to provide the crude product 36 as a foam.

(c) (±)-N-(3-(3,5-bis((((S)-7-methoxy-2-methylene-5-oxo-2,3,5,11a-tetrahydro-1H-pyrrolo[2,1-c][1,4]benzodiazepin-8-yl)oxy)methyl)phenyl)prop-2-yn-1-yl)-1-(4-(pyridin-2-yldisulfanyl)pentanamido)-3,6,9,12-tetraoxapentadecan-15-amide (37)

A solution of 95:5 v/v TFA/H$_2$O (1 mL) was added to a crude sample of the Boc/THP-protected compound 36 (~163 mg, 0.10 mmol) at 0° C. (ice/acetone). After stirring at 0° C. for 1 hour the reaction was deemed complete as judged by LC/MS, desired product peak at retention time 1.44 minutes (ES+) m/z 1144 ([M+H]$^+$, ~3% relative intensity). The reaction mixture was kept cold and added drop-wise to a chilled saturated aqueous solution of NaHCO$_3$ (60 mL). The mixture was extracted with DCM (3×30 mL) and the combined organic layers washed with brine (30 mL), dried (MgSO$_4$), filtered and evaporated in vacuo to provide the crude product. Purification by flash chromatography (gradient elution: 100% CHCl$_3$ to 96:4 v/v CHCl$_3$/MeOH) gave 37 as an orange foam (69 mg, 57% yield): LC/MS (15-minute run), retention time 5.72 minutes (ES+) m/z 1144 ([M+H]$^+$, ~3% relative intensity); $^1$H NMR (400 MHz, CDCl$_3$) δ 8.42 (d, 1H, J=4.3 Hz), 7.72-7.59 (m, 2H), 7.66 (d, 2H, J=4.3 Hz), 7.52 (s, 2H), 7.45-7.40 (m, 3H), 7.09-7.04 (m, 1H), 6.98-6.94 (m, 1H), 6.80 (s, 2H), 6.40-6.35 (m, 1H), 5.23-5.09 (m, 8H), 4.30-4.23 (m, 6H), 4.19-4.10 (m, 4H), 3.96 (s, 6H), 3.91-3.85 (m, 2H), 3.75 (t, 2H, J=5.7 Hz), 3.66-3.58 (m, 8H), 3.51 (t, 2H, J=5.0 Hz), 3.42-3.39 (m, 2H), 3.23-3.08 (m, 2H), 2.96-2.90 (m, 3H), 2.52 (t, 2H, J=5.6 Hz), 2.34 (t, 2H, J=7.4 Hz), 1.94 (q, 2H, J=7.4 Hz), 1.30 (d, 3H, J=6.7 Hz).

Example 8

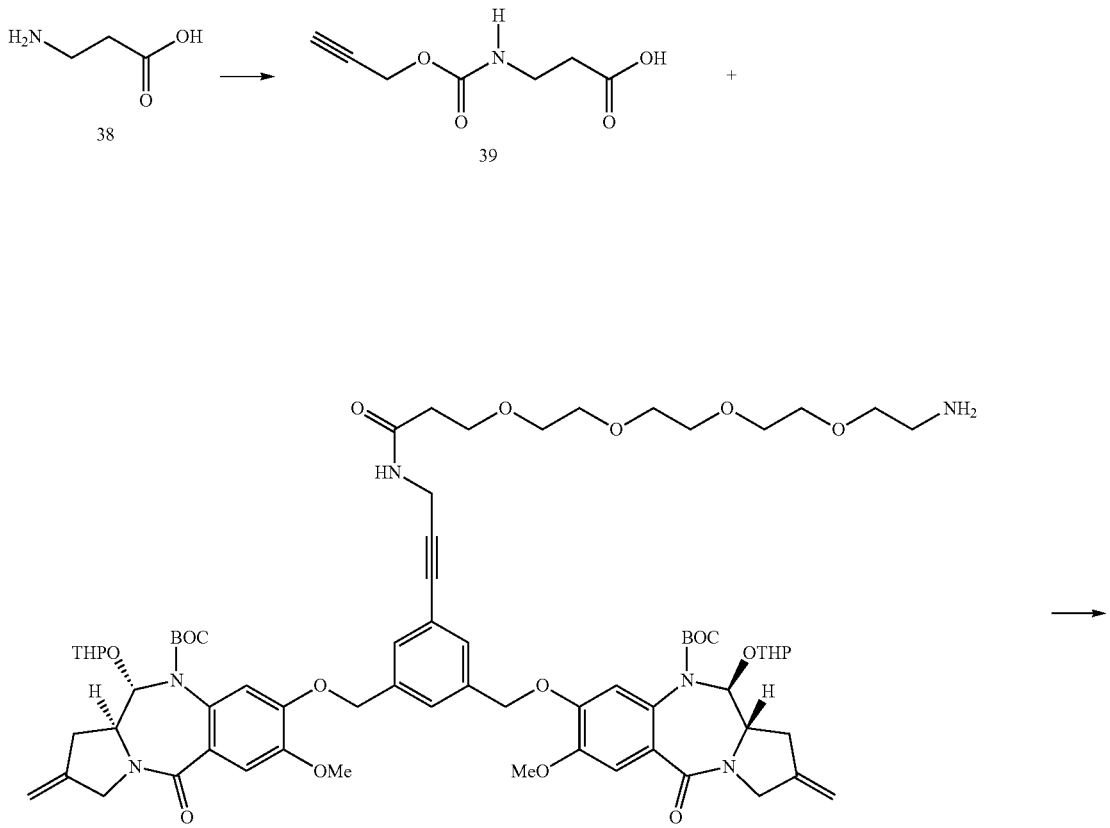

-continued

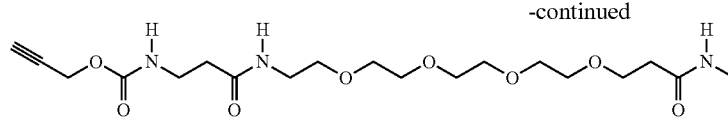
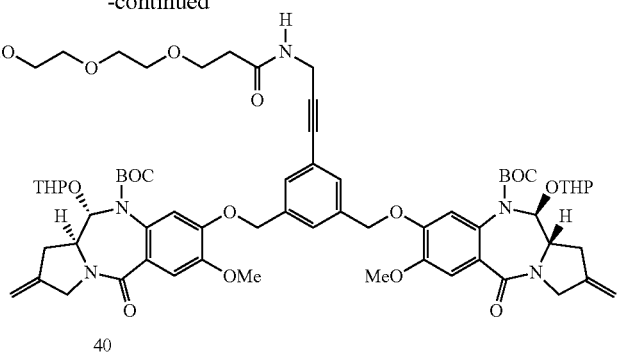

40

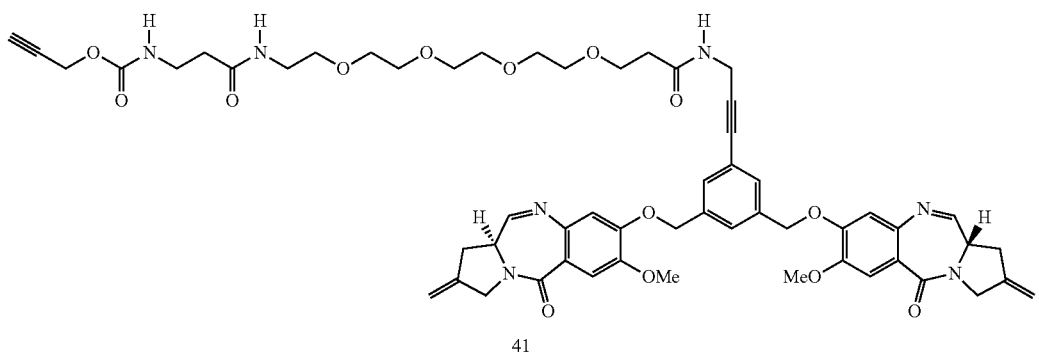

41

(a) 3-(((prop-2-yn-1-yloxy)carbonyl)amino)propanoic acid (39)

A solution of propargyl chloroformate (315 μL, 383 mg, 3.23 mmol) in toluene (2 mL) was added drop-wise to a stirred mixture of β-alanine (38) (250 mg, 2.81 mmol) and NaHCO$_3$ (678 mg, 8.1 mmol) in H$_2$O (7 mL) at room temperature. The reaction mixture was allowed to stir vigorously for 16 hours after which time it was partitioned. The aqueous layer was diluted with H$_2$O (20 mL), washed with Et$_2$O (4×10 mL), chilled to 0-5° C. (ice/acetone) and acidified to pH 2 with concentrated HCl. The acidic solution was extracted with EtOAc (3×20 mL) and the combined organic layers washed with H$_2$O (10 mL), brine (20 mL), dried (MgSO$_4$), filtered and evaporated in vacuo to provide the crude product 39 as an oil, which was carried through to the next step without further purification.

(b) Di-tert-butyl 8,8'-(((5-(5,9,25-trioxo-4, 13, 16, 19,22-pentaoxa-6,10,26-triazanonacosa-1,28-diyn-29-yl)-1,3-phenylene)bis(methylene))bis(oxy))(11S, 11aS,11'S,11a'S)-bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (40)

EDCI (24 mg, 0.13 mmol) was added to a stirred solution of 3-(((prop-2-yn-1-yloxy)carbonyl)amino)propanoic acid (39) (18 mg, 0.10 mmol) and amine 29 (~139 mg, 0.10 mmol) in dry DCM (3 mL) at room temperature. The reaction mixture was stirred under an argon atmosphere for 1.5 hours at which point analysis by LC/MS showed a substantial amount of desired product at retention time 1.84 minutes (ES+) m/z 1477 ([M+H]$^+$, ~20% relative intensity), 1499 ([M+Na]$^+$, ~22% relative intensity) along with product corresponding to 1 N10Boc/1 THP cleaved at retention time 1.60 minutes (ES+) m/z 1274 ([M+H]$^+$, ~10% relative intensity) and unreacted 5 at retention time 1.47 minutes (ES+) m/z 1324 ([M+H]$^+$, ~5% relative intensity). The reaction mixture was diluted with DCM (20 mL) and washed with H₂O (2×10 mL), brine (20 mL), dried (MgSO₄), filtered and evaporated in vacuo to provide the crude product 40 as a foam.

(c) Prop-2-yn-1-yl (23-(3,5-bis((((S)-7-methoxy-2-methylene-5-oxo-2,3,5,11a-tetrahydro-1H-pyrrolo[2,1-c][1,4]benzodiazepin-8-yl)oxy)methyl)phenyl)-3,19-dioxo-7,10,13,16-tetraoxa-4,20-diazatricos-22-yn-1-yl)carbamate (41)

A solution of 95:5 v/v TFA/H₂O (2 mL) was added to a crude sample of the Boc/THP-protected compound 40 (~155 mg, 0.10 mmol) at 0° C. (ice/acetone). After stirring at 0° C. for 1.5 hours the reaction was deemed complete as judged by LC/MS, desired product peak at retention time 1.41 minutes (ES+) m/z 1073 ([M+H]⁺, ~30% relative intensity). The reaction mixture was kept cold and added drop-wise to a chilled saturated aqueous solution of NaHCO₃ (60 mL). The mixture was extracted with DCM (3×20 mL) and the combined organic layers washed with brine (25 mL), dried (MgSO₄), filtered and evaporated in vacuo to provide the crude product. Purification by flash chromatography (gradient elution: 100% CHCl₃ to 95:5 v/v CHCl₃/MeOH) gave 41 as a yellow foam (51 mg, 45% yield): LC/MS (15-minute run), retention time 5.71 minutes (ES+) m/z 1073 ([M+H]⁺, ~30% relative intensity); ¹H NMR (400 MHz, CDCl₃) δ 7.67 (d, 2H, J=4.5 Hz), 7.52 (s, 2H), 7.46-7.43 (m, 3H), 7.07-7.02 (m, 1H), 6.80 (s, 2H), 6.64-6.57 (m, 1H), 5.78-5.72 (m, 1H), 5.21-5.09 (m, 8H), 4.64 (d, 2H, J=2.2 Hz), 4.29-4.25 (m, 6H), 3.96 (s, 6H), 3.90-3.85 (m, 2H), 3.76 (t, 2H, J=5.9 Hz), 3.65-3.35 (m, 18H), 3.16-3.07 (m, 2H), 2.93 (d, 2H, J=16 Hz), 2.52 (t, 2H, J=5.9 Hz), 2.48-2.45 (m, 1H), 2.40 (t, 2H, J=5.9 Hz).

Example 9

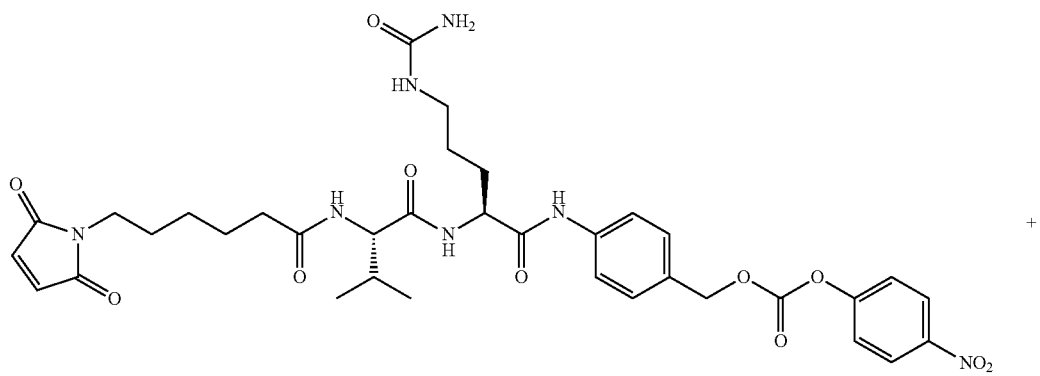

42

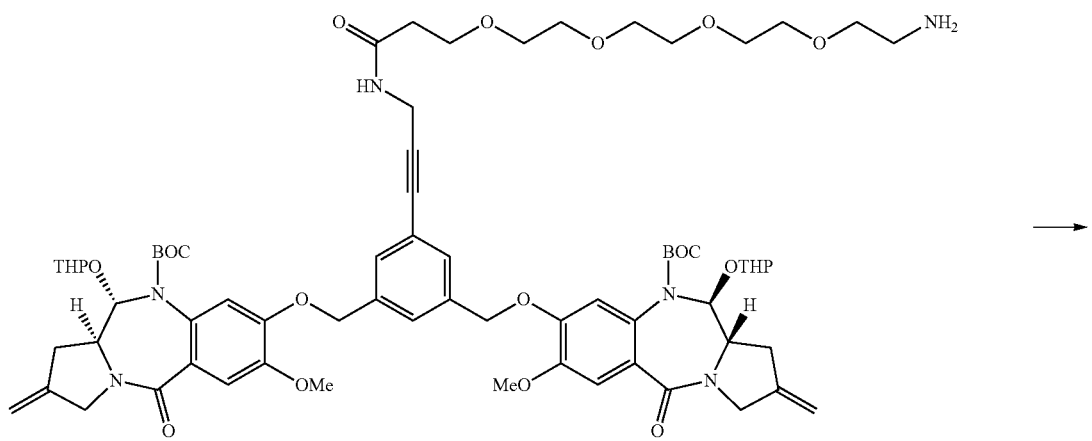

29

-continued

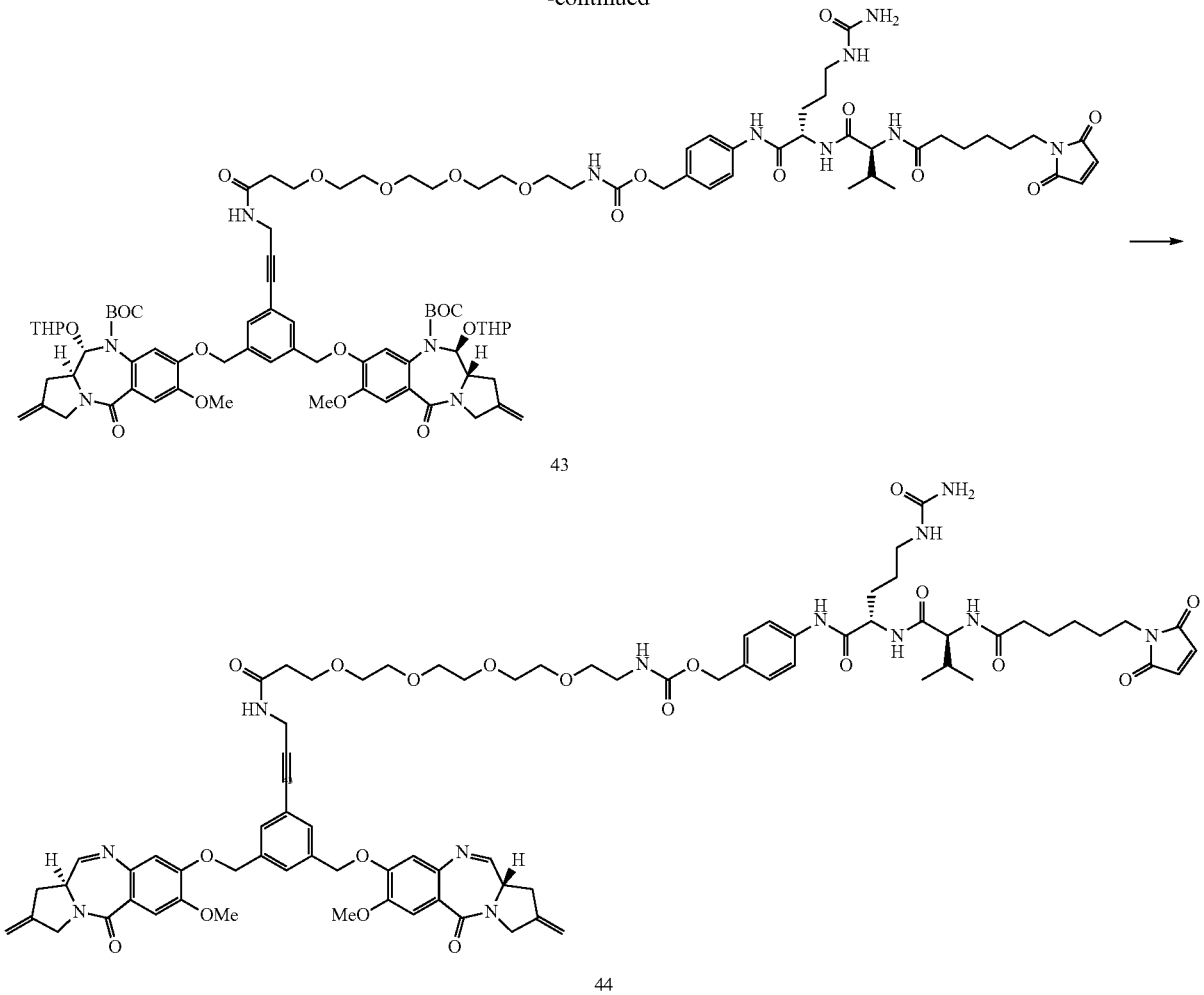

43

44

(a) Di-tert-butyl 8,8'-(((5-(1-(4-((S)-2-((S)-2-(6-(2,5-dioxo-2,5-dihydro-1H-pyrrol-1-yl)hexanamido)-3-methylbutanamido)-5-ureidopentanamido)phenyl)-3,19-dioxo-2,7,10,13,16-pentaoxa-4,20-diazatricos-22-yn-23-yl)-1,3-phenylene)bis(methylene))bis(oxy))(11S,11aS,11'S,11a')-bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (43)

DIPEA (44 µL, 32 mg, 0.25 mmol) was added to a stirred solution of key amine 29 (~155 mg, 0.11 mmol) and the nitrophenyl carbonate 42 (84 mg, 0.11 mmol) in dry DMF (3 mL) at room temperature. The reaction mixture was allowed to stir under an argon atmosphere for 3 days after which time analysis by LC/MS revealed desired product observed at retention time 1.80 minutes (ES+) m/z 1922 ([M+H]$^+$, ~40% relative intensity), 1944 ([M+Na]+$^+$, ~20% relative intensity) along with product corresponding to 1 N10Boc/1 THP cleaved at retention time 1.61 minutes (ES+) m/z 1720 ([M+H]$^+$, ~20% relative intensity). The DMF was removed by evaporation in vacuo and the resulting product 43 carried through to the next step without further purification or analysis.

(b) 4-((S)-2-((S)-2-(6-(2,5-dioxo-2,5-dihydro-1H-pyrrol-1-yl)hexanamido)-3-methylbutanamido)-5-ureidopentanamido)benzyl (19-(3,5-bis((((S)-7-methoxy-2-methylene-5-oxo-2,3,5,11a-tetrahydro-1H-pyrrolo[2,1-c][1,4]benzodiazepin-8-yl)oxy)methyl)phenyl)-15-oxo-3,6,9,12-tetraoxa-16-azanonadec-18-yn-1-yl)carbamate (44)

A solution of 95:5 v/v TFA/H$_2$O (3 mL) was added to a crude sample of the Boc/THP-protected compound 43 (~173 mg, 0.11 mmol) at 0° C. (ice/acetone). After stirring at 0° C. for 1.5 hours the reaction was deemed complete as judged by LC/MS, desired product peak at retention time 1.42 minutes (ES+) m/z 1518 ([M+H]$^+$, ~40% relative intensity). The reaction mixture was kept cold and added drop-wise to a chilled saturated aqueous solution of NaHCO$_3$ (100 mL). The mixture was extracted with DCM (3×30 mL) and the combined organic layers washed with brine (20 mL), dried (MgSO$_4$), filtered and evaporated in vacuo to provide the crude product. Purification by flash chromatography (gradient elution: 100% CHCl$_3$ to 80:20 v/v CHCl$_3$/MeOH) gave crude product as a yellow foam (72 mg, 42% crude yield). The material was further purified by preparative HPLC to provide pure 44 as a thin film (4.5 mg, 3% yield): LC/MS (15-minute run), retention time 5.44 minutes (ES+) m/z 1518 ([M+H]$^+$, ~30% relative intensity).

Example 10
(a) 1-(3-aminopropanamido)-N-(3-(3,5-bis((((S)-7-methoxy-2-methylene-5-oxo-2,3,5,11a-tetrahydro-1H-pyrrolo[2,1-c][1,4]benzodiazepin-8-yl)oxy)methyl)phenyl)prop-2-yn-1-yl)-3,6,9,12-tetraoxapentadecan-15-amide (47)
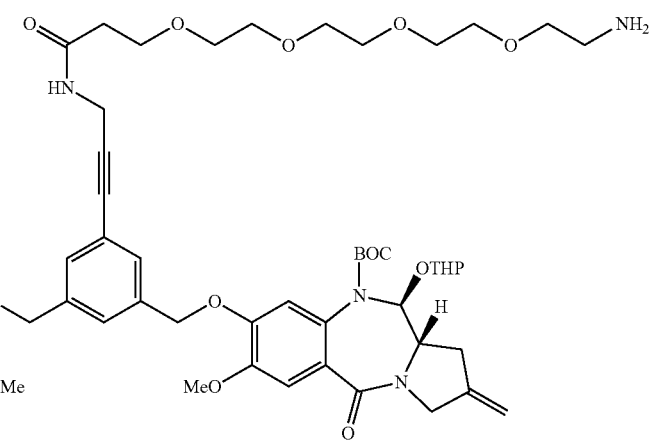
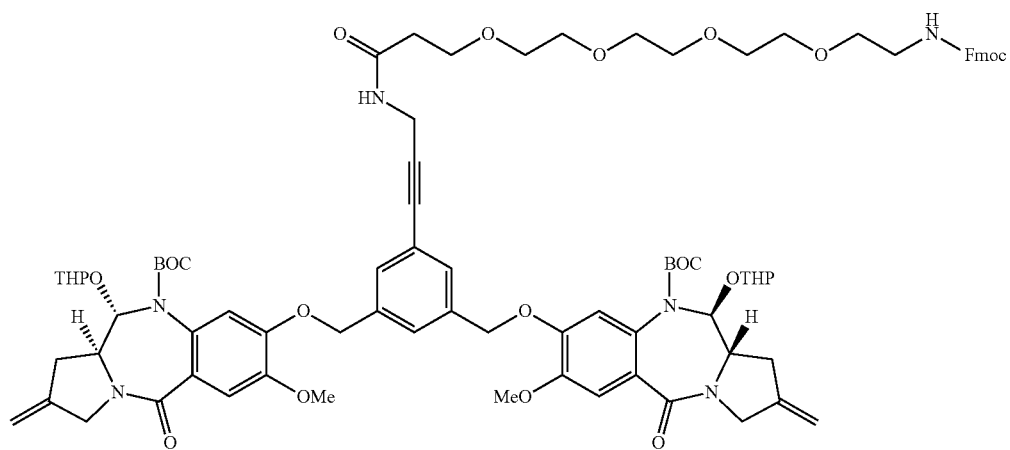

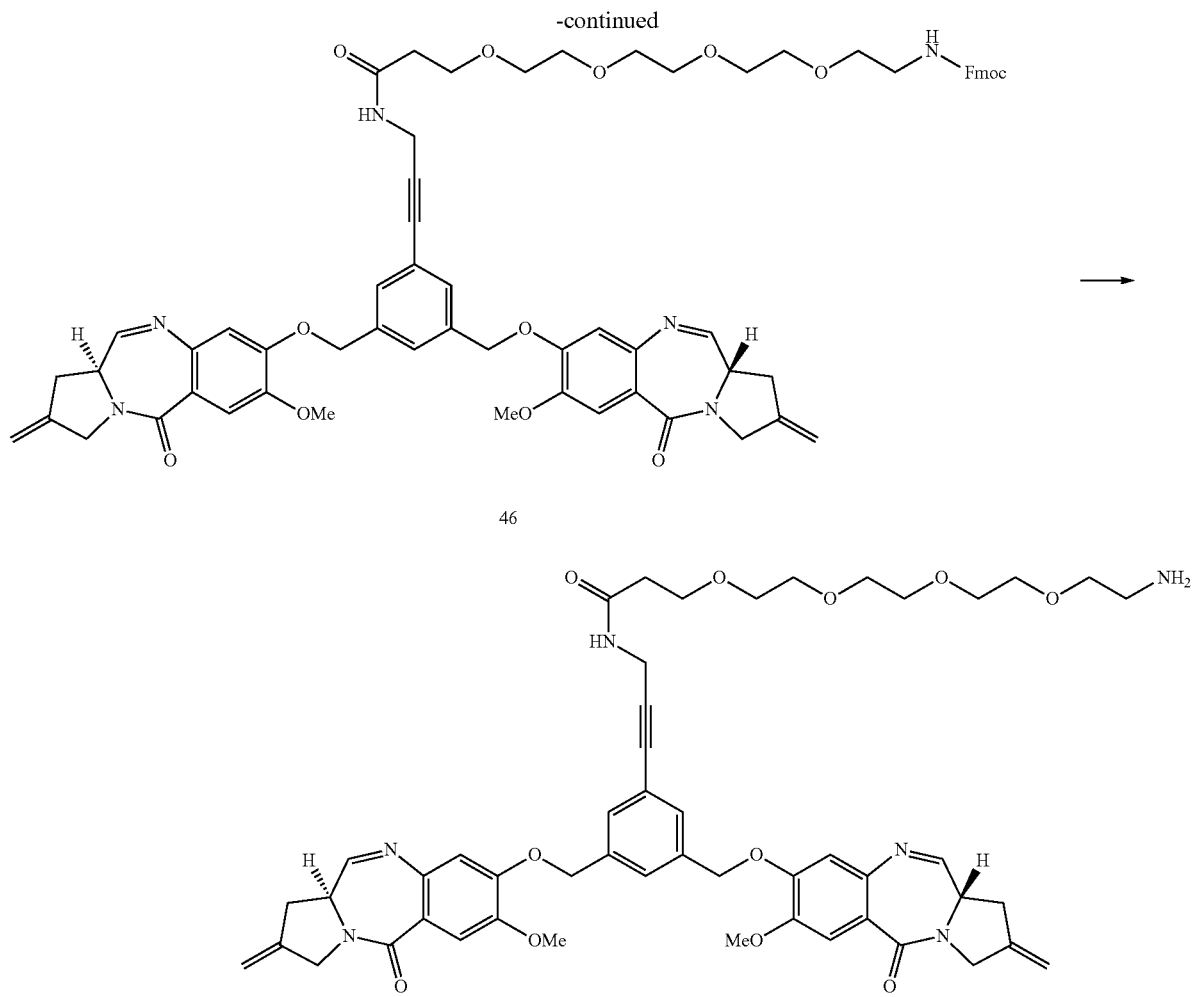

(i) Di-tert-butyl 8,8'-(((5-(1-(9H-fluoren-9-yl)-3,7,23-trioxo-2,11,14,17,20-pentaoxa-4,8,24-triazaheptacos-26-yn-27-yl)-1,3-phenylene)bis(methylene))bis(oxy))(11S,11aS,11'S, 11a'S)-bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (45)

EDCI (49 mg, 0.25 mmol) was added to a stirred solution of Fmoc-β-alanine (66 mg, 0.21 mmol) and amine 29 (~279 mg, 0.21 mmol) in dry DCM (5 mL) at room temperature. The reaction mixture was stirred under an argon atmosphere for 3 hours at which point analysis by LC/MS showed a substantial amount of desired product at retention time 1.76 minutes (ES+) m/z 1617 ([M+H]⁺, ~10% relative intensity), 1639 ([M+Na]⁺, ~80% relative intensity) along with product corresponding to 1 N10Boc/1 THP cleaved at retention time 1.56 minutes (ES+) m/z 1415 ([M+H]⁺, ~10% relative intensity). The reaction mixture was diluted with DCM (30 mL) and washed with H₂O (20 mL), brine (20 mL), dried (MgSO₄), filtered and evaporated in vacuo to provide the crude product 45 as a foam.

(ii) (9H-fluoren-9-yl)methyl (23-(3,5-bis((((S)-7-methoxy-2-methylene-5-oxo-2,3,5,11a-tetrahydro-1H-pyrrolo[2,1-c][1,4]benzodiazepin-8-yl)oxy)methyl)phenyl)-3,19-dioxo-7,10,13,16-tetraoxa-4,20-diazatricos-22-yn-1-yl)carbamate (46)

A solution of 95:5 v/v TFA/H₂O (4 mL) was added to a crude sample of the Boc/THP-protected compound 45 (~341 mg, 0.21 mmol) at 0° C. (ice/acetone). After stirring at 0° C. for 1 hour the reaction was deemed complete as judged by LC/MS, desired product peak at retention time 1.44 minutes (ES+) m/z 1212 ([M+H]⁺, ~30% relative intensity). The reaction mixture was kept cold and added drop-wise to a chilled saturated aqueous solution of NaHCO₃ (80 mL). The mixture was extracted with DCM (3×20 mL) and the combined organic layers washed with NaHCO₃ (2×20 mL), brine (20 mL), dried (MgSO₄), filtered and evaporated in vacuo to provide the crude product. Purification by flash chromatography (gradient elution: 100% CHCl₃ to 95:5 v/v CHCl₃/MeOH) gave pure product 46 as a yellow foam (179 mg, 70% yield).

(iii) 1-(3-aminopropanamido)-N-(3-(3,5-bis((((S)-7-methoxy-2-methylene-5-oxo-2,3,5,1a-tetrahydro-1H-pyrrolo[2,1-c][1,4]benzodiazepin-8-yl)oxy)methyl)phenyl)prop-2-yn-1-yl)-3,6,9,12-tetraoxapentadecan-15-amide (47)

Dimethylamine (735 µL of a 2.0M solution in THF, 1.47 mmol) was added to a stirred solution of the Fmoc protected compound 46 (89 mg, 73.5 µmol) in THF (3 mL) at room temperature. After stirring for 3 hours at room temperature, analysis by LC/MS revealed reaction completion with desired product at retention time 1.14 minutes (ES+) m/z 990 ([M+H]$^+$, ~8% relative intensity), 1008 ([M+H$_2$O]$^+$, ~10% relative intensity), 1026 ([M+2H$_2$O]$^+$, ~15% relative intensity) along with Fmoc cleavage by-product at retention time 1.88 minutes. The mixture was evaporated in vacuo and crude 47 was carried through to next step without further purification or analysis.

(b) N-(3-(3,5-bis((((S)-7-methoxy-2-methylene-5-oxo-2,3,5,11a-tetrahydro-1H-pyrrolo[2,1-c][1,4]benzodiazepin-8-yl)oxy)methyl)phenyl)prop-2-yn-1-yl)-1-(3-(2-bromoacetamido)propanamido)-3,6,9,12-tetraoxapentadecan-15-amide (48)

Bromoacetic anhydride (23 mg, 88.2 µmol) was added to a stirred solution of the crude amine 47 (~73 mg, 73.5 µmol) in DCM (3 mL). The reaction mixture was allowed to stir under an argon atmosphere at room temperature for 3 hours at which point analysis by LC/MS revealed completion of reaction with desired product observed at retention time 1.34 minutes (ES+) m/z 1112 ([M+H]$^+$, ~30% relative intensity). The solvent was removed by evaporation in vacuo to provide the crude product. Purification by flash chromatography (gradient elution: 100% CHCl$_3$ to 93:7 v/v CHCl$_3$/MeOH) gave the product as a yellow foam (38 mg, 46% crude yield). The material was further purified by preparative HPLC to provide pure 48 as a thin film (5 mg, 6% yield): LC/MS (15-minute run), retention time 4.96 minutes (ES+) m/z 1112 ([M+H]$^+$, ~10% relative intensity); $^1$H NMR (400 MHz, CDCl$_3$) δ 7.67 (d, 2H, J=4.4 Hz), 7.52 (s, 2H), 7.46-7.43 (m, 4H), 7.10-7.07 (m, 1H), 6.80 (s, 2H), 5.21-5.09 (m, 8H), 4.29-4.25 (m, 6H), 3.96 (s, 6H), 3.90-3.85 (m, 2H), 3.82 (s, 2H), 3.77 (t, 2H, J=5.9 Hz), 3.65-3.40 (m, 18H), 3.16-3.07 (m, 2H), 2.94 (d, 2H, J=16 Hz), 2.53 (t, 2H, J=5.9 Hz), 2.43 (t, 2H, J=5.9 Hz).

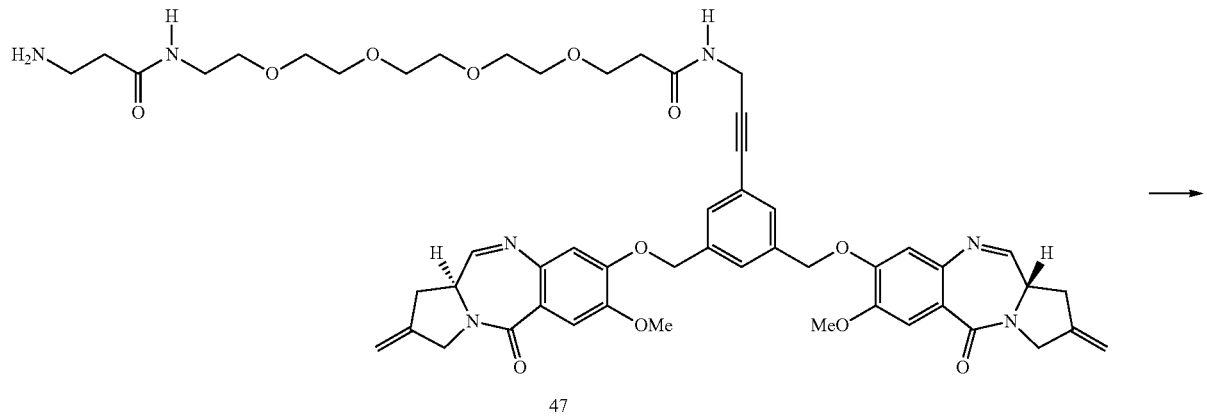

47

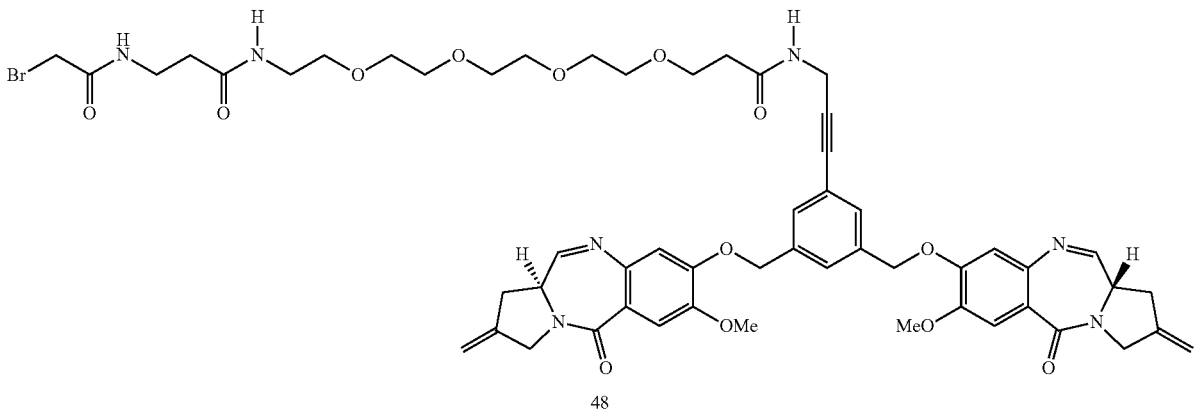

48

Example 11
Alternate Synthesis of 10
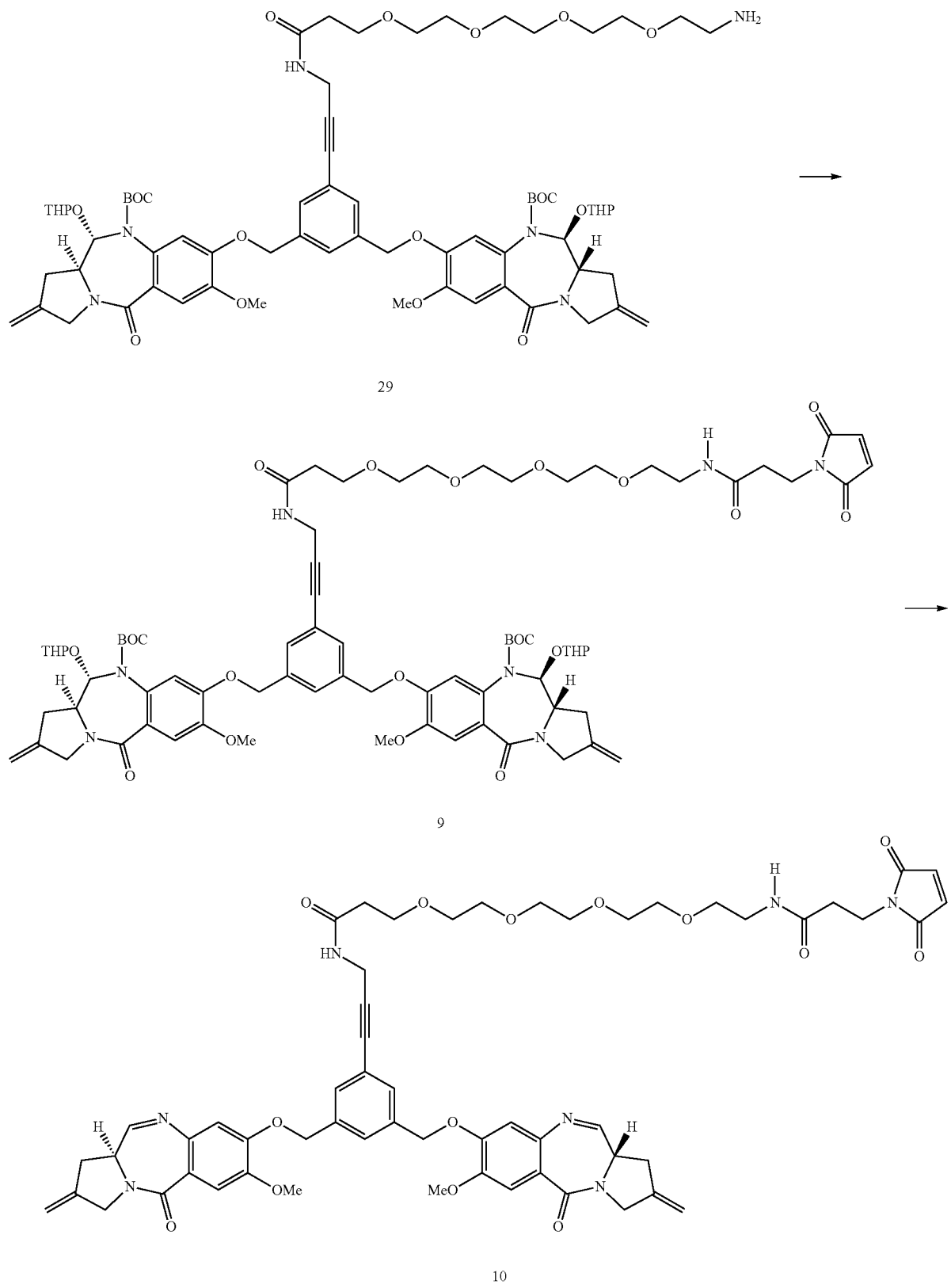

(a) di-tert-Butyl 8,8'-(((5-(1-(2,5-dioxo-2,5-dihydro-1H-pyrrol-1-yl)-3,19-dioxo-7,10,13,16-tetraoxa-4,20-diazatricos-22-yn-23-yl)-1,3-phenylene)bis(methylene))bis(oxy))(11S,11aS,11'S, 11a'S)-bis(7-methoxy-2-methylene-5-oxo-11-((tetrahydro-2H-pyran-2-yl)oxy)-2,3,11,11a-tetrahydro-1H-pyrrolo[2,1-c][1,4]benzodiazepine-10(5H)-carboxylate (9)

EDCI (61 mg, 0.32 mmol) was added to a stirred solution of N-maleoyl-β-alanine (53 mg, 0.32 mmol) and amine 29 (~418 mg, 0.32 mmol) in dry DCM (6 mL) at room temperature. The reaction mixture was stirred under an argon atmosphere for 3 hours at which point analysis by LC/MS showed a substantial amount of desired product at retention time 1.80 minutes (ES+) m/z 1474 ([M+H]$^+$, ~15% relative intensity), 1497 ([M+Na]$^+$, ~100% relative intensity), along with product corresponding to 1 N10Boc/1 THP cleaved at retention time 1.56 minutes 1272 ([M+H]$^+$, ~80% relative intensity), 1295 ([M+Na]$^+$, ~45% relative intensity) and product corresponding to 2 N10 Boc/2 THP cleaved at retention time 1.31 minutes (ES+ M+ not observed). The reaction mixture was diluted with DCM (30 mL) and washed with H$_2$O (15 mL), brine (20 mL), dried (MgSO$_4$), filtered and evaporated in vacuo to provide the crude product 9 as a foam.

(b) N-(3-(3,5-bis((((S)-7-methoxy-2-methylene-5-oxo-2,3,5,11a-tetrahydro-1H-pyrrolo[2,1-c][1,4]benzodiazepin-8-yl)oxy)methyl)phenyl)prop-2-yn-1-yl)-1-(3-(2,5-dioxo-2,5-dihydro-1H-pyrrol-1-yl)propanamido)-3,6,9,12-tetraoxapentadecan-15-amide (10)

A solution of 95:5 v/v TFA/H$_2$O (5 mL) was added to a crude sample of the Boc/THP-protected compound 9 (~466 mg, 0.32 mmol) at 0° C. (ice/acetone). After stirring at 0° C. for 1 hour the reaction was deemed complete as judged by LC/MS, desired product peak at retention time 1.32 minutes (ES+) m/z 1070 ([M+H]$^+$, ~100% relative intensity). The reaction mixture was kept cold and added drop-wise to a chilled saturated aqueous solution of NaHCO$_3$ (120 mL). The mixture was extracted with DCM (3×40 mL) and the combined organic layers washed with brine (50 mL), dried (MgSO$_4$), filtered and evaporated in vacuo to provide the crude product. Purification by flash chromatography (gradient elution: 100% CHCl$_3$ to 96:4 v/v CHCl$_3$/MeOH) gave 10 as an orange foam (202 mg, 60% yield): [α]$^{21}_D$=+351° (c=0.47, CHCl$_3$); LC/MS (15-minute run), retention time 4.88 minutes (ES+) m/z 1070 ([M+H]$^+$, ~100% relative intensity); $^1$H NMR (400 MHz, CDCl$_3$) δ 7.66 (d, 2H, J=4.4 Hz), 7.52 (s, 2H), 7.45-7.40 (m, 3H), 6.98-6.94 (m, 1H), 6.80 (s, 2H), 6.66 (s, 2H), 6.55-6.50 (m, 1H), 5.22-5.07 (m, 8H), 4.30-4.22 (m, 6H), 3.96 (s, 6H), 3.91-3.85 (m, 2H), 3.82 (t, 2H, J=7.2 Hz), 3.76 (t, 2H, J=5.8 Hz), 3.65-3.43 (m, 16H), 3.16-3.08 (m, 2H), 2.94 (d, 2H, J=15.7 Hz), 2.54-2.44 (m, 4H).

Reduction/Oxidation of ThioMabs for Conjugation

Full length, cysteine engineered monoclonal antibodies (ThioMabs—Junutula, et al., 2008b Nature Biotech., 26(8): 925-932; Dornan et al (2009) Blood 114(13):2721-2729; U.S. Pat. No. 7,521,541; U.S. Pat. No. 7,723,485; WO2009/052249, Shen et al (2012) Nature Biotech., 30(2):184-191; Junutula et al (2008) Jour of Immun. Methods 332:41-52) expressed in CHO cells were reduced with about a 20-40 fold excess of TCEP (tris(2-carboxyethyl)phosphine hydrochloride or DTT (dithiothreitol) in 50 mM Tris pH 7.5 with 2 mM EDTA for 3 hrs at 37° C. or overnight at room temperature. (Getz et al (1999) Anal. Biochem. Vol 273:73-80; Soltec Ventures, Beverly, Mass.). The reduced ThioMab was diluted and loaded onto a HiTrap S column in 10 mM sodium acetate, pH 5, and eluted with PBS containing 0.3M sodium chloride. Alternatively, the antibody was acidified by addition of $\frac{1}{20}^{th}$ volume of 10% acetic acid, diluted with 10 mM succinate pH 5, loaded onto the column and then washed with 10 column volumes of succinate buffer. The column was eluted with 50 mM Tris pH7.5, 2 mM EDTA.

The eluted reduced ThioMab was treated with 15 fold molar excess of DHAA (dehydroascorbic acid) or 200 nM aqueous copper sulfate (CuSO$_4$). Oxidation of the interchain disulfide bonds was complete in about three hours or more. Ambient air oxidation was also effective. The re-oxidized antibody was dialyzed into 20 mM sodium succinate pH 5, 150 mM NaCl, 2 mM EDTA and stored frozen at −20° C.

Conjugation of Thio-Mabs with Compounds to Prepare Antibody-Drug Conjugates

The deblocked, reoxidized, thio-antibodies (ThioMab) were reacted with 6-8 fold molar excess of compounds 7, 10, 13, 17, 24, 25, 33, 37, 44, 48 (from a DMSO stock at a concentration of 20 mM) in 50 mM Tris, pH 8, until the reaction was complete (16-24 hours) as determined by LC-MS analysis of the reaction mixture.

The crude antibody-drug conjugates (ADC) were then applied to a cation exchange column after dilution with 20 mM sodium succinate, pH 5. The column was washed with at least 10 column volumes of 20 mM sodium succinate, pH 5, and the antibody was eluted with PBS. The antibody drug conjugates were formulated into 20 mM H is/acetate, pH 5, with 240 mM sucrose using gel filtration columns. The antibody-drug conjugates were characterized by UV spectroscopy to determine protein concentration, analytical SEC (size-exclusion chromatography) for aggregation analysis and LC-MS before and after treatment with Lysine C endopeptidase.

Size exclusion chromatography was performed using a Shodex KW802.5 column in 0.2M potassium phosphate pH 6.2 with 0.25 mM potassium chloride and 15% IPA at a flow rate of 0.75 ml/min. Aggregation state of the conjugate was determined by integration of eluted peak area absorbance at 280 nm.

LC-MS analysis was performed using an Agilent QTOF 6520 ESI instrument. As an example, an antibody-drug conjugate generated using this chemistry was treated with 1:500 w/w Endoproteinase Lys C (Promega) in Tris, pH 7.5, for 30 min at 37° C. The resulting cleavage fragments were loaded onto a 1000A, 8 um PLRP-S column heated to 80° C. and eluted with a gradient of 30% B to 40% B in 5 minutes. Mobile phase A was H$_2$O with 0.05% TFA and mobile phase B was acetonitrile with 0.04% TFA. The flow rate was 0.5 ml/min. Protein elution was monitored by UV absorbance detection at 280 nm prior to electrospray ionization and MS analysis. Chromatographic resolution of the unconjugated Fc fragment, residual unconjugated Fab and drugged Fab was usually achieved. The obtained m/z spectra were deconvoluted using Mass Hunter™ software (Agilent Technologies) to calculate the mass of the antibody fragments.

| ADC Thio-conjugates with 7 | | | |
|---|---|---|---|
| Ab | ADC | DAR (drug to antibody ratio) | LCMS results |
| Thio Hu Anti-Her2 4D5-8 HC A118C | 110 | 1.8 | 23439.82 LC 51681.86 HC |

-continued

| ADC Thio-conjugates with 7 | | | |
|---|---|---|---|
| Ab | ADC | DAR (drug to antibody ratio) | LCMS results |
| Thio Hu Anti-Her2 4D5-8 HC A118C | 111 | 1.9 | |
| Thio hu anti-CD22 10F4v3 HC A118C | 115 | 1.8 | 24034.96 LC 51727.97 HC |

| ADC Thio-conjugates with 10 | | | |
|---|---|---|---|
| Ab | ADC | DAR (drug to antibody ratio) | LCMS results |
| Thio Hu Anti-Her2 4D5-8 HC A118C | 120 | 1.9 | 23440.18 LC 51697.51 HC |
| Thio Hu Anti-Her2 4D5-8 HC A118C | 121 | 1.9 | |
| Thio hu anti-CD22 10F4v3 HC A118C | 125 | 1.7 | 24035.14 LC 51744.95 HC |
| Thio Hu Anti-Her2 4D5-8 HC A118C | 201 | 1.8 | 23440.16 LC 51697.07 HC |
| Thio Hu Anti-Her2 4D5-8 HC A118C | 202 | 1.7 | 51698.55 HC |
| Thio Hu Anti-CD33 GM15.33 HC A118C | 203 | 1.6 | 23932.47 LC 51116.61 HC |
| Thio Hu Anti-LGR5 8E11.v2 HC A118C | 204 | 1.6 | 23956.85 LC 51432.43 HC |
| Thio Hu Anti-Napi3b 10H1.11.4B HC A118C | 205 | 1.4 | |
| Thio hu anti-CD22 10F4v3 HC A118C | 206 | 1.9 | |
| Thio Hu Anti-Her2 4D5-B HC 4118C | 207 | 2.0 | 48502 Fab |

| ADC Thio-conjugates with 13 | | | |
|---|---|---|---|
| Ab | ADC | DAR drug to antibody ratio) | LCMS results |
| Thio Hu Anti-Her2 4D5-8 HC A118C | 211 | 1.7 | |
| Thio Hu Anti-CD22 10F4v3 HC A118C | 212 | 1.7 | |
| Thio Hu Anti-CD33 GM15.33 HC A118C | 213 | 1.5 | 23934.64 LC 51210.40 HC |
| Thio Hu Anti-MUC16 3A5 HC A118C | 214 | 1.8 | 146970 ADC |

| ADC Thio-conjugates with 13 | | | |
|---|---|---|---|
| Ab | ADC | DAR drug to antibody ratio) | LCMS results |
| Thio Hu Anti-CD33 GM15.33 HC A118C | 215 | 1.6 | 147407 ADC |

| ADC Thio-conjugates with 17 | | | |
|---|---|---|---|
| Ab | ADC | DAR (drug to antibody ratio) | LCMS results |
| Thio Hu Anti-Her2 4D5-8 HC A118C | 130 | 1.8 | 23440.15 LC 51728.25 HC |
| Thio Hu Anti-Her2 4D5-8 HC A118C | 131 | 1.9 | 51727.48 HC |
| Thio Hu Anti-CD22 10F4v3 HC A118C | 135 | 1.8 | 23440.15 LC 51728.25 HC |
| Thio Hu Anti-CD22 10F4v3 HC A118C | 221 | 1.9 | 24035.11 LC 51774.92 HC |
| Thio Hu Anti-CD33 GM15.33 HC A118C | 222 | 1.7 | 23932.93 LC 51148.14 HC |
| Thio Hu Anti-Her2 4D5-8 HC A118C | 223 | 2.0 | |
| Thio Hu Anti-Her2 4D5-8 HC A118C | 224 | 0.9 | |

| ADC Thio-conjugates with 24 | | | |
|---|---|---|---|
| Ab | ADC | DAR (drug to antibody ratio) | LCMS results |
| Thio Hu Anti-CD33 GM15.33 HC A118C | | 1.3 | 23932.14 LC 51428.37 HC |
| Thio Hu Anti-MUC16 3A5 HC A118C | | 0.8 | 23479.80 LC 51645.56 HC |

| ADC Thio-conjugates with 25 | | | |
|---|---|---|---|
| Ab | ADC | DAR (drug to antibody ratio) | LCMS results |
| Thio Hu Anti-CD33 GM15.33 HC A118C | | 1.7 | 23933 LC 51431 HC |
| Thio Hu Anti-MUC16 3A5 HC A118C | | 1.7 | |

ADC Thio-conjugates with 33

| Ab | ADC | DAR (drug to antibody ratio) | LCMS results |
|---|---|---|---|
| Thio Hu Anti-CD33 GM15.33 HC A118C | | 1.5 | |
| Thio Hu Anti-Napi3b 10H1.11.4B HC A118C | | 1.4 | |

ADC Thio-conjugates with 37

| Ab | ADC | DAR (drug to antibody ratio) | LCMS results |
|---|---|---|---|
| Thio Hu Anti-CD33 GM15.33 HC A118C | | 1.4 | |
| Thio Hu Anti-Napi3b 10H1.11.4B HC A118C | | 1.6 | |

ADC Thio-conjugates with 44

| Ab | ADC | DAR (drug to antibody ratio) | LCMS results |
|---|---|---|---|
| Thio Hu anti-CD22 10F4v3 HC A118C | | 1.6 | |
| Thio Hu anti-CD33 15G15.3 HC A118C | | 1.6 | |

ADC Thio-conjugates with 48

| Ab | ADC | DAR (drug to antibody ratio) | LCMS results |
|---|---|---|---|
| Thio Hu Anti-Her2 4D5-8 HC A118C | | 1.9 | 147329 ADC |
| Thio Hu Anti-CD22 10F4v3 HC A118C | | 1.7 | |

The following in vitro and in vivo assays are also described in Phillips et al (2008) Cancer Res. 68(22):9280-9290.

In Vitro Cell Proliferation Assay

Efficacy of ADC were measured by a cell proliferation assay employing the following protocol (CellTiter Glo Luminescent Cell Viability Assay, Promega Corp. Technical Bulletin TB288; Mendoza et al (2002) Cancer Res. 62:5485-5488). All cell lines were obtained from American Type Culture Collection:

1. An aliquot of 100 μl of cell culture containing about $10^4$ cells (for example, KPL-4, a human breast cancer cell line, Kurebayashi et al (1999) Brit. Jour. Cancer 79(5-6):707-717), or SKBR-3) in medium was deposited in each well of a 96-well, opaque-walled plate.
2. Control wells were prepared containing medium and without cells.
3. ADC was added to the experimental wells and incubated for 3-5 days.
4. The plates were equilibrated to room temperature for approximately 30 minutes.
5. A volume of CellTiter-Glo Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.

Certain cells are seeded at 1000-2000/well or 2000-3000/well in a 96-well plate, 50 uL/well. After one or two days. ADC are added in 50 μL volumes to final concentration of 9000, 3000, 1000, 333, 111, 37, 12.4, 4.1, or 1.4 ng/mL, with "no ADC" control wells receiving medium alone. Conditions are in duplicate or triplicate After 3-5 days, 100 μL/well Cell TiterGlo II is added (luciferase-based assay; proliferation measured by ATP levels) and cell counts are determined using a luminometer. Data are plotted as the mean of luminescence for each set of replicates, with standard deviation error bars. The protocol is a modification of the CellTiter Glo Luminescent Cell Viability Assay (Promega):

1. Plate 1000 cells/well in 50 μL/well of FBS/glutamine media. Allow cells to attach overnight.
2. ADC is serially diluted 1:3 in media beginning at working concentration 18 μg/ml (this results in a final concentration of 9 μg/ml). 50 μL of diluted ADC is added to the 50 μL of cells and media already in the well.
3. Incubate 72-96 hrs (the standard is 72 hours, but watch the 0 ug/mL concentration to stop assay when the cells are 85-95% confluent).
4. Add 100 μL/well of Promega Cell Titer Glo reagent, shake 3 min. and read on luminometer Results Antibody-drug conjugates, trastuzumab-7 (110) trastuzumab-10 (120) and trastuzumab-17 (130) were tested against SK-BR-3, KPL-4, and MCF-7 (Levenson et al (1997) Cancer Res. 57(15):3071-3078) cells to measure in vitro cell viability in five day studies. The $IC_{50}$ value (ng/mL) for 110 against SK-BR-3 was 22.90. The $IC_{50}$ value for 120 against SK-BR-3 was 11.14. The $IC_{50}$ value for 130 against SK-BR-3 was 16.8. SK-BR-3 cells are HER2+ expressing, trastuzumab sensitive. 110, 120 and 130 were effectively inactive against MCF-7, which is a HER2 non-expressing human breast adenocarcinoma cell line. Thus, conjugates 110, 120 and 130 demonstrate targeted cell killing potency.

Tumor Growth Inhibition, In Vivo Efficacy in High Expressing HER2 Transgenic Explant Mice Animals suitable for transgenic experiments can be obtained from standard commercial sources such as Taconic (Germantown, N.Y.). Many strains are suitable, but FVB female mice are preferred because of their higher susceptibility to tumor formation. FVB males were used for mating and vasectomized CD.1 studs were used to stimulate pseudopregnancy. Vasectomized mice can be obtained from any commercial supplier. Founders were bred with either FVB mice or with 129/BL6xFVB p53 heterozygous mice. The mice with heterozygosity at p53 allele were used to potentially increase tumor formation. However, this has proven unnecessary. Therefore, some F1 tumors are of mixed strain. Founder tumors are FVB only. Six founders were obtained with some developing tumors without having litters.

Animals having tumors (allograft propagated from Fo5 mmtv transgenic mice) were treated with a single or multiple dose by IV injection of ADC. Tumor volume was assessed at various time points after injection.

Tumors arise readily in transgenic mice that express a mutationally activated form of neu, the rat homolog of HER2, but the HER2 that is overexpressed in human breast cancers is not mutated and tumor formation is much less robust in transgenic mice that overexpress nonmutated HER2 (Webster et al (1994) *Semin. Cancer Biol.* 5:69-76).

To improve tumor formation with nonmutated HER2, transgenic mice were produced using a HER2 cDNA plasmid in which an upstream ATG was deleted in order to prevent initiation of translation at such upstream ATG codons, which would otherwise reduce the frequency of translation initiation from the downstream authentic initiation codon of HER2 (for example, see Child et al (1999) *J. Biol. Chem.* 274: 24335-24341). Additionally, a chimeric intron was added to the 5' end, which should also enhance the level of expression as reported earlier (Neuberger and Williams (1988) *Nucleic Acids Res.* 16:6713; Buchman and Berg (1988) *Mol. Cell. Biol.* 8:4395; Brinster et al (1988) *Proc. Natl. Acad. Sci. USA* 85:836). The chimeric intron was derived from a Promega vector, Pci-neo mammalian expression vector (bp 890-1022). The cDNA 3'-end is flanked by human growth hormone exons 4 and 5, and polyadenylation sequences. Moreover, FVB mice were used because this strain is more susceptible to tumor development. The promoter from MMTV-LTR was used to ensure tissue-specific HER2 expression in the mammary gland. Animals were fed the AIN 76A diet in order to increase susceptibility to tumor formation (Rao et al (1997) *Breast Cancer Res. and Treatment* 45:149-158).

Fo5 Murine Mammary Tumor Model

The Fo5 model is a transgenic mouse model in which the human HER2 gene, under transcriptional regulation of the murine mammary tumor virus promoter (MMTV-HER2), is overexpressed in mammary epithelium. The overexpression causes spontaneous development of mammary tumors that overexpress the human HER2 receptor. The mammary tumor of one of the founder animals (founder #5 [Fo5]) has been propagated in subsequent generations of FVB mice by serial transplantation of tumor fragments. Before being used for an in vivo efficacy study, the MMTV-HER2Fo5 transgenic mammary tumor was surgically transplanted into the No. 2/3 mammary fat pad of nu/nu mice (from Charles River Laboratories) in fragments that measured approximately 2×2 mm. When tumors reached desired volumes, the tumor-bearing mice were randomized and given a single dose by IV injection of the ADC.

Results

FIG. 1 shows a plot of the in vivo mean tumor volume change over time in breast cancer-model MMTV-HER2Fo5 mammary allograft tumors inoculated into CRL nu/nu mice after single iv dosing on day 0 with: (1) Vehicle 20 mM Histidine acetate, pH 5.5, 240 mM sucrose, (2) xCD22-7 (115) at 6 mg/kg, (3) trastuzumab-7 (110) at 1 mg/kg, (4) trastuzumab-7 (110) at 3 mg/kg, and (5) trastuzumab-7 (110) at 6 mg/kg. The lines in the figure are indicated with the following symbols:
—✕— Vehicle
—⊖— ADC110 Tmab-7 HC A118C, 1 mg/kg
—▲— ADC110 Tmab-7 HC A118C, 3 mg/kg
—☐— ADC110 Tmab-7 HC A118C, 6 mg/kg
--▼-- ADC115 CD22-7 HC A118C, 6 mg/kg FIG. 2 shows a plot of the in vivo mean tumor volume change over time in breast cancer-model MMTV-HER2Fo5 mammary allograft tumors inoculated into CRL nu/nu mice after single IV dosing on day 0 with: (1) Vehicle 20 mM Histidine acetate, pH 5.5, 240 mM sucrose, (2) xCD22-10 (125) at 3 mg/kg, (3) trastuzumab-10 (120) at 0.3 mg/kg, (4) trastuzumab-10 (120) at 1 mg/kg, and (5) trastuzumab-10 (120) at 3 mg/kg. The lines in the figure are indicated with the following symbols:
—✕— Vehicle
—⊖— ADC20 Tmab-10 HC A118C, 0.3 mg/kg
—◆— ADC120 Tmab-10 HC A118C, 1 mg/kg
—■— ADC120 Tmab-10 HC A118C, 3 mg/kg
--▼-- ADC125 CD22 HC A118C, 3 mg/kg FIG. 3 shows a plot of the in vivo mean tumor volume change over time in breast cancer-model MMTV-HER2Fo5 mammary allograft tumors inoculated into CRL nu/nu mice after single iv dosing on day 0 with: (1) Vehicle 20 mM Histidine acetate, pH 5.5, 240 mM sucrose, (2) xCD22-17 (135) at 3 mg/kg, (3) trastuzumab-17 (130) at 0.3 mg/kg, (4) trastuzumab-17 (130) at 1 mg/kg, and (5) trastuzumab-17 (130) at 3 mg/kg. The lines in the figure are indicated with the following symbols:
—✕— Vehicle
—▲— ADC130 Tmab-17 HC A118C, 0.3 mg/kg
—○— ADC130 Tmab-17 HC A118C, 1 mg/kg
—☐— ADC130 Tmab-17 HC A 118C, 3 mg/kg
--✦-- ADC135 CD22 HC A118C, 3 mg/kg Abbreviations
Ac acetyl
Acm acetamidomethyl
Alloc allyloxycarbonyl
Boc di-tert-butyl dicarbonate
t-Bu tert-butyl
Bzl benzyl, where Bzl-OMe is methoxybenzyl and Bzl-Me is methylbenzene
Cbz or Z benzyloxy-carbonyl, where Z—Cl and Z—Br are chloro- and bromobenzyloxy carbonyl respectively
DMF N,N-dimethylformamide
Dnp dinitrophenyl
DTT dithiothreitol
Fmoc 9H-fluoren-9-ylmethoxycarbonyl
imp N-10 imine protecting group: 3-(2-methoxyethoxy) propanoate-Val-Ala-PAB
MC-OSu maleimidocaproyl-O—N-succinimide
Moc methoxycarbonyl
MP maleimidopropanamide
Mtr 4-methoxy-2,3,6-trimethylbenzenesulfonyl
PAB para-aminobenzyloxycarbonyl
PEG ethyleneoxy
PNZ p-nitrobenzyl carbamate
Psec 2-(phenylsulfonyl)ethoxycarbonyl
TBDMS tert-butyldimethylsilyl
TBDPS tert-butyldiphenylsilyl
Teoc 2-(trimethylsilyl)ethoxycarbonyl
Tos tosyl
Troc 2,2,2-trichloroethoxycarbonyl chloride
Trt trityl
Xan xanthyl

REFERENCES

The following references are incorporated by reference in their entirety:
EP 0522868
EP 0875569

EP 1295944
EP 1347046
EP 1394274
EP 1394274
EP 1439393
JP 05003790
JP 2004113151
JP 58180487
US 2001/055751
US 2002/034749
US 2002/042366
US 2002/150573
US 2002/193567
US 2003/0228319
US 2003/060612
US 2003/064397
US 2003/065143
US 2003/091580
US 2003/096961
US 2003/105292
US 2003/109676
US 2003/118592
US 2003/119121
US 2003/119122
US 2003/119125
US 2003/119126
US 2003/119128
US 2003/119129
US 2003/119130
US 2003/119131
US 2003/124140
US 2003/124579
US 2003/129192
US 2003/134790-A1
US 2003/143557
US 2003/157089
US 2003/165504
US 2003/185830
US 2003/186372
US 2003/186373
US 2003/194704
US 2003/206918
US 2003/219806
US 2003/224411
US 2003/224454
US 2003/232056
US 2003/232350
US 20030096743
US 20030130189
US 2003096743
US 2003130189
US 2004/0001827
US 2004/005320
US 2004/005538
US 2004/005563
US 2004/005598
US 2004/0101899
US 2004/018553
US 2004/022727
US 2004/044179
US 2004/044180
US 2004/101874
US 2004/197325
US 2004/249130
US 20040018194
US 20040052793
US 20040052793
US 20040121940
US 2005/271615
US 2006/116422
U.S. Pat. No. 4,816,567
U.S. Pat. No. 5,362,852
U.S. Pat. No. 5,440,021
U.S. Pat. No. 5,583,024
U.S. Pat. No. 5,621,002
U.S. Pat. No. 5,644,033
U.S. Pat. No. 5,674,713
U.S. Pat. No. 5,700,670
U.S. Pat. No. 5,773,223
U.S. Pat. No. 5,792,616
U.S. Pat. No. 5,854,399
U.S. Pat. No. 5,869,445
U.S. Pat. No. 5,976,551
U.S. Pat. No. 6,011,146
U.S. Pat. No. 6,153,408
U.S. Pat. No. 6,214,345
U.S. Pat. No. 6,218,519
U.S. Pat. No. 6,268,488
U.S. Pat. No. 6,518,404
U.S. Pat. No. 6,534,482
U.S. Pat. No. 6,555,339
U.S. Pat. No. 6,602,677
U.S. Pat. No. 6,677,435
U.S. Pat. No. 6,759,509
U.S. Pat. No. 6,835,807
U.S. Pat. No. 7,223,837
U.S. Pat. No. 7,375,078
U.S. Pat. No. 7,521,541
U.S. Pat. No. 7,723,485
WO 00/012508
WO 00/12507
WO 00/12508
WO 01/16318
WO 01/45746
WO 02/088172
WO 03/026577
WO 03/043583
WO 04/032828
WO 2000/12130
WO 2000/14228
WO 2000/20579
WO 2000/22129
WO 2000/32752
WO 2000/36107
WO 2000/40614
WO 2000/44899
WO 2000/55351
WO 2000/75655
WO 200053216
WO 2001/00244
WO 2001/38490
WO 2001/40269
WO 2001/40309
WO 2001/41787
WO 2001/46232
WO 2001/46261
WO 2001/48204
WO 2001/53463
WO 2001/57188
WO 2001/62794
WO 2001/66689
WO 2001/72830
WO 2001/72962
WO 2001/75177

WO 2001/77172
WO 2001/88133
WO 2001/90304
WO 2001/94641
WO 2001/98351
WO 2002/02587
WO 2002/02624
WO 2002/06317
WO 2002/06339
WO 2002/101075
WO 2002/10187
WO 2002/102235
WO 2002/10382
WO 2002/12341
WO 2002/13847
WO 2002/14503
WO 2002/16413
WO 2002/16429
WO 2002/22153
WO 2002/22636
WO 2002/22660
WO 2002/22808
WO 2002/24909
WO 2002/26822
WO 2002/30268
WO 2002/38766
WO 2002/54940
WO 2002/59377
WO 2002/60317
WO 2002/61087;
WO 2002/64798
WO 2002/71928
WO 2002/72596
WO 2002/78524
WO 2002/81646
WO 2002/83866
WO 2002/86443
WO 2002/88170
WO 2002/89747
WO 2002/92836
WO 2002/94852
WO 2002/98358
WO 2002/99074
WO 2002/99122
WO 2003/000842
WO 2003/002717
WO 2003/003906
WO 2003/003984
WO 2003/004989
WO 2003/008537
WO 2003/009814
WO 2003/014294
WO 2003/016475
WO 2003/016494
WO 2003/018621
WO 2003/022995
WO 2003/023013
WO 2003/024392
WO 2003/025138
WO 2003/025148
WO 2003/025228
WO 2003/026493
WO 2003/029262
WO 2003/029277
WO 2003/029421
WO 2003/034984
WO 2003/035846
WO 2003/042661
WO 2003/045422
WO 2003/048202
WO 2003/054152
WO 2003/055439
WO 2003/055443
WO 2003/062401
WO 2003/062401
WO 2003/072035
WO 2003/072036
WO 2003/077836
WO 2003/081210
WO 2003/083041
WO 2003/083047
WO 2003/083074
WO 2003/087306
WO 2003/087768
WO 2003/088808
WO 2003/089624
WO 2003/089904
WO 2003/093444
WO 2003/097803
WO 2003/101283
WO 2003/101400
WO 2003/104270
WO 2003/104275
WO 2003/105758
WO 2003004529
WO 2003042661
WO 2003104399
WO 2004/000997
WO 2004/001004
WO 2004/009622
WO 2004/011611
WO 2004/015426
WO 2004/016225
WO 2004/020595
WO 2004/022709
WO 2004/022778
WO 2004/027049
WO 2004/031238
WO 2004/032828
WO 2004/032842
WO 2004/040000
WO 2004/043361
WO 2004/043963
WO 2004/044178
WO 2004/045516
WO 2004/045520
WO 2004/045553
WO 2004/046342
WO 2004/047749
WO 2004/048938
WO 2004/053079
WO 2004/063355
WO 2004/063362
WO 2004/063709
WO 2004/065577
WO 2004/074320
WO 2004000221
WO 2004020583
WO 2004042346
WO 2004065576
WO 2005/023814
WO 2005/082023
WO 2005/085251
WO 2006/111759

WO 2007/044515
WO 2007/085930
WO 2009/052249
WO 2010/091150
WO 91/02536
WO 92/07574
WO 92/17497
WO 94/10312
WO 94/28931
WO 9630514
WO 97/07198
WO 97/44452
WO 98/13059
WO 98/37193
WO 98/40403
WO 98/51805
WO 98/51824
WO 99/28468
WO 99/46284
WO 99/58658
Am. J. Hum. Genet. 49 (3):555-565 (1991)
Amiel J., et al Hum. Mol. Genet. 5, 355-357, 1996
Amir et al (2003) Angew. Chem. Int. Ed. 42:4494-4499
Amsberry, et al (1990) J. Org. Chem. 55:5867
Angew Chem. Intl. Ed. Engl. (1994) 33:183-186
Annu. Rev. Neurosci. 21:309-345 (1998)
Arai H., et al J. Biol. Chem. 268, 3463-3470, 1993
Arai H., et al Jpn. Circ. J. 56, 1303-1307, 1992
Arima, et al., J. Antibiotics, 25, 437-444 (1972)
Attie T., et al, Hum. Mol. Genet. 4, 2407-2409, 1995
Auricchio A., et al Hum. Mol. Genet. 5:351-354, 1996
Barel M., et al Mol. Immunol. 35, 1025-1031, 1998
Barella et al (1995) Biochem. J. 309:773-779
Barnett T., et al Genomics 3, 59-66, 1988
Beck et al (1992) J. Mol. Biol. 228:433-441
Beck et al (1996) J. Mol. Biol. 255:1-13
Berge, et al., J. Pharm. Sci., 66, 1-19 (1977)
Biochem. Biophys. Res. Commun. (2000) 275(3):783-788
Biochem. Biophys. Res. Commun. 255 (2), 283-288 (1999)
Blood (2002) 100 (9):3068-3076
Blood 99 (8):2662-2669 (2002)
Blumberg H., et al Cell 104, 9-19, 2001
Bose, et al., Tetrahedron, 48, 751-758 (1992)
Bourgeois C., et al J. Clin. Endocrinol. Metab. 82, 3116-3123, 1997
Brinster et al (1988) Proc. Natl. Acad. Sci. USA 85:836
Buchman and Berg (1988) Mol. Cell. Biol. 8:4395
Cancer Res. 61 (15), 5857-5860 (2001)
Carl et al (1981) J. Med. Chem. 24:479-480
Carlsson et al (1978) Biochem. J. 173:723-737
Carter, P. (2006) Nature Reviews Immunology 6:343-357
Cell 109 (3):397-407 (2002)
CellTiter Glo Luminescent Cell Viability Assay, Promega Corp. Technical Bulletin TB288
Chakravarty et al (1983) J. Med. Chem. 26:638-644
Chan, J. and Watt, V. M., Oncogene 6 (6), 1057-1061 (1991)
Child et al (1999) J. Biol. Chem. 274: 24335-24341
Cho H.-S., et al Nature 421, 756-760, 2003
Ciccodicola, A., et al EMBO J. 8(7):1987-1991 (1989)
Clackson et al (1991) Nature, 352:624-628
Clark H. F., et al Genome Res. 13, 2265-2270, 2003
Corey E, Quinn J E, Buhler K R, et al. LuCap35: a new model of prostate cancer progression to androgen independence. The Prostate 2003; 55:239-46
Coussens L., et al Science (1985) 230(4730):1132-1139
Cree et al (1995) AntiCancer Drugs 6:398-404
Crouch et al (1993) J. Immunol. Meth. 160:81-88
Davis et al (2001) Proc. Natl. Acad. Sci. USA 98(17):9772-9777
de Groot et al (2001) J. Org. Chem. 66:8815-8830
de Groot et al (2003) Angew. Chem. Int. Ed. 42:4490-4494
Dennis et al. (2002) "Albumin Binding As A General Strategy For Improving The Pharmacokinetics Of Proteins" J Biol. Chem. 277:35035-35043
Dobner et al (1992) Eur. J. Immunol. 22:2795-2799
Dornan et al (2009) Blood 114(13):2721-2729
Doronina et al (2006) Bioconj. Chem. 17:114-124
Dubowchik et al. Bioconjugate Chemistry, 2002, 13, 855-869
Dubowchik, et al. (1997) Tetrahedron Letters, 38:5257-60
Dumoutier L., et al J. Immunol. 167, 3545-3549, 2001
E. Schröder and K. Lübke, The Peptides, volume 1, pp 76-136 (1965) Academic Press
Ehsani A., et al (1993) Genomics 15, 426-429
Eliel, E. and Wilen, S., "Stereochemistry of Organic Compounds", John Wiley & Sons, Inc., New York, 1994
Elshourbagy N. A., et al J. Biol. Chem. 268, 3873-3879, 1993
Erickson et al (2006) Cancer Res. 66(8):1-8
Feild, J. A., et al (1999) Biochem. Biophys. Res. Commun. 258 (3):578-582
Fields, G. and Noble, R. (1990) "Solid phase peptide synthesis utilizing 9-fluoroenylmethoxycarbonyl amino acids", Int. J. Peptide Protein Res. 35:161-214
Fuchs S., et al Mol. Med. 7, 115-124, 2001
Fujisaku et al (1989) J. Biol. Chem. 264 (4):2118-2125)
Gary S. C., et al Gene 256, 139-147, 2000
Gaugitsch, H. W., et al (1992) J. Biol. Chem. 267 (16): 11267-11273)
Geiser et al "Automation of solid-phase peptide synthesis" in Macromolecular Sequencing and Synthesis, Alan R. Liss, Inc., 1988, pp. 199-218
Genome Res. 13 (10):2265-2270 (2003)
Genomics 62 (2):281-284 (1999)
Geoghegan & Stroh, (1992) Bioconjugate Chem. 3:138-146
Getz et al (1999) Anal. Biochem. Vol 273:73-80
Glynne-Jones et al (2001) Int J Cancer. October 15; 94(2): 178-84
Gregson et al., Chem. Commun. 1999, 797-798
Gregson et al., J. Med. Chem. 2001, 44, 1161-1174
Gu Z., et al Oncogene 19, 1288-1296, 2000
Ha et al (1992) J. Immunol. 148(5):1526-1531
Haendler B., et al J. Cardiovasc. Pharmacol. 20, s1-S4, 1992
Hamann P. (2005) Expert Opin. Ther. Patents 15(9):1087-1103
Hamblett et al (2004) Clin. Cancer Res. 10:7063-7070
Handbook of Pharmaceutical Additives, 2nd Edition (eds. M. Ash and I. Ash), 2001 (Synapse Information Resources, Inc., Endicott, N.Y., USA)
Handbook of Pharmaceutical Excipients, 2nd edition, 1994
Hara, et al., J. Antibiotics, 41, 702-704 (1988)
Hashimoto et al (1994) Immunogenetics 40(4):287-295
Hay et al. (1999) Bioorg. Med. Chem. Lett. 9:2237
Herdwijn, P. et al., Canadian Journal of Chemistry. 1982, 60, 2903-7
Hermanson, G. T. (1996) Bioconjugate Techniques; Academic Press: New York, p 234-242
Hochlowski, et al., J. Antibiotics, 40, 145-148 (1987)
Hofstra R. M. W., et al Eur. J. Hum. Genet. 5, 180-185, 1997
Hofstra R. M. W., et al Nat. Genet. 12, 445-447, 1996
Horie et al (2000) Genomics 67:146-152
Hubert, R. S., et al (1999) Proc. Natl. Acad. Sci. U.S.A. 96 (25):14523-14528)

Hurley and Needham-VanDevanter, Acc. Chem. Res., 19, 230-237 (1986)
Immunogenetics 54 (2):87-95 (2002)
Int. Rev. Cytol. 196:177-244 (2000)
Itoh, et al., J. Antibiotics, 41, 1281-1284 (1988)
J. Biol. Chem. 270 (37):21984-21990 (1995)
J. Biol. Chem. 276 (29):27371-27375 (2001)
J. Biol. Chem. 277 (22):19665-19672 (2002)
J. Biol. Chem. 278 (33):30813-30820 (2003)
Janeway, C., Travers, P., Walport, M., Shlomchik (2001) Immuno Biology, 5th Ed., Garland Publishing, New York
Jeffrey et al (2005) J. Med. Chem. 48:1344-1358
Jonsson et al (1989) Immunogenetics 29(6):411-413
Junutula, et al., 2008b Nature Biotech., 26(8):925-932
Kang, G-D., et al., Chem. Commun., 2003, 1680-1689
Kasahara et al (1989) Immunogenetics 30(1):66-68
King et al (2002) Tetrahedron Letters 43:1987-1990
Kingsbury et al (1984) J. Med. Chem. 27:1447
Kohler et al (1975) Nature 256:495
Kohn, in Antibiotics III. Springer-Verlag, New York, pp. 3-11 (1975).
Konishi, et al., J. Antibiotics, 37, 200-206 (1984)
Kovtun et al (2006) Cancer Res. 66(6):3214-3121
Kuhns J. J., et al J. Biol. Chem. 274, 36422-36427, 1999
Kuminoto, et al., J. Antibiotics, 33, 665-667 (1980)
Kurebayashi et al (1999) Brit. Jour. Cancer 79(5-6):707-717
Lab. Invest. 82 (11):1573-1582 (2002)
Lambert J. (2005) Current Opin. in Pharmacol. 5:543-549
Langley and Thurston, J. Org. Chem., 52, 91-97 (1987)
Larhammar et al (1985) J. Biol. Chem. 260(26):14111-14119
Law et al (2006) Cancer Res. 66(4):2328-2337
Le et al (1997) FEBS Lett. 418(1-2):195-199
Leber, et al., J. Am. Chem. Soc., 110, 2992-2993 (1988)
Leimgruber, et al., J. Am. Chem. Soc., 87, 5791-5793 (1965)
Leimgruber, et al., J. Am. Chem. Soc., 87, 5793-5795 (1965)
Levenson et al (1997) Cancer Res. 57(15):3071-3078
Liang et al (2000) Cancer Res. 60:4907-12
Manfré, F. et al., J. Org. Chem. 1992, 57, 2060-2065
Marks et al (1991) J. Mol. Biol., 222:581-597
McDonagh (2006) Protein Eng. Design & Sel., 19(7): 299-307
Mendoza et al (2002) Cancer Res. 62:5485-5488
Miller et al (2003) Jour. of Immunology 170:4854-4861
Miura et al (1996) Genomics 38(3):299-304
Miura et al (1998) Blood 92:2815-2822
Moore M., et al Proc. Natl. Acad. Sci. U.S.A. 84, 9194-9198, 1987
Morrison et al (1984) Proc. Natl. Acad. Sci. USA, 81:6851-6855
Muller et al (1992) Eur. J. Immunol. 22 (6):1621-1625
Mungall A. J., et al Nature 425, 805-811, 2003
Nagase T., et al (2000) DNA Res. 7 (2):143-150)
Nakamuta M., et al Biochem. Biophys. Res. Commun. 177, 34-39, 1991
Nakayama et al (2000) Biochem. Biophys. Res. Commun. 277(1):124-127
Naruse et al (2002) Tissue Antigens 59:512-519
Nature 395 (6699):288-291 (1998)
Neuberger and Williams (1988) Nucleic Acids Res. 16:6713
Novabiochem Catalog 2006/2007
Ogawa Y., et al Biochem. Biophys. Res. Commun. 178, 248-255, 1991
Okamoto Y., et al Biol. Chem. 272, 21589-21596, 1997
Oncogene 10 (5):897-905 (1995)
Oncogene 14(11):1377-1382 (1997))
Parrish-Novak J., et al J. Biol. Chem. 277, 47517-47523, 2002
Payne, G. (2003) Cancer Cell 3:207-212
Phillips et al (2008) Cancer Res. 68(22):9280-9290
Pingault V., et al (2002) Hum. Genet. 111, 198-206
Pletnev S., et al (2003) Biochemistry 42:12617-12624
Preud'homme et al (1992) Clin. Exp. Immunol. 90(1):141-146
Proc. Natl. Acad. Sci. U.S.A. (2003) 100 (7):4126-4131
Proc. Natl. Acad. Sci. U.S.A. 93 (1):136-140 (1996)
Proc. Natl. Acad. Sci. U.S.A. 98 (17):9772-9777 (2001)
Proc. Natl. Acad. Sci. U.S.A. 99 (26):16899-16903 (2002)
Proc. Natl. Acad. Sci. U.S.A. 96 (20):11531-11536 (1999)
Protective Groups in Organic Synthesis, Greene and Wuts, $3^{rd}$ Edition, 1999, John Wiley & Sons Inc.
Puffenberger E. G., et al Cell 79, 1257-1266, 1994
Rao et al (1997) Breast Cancer Res. and Treatment 45:149-158
Reiter R. E., et al Proc. Natl. Acad. Sci. U.S.A. 95, 1735-1740, 1998
Remington's Pharmaceutical Sciences, 20th edition, pub. Lippincott, Williams & Wilkins, 2000
Rodrigues et al (1995) Chemistry Biology 2:223
Ross et al (2002) Cancer Res. 62:2546-2553
S. P. Parker, Ed., McGraw-Hill Dictionary of Chemical Terms (1984) McGraw-Hill Book Company, New York
Sakaguchi et al (1988) EMBO J. 7(11):3457-3464
Sakamoto A., Yanagisawa M., et al Biochem. Biophys. Res. Commun. 178, 656-663, 1991
Sanderson et al (2005) Clin. Cancer Res. 11:843-852
Semba K., et al Proc. Natl. Acad. Sci. U.S.A. 82, 6497-6501, 1985
Servenius et al (1987) J. Biol. Chem. 262:8759-8766
Shamis et al (2004) J. Am. Chem. Soc. 126:1726-1731
Sheikh F., et al (2004) J. Immunol. 172, 2006-2010
Shimizu, et al, J. Antibiotics, 29, 2492-2503 (1982)
Sinha S. K., et al (1993) J. Immunol. 150, 5311-5320
Storm et al (1972) J. Amer. Chem. Soc. 94:5815
Strausberg et al (2002) Proc. Natl. Acad. Sci. USA 99:16899-16903
Sun et al (2002) Bioorganic & Medicinal Chemistry Letters 12:2213-2215
Sun et al (2003) Bioorganic & Medicinal Chemistry 11:1761-1768
Svensson P. J., et al Hum. Genet. 103, 145-148, 1998
Swiercz J. M., et al J. Cell Biol. 165, 869-880, 2004
Syrigos and Epenetos (1999) Anticancer Research 19:605-614
Takeuchi, et al., J. Antibiotics, 29, 93-96 (1976)
Tawaragi Y., et al Biochem. Biophys. Res. Commun. 150, 89-96, 1988
ten Dijke, P., et al Science 264 (5155):101-104 (1994)
Thompson, J. S., et al Science 293 (5537), 2108-2111 (2001)
WO 2004/058309
Thurston, et al., Chem. Brit., 26, 767-772 (1990)
Thurston, et al., Chem. Rev. 1994, 433-465 (1994)
Toki et al (2002) J. Org. Chem. 67:1866-1872
Tonnelle et al (1985) EMBO J. 4(11):2839-2847
Touchman et al (2000) Genome Res. 10:165-173
Trail et al (2003) Cancer Immunol. Immunother. 52:328-337
Tsunakawa, et al., J. Antibiotics, 41, 1366-1373 (1988)
Tsutsumi M., et al Gene 228, 43-49, 1999
Uchida et al (1999) Biochem. Biophys. Res. Commun. 266:593-602
Verheij J. B., et al Am. J. Med. Genet. 108, 223-225, 2002
Von Hoegen et al (1990) J. Immunol. 144(12):4870-4877
Webster et al (1994) Semin. Cancer Biol. 5:69-76

Weis J. J., et al J. Exp. Med. 167, 1047-1066, 1988
Weis J. J., et al Proc. Natl. Acad. Sci. U.S.A. 83, 5639-5643, 1986
Wilson et al (1991) J. Exp. Med. 173:137-146
Wu et al (2005) Nature Biotech. 23(9):1137-1145
Xie et al (2006) Expert. Opin. Biol. Ther. 6(3):281-291
Xu, M. J., et al (2001) Biochem. Biophys. Res. Commun. 280 (3):768-775 WO 2004/016225
Xu, X. Z., et al Proc. Natl. Acad. Sci. U.S.A. 98 (19):10692-10697 (2001)
Yamaguchi, N., et al Biol. Chem. 269 (2), 805-808 (1994)
Yamamoto T., et al Nature 319, 230-234, 1986
Yu et al (1992) J. Immunol. 148(2) 633-637

The invention claimed is:
1. An antibody-drug conjugate compound comprising an antibody attached to one or more PBD drug moieties, and prepared by reacting the antibody and a PBD compound selected from:
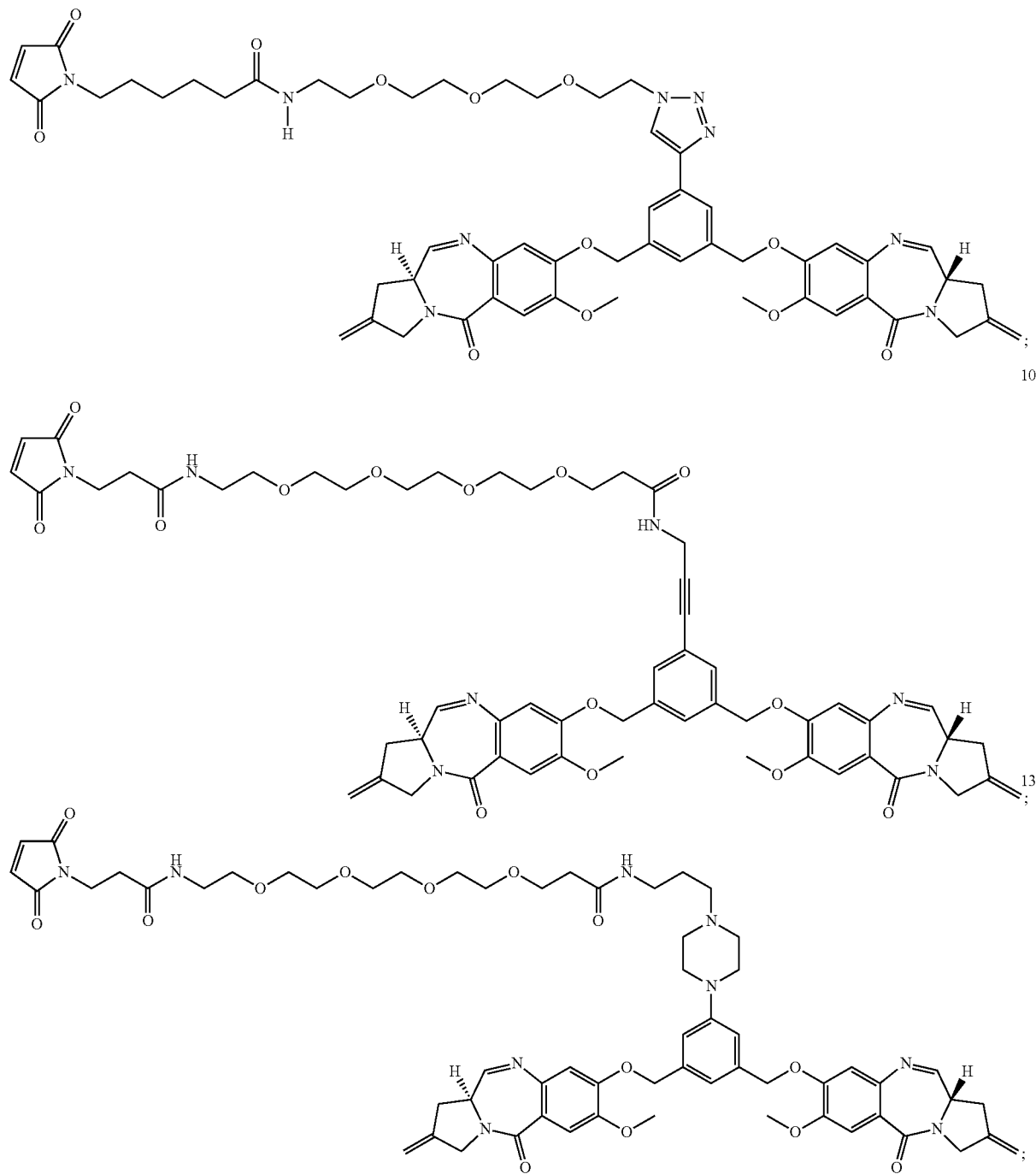

17
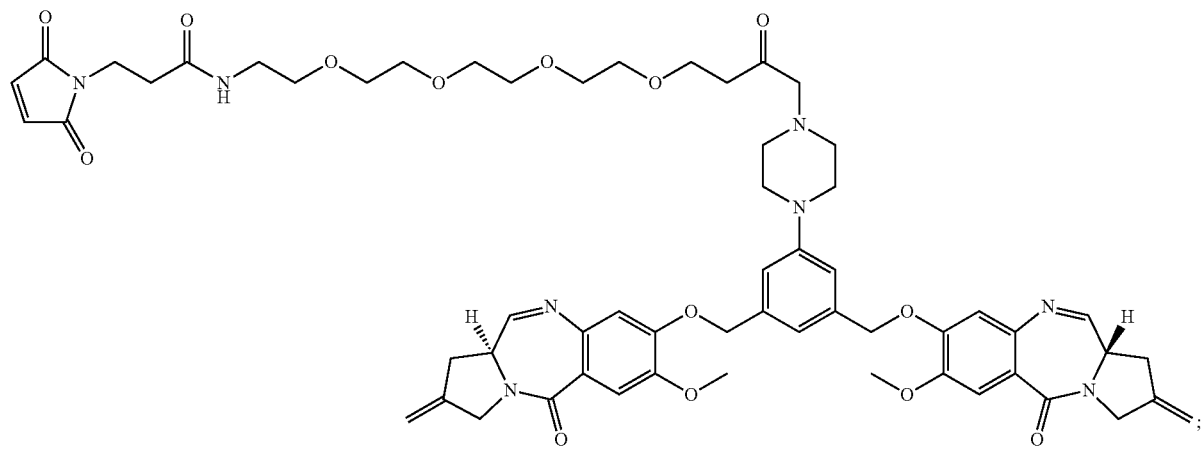
24
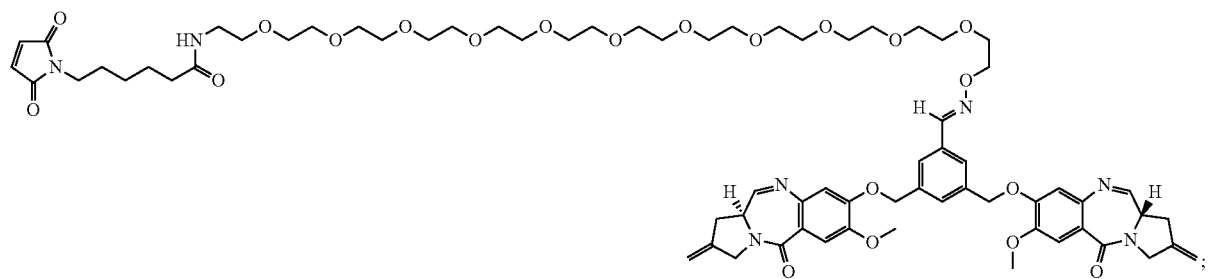
25
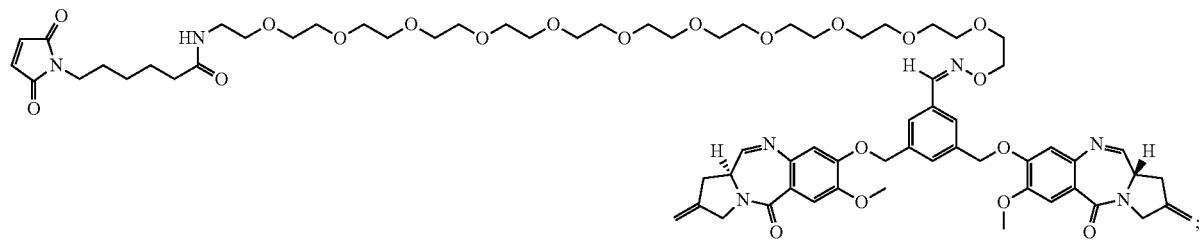
33
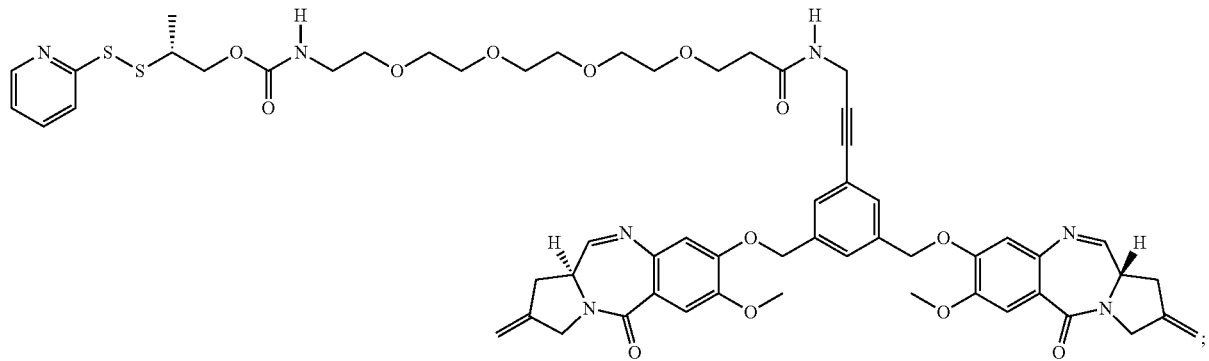

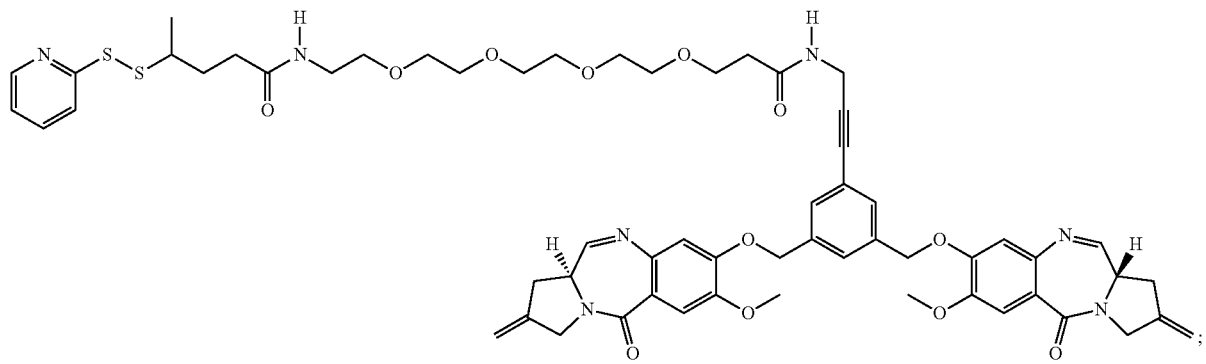

37 and

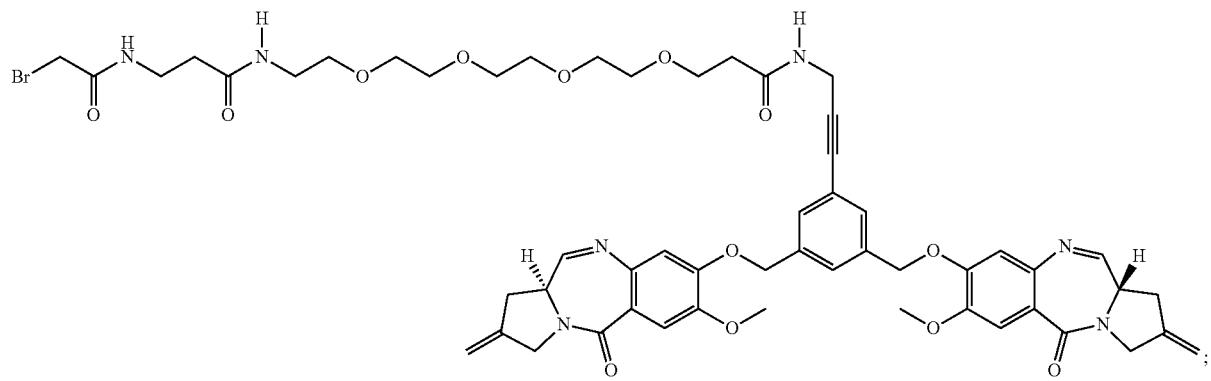

48 wherein the antibody binds to one or more tumor-associated antigens or cell-surface receptors selected from:
(4) 0772P (CA125, MUC16);
(6) Napi3b (NAPI-3B, Napi2b, NPTIIb, SLC34A2, solute carrier family 34 (sodium phosphate), member 2, type II sodium-dependent phosphate transporter 3b);
(17) HER2;
(27) CD22 (B-cell receptor CD22-B isoform);
(37) CD33 (CD33 molecule, SIGLEC-3, SIGLEC3, p67; CD33 antigen (gp67); gp67; myeloid cell surface antigen CD33; sialic acid binding Ig-like lectin 3; sialic acid-binding Ig-like lectin); and
(38) LGR5/GPR49.

2. The antibody-drug conjugate compound of claim 1 wherein the antibody is a cysteine-engineered antibody.

3. The antibody-drug conjugate compound of claim 2 wherein the antibody is an antibody which binds to an ErbB receptor.

4. The antibody-drug conjugate compound of claim 3 wherein the antibody is trastuzumab.

5. The antibody-drug conjugate compound of claim 1 wherein the antibody is selected from an anti-HER2 antibody, an anti-CD33 antibody, an anti-LGR5 antibody, an anti-Napi3b antibody, an anti-MUC16 antibody, and an anti-CD22 antibody.

6. The antibody-drug conjugate compound according to claim 1 comprising a mixture of the antibody-drug conjugate compounds, wherein the average drug loading per antibody in the mixture of antibody-drug conjugate compounds is about 2 to about 5.

7. A pharmaceutical composition comprising the antibody-drug conjugate compound of claim 1, and a pharmaceutically acceptable diluent, carrier or excipient.

8. A method of treating a patient with cancer, comprising administering an effective amount of the pharmaceutical composition according to claim 7 to the patient.

* * * * *